United States Patent
Weikart et al.

(10) Patent No.: US 12,257,371 B2
(45) Date of Patent: **\*Mar. 25, 2025**

(54) SiO$_x$ BARRIER FOR PHARMACEUTICAL PACKAGE AND COATING PROCESS

(71) Applicant: SiO2 Medical Products, Inc., Auburn, AL (US)

(72) Inventors: Christopher Weikart, Auburn, AL (US); John T. Felts, Alameda, CA (US); Thomas E. Fisk, Green Valley, AZ (US); Robert S. Abrams, Albany, NY (US); John Ferguson, Auburn, AL (US); Jonathan R. Freedman, Auburn, AL (US); Robert J. Pangborn, Harbor Springs, MI (US); Peter J. Sagona, Pottstown, PA (US)

(73) Assignee: SIO2 MEDICAL PRODUCTS, LLC, Auburn, AL (US)

( * ) Notice: Subject to any disclaimer, the term of this patent is extended or adjusted under 35 U.S.C. 154(b) by 969 days.

This patent is subject to a terminal disclaimer.

(21) Appl. No.: 17/306,621

(22) Filed: May 3, 2021

(65) Prior Publication Data

US 2021/0330869 A1 Oct. 28, 2021

Related U.S. Application Data

(63) Continuation of application No. 14/412,472, filed as application No. PCT/US2013/048709 on Jun. 28, 2013, now abandoned.

(Continued)

(51) Int. Cl.
*A61L 31/08* (2006.01)
*A61F 9/00* (2006.01)
(Continued)

(52) U.S. Cl.
CPC .............. *A61L 31/088* (2013.01); *A61J 1/035* (2013.01); *A61J 1/05* (2013.01); *A61L 29/106* (2013.01);
(Continued)

(58) Field of Classification Search
CPC ..................... A61J 1/1468; A61J 2205/0238
See application file for complete search history.

(56) References Cited

U.S. PATENT DOCUMENTS 3,274,267 A 9/1966 Chow
3,297,465 A 1/1967 Connell
(Continued)

FOREIGN PATENT DOCUMENTS

AT 414209 B 10/2006
AT 504533 A1 6/2008
(Continued)

OTHER PUBLICATIONS

US 5,645,643 A, 07/1997, Thomas (withdrawn)
(Continued)

*Primary Examiner* — Michael C Miggins
(74) *Attorney, Agent, or Firm* — McAndrews, Held & Malloy, Ltd.

(57) ABSTRACT

A vessel including a thermoplastic wall enclosing a lumen is disclosed. The wall supports an SiO$_x$ composite barrier coating or layer, for which x is from 1.8 to 2.4, between the wall and the lumen. High Resolution X-ray Photoelectron Spectroscopy (XPS) shows the presence of an interface between the composite barrier coating or layer and the wall or substrate. In one aspect, the interface has at least 1 mol. % O$_3$—Si—C covalent bonding, as a proportion of the O$_3$—Si—C covalent bonding plus SiO$_4$ bonding. In another aspect, the interface has an Si 2p chemical shift to lower binding energy (eV), compared to the binding energy of (Continued)

SiO$_4$ bonding. The result is a tightly adherent composite barrier coating or layer having a high degree of adhesion to the substrate under practical use conditions. Methods of applying the composite barrier coating or layer are also disclosed.

19 Claims, 10 Drawing Sheets

Related U.S. Application Data

(60) Provisional application No. 61/800,494, filed on Mar. 15, 2013, provisional application No. 61/792,952, filed on Mar. 15, 2013, provisional application No. 61/800,746, filed on Mar. 15, 2013, provisional application No. 61/800,660, filed on Mar. 15, 2013, provisional application No. 61/776,733, filed on Mar. 11, 2013, provisional application No. 61/771,644, filed on Mar. 1, 2013, provisional application No. 61/747,584, filed on Dec. 31, 2012, provisional application No. 61/732,180, filed on Nov. 30, 2012, provisional application No. 61/713,435, filed on Oct. 12, 2012.

(51) Int. Cl.
| | | |
|---|---|---|
| A61J 1/03 | | (2023.01) |
| A61J 1/05 | | (2006.01) |
| A61J 1/14 | | (2023.01) |
| A61L 29/10 | | (2006.01) |
| A61M 5/31 | | (2006.01) |
| A61M 15/00 | | (2006.01) |
| C23C 16/40 | | (2006.01) |

(52) U.S. Cl.
CPC ......... *A61M 5/3129* (2013.01); *C23C 16/401* (2013.01); *A61F 9/0008* (2013.01); *A61J 1/1468* (2015.05); *A61L 2420/02* (2013.01); *A61M 15/0001* (2014.02); *A61M 2202/048* (2013.01); *A61M 2205/0238* (2013.01); *A61M 2205/19* (2013.01)

(56) References Cited

U.S. PATENT DOCUMENTS

| | | |
|---|---|---|
| 3,355,947 A | 12/1967 | Karlby |
| 3,442,686 A | 5/1969 | Jones |
| 3,448,614 A | 6/1969 | Muger |
| 3,590,634 A | 7/1971 | Pasternak |
| 3,838,598 A | 10/1974 | Tomkins |
| 3,957,653 A | 5/1976 | Blecher |
| 4,111,326 A | 9/1978 | Percarpio |
| 4,134,832 A | 1/1979 | Heimreid |
| 4,136,794 A | 1/1979 | Percapio |
| 4,162,528 A | 7/1979 | Maldonado |
| 4,168,330 A | 9/1979 | Kaganowicz |
| 4,186,840 A | 2/1980 | Percarpio |
| 4,187,952 A | 2/1980 | Percarpio |
| 4,226,333 A | 10/1980 | Percarpio |
| 4,289,726 A | 9/1981 | Potoczky |
| 4,290,534 A | 9/1981 | Percarpio |
| 4,293,078 A | 10/1981 | Percarpio |
| 4,338,764 A | 7/1982 | Percarpio |
| 4,391,128 A | 7/1983 | McWorter |
| 4,392,218 A | 7/1983 | Plunkett, Jr. |
| 4,422,896 A | 12/1983 | Class |
| 4,452,679 A | 6/1984 | Dunn |
| 4,478,873 A | 10/1984 | Masso |
| 4,481,229 A | 11/1984 | Suzuki |
| 4,483,737 A | 11/1984 | Mantei |
| 4,484,479 A | 11/1984 | Eckhardt |
| 4,486,378 A | 12/1984 | Hirata |
| 4,522,510 A | 6/1985 | Rosencwaig |
| 4,524,089 A | 6/1985 | Haque |
| 4,524,616 A | 6/1985 | Drexel |
| 4,552,791 A | 11/1985 | Hahn |
| 4,576,204 A | 3/1986 | Smallborn |
| 4,609,428 A | 9/1986 | Fujimura |
| 4,610,770 A | 9/1986 | Saito |
| 4,648,107 A | 3/1987 | Latter |
| 4,648,281 A | 3/1987 | Morita |
| 4,652,429 A | 3/1987 | Konrad |
| 4,664,279 A | 5/1987 | Obrist |
| 4,667,620 A | 5/1987 | White |
| 4,668,365 A | 5/1987 | Foster |
| 4,683,838 A | 8/1987 | Kimura |
| 4,697,717 A | 10/1987 | Grippi |
| 4,703,187 A | 10/1987 | Hofling |
| 4,716,491 A | 12/1987 | Ohno |
| 4,721,553 A | 1/1988 | Saito |
| 4,725,481 A | 2/1988 | Ostapchenko |
| 4,741,446 A | 5/1988 | Miller |
| 4,756,964 A | 7/1988 | Kincaid |
| 4,767,414 A | 8/1988 | Williams |
| 4,778,721 A | 10/1988 | Sliemers |
| 4,799,246 A | 1/1989 | Fischer |
| 4,808,453 A | 2/1989 | Romberg |
| 4,809,876 A | 3/1989 | Tomaswick |
| 4,824,444 A | 4/1989 | Nomura |
| 4,841,776 A | 6/1989 | Kawachi |
| 4,842,704 A | 6/1989 | Collins |
| 4,844,986 A | 7/1989 | Karakelle |
| 4,846,101 A | 7/1989 | Montgomery |
| 4,853,102 A | 8/1989 | Tateishi |
| 4,869,203 A | 9/1989 | Pinkhasov |
| 4,872,758 A | 10/1989 | Miyazaki |
| 4,874,497 A | 10/1989 | Matsuoka |
| 4,880,675 A | 11/1989 | Mehta |
| 4,883,686 A | 11/1989 | Doehler |
| 4,886,086 A | 12/1989 | Etchells |
| 4,894,256 A | 1/1990 | Gartner |
| 4,894,510 A | 1/1990 | Nakanishi |
| 4,897,285 A | 1/1990 | Wilhelm |
| 4,926,791 A | 5/1990 | Hirose |
| 4,948,628 A | 8/1990 | Montgomery |
| 4,973,504 A | 11/1990 | Romberg |
| 4,991,104 A | 2/1991 | Miller |
| 4,999,014 A | 3/1991 | Gold |
| 5,000,994 A | 3/1991 | Romberg |
| 5,016,564 A | 5/1991 | Nakamura |
| 5,021,114 A | 6/1991 | Saito |
| 5,028,566 A | 7/1991 | Lagendijk |
| 5,030,475 A | 7/1991 | Ackermann |
| 5,032,202 A | 7/1991 | Tsai |
| 5,039,548 A | 8/1991 | Hirose |
| 5,041,303 A | 8/1991 | Wertheimer |
| 5,042,951 A | 8/1991 | Gold |
| 5,044,199 A | 9/1991 | Drexel |
| 5,064,083 A | 11/1991 | Alexander |
| 5,067,491 A | 11/1991 | Taylor |
| 5,079,481 A | 1/1992 | Moslehi |
| 5,082,542 A | 1/1992 | Moslehi |
| 5,084,356 A | 1/1992 | Deak |
| 5,085,904 A | 2/1992 | Deak |
| 5,099,881 A | 3/1992 | Nakajima |
| 5,113,790 A | 5/1992 | Geisler |
| 5,120,966 A | 6/1992 | Kondo |
| 5,131,752 A | 7/1992 | Yu |
| 5,144,196 A | 9/1992 | Gegenwart |
| 5,147,678 A | 9/1992 | Foerch |
| 5,154,943 A | 10/1992 | Etzkorn |
| 5,189,446 A | 2/1993 | Barnes |
| 5,192,849 A | 3/1993 | Moslehi |
| 5,198,725 A | 3/1993 | Chen |
| 5,203,959 A | 4/1993 | Hirose |
| 5,204,141 A | 4/1993 | Roberts |
| 5,209,882 A | 5/1993 | Hattori |
| 5,216,329 A | 6/1993 | Pelleteir |
| 5,224,441 A | 7/1993 | Felts |
| 5,225,024 A | 7/1993 | Hanley |

(56) References Cited

U.S. PATENT DOCUMENTS

| | | |
|---|---|---|
| 5,232,111 A | 8/1993 | Burns |
| 5,252,178 A | 10/1993 | Moslehi |
| 5,260,095 A | 11/1993 | Affinito |
| 5,266,398 A | 11/1993 | Hioki |
| 5,271,274 A | 12/1993 | Khuri-Yakub |
| 5,272,417 A | 12/1993 | Ohmi |
| 5,272,735 A | 12/1993 | Bryan |
| 5,275,299 A | 1/1994 | Konrad |
| 5,286,297 A | 2/1994 | Moslehi |
| 5,292,370 A | 3/1994 | Tsai |
| 5,294,011 A | 3/1994 | Konrad |
| 5,294,464 A | 3/1994 | Geisler |
| 5,297,561 A | 3/1994 | Hulon |
| 5,298,587 A | 3/1994 | Hu |
| 5,300,901 A | 4/1994 | Krummel |
| 5,302,266 A | 4/1994 | Grabarz |
| 5,308,649 A | 5/1994 | Babacz |
| 5,314,561 A | 5/1994 | Komiya |
| 5,320,875 A | 6/1994 | Hu |
| 5,321,634 A | 6/1994 | Obata |
| 5,330,578 A | 7/1994 | Sakama |
| 5,333,049 A | 7/1994 | Ledger |
| 5,338,579 A | 8/1994 | Ogawa et al. |
| 5,346,579 A | 9/1994 | Cook |
| 5,354,286 A | 10/1994 | Mesa |
| 5,356,029 A | 10/1994 | Hogan |
| 5,361,921 A | 11/1994 | Burns |
| 5,364,665 A | 11/1994 | Felts |
| 5,364,666 A | 11/1994 | Williams |
| 5,372,851 A | 12/1994 | Ogawa et al. |
| 5,374,314 A | 12/1994 | Babacz |
| 5,378,510 A | 1/1995 | Thomas |
| 5,381,228 A | 1/1995 | Brace |
| 5,395,644 A | 3/1995 | Affinito |
| 5,396,080 A | 3/1995 | Hannotiau |
| 5,397,956 A | 3/1995 | Araki |
| 5,409,782 A | 4/1995 | Murayama |
| 5,413,813 A | 5/1995 | Cruse |
| 5,423,915 A | 6/1995 | Murata |
| 5,429,070 A | 7/1995 | Campbell |
| 5,433,786 A | 7/1995 | Hu |
| 5,434,008 A | 7/1995 | Felts |
| 5,439,736 A | 8/1995 | Nomura |
| 5,440,446 A | 8/1995 | Shaw |
| 5,443,645 A | 8/1995 | Otoshi |
| 5,444,207 A | 8/1995 | Sekine |
| 5,449,432 A | 9/1995 | Hanawa |
| 5,452,082 A | 9/1995 | Sanger |
| 5,468,520 A | 11/1995 | Williams |
| 5,470,388 A | 11/1995 | Goedicke |
| 5,472,660 A | 12/1995 | Fortin |
| 5,485,091 A | 1/1996 | Verkuil |
| 5,486,701 A | 1/1996 | Norton |
| 5,494,170 A | 2/1996 | Burns |
| 5,494,712 A | 2/1996 | Hu |
| 5,495,958 A | 3/1996 | Konrad |
| 5,508,075 A | 4/1996 | Roulin |
| 5,510,155 A | 4/1996 | Williams |
| 5,513,515 A | 5/1996 | Mayer |
| 5,514,276 A | 5/1996 | Babock |
| 5,521,351 A | 5/1996 | Mahoney |
| 5,522,518 A | 6/1996 | Konrad |
| 5,531,060 A | 7/1996 | Fayet |
| 5,531,683 A | 7/1996 | Kriesel |
| 5,536,253 A | 7/1996 | Haber |
| 5,543,919 A | 8/1996 | Mumola |
| 5,545,375 A | 8/1996 | Tropsha |
| 5,547,508 A | 8/1996 | Affinito |
| 5,547,723 A | 8/1996 | Williams |
| 5,554,223 A | 9/1996 | Imahashi |
| 5,555,471 A | 9/1996 | Xu |
| 5,565,248 A | 10/1996 | Piester |
| 5,569,810 A | 10/1996 | Tsuji |
| 5,571,366 A | 11/1996 | Ishii |
| 5,578,103 A | 11/1996 | Araujo |
| 5,591,898 A | 1/1997 | Mayer |
| 5,593,550 A | 1/1997 | Stewart |
| 5,597,456 A | 1/1997 | Maruyama |
| 5,616,369 A | 4/1997 | Williams |
| 5,620,523 A | 4/1997 | Maeda |
| 5,632,396 A | 5/1997 | Burns |
| 5,633,711 A | 5/1997 | Nelson |
| 5,643,638 A | 7/1997 | Otto |
| 5,652,030 A | 7/1997 | Delperier |
| 5,654,054 A | 8/1997 | Tropsha |
| 5,656,141 A | 8/1997 | Betz |
| 5,658,438 A | 8/1997 | Givens |
| 5,665,280 A | 9/1997 | Tropsha |
| 5,667,840 A | 9/1997 | Tingey |
| 5,674,321 A | 10/1997 | Pu |
| 5,677,010 A | 10/1997 | Esser |
| 5,679,412 A | 10/1997 | Kuehnle |
| 5,679,413 A | 10/1997 | Petrmichl |
| 5,683,771 A | 11/1997 | Tropsha |
| 5,686,157 A | 11/1997 | Harvey |
| 5,690,745 A | 11/1997 | Grunwald |
| 5,691,007 A | 11/1997 | Montgomery |
| 5,693,196 A | 12/1997 | Stewart |
| 5,699,923 A | 12/1997 | Burns |
| 5,702,770 A | 12/1997 | Martin |
| 5,704,983 A | 1/1998 | Thomas et al. |
| 5,716,683 A | 2/1998 | Harvey |
| 5,718,967 A | 2/1998 | Hu |
| 5,725,909 A | 3/1998 | Shaw |
| 5,733,405 A | 3/1998 | Taki |
| 5,736,207 A | 4/1998 | Walther |
| 5,737,179 A | 4/1998 | Shaw |
| 5,738,233 A | 4/1998 | Burns |
| 5,738,920 A | 4/1998 | Knors |
| 5,744,360 A | 4/1998 | Hu |
| 5,750,892 A | 5/1998 | Huang |
| 5,763,033 A | 6/1998 | Tropsha |
| 5,766,362 A | 6/1998 | Montgomery |
| 5,769,273 A | 6/1998 | Sasaki |
| 5,779,074 A | 7/1998 | Burns |
| 5,779,716 A | 7/1998 | Cano |
| 5,779,802 A | 7/1998 | Borghs |
| 5,779,849 A | 7/1998 | Blalock |
| 5,788,670 A | 8/1998 | Reinhard |
| 5,792,940 A | 8/1998 | Ghandhi |
| 5,798,027 A | 8/1998 | Lefebvre |
| 5,800,880 A | 9/1998 | Laurent |
| 5,807,343 A | 9/1998 | Tucker |
| 5,807,605 A | 9/1998 | Tingey |
| 5,812,261 A | 9/1998 | Nelson |
| 5,814,257 A | 9/1998 | Kawata |
| 5,814,738 A | 9/1998 | Pinkerton |
| 5,820,603 A | 10/1998 | Tucker |
| 5,823,373 A | 10/1998 | Sudo |
| 5,824,198 A | 10/1998 | Williams |
| 5,824,607 A | 10/1998 | Trow |
| 5,833,752 A | 11/1998 | Martin |
| 5,837,888 A | 11/1998 | Mayer |
| 5,837,903 A | 11/1998 | Weingand |
| 5,840,167 A | 11/1998 | Kim |
| 5,849,368 A | 12/1998 | Hostettler |
| 5,853,833 A | 12/1998 | Sudo |
| 5,855,686 A | 1/1999 | Rust |
| 5,861,546 A | 1/1999 | Sagi |
| 5,871,700 A | 2/1999 | Konrad |
| 5,877,895 A | 3/1999 | Shaw |
| 5,880,034 A | 3/1999 | Keller |
| 5,888,414 A | 3/1999 | Collins |
| 5,888,591 A | 3/1999 | Gleason |
| 5,897,508 A | 4/1999 | Konrad |
| 5,900,284 A | 5/1999 | Hu |
| 5,900,285 A | 5/1999 | Walther |
| 5,902,461 A | 5/1999 | Xu |
| 5,904,952 A | 5/1999 | Lopata |
| 5,913,140 A | 6/1999 | Roche |
| 5,914,189 A | 6/1999 | Hasz |
| 5,919,328 A | 7/1999 | Tropsha |
| 5,919,420 A | 7/1999 | Niermann |
| 5,935,391 A | 8/1999 | Nakahigashi |

(56) References Cited

U.S. PATENT DOCUMENTS

| | | |
|---|---|---|
| 5,945,187 A | 8/1999 | Buch-Rasmussen |
| 5,951,527 A | 9/1999 | Sudo |
| 5,952,069 A | 9/1999 | Tropsha |
| 5,955,161 A | 9/1999 | Tropsha |
| 5,961,911 A | 10/1999 | Hwang |
| 5,968,620 A | 10/1999 | Harvey |
| 5,972,297 A | 10/1999 | Niermann |
| 5,972,436 A | 10/1999 | Walther |
| 5,985,103 A | 11/1999 | Givens |
| 6,001,429 A | 12/1999 | Martin |
| 6,009,743 A | 1/2000 | Mayer |
| 6,013,337 A | 1/2000 | Knors |
| 6,017,317 A | 1/2000 | Newby |
| 6,018,987 A | 2/2000 | Mayer |
| 6,020,196 A | 2/2000 | Hu |
| 6,027,619 A | 2/2000 | Cathey |
| 6,032,813 A | 3/2000 | Niermann |
| 6,035,717 A | 3/2000 | Carodiskey |
| 6,050,400 A | 4/2000 | Taskis |
| 6,051,151 A | 4/2000 | Keller |
| 6,054,016 A | 4/2000 | Tuda |
| 6,054,188 A | 4/2000 | Tropsha |
| 6,068,884 A | 5/2000 | Rose |
| 6,077,403 A | 6/2000 | Kobayashi |
| 6,081,330 A | 6/2000 | Nelson |
| 6,082,295 A | 7/2000 | Lee |
| 6,083,313 A | 7/2000 | Venkatraman et al. |
| 6,085,927 A | 7/2000 | Kusz |
| 6,090,081 A | 7/2000 | Sudo |
| 6,106,678 A | 8/2000 | Shufflebotham |
| 6,110,395 A | 8/2000 | Gibson, Jr. |
| 6,110,544 A | 8/2000 | Yang |
| 6,112,695 A | 9/2000 | Felts |
| 6,116,081 A | 9/2000 | Ghandhi |
| 6,117,243 A | 9/2000 | Walther |
| 6,118,844 A | 9/2000 | Fischer |
| 6,124,212 A | 9/2000 | Fan |
| 6,125,687 A | 10/2000 | McClelland |
| 6,126,640 A | 10/2000 | Tucker |
| 6,136,275 A | 10/2000 | Niermann |
| 6,139,802 A | 10/2000 | Niermann |
| 6,143,140 A | 11/2000 | Wang |
| 6,149,982 A | 11/2000 | Plester |
| 6,153,269 A | 11/2000 | Gleason |
| 6,156,152 A | 12/2000 | Ogino |
| 6,156,399 A | 12/2000 | Spallek |
| 6,156,435 A | 12/2000 | Gleason |
| 6,160,350 A | 12/2000 | Sakemi |
| 6,161,712 A | 12/2000 | Savitz |
| 6,163,006 A | 12/2000 | Doughty |
| 6,165,138 A | 12/2000 | Miller |
| 6,165,542 A | 12/2000 | Jaworowski |
| 6,165,566 A | 12/2000 | Tropsha |
| 6,171,670 B1 | 1/2001 | Sudo |
| 6,175,612 B1 | 1/2001 | Sato |
| 6,177,142 B1 | 1/2001 | Felts |
| 6,180,185 B1 | 1/2001 | Felts |
| 6,180,191 B1 | 1/2001 | Felts |
| 6,188,079 B1 | 2/2001 | Juvinall |
| 6,189,484 B1 | 2/2001 | Yin |
| 6,190,992 B1 | 2/2001 | Sandhu |
| 6,193,853 B1 | 2/2001 | Yumshtyk |
| 6,196,155 B1 | 3/2001 | Setoyama |
| 6,197,166 B1 | 3/2001 | Moslehi |
| 6,200,658 B1 | 3/2001 | Walther |
| 6,200,675 B1 | 3/2001 | Neerinck |
| 6,204,922 B1 | 3/2001 | Chalmers |
| 6,210,791 B1 | 4/2001 | Skoog |
| 6,213,985 B1 | 4/2001 | Niedospial |
| 6,214,422 B1 | 4/2001 | Yializis |
| 6,217,716 B1 | 4/2001 | Fai Lai |
| 6,223,683 B1 | 5/2001 | Plester |
| 6,236,459 B1 | 5/2001 | Negahdaripour |
| 6,245,190 B1 | 6/2001 | Masuda |
| 6,248,219 B1 | 6/2001 | Wellerdieck |
| 6,248,397 B1 | 6/2001 | Ye |
| 6,251,792 B1 | 6/2001 | Collins |
| 6,254,983 B1 | 7/2001 | Namiki |
| 6,261,643 B1 | 7/2001 | Hasz |
| 6,263,249 B1 | 7/2001 | Stewart |
| 6,271,047 B1 | 8/2001 | Ushio |
| 6,276,296 B1 | 8/2001 | Plester |
| 6,277,331 B1 | 8/2001 | Konrad |
| 6,279,505 B1 | 8/2001 | Plester |
| 6,284,986 B1 | 9/2001 | Dietze |
| 6,306,132 B1 | 10/2001 | Moorman |
| 6,308,556 B1 | 10/2001 | Sagi |
| 6,322,661 B1 | 11/2001 | Bailey, III |
| 6,331,174 B1 | 12/2001 | Reinhard et al. |
| 6,346,596 B1 | 2/2002 | Mallen |
| 6,348,967 B1 | 2/2002 | Nelson |
| 6,350,415 B1 | 2/2002 | Niermann |
| 6,351,075 B1 | 2/2002 | Barankova |
| 6,352,629 B1 | 3/2002 | Wang |
| 6,354,452 B1 | 3/2002 | DeSalvo |
| 6,355,033 B1 | 3/2002 | Moorman |
| 6,365,013 B1 | 4/2002 | Beele |
| 6,375,022 B1 | 4/2002 | Zurcher |
| 6,376,028 B1 | 4/2002 | Laurent |
| 6,379,757 B1 | 4/2002 | Iacovangelo |
| 6,382,441 B1 | 5/2002 | Carano |
| 6,394,979 B1 | 5/2002 | Sharp |
| 6,396,024 B1 | 5/2002 | Doughty |
| 6,399,944 B1 | 6/2002 | Vasilyev |
| 6,402,885 B2 | 6/2002 | Loewenhardt |
| 6,410,926 B1 | 6/2002 | Munro |
| 6,413,645 B1 | 7/2002 | Graff |
| 6,432,494 B1 | 8/2002 | Yang |
| 6,432,510 B1 | 8/2002 | Kim |
| 6,470,650 B1 | 10/2002 | Lohwasser |
| 6,471,822 B1 | 10/2002 | Yin |
| 6,475,622 B2 | 11/2002 | Namiki |
| 6,482,509 B2 | 11/2002 | Buch-Rasmussen et al. |
| 6,486,081 B1 | 11/2002 | Ishikawa |
| 6,500,500 B1 | 12/2002 | Okamura |
| 6,503,579 B1 | 1/2003 | Murakami |
| 6,518,195 B1 | 2/2003 | Collins |
| 6,524,448 B2 | 2/2003 | Brinkmann |
| 6,539,890 B1 | 4/2003 | Felts |
| 6,544,610 B1 | 4/2003 | Minami |
| 6,551,267 B1 | 4/2003 | Cohen |
| 6,558,679 B2 | 5/2003 | Flament-Garcia et al. |
| 6,562,189 B1 | 5/2003 | Quiles |
| 6,565,791 B1 | 5/2003 | Laurent |
| 6,582,426 B2 | 6/2003 | Moorman |
| 6,582,823 B1 | 6/2003 | Sakhrani et al. |
| 6,584,828 B2 | 7/2003 | Sagi |
| 6,595,961 B2 | 7/2003 | Hetzler |
| 6,597,193 B2 | 7/2003 | Lagowski |
| 6,599,569 B1 | 7/2003 | Humele |
| 6,599,594 B1 | 7/2003 | Walther |
| 6,602,206 B1 | 8/2003 | Niermann |
| 6,616,632 B2 | 9/2003 | Sharp |
| 6,620,139 B1 | 9/2003 | Plicchi |
| 6,620,334 B2 | 9/2003 | Kanno |
| 6,623,861 B2 | 9/2003 | Martin |
| 6,638,403 B1 | 10/2003 | Inaba |
| 6,638,876 B2 | 10/2003 | Levy |
| 6,645,354 B1 | 11/2003 | Gorokhovsky |
| 6,651,835 B2 | 11/2003 | Iskra |
| 6,652,520 B2 | 11/2003 | Moorman |
| 6,656,540 B2 | 12/2003 | Sakamoto |
| 6,658,919 B2 | 12/2003 | Chatard |
| 6,662,957 B2 | 12/2003 | Zurcher |
| 6,663,601 B2 | 12/2003 | Hetzler |
| 6,670,200 B2 | 12/2003 | Ushio |
| 6,673,199 B2 | 1/2004 | Yamartino |
| 6,680,091 B2 | 1/2004 | Buch-Rasmussen et al. |
| 6,680,621 B2 | 1/2004 | Savtchouk |
| 6,683,308 B2 | 1/2004 | Itagaki |
| 6,684,683 B2 | 2/2004 | Potyrailo |
| 6,702,898 B2 | 3/2004 | Hosoi |
| 6,706,412 B2 | 3/2004 | Yializis |
| 6,746,430 B2 | 6/2004 | Lubrecht |

(56) References Cited

U.S. PATENT DOCUMENTS

| | | |
|---|---|---|
| 6,749,078 B2 | 6/2004 | Iskra |
| 6,752,899 B1 | 6/2004 | Singh |
| 6,753,972 B1 | 6/2004 | Hirose |
| 6,757,056 B1 | 6/2004 | Meeks |
| 6,764,714 B2 | 7/2004 | Wei |
| 6,765,466 B2 | 7/2004 | Miyata |
| 6,766,682 B2 | 7/2004 | Engle |
| 6,774,018 B2 | 8/2004 | Mikhael |
| 6,796,780 B1 | 9/2004 | Chatard |
| 6,800,852 B2 | 10/2004 | Larson |
| 6,808,753 B2 | 10/2004 | Rule |
| 6,810,106 B2 | 10/2004 | Sato |
| 6,815,014 B2 | 11/2004 | Gabelnick |
| 6,818,310 B2 | 11/2004 | Namiki |
| 6,827,972 B2 | 12/2004 | Darras |
| 6,837,954 B2 | 1/2005 | Carano |
| 6,844,075 B1 | 1/2005 | Saak |
| 6,853,141 B2 | 2/2005 | Hoffman |
| 6,858,259 B2 | 2/2005 | Affinito |
| 6,863,731 B2 | 3/2005 | Elsayed-Ali |
| 6,864,773 B2 | 3/2005 | Perrin |
| 6,866,656 B2 | 3/2005 | Tingey |
| 6,872,428 B2 | 3/2005 | Yang |
| 6,876,154 B2 | 4/2005 | Appleyard |
| 6,885,727 B2 | 4/2005 | Tamura |
| 6,887,578 B2 | 5/2005 | Gleason |
| 6,891,158 B2 | 5/2005 | Larson |
| 6,892,567 B1 | 5/2005 | Morrow |
| 6,899,054 B1 | 5/2005 | Bardos |
| 6,905,769 B2 | 6/2005 | Komada |
| 6,910,597 B2 | 6/2005 | Iskra |
| 6,911,779 B2 | 6/2005 | Madocks |
| 6,919,107 B2 | 7/2005 | Schwarzenbach |
| 6,919,114 B1 | 7/2005 | Darras |
| 6,933,460 B2 | 8/2005 | Vanden Brande |
| 6,946,164 B2 | 9/2005 | Huang |
| 6,952,949 B2 | 10/2005 | Moore |
| 6,960,393 B2 | 11/2005 | Yializis |
| 6,962,671 B2 | 11/2005 | Martin |
| 6,965,221 B2 | 11/2005 | Lipcsei |
| 6,981,403 B2 | 1/2006 | Ascheman |
| 6,989,675 B2 | 1/2006 | Kesil |
| 6,995,377 B2 | 2/2006 | Darr |
| 7,029,755 B2 | 4/2006 | Terry |
| 7,029,803 B2 | 4/2006 | Becker |
| 7,039,158 B1 | 5/2006 | Janik |
| 7,052,736 B2 | 5/2006 | Wei |
| 7,052,920 B2 | 5/2006 | Ushio |
| 7,059,268 B2 | 6/2006 | Russell |
| 7,067,034 B2 | 6/2006 | Bailey, III |
| 7,074,501 B2 | 7/2006 | Czeremuszkin |
| 7,098,453 B2 | 8/2006 | Ando |
| 7,109,070 B2 | 9/2006 | Behle |
| 7,112,352 B2 | 9/2006 | Schaepkens |
| 7,112,541 B2 | 9/2006 | Xia |
| 7,115,310 B2 | 10/2006 | Jacoud |
| 7,118,538 B2 | 10/2006 | Konrad |
| 7,119,908 B2 | 10/2006 | Nomoto |
| 7,121,135 B2 | 10/2006 | Moore |
| 7,130,373 B2 | 10/2006 | Omote |
| 7,150,299 B2 | 12/2006 | Hertzler |
| 7,160,292 B2 | 1/2007 | Moorman |
| 7,180,849 B2 | 2/2007 | Hirokane |
| 7,183,197 B2 | 2/2007 | Won |
| 7,188,734 B2 | 3/2007 | Konrad |
| 7,189,218 B2 | 3/2007 | Lichtenberg |
| 7,189,290 B2 | 3/2007 | Hama |
| 7,193,724 B2 | 3/2007 | Isei |
| 7,198,685 B2 | 4/2007 | Hetzler |
| 7,206,074 B2 | 4/2007 | Fujimoto |
| 7,244,381 B2 | 7/2007 | Chatard |
| 7,253,892 B2 | 8/2007 | Semersky |
| 7,286,242 B2 | 10/2007 | Kim |
| 7,288,293 B2 | 10/2007 | Koulik |
| 7,297,216 B2 | 11/2007 | Hetzler |
| 7,297,640 B2 | 11/2007 | Xie |
| 7,300,684 B2 | 11/2007 | Boardman |
| 7,303,789 B2 | 12/2007 | Saito |
| 7,303,790 B2 | 12/2007 | Delaunay |
| 7,306,852 B2 | 12/2007 | Komada |
| 7,332,227 B2 | 2/2008 | Hardman |
| 7,338,576 B2 | 3/2008 | Ono |
| 7,339,682 B2 | 3/2008 | Aiyer |
| 7,344,766 B1 | 3/2008 | Sorensen |
| 7,348,055 B2 | 3/2008 | Chappa |
| 7,348,192 B2 | 3/2008 | Mikami |
| 7,362,425 B2 | 4/2008 | Meeks |
| 7,381,469 B2 | 6/2008 | Moelle |
| 7,390,573 B2 | 6/2008 | Korevaar |
| 7,399,500 B2 | 7/2008 | Bicker |
| 7,404,278 B2 | 7/2008 | Wittland |
| 7,405,008 B2 | 7/2008 | Domine |
| 7,409,313 B2 | 8/2008 | Ringermacher |
| 7,411,685 B2 | 8/2008 | Takashima |
| RE40,531 E | 10/2008 | Graff |
| 7,431,989 B2 | 10/2008 | Sakhrani |
| 7,438,783 B2 | 10/2008 | Miyata |
| 7,444,955 B2 | 11/2008 | Boardman |
| 7,455,892 B2 | 11/2008 | Goodwin |
| 7,480,363 B2 | 1/2009 | Lasiuk |
| 7,488,683 B2 | 2/2009 | Kobayashi |
| 7,494,941 B2 | 2/2009 | Kasahara |
| 7,507,378 B2 | 3/2009 | Reichenbach |
| 7,513,953 B1 | 4/2009 | Felts |
| 7,520,965 B2 | 4/2009 | Wei |
| 7,521,022 B2 | 4/2009 | Konrad |
| 7,534,615 B2 | 5/2009 | Havens |
| 7,534,733 B2 | 5/2009 | Bookbinder |
| RE40,787 E | 6/2009 | Martin |
| 7,541,069 B2 | 6/2009 | Tudhope |
| 7,552,620 B2 | 6/2009 | DeRoos |
| 7,553,529 B2 | 6/2009 | Sakhrani |
| 7,555,934 B2 | 7/2009 | DeRoos |
| 7,569,035 B1 | 8/2009 | Wilmot |
| 7,571,122 B2 | 8/2009 | Howes |
| 7,579,056 B2 | 8/2009 | Brown |
| 7,586,824 B2 | 8/2009 | Hirokane |
| 7,582,868 B2 | 9/2009 | Jiang |
| 7,595,097 B2 | 9/2009 | Iacovangelo |
| 7,608,151 B2 | 10/2009 | Tudhope |
| 7,609,605 B2 | 10/2009 | Hirokane |
| 7,618,686 B2 | 11/2009 | Colpo |
| 7,624,622 B1 | 12/2009 | Mayer |
| 7,625,494 B2 | 12/2009 | Honda |
| 7,641,636 B2 | 1/2010 | Moesli |
| 7,645,696 B1 | 1/2010 | Dulkin |
| 7,648,481 B2 | 1/2010 | Geiger |
| 7,648,762 B2 | 1/2010 | Sohn |
| 7,682,816 B2 | 3/2010 | Kim |
| 7,694,403 B2 | 4/2010 | Moulton |
| 7,699,933 B2 | 4/2010 | Lizenberg |
| 7,704,683 B2 | 4/2010 | Wittenberg |
| 7,713,638 B2 | 5/2010 | Moelle |
| 7,736,689 B2 | 6/2010 | Chappa |
| 7,740,610 B2 | 6/2010 | Moh |
| 7,744,567 B2 | 6/2010 | Glowacki |
| 7,744,790 B2 | 6/2010 | Behle |
| 7,745,228 B2 | 6/2010 | Schwind |
| 7,745,547 B1 | 6/2010 | Auerbach |
| 7,749,914 B2 | 7/2010 | Honda |
| 7,754,302 B2 | 7/2010 | Yamaski |
| 7,766,882 B2 | 8/2010 | Sudo |
| 7,780,866 B2 | 8/2010 | Miller |
| 7,785,862 B2 | 8/2010 | Kim |
| 7,790,475 B2 | 9/2010 | Galbraith |
| 7,798,993 B2 | 9/2010 | Lim |
| 7,803,305 B2 | 9/2010 | Ahern |
| 7,807,242 B2 | 10/2010 | Sorensen |
| 7,810,448 B2 | 10/2010 | Behle |
| 7,815,922 B2 | 10/2010 | Chaney |
| 7,846,293 B2 | 12/2010 | Iwasaki |
| 7,854,889 B2 | 12/2010 | Perot |
| 7,867,366 B1 | 1/2011 | McFarland |
| 7,901,783 B2 | 3/2011 | Rose |

(56) References Cited

U.S. PATENT DOCUMENTS

| | | |
|---|---|---|
| 7,905,866 B2 | 3/2011 | Haider |
| 7,922,880 B1 | 4/2011 | Pradhan |
| 7,922,958 B2 | 4/2011 | D'Arrigo |
| 7,926,446 B2 | 4/2011 | Behle |
| 7,931,955 B2 | 4/2011 | Behle |
| 7,932,678 B2 | 4/2011 | Madocks |
| 7,934,613 B2 | 5/2011 | Sudo |
| 7,943,205 B2 | 5/2011 | Schaepkens |
| 7,947,337 B2 | 5/2011 | Kuepper |
| 7,955,986 B2 | 6/2011 | Hoffman |
| 7,960,043 B2 | 6/2011 | Harris |
| 7,964,438 B2 | 6/2011 | Roca I Cabarrocas |
| 7,967,945 B2 | 6/2011 | Glukhoy |
| 7,975,646 B2 | 7/2011 | Rius |
| 7,985,188 B2 | 7/2011 | Felts |
| 8,025,915 B2 | 9/2011 | Haines |
| 8,038,858 B1 | 10/2011 | Bures |
| 8,039,524 B2 | 10/2011 | Chappa |
| 8,056,719 B2 | 11/2011 | Porret |
| 8,062,266 B2 | 11/2011 | Mckinnon |
| 8,066,854 B2 | 11/2011 | Storey |
| 8,067,070 B2 | 11/2011 | Klein |
| 8,070,917 B2 | 12/2011 | Tsukamoto |
| 8,075,995 B2 | 12/2011 | Zhao |
| 8,092,605 B2 | 1/2012 | Shannon |
| 8,101,246 B2 | 1/2012 | Fayet |
| 8,197,452 B2 | 6/2012 | Harding |
| 8,258,486 B2 | 9/2012 | Avnery |
| 8,268,410 B2 | 9/2012 | Moelle |
| 8,273,222 B2 | 9/2012 | Wei |
| 8,277,025 B2 | 10/2012 | Nakazawa |
| 8,313,455 B2 | 11/2012 | DiGregorio |
| 8,323,166 B2 | 12/2012 | Haines |
| 8,389,958 B2 | 3/2013 | Vo-Dinh |
| 8,397,667 B2 | 3/2013 | Behle |
| 8,409,441 B2 | 4/2013 | Wilt |
| 8,418,650 B2 | 4/2013 | Goto |
| 8,435,605 B2 | 5/2013 | Aitken et al. |
| 8,450,113 B2 | 5/2013 | Luepke |
| 8,475,886 B2 | 7/2013 | Chen et al. |
| 8,512,796 B2 | 8/2013 | Felts |
| 8,524,331 B2 | 9/2013 | Honda |
| 8,592,015 B2 | 11/2013 | Bicker |
| 8,603,638 B2 | 12/2013 | Liu |
| 8,618,509 B2 | 12/2013 | Vo-Dinh |
| 8,623,324 B2 | 1/2014 | Diwu |
| 8,633,034 B2 | 1/2014 | Trotter |
| 8,747,962 B2 | 6/2014 | Bicker |
| 8,802,603 B2 | 8/2014 | D'Souza |
| 8,816,022 B2 | 8/2014 | Zhao |
| 9,067,706 B2 | 6/2015 | Joergensen |
| 9,068,565 B2 | 6/2015 | Alarcon |
| 2001/0000279 A1 | 4/2001 | Daniels |
| 2001/0021356 A1 | 9/2001 | Konrad |
| 2001/0038894 A1 | 11/2001 | Komada |
| 2001/0042510 A1 | 11/2001 | Plester |
| 2001/0043997 A1 | 11/2001 | Uddin |
| 2002/0006487 A1 | 1/2002 | O'Connor |
| 2002/0007796 A1 | 1/2002 | Gorokhovsky |
| 2002/0070647 A1 | 6/2002 | Ginovker |
| 2002/0117114 A1 | 8/2002 | Ikenaga |
| 2002/0125900 A1 | 9/2002 | Savtchouk |
| 2002/0130100 A1 | 9/2002 | Smith |
| 2002/0130674 A1 | 9/2002 | Logowski |
| 2002/0141477 A1 | 10/2002 | Akahori |
| 2002/0153103 A1 | 10/2002 | Madocks |
| 2002/0155218 A1 | 10/2002 | Meyer |
| 2002/0170495 A1 | 11/2002 | Nakamura |
| 2002/0176947 A1 | 11/2002 | Darras |
| 2002/0182101 A1 | 12/2002 | Koulik |
| 2002/0185226 A1 | 12/2002 | Lea |
| 2002/0190207 A1 | 12/2002 | Levy |
| 2003/0010454 A1 | 1/2003 | Bailey, III |
| 2003/0013818 A1 | 1/2003 | Hakuta |
| 2003/0029837 A1 | 2/2003 | Trow |
| 2003/0031806 A1 | 2/2003 | Jinks |
| 2003/0046982 A1 | 3/2003 | Chartard |
| 2003/0058413 A1 | 3/2003 | Barnhurst |
| 2003/0102087 A1 | 6/2003 | Ito |
| 2003/0119193 A1 | 6/2003 | Hess |
| 2003/0148028 A1 | 8/2003 | Kimura et al. |
| 2003/0159654 A1 | 8/2003 | Arnold |
| 2003/0215652 A1 | 11/2003 | O'Connor |
| 2003/0219547 A1 | 11/2003 | Arnold |
| 2003/0232150 A1 | 12/2003 | Arnold |
| 2004/0024371 A1 | 2/2004 | Plicchi |
| 2004/0039401 A1 | 2/2004 | Chow |
| 2004/0040372 A1 | 3/2004 | Plester |
| 2004/0045811 A1 | 3/2004 | Wang |
| 2004/0050744 A1 | 3/2004 | Hama |
| 2004/0055538 A1 | 3/2004 | Gorokhovsky |
| 2004/0071960 A1 | 4/2004 | Weber |
| 2004/0082917 A1 | 4/2004 | Hetzler |
| 2004/0084151 A1 | 5/2004 | Kim |
| 2004/0125913 A1 | 7/2004 | Larson |
| 2004/0135081 A1 | 7/2004 | Larson |
| 2004/0149225 A1 | 8/2004 | Weikart |
| 2004/0175961 A1 | 9/2004 | Olsen |
| 2004/0177676 A1 | 9/2004 | Moore |
| 2004/0195960 A1 | 10/2004 | Czeremuszkin |
| 2004/0206309 A1 | 10/2004 | Bera |
| 2004/0217081 A1 | 11/2004 | Konrad |
| 2004/0247948 A1 | 12/2004 | Behle |
| 2004/0267194 A1 | 12/2004 | Sano |
| 2005/0000962 A1 | 1/2005 | Crawford |
| 2005/0010175 A1 | 1/2005 | Beedon |
| 2005/0019503 A1 | 1/2005 | Komada |
| 2005/0037165 A1 | 2/2005 | Ahern |
| 2005/0039854 A1 | 2/2005 | Matsuyama |
| 2005/0045472 A1 | 3/2005 | Nagata |
| 2005/0057754 A1 | 3/2005 | Smith |
| 2005/0073323 A1 | 4/2005 | Kohno |
| 2005/0075611 A1 | 4/2005 | Heltzer |
| 2005/0075612 A1 | 4/2005 | Lee |
| 2005/0161149 A1 | 7/2005 | Yokota |
| 2005/0169803 A1 | 8/2005 | Betz |
| 2005/0190450 A1 | 9/2005 | Becker |
| 2005/0196629 A1 | 9/2005 | Bariatinsky |
| 2005/0199571 A1 | 9/2005 | Geisler |
| 2005/0206907 A1 | 9/2005 | Fujimoto |
| 2005/0211383 A1 | 9/2005 | Miyata |
| 2005/0223988 A1 | 10/2005 | Behle |
| 2005/0227002 A1 | 10/2005 | Lizenberg |
| 2005/0227022 A1 | 10/2005 | Domine |
| 2005/0229850 A1 | 10/2005 | Behle |
| 2005/0233077 A1 | 10/2005 | Lizenberg |
| 2005/0233091 A1 | 10/2005 | Kumar |
| 2005/0236346 A1 | 10/2005 | Whitney |
| 2005/0260504 A1 | 11/2005 | Becker |
| 2005/0284550 A1 | 12/2005 | Bicker |
| 2006/0005608 A1 | 1/2006 | Kutzhoffer |
| 2006/0013997 A1 | 1/2006 | Kuepper |
| 2006/0014309 A1 | 1/2006 | Sachdev |
| 2006/0024849 A1 | 2/2006 | Zhu |
| 2006/0042755 A1 | 3/2006 | Holmberg |
| 2006/0046006 A1 | 3/2006 | Bastion |
| 2006/0051252 A1 | 3/2006 | Yuan |
| 2006/0051520 A1 | 3/2006 | Behle |
| 2006/0076231 A1 | 4/2006 | Wei |
| 2006/0086320 A1 | 4/2006 | Lizenberg |
| 2006/0099340 A1 | 5/2006 | Behle |
| 2006/0121222 A1 | 6/2006 | Audrich |
| 2006/0121613 A1 | 6/2006 | Havens |
| 2006/0121623 A1 | 6/2006 | He |
| 2006/0127699 A1 | 6/2006 | Moelle |
| 2006/0135945 A1 | 6/2006 | Bankiewicz |
| 2006/0138326 A1 | 6/2006 | Jiang |
| 2006/0150909 A1 | 7/2006 | Behle |
| 2006/0169026 A1 | 8/2006 | Kage |
| 2006/0178627 A1 | 8/2006 | Geiger |
| 2006/0183345 A1 | 8/2006 | Nguyen |
| 2006/0192973 A1 | 8/2006 | Aiyer |
| 2006/0196419 A1 | 9/2006 | Tudhope |
| 2006/0198903 A1 | 9/2006 | Storey |

(56) References Cited

U.S. PATENT DOCUMENTS

| | | |
|---|---|---|
| 2006/0198965 A1 | 9/2006 | Tudhope |
| 2006/0200078 A1 | 9/2006 | Konrad |
| 2006/0200084 A1 | 9/2006 | Ito |
| 2006/0210425 A1 | 9/2006 | Mirkarimi |
| 2006/0228497 A1 | 10/2006 | Kumar |
| 2006/0260360 A1 | 11/2006 | Dick |
| 2007/0003441 A1 | 1/2007 | Wohleb |
| 2007/0009673 A1 | 1/2007 | Fukazawa et al. |
| 2007/0017870 A1 | 1/2007 | Belov |
| 2007/0031457 A1 | 2/2007 | Nakata et al. |
| 2007/0048456 A1 | 3/2007 | Keshner |
| 2007/0049048 A1 | 3/2007 | Rauf |
| 2007/0051629 A1 | 3/2007 | Donlik |
| 2007/0065680 A1 | 3/2007 | Schultheis |
| 2007/0076833 A1 | 4/2007 | Becker |
| 2007/0102344 A1 | 5/2007 | Konrad |
| 2007/0110907 A1 | 5/2007 | Brown |
| 2007/0123920 A1 | 5/2007 | Inokuti |
| 2007/0148326 A1 | 6/2007 | Hatings |
| 2007/0166187 A1 | 7/2007 | Song |
| 2007/0184657 A1 | 8/2007 | Iijima |
| 2007/0187229 A1 | 8/2007 | Aksenov |
| 2007/0187280 A1 | 8/2007 | Haines |
| 2007/0205096 A1 | 9/2007 | Nagashima |
| 2007/0215009 A1 | 9/2007 | Shimazu |
| 2007/0215046 A1 | 9/2007 | Lupke |
| 2007/0218265 A1 | 9/2007 | Harris |
| 2007/0224236 A1 | 9/2007 | Boden |
| 2007/0229844 A1 | 10/2007 | Holz |
| 2007/0231655 A1 | 10/2007 | Ha |
| 2007/0232066 A1 | 10/2007 | Bicker |
| 2007/0235890 A1 | 10/2007 | Lewis |
| 2007/0243618 A1 | 10/2007 | Hatchett |
| 2007/0251458 A1 | 11/2007 | Mund |
| 2007/0258894 A1 | 11/2007 | Melker et al. |
| 2007/0259184 A1 | 11/2007 | Martin |
| 2007/0281108 A1 | 12/2007 | Weikart |
| 2007/0281117 A1 | 12/2007 | Kaplan |
| 2007/0287950 A1 | 12/2007 | Kjeken |
| 2007/0287954 A1 | 12/2007 | Zhao |
| 2007/0298189 A1 | 12/2007 | Straemke |
| 2008/0011232 A1 | 1/2008 | Ruis |
| 2008/0017113 A1 | 1/2008 | Goto |
| 2008/0023414 A1 | 1/2008 | Konrad |
| 2008/0027400 A1 | 1/2008 | Harding |
| 2008/0045880 A1 | 2/2008 | Kjeken |
| 2008/0050567 A1 | 2/2008 | Kawashima |
| 2008/0050932 A1 | 2/2008 | Lakshmanan |
| 2008/0053373 A1 | 3/2008 | Mund |
| 2008/0069970 A1 | 3/2008 | Wu |
| 2008/0071228 A1 | 3/2008 | Wu |
| 2008/0081184 A1 | 4/2008 | Kubo |
| 2008/0090039 A1 | 4/2008 | Klein |
| 2008/0093245 A1 | 4/2008 | Periasamy |
| 2008/0102206 A1 | 5/2008 | Wagner |
| 2008/0109017 A1 | 5/2008 | Herweck |
| 2008/0110852 A1 | 5/2008 | Kuroda |
| 2008/0113109 A1 | 5/2008 | Moelle |
| 2008/0118734 A1 | 5/2008 | Goodwin |
| 2008/0131628 A1 | 6/2008 | Abensour |
| 2008/0131638 A1 | 6/2008 | Hutton |
| 2008/0139003 A1 | 6/2008 | Pirzada |
| 2008/0144185 A1 | 6/2008 | Wang et al. |
| 2008/0145271 A1 | 6/2008 | Kidambi |
| 2008/0187681 A1 | 8/2008 | Hofrichter |
| 2008/0202414 A1 | 8/2008 | Yan |
| 2008/0206477 A1 | 8/2008 | Leontaris |
| 2008/0210550 A1 | 9/2008 | Walther |
| 2008/0220164 A1 | 9/2008 | Bauch |
| 2008/0223815 A1 | 9/2008 | Konrad |
| 2008/0233355 A1 | 9/2008 | Henze |
| 2008/0260966 A1 | 10/2008 | Hanawa |
| 2008/0277332 A1 | 11/2008 | Liu |
| 2008/0289957 A1 | 11/2008 | Takigawa |
| 2008/0292806 A1 | 11/2008 | Wei |
| 2008/0295772 A1 | 12/2008 | Park |
| 2008/0303131 A1 | 12/2008 | McElrea |
| 2008/0312607 A1 | 12/2008 | Delmotte |
| 2008/0314318 A1 | 12/2008 | Han |
| 2009/0004091 A1 | 1/2009 | Kang |
| 2009/0004363 A1 | 1/2009 | Keshner |
| 2009/0017217 A1 | 1/2009 | Hass |
| 2009/0022981 A1 | 1/2009 | Yoshida |
| 2009/0029402 A1 | 1/2009 | Papkovsky |
| 2009/0031953 A1 | 2/2009 | Ingle |
| 2009/0032393 A1 | 2/2009 | Madocks |
| 2009/0039240 A1 | 2/2009 | Van Nijnatten |
| 2009/0053491 A1 | 2/2009 | Laboda |
| 2009/0061237 A1 | 3/2009 | Gates |
| 2009/0065485 A1 | 3/2009 | O'Neill |
| 2009/0069790 A1 | 3/2009 | Yokley |
| 2009/0081797 A1 | 3/2009 | Fadeev |
| 2009/0099512 A1 | 4/2009 | Digregorio |
| 2009/0104392 A1 | 4/2009 | Takada |
| 2009/0117268 A1 | 5/2009 | Lewis |
| 2009/0117389 A1 | 5/2009 | Amberg-Schwab |
| 2009/0122832 A1 | 5/2009 | Feist |
| 2009/0134884 A1 | 5/2009 | Bosselmann |
| 2009/0137966 A1 | 5/2009 | Rueckert |
| 2009/0142227 A1 | 6/2009 | Fuchs |
| 2009/0142514 A1 | 6/2009 | O'Neill |
| 2009/0147719 A1 | 6/2009 | Rak |
| 2009/0149816 A1 | 6/2009 | Hetzler |
| 2009/0155490 A1 | 6/2009 | Bicker |
| 2009/0162571 A1 | 6/2009 | Haines |
| 2009/0166312 A1 | 7/2009 | Giraud |
| 2009/0176031 A1 | 7/2009 | Armellin |
| 2009/0214801 A1 | 8/2009 | Higashi |
| 2009/0220948 A1 | 9/2009 | Oviso et al. |
| 2009/0263668 A1 | 10/2009 | David |
| 2009/0274851 A1 | 11/2009 | Goudar |
| 2009/0280268 A1 | 11/2009 | Glukhoy |
| 2009/0297730 A1 | 12/2009 | Glukhoy |
| 2009/0306595 A1 | 12/2009 | Shih |
| 2009/0326517 A1 | 12/2009 | Bork |
| 2010/0021998 A1 | 1/2010 | Sanyal |
| 2010/0028238 A1 | 2/2010 | Maschwitz |
| 2010/0034985 A1 | 2/2010 | Krueger |
| 2010/0075077 A1 | 3/2010 | Bicker et al. |
| 2010/0086808 A1 | 4/2010 | Nagata |
| 2010/0089097 A1 | 4/2010 | Brack |
| 2010/0104770 A1 | 4/2010 | Goudar |
| 2010/0105208 A1 | 4/2010 | Winniczek |
| 2010/0132762 A1 | 6/2010 | Graham, Jr. |
| 2010/0145284 A1 | 6/2010 | Togashi |
| 2010/0149540 A1 | 6/2010 | Boukherroub |
| 2010/0174239 A1 | 7/2010 | Yodfat |
| 2010/0174245 A1 | 7/2010 | Halverson |
| 2010/0178490 A1 | 7/2010 | Cerny |
| 2010/0186740 A1 | 7/2010 | Lewis |
| 2010/0190036 A1 | 7/2010 | Komvopoulos |
| 2010/0193461 A1 | 8/2010 | Boutroy |
| 2010/0195471 A1 | 8/2010 | Hirokane |
| 2010/0204648 A1 | 8/2010 | Stout |
| 2010/0230281 A1 | 9/2010 | Park |
| 2010/0231194 A1 | 9/2010 | Bauch |
| 2010/0237545 A1 | 9/2010 | Haury |
| 2010/0273261 A1 | 10/2010 | Chen |
| 2010/0275847 A1 | 11/2010 | Yamasaki |
| 2010/0279397 A1 | 11/2010 | Crawford |
| 2010/0298738 A1 | 11/2010 | Felts |
| 2010/0298779 A1 | 11/2010 | Hetzler |
| 2011/0037159 A1 | 2/2011 | McElrea |
| 2011/0046570 A1 | 2/2011 | Stout |
| 2011/0056912 A1 | 3/2011 | Magsuyama |
| 2011/0065798 A1 | 3/2011 | Hoang |
| 2011/0079582 A1 | 4/2011 | Yonesu |
| 2011/0093056 A1 | 4/2011 | Kaplan |
| 2011/0111132 A1 | 5/2011 | Wei |
| 2011/0117202 A1 | 5/2011 | Bourke, Jr |
| 2011/0117288 A1 | 5/2011 | Honda |
| 2011/0137263 A1 | 6/2011 | Ashmead |
| 2011/0152820 A1 | 6/2011 | Chattaraj |
| 2011/0159101 A1 | 6/2011 | Kurdyumov et al. |

(56) References Cited

U.S. PATENT DOCUMENTS

| | | |
|---|---|---|
| 2011/0160662 A1 | 6/2011 | Stout |
| 2011/0160663 A1 | 6/2011 | Stout |
| 2011/0174220 A1 | 7/2011 | Laure |
| 2011/0186537 A1 | 8/2011 | Rodriguez San Juan |
| 2011/0220490 A1 | 9/2011 | Wei |
| 2011/0253674 A1 | 10/2011 | Chung |
| 2011/0313363 A1 | 12/2011 | D'Souza |
| 2011/0319758 A1 | 12/2011 | Wang |
| 2011/0319813 A1 | 12/2011 | Kamen |
| 2012/0003497 A1 | 1/2012 | Handy |
| 2012/0004339 A1 | 1/2012 | Chappa |
| 2012/0021136 A1 | 1/2012 | Dzengeleski |
| 2012/0031070 A1 | 2/2012 | Slough |
| 2012/0035543 A1 | 2/2012 | Kamen |
| 2012/0052123 A9 | 3/2012 | Kurdyumov et al. |
| 2012/0053530 A1 | 3/2012 | Zhao |
| 2012/0058351 A1 | 3/2012 | Zhao |
| 2012/0065612 A1 | 3/2012 | Stout |
| 2012/0097527 A1 | 4/2012 | Kodaira |
| 2012/0097870 A1 | 4/2012 | Leray |
| 2012/0108058 A1 | 5/2012 | Ha |
| 2012/0123345 A1 | 5/2012 | Felts |
| 2012/0141913 A1 | 6/2012 | Lee |
| 2012/0143148 A1 | 6/2012 | Zhao |
| 2012/0149871 A1 | 6/2012 | Saxena |
| 2012/0171386 A1 | 7/2012 | Bicker |
| 2012/0175384 A1 | 7/2012 | Greter |
| 2012/0183954 A1 | 7/2012 | Diwu |
| 2012/0205374 A1 | 8/2012 | Klumpen |
| 2012/0231182 A1 | 9/2012 | Stevens |
| 2012/0234720 A1 | 9/2012 | Digregorio |
| 2012/0252709 A1 | 10/2012 | Felts |
| 2013/0041241 A1 | 2/2013 | Felts |
| 2013/0046375 A1 | 2/2013 | Chen |
| 2013/0057677 A1 | 3/2013 | Weil |
| 2013/0072025 A1 | 3/2013 | Singh |
| 2013/0081953 A1 | 4/2013 | Bruna et al. |
| 2013/0190695 A1 | 7/2013 | Wu |
| 2013/0209704 A1 | 8/2013 | Krueger |
| 2013/0220152 A1 | 8/2013 | Shibusawa |
| 2013/0264303 A1 | 10/2013 | Andersen et al. |
| 2013/0296235 A1 | 11/2013 | Alarcon |
| 2014/0010969 A1 | 1/2014 | Bicker |
| 2014/0052076 A1 | 2/2014 | Zhao |
| 2014/0054803 A1 | 2/2014 | Chen |
| 2014/0099455 A1 | 4/2014 | Stanley |
| 2014/0110297 A1 | 4/2014 | Trotter |
| 2014/0147654 A1 | 5/2014 | Walthe |
| 2014/0151320 A1 | 6/2014 | Chang |
| 2014/0151370 A1 | 6/2014 | Chang |
| 2014/0187666 A1 | 7/2014 | Aizenberg |
| 2014/0190846 A1 | 7/2014 | Belt |
| 2014/0221934 A1 | 8/2014 | Janvier |
| 2014/0251856 A1 | 9/2014 | Larsson |
| 2014/0251859 A1 | 9/2014 | Weikart |
| 2014/0305830 A1 | 10/2014 | Bicker |
| 2015/0105734 A1 | 4/2015 | Bryant |
| 2015/0165125 A1 | 6/2015 | Foucher |
| 2015/0224263 A1 | 8/2015 | Dugand |
| 2016/0186009 A1 | 6/2016 | Goto |

FOREIGN PATENT DOCUMENTS

| | | |
|---|---|---|
| AU | 2002354470 B2 | 5/2007 |
| CA | 2085805 | 12/1992 |
| CA | 2277679 A1 | 7/1997 |
| CA | 2355681 | 7/2000 |
| CA | 2571380 A1 | 7/2006 |
| CA | 2718253 | 9/2009 |
| CA | 2268719 C | 8/2010 |
| CA | 2879732 A1 | 1/2014 |
| CN | 1245439 A | 2/2000 |
| CN | 2546041 Y | 4/2003 |
| CN | 1436104 A | 8/2003 |
| CN | 1639775 A | 7/2005 |
| CN | 1711310 A | 12/2005 |
| CN | 2766863 Y | 3/2006 |
| CN | 1898172 A | 1/2007 |
| CN | 101035630 A | 9/2007 |
| CN | 201002786 Y | 1/2008 |
| CN | 101147813 A | 3/2008 |
| CN | 201056331 Y | 5/2008 |
| CN | 102027159 A | 4/2011 |
| CN | 102036814 A | 4/2011 |
| CN | 102414343 A | 4/2012 |
| CN | 102581274 A | 7/2012 |
| CN | 102917805 A | 2/2013 |
| DE | 1147836 | 4/1969 |
| DE | 1147838 | 4/1969 |
| DE | 3632748 A1 | 4/1988 |
| DE | 3908418 A1 | 9/1990 |
| DE | 4214401 C1 | 3/1993 |
| DE | 4204082 A1 | 8/1993 |
| DE | 4316349 A1 | 11/1994 |
| DE | 4438359 | 5/1996 |
| DE | 19707645 A1 | 8/1998 |
| DE | 19830794 A1 | 1/2000 |
| DE | 19912737 A1 | 6/2000 |
| DE | 10010831 A1 | 9/2001 |
| DE | 10154404 C1 | 6/2003 |
| DE | 10201110 A1 | 10/2003 |
| DE | 10242698 | 3/2004 |
| DE | 10246181 A1 | 4/2004 |
| DE | 10353540 A1 | 5/2004 |
| DE | 102004017236 A1 | 10/2005 |
| DE | 102006061585 A1 | 2/2008 |
| DE | 102008023027 A1 | 11/2009 |
| EP | 0121340 A2 | 10/1984 |
| EP | 0221005 A2 | 5/1987 |
| EP | 0275965 A2 | 7/1988 |
| EP | 0284867 A2 | 10/1988 |
| EP | 0306307 | 3/1989 |
| EP | 0329041 A2 | 8/1989 |
| EP | 0343017 A2 | 11/1989 |
| EP | 0396919 A2 | 11/1990 |
| EP | 0482613 A1 | 10/1991 |
| EP | 0484746 A2 | 10/1991 |
| EP | 0495447 A1 | 7/1992 |
| EP | 0520519 A1 | 12/1992 |
| EP | 0535810 A1 | 4/1993 |
| EP | 0375778 B1 | 9/1993 |
| EP | 0571116 A1 | 11/1993 |
| EP | 0580094 A1 | 1/1994 |
| EP | 0603717 A2 | 6/1994 |
| EP | 0619178 | 10/1994 |
| EP | 0645470 A1 | 3/1995 |
| EP | 0697378 A2 | 2/1996 |
| EP | 0709485 B1 | 5/1996 |
| EP | 0719877 A1 | 7/1996 |
| EP | 0728676 A1 | 8/1996 |
| EP | 0787824 A2 | 8/1997 |
| EP | 0787828 A2 | 8/1997 |
| EP | 0814114 A1 | 12/1997 |
| EP | 0251812 A2 | 1/1998 |
| EP | 0833366 A2 | 4/1998 |
| EP | 0879611 A2 | 11/1998 |
| EP | 0940183 A2 | 9/1999 |
| EP | 0962229 A2 | 12/1999 |
| EP | 0992610 A2 | 4/2000 |
| EP | 1119034 A1 | 7/2001 |
| EP | 0954272 B1 | 3/2002 |
| EP | 1245694 A1 | 10/2002 |
| EP | 1388594 B1 | 1/2003 |
| EP | 1317937 A1 | 6/2003 |
| EP | 1365043 A1 | 11/2003 |
| EP | 1367145 | 12/2003 |
| EP | 1388593 A1 | 2/2004 |
| EP | 1439241 A2 | 7/2004 |
| EP | 1447459 A2 | 8/2004 |
| EP | 1990639 A1 | 2/2005 |
| EP | 1510595 A1 | 3/2005 |
| EP | 1522403 A2 | 4/2005 |
| EP | 1901067 A2 | 8/2005 |
| EP | 1507894 | 12/2005 |

(56) References Cited

FOREIGN PATENT DOCUMENTS

| | | |
|---|---|---|
| EP | 1507723 | 3/2006 |
| EP | 1653192 A1 | 5/2006 |
| EP | 1810758 A1 | 7/2007 |
| EP | 1356260 B1 | 12/2007 |
| EP | 1870117 A2 | 12/2007 |
| EP | 1881088 A1 | 1/2008 |
| EP | 1507887 | 7/2008 |
| EP | 1415018 | 10/2008 |
| EP | 1756565 A4 | 7/2009 |
| EP | 2199264 A1 | 11/2009 |
| EP | 2178109 A1 | 4/2010 |
| EP | 1507895 | 7/2010 |
| EP | 2218465 A1 | 8/2010 |
| EP | 2243751 A1 | 10/2010 |
| EP | 2251671 | 11/2010 |
| EP | 2261185 | 12/2010 |
| EP | 2369038 A2 | 9/2011 |
| EP | 1960279 B1 | 10/2011 |
| EP | 2444771 A2 | 4/2012 |
| EP | 2602354 A1 | 6/2013 |
| EP | 2639330 A1 | 9/2013 |
| EP | 3381444 A1 | 10/2018 |
| FR | 891892 A | 11/1942 |
| GB | 752822 | 7/1956 |
| GB | 1363762 | 8/1974 |
| GB | 1513426 A | 6/1978 |
| GB | 1566251 | 4/1980 |
| GB | 2210826 A | 6/1989 |
| GB | 2231197 A | 11/1990 |
| GB | 2246794 A | 2/1992 |
| GB | 2246795 A | 2/1992 |
| GB | 2387964 A | 10/2003 |
| IT | 1304783 B1 | 3/2001 |
| IT | 1310330 B1 | 2/2002 |
| JP | 56027330 A | 3/1981 |
| JP | 58154602 A | 9/1983 |
| JP | 59087307 A | 5/1984 |
| JP | 59154029 | 9/1984 |
| JP | S61183462 A | 8/1986 |
| JP | S62180069 A | 8/1987 |
| JP | S62290866 A | 12/1987 |
| JP | 63124521 A2 | 5/1988 |
| JP | 1023105 A | 1/1989 |
| JP | H01225775 A | 9/1989 |
| JP | 1279745 | 11/1989 |
| JP | 2501490 | 5/1990 |
| JP | 3183759 A2 | 8/1991 |
| JP | H03260065 A | 11/1991 |
| JP | H03271374 A | 12/1991 |
| JP | 4000373 A | 1/1992 |
| JP | 4000374 A | 1/1992 |
| JP | 4000375 A | 1/1992 |
| JP | 4014440 A | 1/1992 |
| JP | H04124273 A | 4/1992 |
| JP | H04249766 | 9/1992 |
| JP | H0578844 A | 3/1993 |
| JP | H05263223 A | 10/1993 |
| JP | 6010132 A | 1/1994 |
| JP | 6289401 | 10/1994 |
| JP | 7041579 A | 2/1995 |
| JP | 7068614 A | 3/1995 |
| JP | 7126419 A | 5/1995 |
| JP | 7-304127 | 11/1995 |
| JP | 8025244 A | 1/1996 |
| JP | 8084773 A | 4/1996 |
| JP | H08296038 A | 11/1996 |
| JP | 9005038 A | 1/1997 |
| JP | 10008254 A | 1/1998 |
| JP | 10-130844 | 5/1998 |
| JP | 11-108833 A | 4/1999 |
| JP | 11106920 | 4/1999 |
| JP | H11256331 A | 9/1999 |
| JP | 11344316 A | 12/1999 |
| JP | 2000064040 A | 2/2000 |
| JP | 2000109076 A | 4/2000 |
| JP | 2001033398 A | 2/2001 |
| JP | 2001231841 A | 8/2001 |
| JP | 2002177364 A | 6/2002 |
| JP | 2002206167 A | 7/2002 |
| JP | 2002371364 A | 12/2002 |
| JP | 2003171771 A | 6/2003 |
| JP | 2003-268550 A | 9/2003 |
| JP | 2003294431 A | 10/2003 |
| JP | 2003305121 A | 10/2003 |
| JP | 2004002928 A | 1/2004 |
| JP | 2004008509 A | 1/2004 |
| JP | 2004043789 A | 2/2004 |
| JP | 2004100036 A | 4/2004 |
| JP | 2004156444 A | 6/2004 |
| JP | 2004168359 A | 6/2004 |
| JP | 2004169087 A | 6/2004 |
| JP | 2004200646 A | 7/2004 |
| JP | 2004203682 A | 7/2004 |
| JP | 2004-253683 A | 9/2004 |
| JP | 2004532756 | 10/2004 |
| JP | 2004307935 A | 11/2004 |
| JP | 2005035597 A | 2/2005 |
| JP | 2005043285 A | 2/2005 |
| JP | 2005132416 A | 5/2005 |
| JP | 2005160888 A | 6/2005 |
| JP | 2005-200044 | 7/2005 |
| JP | 2005200044 A | 7/2005 |
| JP | 2005-241524 A | 9/2005 |
| JP | 2005271997 A | 10/2005 |
| JP | 2005290561 A | 10/2005 |
| JP | 2006-064416 | 3/2006 |
| JP | 2006111967 A | 4/2006 |
| JP | 2006160268 A | 6/2006 |
| JP | 2006179948 A | 7/2006 |
| JP | 2006-224992 A | 8/2006 |
| JP | 2006249577 A | 9/2006 |
| JP | 2007050898 A | 3/2007 |
| JP | 2007231386 A | 9/2007 |
| JP | 2007246974 A | 9/2007 |
| JP | 2008174793 A | 7/2008 |
| JP | 2009-506201 | 2/2009 |
| JP | 2009062620 A | 3/2009 |
| JP | 2009079298 A | 4/2009 |
| JP | 2009084203 A | 4/2009 |
| JP | 2009185330 A | 8/2009 |
| JP | 2010155134 A | 7/2010 |
| JP | 2010270117 A | 12/2010 |
| JP | 2012006390 A | 1/2012 |
| JP | 2012149278 A | 8/2012 |
| JP | 2012210315 A | 11/2012 |
| JP | 2012526921 A | 11/2012 |
| JP | 2013233716 A | 11/2013 |
| JP | 5362941 B2 | 12/2013 |
| KR | 10-2005-0100367 A | 10/2005 |
| KR | 10-2006-0029694 | 4/2006 |
| KR | 20060038945 | 5/2006 |
| KR | 10-0685594 B1 | 2/2007 |
| SU | 1530913 | 12/1989 |
| TW | 200703536 A | 1/2007 |
| WO | WO9324243 A1 | 12/1993 |
| WO | WO9400247 A1 | 1/1994 |
| WO | WO9426497 A1 | 11/1994 |
| WO | WO95/24275 | 9/1995 |
| WO | WO97/11482 | 3/1997 |
| WO | WO97/13802 | 4/1997 |
| WO | WO98-27926 | 7/1998 |
| WO | WO98/45871 | 10/1998 |
| WO | WO9917334 A1 | 4/1999 |
| WO | WO99/41425 | 8/1999 |
| WO | WO9945984 A1 | 9/1999 |
| WO | WO9945985 A1 | 9/1999 |
| WO | WO9947192 A1 | 9/1999 |
| WO | WO99/50471 | 10/1999 |
| WO | WO0038566 A2 | 7/2000 |
| WO | WO0104668 A1 | 1/2001 |
| WO | WO0125788 | 4/2001 |
| WO | WO0154816 A1 | 8/2001 |
| WO | WO0156706 A1 | 8/2001 |
| WO | WO0170403 A1 | 9/2001 |

(56) References Cited

FOREIGN PATENT DOCUMENTS

| | | |
|---|---|---|
| WO | WO0222192 A1 | 3/2002 |
| WO | WO03033426 | 4/2002 |
| WO | WO02/43116 A2 | 5/2002 |
| WO | WO0249925 A1 | 6/2002 |
| WO | WO02/056333 A1 | 7/2002 |
| WO | WO02072914 | 9/2002 |
| WO | WO02076709 A1 | 10/2002 |
| WO | 02100928 A1 | 12/2002 |
| WO | WO03014415 A1 | 2/2003 |
| WO | WO03038143 | 5/2003 |
| WO | WO03040649 A1 | 5/2003 |
| WO | WO03044240 A1 | 5/2003 |
| WO | 2004044039 A2 | 5/2004 |
| WO | WO2005035147 A1 | 4/2005 |
| WO | WO2005/052555 A1 | 6/2005 |
| WO | WO2005051525 A1 | 6/2005 |
| WO | WO2005094214 A2 | 10/2005 |
| WO | WO2005103605 A1 | 11/2005 |
| WO | WO2006012281 A1 | 2/2006 |
| WO | WO2006017186 A1 | 2/2006 |
| WO | WO2006027568 A1 | 3/2006 |
| WO | WO2006029743 A1 | 3/2006 |
| WO | WO2006044254 A1 | 4/2006 |
| WO | WO2006/048650 | 5/2006 |
| WO | WO2006048276 | 5/2006 |
| WO | WO2006048277 A1 | 5/2006 |
| WO | WO2006069774 A1 | 7/2006 |
| WO | 2006121556 A3 | 11/2006 |
| WO | WO2006135755 A2 | 12/2006 |
| WO | WO2007028061 A2 | 3/2007 |
| WO | WO2007035741 A2 | 3/2007 |
| WO | WO2007036544 A1 | 4/2007 |
| WO | WO2007/081814 | 7/2007 |
| WO | WO2007/089216 A1 | 8/2007 |
| WO | WO2007112328 A2 | 10/2007 |
| WO | WO2007120507 A2 | 10/2007 |
| WO | WO2007133378 A1 | 11/2007 |
| WO | WO2007134347 A2 | 11/2007 |
| WO | WO2008014438 A2 | 1/2008 |
| WO | WO2008024566 A2 | 2/2008 |
| WO | WO2008040531 A1 | 4/2008 |
| WO | WO2008047541 A1 | 4/2008 |
| WO | 2008071458 | 6/2008 |
| WO | WO2008067574 A1 | 6/2008 |
| WO | WO2008071458 A1 | 6/2008 |
| WO | WO2008093335 A2 | 8/2008 |
| WO | 2008/121478 A2 | 10/2008 |
| WO | WO2009/015862 A1 | 2/2009 |
| WO | WO2009020550 A2 | 2/2009 |
| WO | WO2009021257 A1 | 2/2009 |
| WO | WO2009030974 | 3/2009 |
| WO | WO2009030975 A1 | 3/2009 |
| WO | WO2009030976 A1 | 3/2009 |
| WO | WO2009031838 A1 | 3/2009 |
| WO | WO2009040109 | 4/2009 |
| WO | WO2009053947 A2 | 4/2009 |
| WO | WO2009112053 A1 | 9/2009 |
| WO | WO2009117032 | 9/2009 |
| WO | WO2009118361 A1 | 10/2009 |
| WO | WO2009158613 | 12/2009 |
| WO | WO2010047825 A1 | 4/2010 |
| WO | WO2010095011 A1 | 8/2010 |
| WO | WO2010/132581 | 11/2010 |
| WO | WO2010/132584 | 11/2010 |
| WO | WO2010/132585 | 11/2010 |
| WO | WO2010034004 A1 | 11/2010 |
| WO | WO2010132579 | 11/2010 |
| WO | WO2010132579 A2 | 11/2010 |
| WO | WO2010132589 | 11/2010 |
| WO | WO2010132591 | 11/2010 |
| WO | WO2011029628 | 3/2011 |
| WO | WO2011059823 A1 | 5/2011 |
| WO | WO2011007055 A1 | 6/2011 |
| WO | WO2011080543 A1 | 7/2011 |
| WO | WO2011082296 A1 | 7/2011 |
| WO | WO2011090717 A1 | 7/2011 |
| WO | WO2011/143509 | 11/2011 |
| WO | WO2011/143509 A1 | 11/2011 |
| WO | WO2011137437 | 11/2011 |
| WO | WO2011143329 | 11/2011 |
| WO | WO2011159975 A1 | 12/2011 |
| WO | WO2012003221 | 1/2012 |
| WO | WO2012009653 | 1/2012 |
| WO | WO2012166515 A1 | 12/2012 |
| WO | WO2013045671 A1 | 4/2013 |
| WO | WO2013/071138 | 5/2013 |
| WO | WO2013/071138 A1 | 5/2013 |
| WO | WO2013106588 A1 | 7/2013 |
| WO | WO2013/170044 | 11/2013 |
| WO | WO2013/170052 | 11/2013 |
| WO | 214-005728 A1 | 1/2014 |
| WO | WO2014/008138 | 1/2014 |
| WO | WO2014012039 A1 | 1/2014 |
| WO | WO2014012052 A1 | 1/2014 |
| WO | WO2014012072 A2 | 1/2014 |
| WO | WO2014012078 A2 | 1/2014 |
| WO | WO2014012079 A1 | 1/2014 |
| WO | WO2014014641 A1 | 1/2014 |
| WO | WO2014/059012 | 4/2014 |
| WO | WO2014/071061 | 5/2014 |
| WO | WO2014/078666 | 5/2014 |
| WO | WO2014/085346 | 6/2014 |
| WO | WO2014/085348 | 6/2014 |
| WO | WO2014/134577 | 9/2014 |
| WO | WO2014/144926 | 9/2014 |
| WO | WO2014/164928 | 10/2014 |
| WO | WO2015049972 A1 | 4/2015 |
| WO | WO2016057068 A1 | 4/2016 |
| WO | WO2016094387 A2 | 6/2016 |

OTHER PUBLICATIONS

Hanlon, Adriene Lepiane, PAK, Chung K., Pawlikowski, Beverly A., Decision on Appeal, Appeal No. 2005-1693, U.S. Appl. No. 10/192,333, dated Sep. 30, 2005.

Arganguren, Mirta I., Macosko, Christopher W., Thakkar, Bimal, and Tirrel, Matthew, "Interfacial Interactions in Silica Reinforced Silicones," Materials Research Society Symposium Proceedings, vol. 170, 1990, pp. 303-308.

Patent Cooperation Treaty, International Preliminary Examining Authority, Notification of Transmittal of International Preliminary Report on Patentability, in international application No. PCT/US2011/036097, dated Nov. 13, 2012.

Australian Government, IP Australia, Patent Examination Report No. 1, in Application No. 2010249031, dated Mar. 13, 2014. (4 pages).

Australian Government, IP Australia, Patent Examination Report No. 1, in Application No. 2013202893, dated Mar. 13, 2014. (4 pages).

European Patent Office, Communication pursuant to Article 93(3) EPC, in Application No. 11 731 554.9 dated Apr. 15, 2014. (7 pages).

PCT, Notification Concerning Transmittal of Copy of International Preliminary Report on Patentability, in International application No. PCT/US2012/064489, dated May 22, 2014. (10 pages).

PCT, Notification of Transmittal of the International Search Report and the Written Opinion of the International Searching Authority, or the Declaration, in International application No. PCT/US2013/071750, dated Apr. 4, 2014. (13 pages).

PCT, Notification of Transmittal of the International Search Report and the Written Opinion of the International Searching Authority, or the Declaration, in International application No. PCT/US2014/019684, dated May 23, 2014. (16 pages).

PCT, Notification of Transmittal of the International Search Report and the Written Opinion of the International Searching Authority, or the Declaration, in International application No. PCT/US2014/023813, dated May 22, 2014. (11 pages).

European Patent Office, Communication pursuant to Article 94(3) EPC, in Application No. 11 736 511.4, dated Mar. 28, 2014.

(56) References Cited

OTHER PUBLICATIONS

PCT, Notification Concerning Transmittal of Copy of International Preliminary Report on Patentability, in International application No. PCT/US2011/042387, dated Jan. 17, 2013. (7 pages).
State Intellectual Property Office of the People's Republic of China, Notification of the First Office Action, in Application No. 201180032145.4, dated Jan. 30, 2014. (16 pages).
PCT, Notification Concerning Transmittal of Copy of International Preliminary Report on Patentability, in International application No. PCT/US2011/044215, dated Jan. 31, 2013. (14 pages).
Da Silva Sobrinho A S et al., "Transparent barrier coatings on polyethylene terephthalate by single-and dual-frequency plasma-enhanced chemical vapor deposition", Journal of Vacuum Science and Technology; Part A, AVS/AIP, Melville, NY, US, vol. 16, No. 6, Nov. 1, 1998 (Nov. 1, 1998), pp. 3190-3198, KP01200471, Issn: 0734-2101, DOI: 10.1116/1.581519 (9 pages).
State Intellectual Property Office of the People's Republic of China, Notification of the Third Office Action, in Application No. 201080029201.4, dated Jul. 7, 2014 (15 pages).
PCT, Notification of Transmittal of the International Search Report and the Written Opinion of the International Searching Authority, or the Declaration, in International application No. PCT/US2014/029531, dated Jun. 20, 2014 (12 pages).
State Intellectual Property Office of the People's Republic of China, Notification of the Third Office Action, with translation, in Application No. 201080029199.0, dated Jun. 27, 2014 (19 pages).
Intellectual Property Office of Singapore, Invitation to Respond to Written Opinion, in Application No. 2012083077, dated Jun. 30, 2014 (12 pages).
PCT, Notification of Transmittal of International Preliminary Report on Patentability, in International application No. PCT/US13/40368, dated Jul. 16, 2014 (6 pages).
Australian Government, IP Australia, Patent Examination Report No. 1, in Application No. 2012318242, dated Apr. 30, 2014. (6 pages).
State Intellectual Property Office of the People's Republic of China, Notification of the First Office Action, in Application No. 201180023461.5, dated May 21, 2014. (25 pages).
European Patent Office, Communication pursuant to Article 94(3) EPC, in Application No. 10162758.6 dated May 27, 2014. (7 pages).
Australian Government, IP Australia, Patent Examination Report No. 1, in Application No. 2011252925, dated Sep. 6, 2013 (3 pages).
Hopwood J (ED-CRC Press), "Plasma-assisted deposition", Handbook of Nanophase Materials, pp. 184-196, Aug. 17, 1997 (Aug. 17, 1997).
P.G. Pai, S.S. Chao, and Y Takagi, "Infrared Spectroscopic Study of SiOx Films Produced by Plasma Enhanced Chemical Vapor Deposition", Journal of Vacuum Science & Technology A: Vacuum Surfaces and Films, Jun. 1986, p. 689-694; retrieved on Jun. 1, 2014 (7 pages).
C. Weikart and T. Smith, The Dow Chemical Company, "Microwave Plasma Barrier Coating Technology for PET Beverages Containers", Society of Vacuum Coaters, 46th Annual Technical Conference Proceedings, ISSN 0737-5921, pp. 486-490, 2003 (5 pages).
C. Weikart, T. Fisk, and M. Larive, The Dow Chemical Company; T. Glass, H. Pham, and A. Taha, The Dow Chemical Company, J. Felts, Nano Scale Surface Systems, Inc.; "Advances in PECVD Barrier Coating Development for ISBM PP Containers", Society of Vacuum Coaters, 51st Annual Technical Conference Proceedings, ISSN 0737-5921, pp. 569-573, Apr. 19-24, 2008 (5 pages).
C. Weikart, H. Yasuda, "Modification, Degradation, and Stability of Polymeric Surfaces Treated with Reactive Plasmas", Journal of Polymer Science: Part A: Polymer Chemistry, vol. 38, 3028-3042, John Wiley & Sons, Inc., 2000 (15 pages).
PCT, Written Opinion of the International Preliminary Examining Authority, in International application No. PCT/USUS13/048709, dated Sep. 30, 2014 (4 pages).
PCT, Notification of Transmittal of the International Preliminary Report on Patentability, in International application No. PCT/USUS13/048709, dated Oct. 15, 2014 (7 pages).
PCT, Written Opinion of the International Preliminary Examining Authority, in International application No. PCT/USUS13/064121, dated Nov. 19, 2014 (8 pages).
PCT, Written Opinion of the International Preliminary Examining Authority, in International application No. PCT/USUS13/064121, dated Nov. 21, 2014 (7 pages).
Intellectual Property Corporation of Malaysia, Substantive Examintion Adverse Report (section 30(1)/30(2)), in Application No. PI 2011005486, dated Oct. 31, 2014 (3 pages).
Patent Office of the Russian Federation, Official Action, in Application No. 2011150499, dated Sep. 25, 2014 (4 pages).
Instituto Mexicano de la Propiedad Indutrial, Official Action, in Appilcation No. MX/a/2012/013129, dated Sep. 22, 2014 (5 pages).
Australian Government, Patent Examination Report No. 2 in Application No. 2010249031 dated Apr. 21, 2015.
Japanese Patent Office, Notice of Reasons for Refusal in application No. 2013-510276, dated Mar. 31, 2015.
Bose, Sagarika and Constable, Kevin, Advanced Delivery Devices, Design & Evaluation of a Polymer-Based Prefillable Syringe for Biopharmaceuticals With Improved Functionality & Performance, JR Automation Technologies, May 2015.
Hopwood J Ed—CRC Press: "Plasma-assisted deposition", Aug. 17, 1997 (Aug. 17, 1997), Handbook of Nanophase Materials, Chapter 6, pp. 141-197, XP008107730, ISBN: 978-0-8247-9469-9.
PCT, Written Opinion of the International Preliminary Examining Authority, International application No. PCT/SU2013/071752, dated May 6, 2015.
Hlobik, "Plastic Pre-Fillable Syringe Systems" (http://www.healthcarepackaging.com/package-type/Containers/plastic-brefillablesyringe-systems, Jun. 8, 2010).
PCT, Written Opinion of the International Preliminary Examining Authority, in International application No. PCT/US2013/071750, dated Jan. 20, 2015 (9 pages).
PCT, Written Opinion of the International Preliminary Examining Authority, in International application No. PCT/US2013/064121, dated Nov. 21, 2014 (7 pages).
Japanese Patent Office, Decision of Rejection in Application No. 2012-510983, dated Jan. 20, 2015 (4 pages).
Australian Government, IP Australia, Patent Examination Report No. 1, in Application No. 2010249033, dated Dec. 19, 2014 (7 pages).
Australian Government, IP Australia, Patent Examination Report No. 1, in Application No. 2011252925, dated Dec. 2, 2014 (3 pages).
State Intellectual Property Office of the People's Republic of China, Notification of the Fourth Office Action in Application No. 201080029199.0, dated Mar. 18, 2015 (15 pages).
Reh, et al., Evaluation of stationary phases for 2-dimensional HPLC of Proteins—Validation of commercial RP-columns, Published by Elsevier B.V., 2000.
Korean Patent Office, Office Action dated Jun. 21, 2016 in Patent Application No. 10-2011-7028713.
Mexican Patent Office, Office Action dated Jun. 7, 2016 in Patent Application No. MX/a/2011/012038 (3 pages).
Japanese Patent Office, Notice of Reasons for Refusal, Patent Application No. 2013-510276, mailed Mar. 8, 2016 (15 pages).
European Patent Office, Communication pursuant to Article 94(3) EPC, in Application No. 13 726 337.2, dated Dec. 2, 2016 (6 pages).
Allison, H.L., The Real Markets for Transparent Barrier Films, 37th Annual Technical Conference Proceedings, 1994, ISBN 1-878068-13-X, pp. 458.
Bailey, R. et al., Thin-Film Multilayer Capacitors Using Pyrolytically Deposited Silicon Dioxide, IEEE Transactions on Parts, Hybrids, and Packaging, vol. PHP-12, No. 4, Dec. 1976, pp. 361-364.
Banks, B.A., et al., Fluoropolymer Filled SiO2 Coatings; Properties and Potential Applications, Society of Vacuum Coaters, 35th Annual Technical Conference Proceedings, 1992, ISBN 1-878068-11-3, pp. 89-93.
Baouchi, W., X-Ray Photoelectron Spectroscopy Study of Sodium Ion Migration through Thin Films of SiO2 Deposited on Sodalime Glass, 37th Annual Technical Conference Proceedings, 1994, ISBN 1-878068-13-X, pp. 419-422.

(56) References Cited

OTHER PUBLICATIONS

Boebel, F. et al., Simultaneous in Situ Measurement of Film Thickness and Temperature by Using Multiple Wavelengths Pyrometric Interferometry (MWPI), IEEE Transaction on Semiconductor Manufacturing, vol. 6, No. 2, May 1993, , pp. 112-118.
Bush, V. et al., The Evolution of Evacuated Blood Collection Tubes, BD Diagnostics—Preanalytical Systems Newsletter, vol. 19, No. 1, 2009.
Chahroudi, D., Deposition Technology for Glass Barriers, 33rd Annual Technical Conference Proceedings, 1990, ISBN 1-878068-09-1, pp. 212-220.
Chahroudi, D., et al., Transparent Glass Barrier Coatings for Flexible Film Packaging, Society of Vacuum Coaters, 34th Annual Technical Conference Proceedings, 1991, ISBN 1-878068-10-5, pp. 130-133.
Chahroudi, D., Glassy Barriers from Electron Beam Web Coaters, 32nd Annual Technical Conference Proceedings, 1989, pp. 29-39.
Czeremuszkin, G. et al., Ultrathin Silicon-Compound Barrier Coatings for Polymeric Packaging Materials: An Industrial Perspective, Plasmas and Polymers, vol. 6, Nos. 1/2, Jun. 2001, pp. 107-120.
Ebihara, K. et al., Application of the Dielectric Barrier Discharge to Detect Defects in a Teflon Coated Metal Surface, 2003 J. Phys. D: Appl. Phys. 36 2883-2886, doi: 10.1088/0022-3727/36/23/003, IOP Electronic Journals, http://www.iop.org/EJ/abstract/0022-3727/36/23/003, printed Jul. 14, 2009.
Egitto, F.D., et al., Plasma Modification of Polymer Surfaces, Society of Vacuum Coaters, 36th Annual Technical Conference Proceedings, 1993, ISBN 1-878068-12-1, pp. 10-21.
Erlat, A.G. et al., SIOx Gas Barrier Coatings on Polymer Substrates: Morphology and Gas Transport Considerations, ACS Publications, Journal of Physical Chemistry, published Jul. 2, 1999, http://pubs.acs.org/doi/abs/10.1021/jp990737e, printed Jul. 14, 2009.
Fayet, P., et al., Commercialism of Plasma Deposited Barrier Coatings for Liquid Food Packaging, 37th Annual Technical Conference Proceedings, 1995, ISBN 1-878068-13-X, pp. 15-16.
Felts, J., Hollow Cathode Based Multi-Component Depositions, Vacuum Technology & Coating, Mar. 2004, pp. 48-55.
Felts, J.T., Thickness Effects on Thin Film Gas Barriers: Silicon-Based Coatings, Society of Vacuum Coaters, 34th Annual Technical Conference Proceedings, 1991, ISBN 1-878068-10-5, pp. 99-104.
Felts, J.T., Transparent Barrier Coatings Update: Flexible Substrates, Society of Vacuum Coaters, 36th Annual Technical Conference Proceedings, 1993, ISBN 1-878068-12-1, pp. 324-331.
Felts, J.T., Transparent Gas Barrier Technologies, 33rd Annual Technical Conference Proceedings, 1990, ISBN 1-878068-09-1, pp. 184-193.
Finson, E., et al., Transparent SiO2 Barrier Coatings: Conversion and Production Status, 37th Annual Technical Conference Proceedings, 1994, ISBN 1-878068-13-X, pp. 139-143.
Flaherty, T. et al., Application of Spectral Reflectivity to the Measurement of Thin-Film Thickness, Opto-Ireland 2002: Optics and Photonics Technologies and Applications, Proceedings of SPIE vol. 4876, 2003, pp. 976-983.
Hora, R., et al., Plasma Polymerization: A New Technology for Functional Coatings on Plastics, 36th Annual Technical Conference Proceedings, 1993, ISBN 1-878068-12-1, pp. 51-55.
Izu, M., et al., High Performance Clear CoatTM Barrier Film, 36th Annual Technical Conference Proceedings, 1993, ISBN 1-878068-12-1, pp. 333-340.
Jost, S., Plasma Polymerized Organosilicon Thin Films on Reflective Coatings, 33rd Annual Technical Conference Proceedings, 1990, ISBN 1-878068-09-1, pp. 344-346.
Kaganowicz, G., et al., Plasma-Deposited Coatings—Properties and Applications, 23rd Annual Technical Conference Proceedings, 1980, pp. 24-30.
Kamineni, V. et al., Thickness Measurement of Thin Metal Films by Optical Metrology, College of Nanoscale Science and Engineering, University of Albany, Albany, NY.
Klemberg-Sapieha, J.E., et al., Transparent Gas Barrier Coatings Produced by Dual Frequency PECVD, 36th Annual Technical Conference Proceedings, 1993, ISBN 1-878068-12-1, pp. 445-449.
Krug, T., et al., New Developments in Transparent Barrier Coatings, 36th Annual Technical Conference Proceedings, 1993, ISBN 1-878068-12-1, pp. 302-305.
Kuhr, M. et al., Multifunktionsbeschichtungen für innovative Applikationen von Kunststoff-Substraten, HiCotec Smart Coating Solutions.
Kulshreshtha, D.S., Specifications of a Spectroscopic Ellipsometer, Department of Physics & Astrophysics, University of Delhi, Delhi-110007, Jan. 16, 2009.
Krug, T.G., Transparent Barriers for Food Packaging, 33rd Annual Technical Conference Proceedings, 1990, ISBN 1-878068-09-1, pp. 163-169.
Lee, K. et al., The Ellipsometric Measurements of a Curved Surface, Japanese Journal of Applied Physics, vol. 44, No. 32, 2005, pp. L1015-L1018.
Lelait, L. et al., Microstructural Investigations of EBPVD Thermal Barrier Coatings, Journal De Physique IV, Colloque C9, supplément au Journal de Physique III, vol. 3, Dec. 1993, pp. 645-654.
Masso, J.D., Evaluation of Scratch Resistant and Antireflective Coatings for Plastic Lenses, 32nd Annual Technical Conference Proceedings, 1989, p. 237-240.
Misiano, C., et al., New Colourless Barrier Coatings (Oxygen & Water Vapor Transmission Rate) on Plastic Substrates, 35th Annual Technical Conference Proceedings, 1992, ISBN 1-878068-11-3, pp. 28-40.
Misiano, C., et al., Silicon Oxide Barrier Improvements on Plastic Substrate, Society of Vacuum Coaters, 34th Annual Technical Conference Proceedings, 1991, ISBN 1-878068-10-5, pp. 105-112.
Mount, E., Measuring Pinhole Resistance of Packaging, Corotec Corporation website, http://www.convertingmagazine.com, printed Jul. 13, 2009.
Murray, L. et al., The Impact of Foil Pinholes and Flex Cracks on the Moisture and Oxygen Barrier of Flexible Packaging.
Nelson, R.J., et al., Double-Sided QLF® Coatings for Gas Barriers, Society of Vacuum Coaters, 34th Annual Technical Conference Proceedings, 1991, ISBN 1-878068-10-5, pp. 113-117.
Nelson, R.J., Scale-Up of Plasma Deposited SiOx Gas Diffusion Barrier Coatings, 35th Annual Technical Conference Proceedings, 1992, ISBN 1-878068-11-3, pp. 75-78.
Novotny, V. J., Ultrafast Ellipsometric Mapping of Thin Films, IBM Technical Disclosure Bulletin, vol. 37, No. 02A, Feb. 1994, pp. 187-188.
Rüger, M., Die Pulse Sind das Plus, PICVD-Beschichtungsverfahren.
Schultz, A. et al., Detection and Identification of Pinholes in Plasma-Polymerised Thin Film Barrier Coatings on Metal Foils, Surface & Coatings Technology 200, 2005, pp. 213-217.
Stchakovsky, M. et al., Characterization of Barrier Layers by Spectroscopic Ellipsometry for Packaging Applications, Horiba Jobin Yvon, Application Note, Spectroscopic Ellipsometry, SE 14, Nov. 2005.
Teboul, E., Thi-Film Metrology: Spectroscopic Ellipsometer Becomes Industrial Thin-Film Tool, LaserFocusWorld, http://www.laserfocusworld.com/display_article, printed Jul. 14, 2009.
Teyssedre, G. et al., Temperature Dependence of the Photoluminescence in Poly(Ethylene Terephthalate) Films, Polymer 42, 2001, pp. 8207-8216.
Tsung, L. et al., Development of Fast CCD Cameras for In-Situ Electron Microscopy, Microsc Microanal 14(Supp 2), 2008.
Wood, L. et al., A Comparison of SiO2 Barrier Coated Polypropylene to Other Coated Flexible Substrates, 35th Annual Technical Conference Proceedings, 1992, ISBN 1-878068-11-3, pp. 59-62.
Yang, et al., Microstructure and tribological properties of SiOx/DLC films grown by PECVD, Surface and Coatings Technology, vol. 194, Issue 1, Apr. 20, 2005, pp. 128-135.
AN 451, Accurate Thin Film Measurements by High-Resoluiton Transmission Electron Microscopy (HRTEM), Evans Alalytical Group, Version 1.0, Jun. 12, 2008, pp. 1-2.
Benefits of TriboGlide, TriboGlide Silicone-Free Lubrication Systems, http://www.triboglide.com/benfits.htm, printed Aug. 31, 2009.

(56) References Cited

OTHER PUBLICATIONS

Coating Syringes, http://www.triboglide.com/syringes.htm, printed Aug. 31, 2009.
Coating/Production Process, http://www.triboglide.com/process.htm, printed Aug. 31, 2009.
Munich Exp, Materialica 2005: Fundierte Einblicke in den Werkstofsektor, Seite 1, von 4, ME095-6.
Schott Developing Syringe Production in United States, Apr. 14, 2009, http://www.schott.com/pharmaceutical_packaging, printed Aug. 31, 2009.
Sterile Prefillable Glass and Polymer Syringes, Schott forma vitrum, http://www.schott.com/pharmaceutical_packaging.
Transparent und recyclingfähig, neue verpackung, Dec. 2002, pp. 54-57.
European Patent Office, Communication with European Search Report, in Application No. 10162758.6, dated Aug. 19, 2010.
Griesser, Hans J., et al., Elimination of Stick-Slip of Elastomeric Sutures by Radiofrequency Glow Discharge Deposited Coatings, Biomed Mater. Res. Appl Biomater, 2000, vol. 53, 235-243, John Wiley & Sons, Inc.
European Patent Office, Communication with extended Search Report, in Application No. EP 10162761.0, dated Feb. 10, 2011.
European Patent Office, Communication with partial Search Report, in Application No. EP 10162758.6, dated Aug. 19, 2010.
European Patent Office, Communication with extended Search Report, in Application No. EP 10162758.6, dated Dec. 21, 2010.
Yang, et al., Microstructure and tribological properties of SiOx/DLC films grown by PECVD, Surface and Coatings Technology, vol. 194 (2005), Apr. 20, 2005, pp. 128-135.
European Patent Office, Communication with extended European search report, in Application No. EP10162756.0, dated Nov. 17, 2010.
Prasad, G.R. et al., "Biocompatible Coatings with Silicon and Titanium Oxides Deposited by PECVD", 3rd Mikkeli International Industrial Coating Seminar, Mikkeli, Finland, Mar. 16-18, 2006.
European Patent Office, Communication with extended European search report, in Application No. EP10162757.8, dated Nov. 10, 2010.
Patent Cooperation Treaty, Notification of Transmittal of the International Search Report and the Written Opinion of the International Searching Authority, in PCT/US2010/034568, dated Jan. 21, 2011.
Patent Cooperation Treaty, Notification of Transmittal of the International Search Report and the Written Opinion of the International Searching Authority, in PCT/US2010/034571, dated Jan. 26, 2011.
Patent Cooperation Treaty, Notification of Transmittal of the International Search Report and the Written Opinion of the International Searching Authority, in PCT/US2010/034576, dated Jan. 25, 2011.
Patent Cooperation Treaty, Notification of Transmittal of the International Search Report and the Written Opinion of the International Searching Authority, in PCT/US2010/034577, dated Jan. 21, 2011.
Patent Cooperation Treaty, Notification of Transmittal of the International Search Report and the Written Opinion of the International Searching Authority, in PCT/US2010/034582, dated Jan. 24, 2011.
European Patent Office, Communication with Extended Search Report, in Application No. EP 10162755.2, dated Nov. 9, 2010.
European Patent Office, Communication with Extended Search Report, in Application No. EP 10162760.2, dated Nov. 12, 2010.
PCT, Written Opinion of the International Searching Authority with International Search Report in Application No. PCT/US2010/034586, dated Mar. 15, 2011.
Shimojima, Atsushi et al., Structure and Properties of Multilayered Siloxane-Organic Hybrid Films Prepared Using Long-Chain Organotrialkoxysilanes Containing C=C Double Bonds, Journal of Materials Chemistry, 2007, vol. 17, pp. 658-663, © The Royal Society of Chemistry, 2007.
Sone, Hayato et al., Picogram Mass Sensor Using Resonance Frequency Shift of Cantilever, Japanese Journal of Applied Physics, vol. 43, No. 6A, 2004, pp. 3648-3651, © The Japan Society of Applied Physics.
Sone, Hayato et al., Femtogram Mass Sensor Using Self-Sensing Cantilever for Allergy Check, Japanese Journal of Applied Physics, vol. 45, No. 3B, 2006, pp. 2301-2304, © The Japan Society of Applied Physics.
Mallikarjunan, Anupama et al., The Effect of Interfacial Chemistry on Metal Ion Penetration into Polymeric Films, Mat. Res. Soc. Symp. Proc. vol. 734, 2003, © Materials Research Society.
Schonher, H., et al., Friction and Surface Dynamics of Polymers on the Nanoscale by AFM, STM and AFM Studies on (Bio)molecular Systems: Unravelling the Nanoworld. Topics in Current Chemistry, 2008, vol. 285, pp. 103-156, © Springer-Verlag Berlin Heidelberg.
Lang, H.P., Gerber, C., Microcantilever Sensors, STM and AFM Studies on (Bio)molecular Systems: Unravelling the Nanoworld. Topics in Current Chemistry, 2008, vol. 285, pp. 1-28, © Springer-Verlag Berlin Heidelberg.
Patent Cooperation Treaty, Notification of Transmittal of International Preliminary Report on Patentability, in Application No. PCT/US2010/034576, dated Sep. 14, 2011.
Patent Cooperation Treaty, Notification of Transmittal of International Preliminary Report on Patentability, in Application No. PCT/US2010/034568, dated Sep. 14, 2011.
Patent Cooperation Treaty, International Search Report and Written Opinion, in Application No. PCT/US2011/036358, dated Sep. 9, 2011.
Patent Cooperation Treaty, International Search Report and Written Opinion, in Application No. PCT/US2011/036340, dated Aug. 1, 2011.
MacDonald, Gareth, "West and Daikyo Seiko Launch Ready Pack", http://www.in-pharmatechnologist.com/Packaging/West-and-Daikyo-Seiko-launch-Ready-Pack, 2 pages, retrieved from the internet Sep. 22, 2011.
Kumer, Vijai, "Development of Terminal Sterilization Cycle for Pre-Filled Cyclic Olefin Polymer (COP) Syringes", http://abstracts.aapspharmaceutica.com/ExpoAAPS09/CC/forms/attendee/index.aspx?content=sessionInfo&sessionId=401, 1 page, retrieved from the internet Sep. 22, 2011.
Quinn, F.J., "Biotech Lights Up the Glass Packaging Picture", http://www.pharmaceuticalcommerce.com/frontEnd/main.php?idSeccion=840, 4 pages, retrieved from the internet Sep. 21, 2011.
Wen, Zai-Qing et al., Distribution of Silicone Oil in Prefilled Glass Syringes Probed with Optical and Spectroscopic Methods, PDA Journal of Pharmaceutical Science and Technology 2009, 63, pp. 149-158.
ZebraSci—Intelligent Inspection Products, webpage, http://zebrasci.com/index.html, retrieved from the internet Sep. 30, 2011.
Google search re "cyclic olefin polymer resin" syringe OR vial, http://www.google.com/search?sclient=psy-ab&hl=en&lr=&source=hp&q=%22cyclic+olefin+polymer+resin%22+syringe+OR+vial&btnG=Search&pbx=1&oq=%22cyclic+olefin+polymer+resin%22+syringe+OR+vial&aq, 1 page, retrieved from the internet Sep. 22, 2011.
Taylor, Nick, "West to Add CZ Vials as Glass QC Issues Drive Interest", ttp://twitter.com/WestPharma/status/98804071674281986, 2 pages, retrieved from the internet Sep. 22, 2011.
Patent Cooperation Treaty, International Preliminary Examining Authority, Notification of Transmittal of International Preliminary Report on Patentability, in international application No. PCT/US2010/034571, dated Jun. 13, 2011.
Patent Cooperation Treaty, International Preliminary Examining Authority, Written Opinion of the International Preliminary Examining Authority, in international application No. PCT/US2010/034586, dated Aug. 23, 2011.
Patent Cooperation Treaty, International Preliminary Examining Authority, Written Opinion of the International Preliminary Examining Authority, in international application No. PCT/US2010/034568, dated May 30, 2011.
Silicone Oil Layer, Contract Testing, webpage, http://www.siliconization.com/downloads/siliconeoillayercontracttesting.pdf, retrieved from the internet Oct. 28, 2011.
Patent Cooperation Treaty, Notification of Transmittal of Copy of International Preliminary Report on Patentability, in PCT/US2010/034577, dated Nov. 24, 2011.

(56) References Cited

OTHER PUBLICATIONS

Patent Cooperation Treaty, Notification of Transmittal of Copy of International Preliminary Report on Patentability, in PCT/US2010/034582, dated Nov. 24, 2011.
Patent Cooperation Treaty, Notification of Transmittal of Copy of International Preliminary Report on Patentability, in PCT/US2010/034586, dated Dec. 20, 2011.
Patent Cooperation Treaty, Notification of Transmittal of the International Search Report and the Written Opinion of the International Searching Authority, in PCT/US2011/036097, dated Dec. 29, 2011.
"Oxford instruments plasmalab 80plus", XP55015205, retrieved from the Internet on Dec. 20, 2011, URL:http://www.oxfordplasma.de/pdf_inst/plas_80.pdf.
Patent Cooperation Treaty, Notification of Transmittal of the International Search Report and the Written Opinion of the International Searching Authority, in PCT/US2011/044215, dated Dec. 29, 2011.
European Patent Office, Communication pursuant to Article 94(3) EPC, in Application No. 10 162 758.6-1234, dated May 8, 2012 (6 pages).
Sahagian, Khoren; Larner, Mikki; Kaplan, Stephen L., "Altering Biological Interfaces with Gas Plasma: Example Applications", Plasma Technology Systems, Belmont, CA, In SurFACTS in Biomaterials, Surfaces In Biomaterials Foundation, Summer 2013, 18(3), p. 1-5.
Daikyo Cyrystal Zenith Insert Needle Syringe System, West Delivering Innovative Services, West Pharmaceutical Services, Inc., 2010.
Daikyo Crystal Zenigh Syringes, West Pharmaceutical Services, Inc., www. WestPFSsolutions.com, #5659, 2011.
Zhang, Yongchao and Heller, Adam, Reduction of the Nonspecific Binding of a Target Antibody and of Its Enzyme-Labeled Detection Probe Enabling Electrochemical Immunoassay of Antibody through the 7 pg/mL-100 ng/mL (40 fM-400 pM) Range, Department of Chemical Engineering and Texas Materials Institute, University of Texas at Austin, Anal. Chem. 2005, 7, 7758-7762. (6 pages).
Principles and Applications of Liquid Scintillation Counting, LSC Concepts—Fundamentals of Liquid Scintillation Counting, National Diagnostics, 2004, pp. 1-15.
Chikkaveeraiah, Bhaskara V. and Rusling, Dr. James, Non Specific Binding (NSB) in Antigen-Antibody Assays, University of Connecticut, Spring 2007. (13 pages).
Sahagian, Khoren; Larner, Mikki; Kaplan, Stephen L., "Cold Gas Plasma in Surface Modification of Medical Plastics", Plasma Technology Systems, Belmont, CA, Publication pending. Presented at SPE Antec Medical Plastics Division, Apr. 23, 2013, Ohio.
Lipman, Melissa, "Jury Orders Becton to Pay $114M in Syringe Antitrust Case", © 2003-2013, Portfolio Media, Inc., Law360, New York (Sep. 20, 2013, 2:53 PM ET), http://www.law360.com/articles/474334/print?section=ip, [retrieved Sep. 23, 2013].
Wikipedia, the free encyclopedia, http://en.wikipedia.org/wiki/Birefringence, page last modified Sep. 18, 2013 at 11:39. [retrieved on Oct. 8, 2013]. (5 pages).
Wikipedia, the free encyclopedia, http://en.wikipedia.org/wiki/Confocal_microscopy, page last modified Aug. 28, 2013 at 11:12. [retrieved on Oct. 8, 2013]. (4 pages).
Wang, Jun et al., "Fluorocarbon thin film with superhydrophobic property prepared by pyrolysis of hexafluoropropylene oxide", Applied Surface Science, vol. 258, 2012, pp. 9782-9784 (4 pages).
Wang, Hong et al., "Ozone-Initiated Secondary Emission Rates of Aldehydes from Indoor surfaces in Four Homes", American Chemical Society, Environmental Science & Technology, vol. 40, No. 17, 2006, pp. 5263-5268 (6 pages).
Lewis, Hilton G. Pryce, et al., "HWCVD of Polymers: Commercialization and Scale-Up", Thin Solid Films 517, 2009, pp. 3551-3554.
Wolgemuth, Lonny, "Challenges With Prefilled Syringes: The Parylene Solution", Frederick Furness Publishing, www.ongrugdelivery.com, 2012, pp. 44-45.
History of Parylene (12 pages).

SCS Parylene HTX brochure, Stratamet Thin Film Corporation, Fremont, CA, 2012, retrieved from the Internet Feb. 13, 2013, http://www.stratametthinfilm.com/parylenes/htx. (2 pages).
SCS Parylene Properties, Specialty Coating Systems, Inc., Indianapolis, IN, 2011. (12 pages).
Werthheimer, M.R., Studies of the earliest stages of plasma-enhanced chemical vapor deposition of $SiO_2$ on polymeric substrates, Thin Solid Films 382 (2001) 1-3, and references therein, United States Pharmacopeia 34. In General Chapters <1>, 2001.
Gibbins, Bruce and Warner, Lenna, The Role of Antimicrobial Silver Nanotechnology, Medical Device & Diagnostic Industry, August 205, pp. 2-6.
MTI CVD Tube Furnace w Gas Delivery & Vacuum Pump, http://mtixtl.com/MiniCVDTubeFurnace2ChannelsGasVacuum-OTF-1200X-S50-2F.aspx (2 pages).
Lab-Built HFPO CVD Coater, HFPO Decomp to Give Thin Fluorocarbon Films, Applied Surface Science 2012 258 (24) 9782.
Technical Report No. 10, Journal of Parenteral Science and Technology, 42, Supplement 1988, Parenteral Formulation of Proteins and Peptides: Stability and Stabilizers, Parenteral Drug Association, 1988.
Technical Report No. 12, Journal of Parenteral Science and Technology, 42, Supplement 1988, Siliconization of Parenteral Drug Packaging Components, Parenteral Drug Association, 1988.
European Patent Office, Communication under Rule 71(3) EPC, in Application No. 10 162 760.2-1353, dated Oct. 25, 2013. (366 pages).
Wikipedia, the free encyclopedia, http://en.wikipedia.org/wiki/Difluorocarbene, page last modified Feb. 20, 2012 at 14:41. [retrieved on Sep. 7, 2012]. (4 pages).
O'Shaughnessy, W.S., et al., "Initiated Chemical Vapor Deposition of a Siloxane Coating for Insulation of Neutral Probes", Thin Solid Films 517 (2008) 3612-3614. (3 pages).
Denler, et al., Investigations of SiOx-polymer "interphases" by glancing angle RBS with Li+ and Be+ ions, Nuclear Instruments and Methods in Physical Research B 208 (2003) 176-180, United States Pharmacopeia 34. In General Chapters <1>, 2003.
PCT, Invitation to Pay Additional Fees and Annex to Form PCT/ISA/206 Communication relating to the results of the partial international search in International application No. PCT/US2013/071750, dated Feb. 14, 2014. (6 pages).
PCT, Notification of Transmittal of the International Search Report and the Written Opinion of the International Searching Authority, or the Declaration, in International application No. PCT/US2013/62247, dated Dec. 30, 2013. (13 pages).
PCT, Notification of Transmittal of the International Search Report and the Written Opinion of the International Searching Authority, or the Declaration, in International application No. PCT/US2013/043642, dated Dec. 5, 2013. (21 pages).
Japanese Patent Office, Notice of Reason(s) for Rejection in Patent application No. 2012-510983, dated Jan. 7, 2014. (6 pages).
Chinese Patent Office, Notification of the Second Office Action in Application No. 201080029199.0, dated Jan. 6, 2014. (26 pages).
Chinese Patent Office, Notification of the First Office Action in Application No. 201180023474.2, dated Dec. 23, 2013. (18 pages).
PCT, Notification of Transmittal of the International Search Report and the Written Opinion of the International Searching Authority, or the Declaration, in International application No. PCT/US2013/067852, dated Jan. 22, 2014. (9 pages).
PCT, Notification of Transmittal of the International Search Report and the Written Opinion of the International Searching Authority, or the Declaration, in International application No. PCT/US2013/064121, dated Mar. 24, 2014. (8 pages).
PCT, Notification of Transmittal of the International Search Report and the Written Opinion of the International Searching Authority, or the Declaration, in International application No. PCT/US2013/070325, dated Mar. 24, 2014. (16 pages).
L. Martinu, O. Zabeida, and J.E. Klemberg-Sapieha, "Plasma-Enhanced Chemical Vapor Deposition of Functional Coatings", Handbook of Deposition Technologies for Films and Coating, Chapter 9, pp. 392-464, 2010.

(56) References Cited

OTHER PUBLICATIONS

Patent Cooperation Treaty, Written Opinion of the International Searching Authority with International Search Report in Application No. PCT/US2012/064489, dated Jan. 25, 2013.

Danish Patent and Trademark Office, Singapore Written Opinion, in Application No. 201108308-6, dated Dec. 6, 2012.

Danish Patent and Trademark Office, Singapore Search Report, in Application No. 201108308-6, dated Dec. 12, 2012.

Tao, Ran et al., Condensationand Polymerization of Supersaturated Monomer Vapor, ACS Publications, 2012 American Chemical Society, ex.doi.org/10.1021/la303462q/Langmuir 2012, 28, 16580-16587.

State Intellectual Property Office of Teh People's Republic of China, Notification of First Office Action in Application No. 201080029201.4, dated Mar. 37, 2013. (15 pages).

PCT, Notification of Transmittal of the International Search Report and the Written Opinion of the International Searching Authority, or the Declaration, in International application No. PCT/US2013/040380, dated Sep. 3, 2013. (13 pages).

PCT, Notification of Transmittal of the International Search Report and the Written Opinion of the International Searching Authority, or the Declaration, in International application No. PCT/US2013/040368, dated Oct. 21, 2013. (21 pages).

PCT, Notification of Transmittal of the International Search Report and the Written Opinion of the International Searching Authority, or the Declaration, in International application No. PCT/US2013/048709, dated Oct. 2, 2013. (7 pages).

Coclite A.M. et al., "On the relationship between the structure and the barrier performance of plasma deposited silicon dioxide-like films", Surface and Coatings Technology, Elsevier, Amsterdam, NL, vol. 204, No. 24, Sep. 15, 2010 (Sep. 15, 2010), pp. 4012-4017, XPO27113381, ISSN: 0257-8972 [retrieved on Jun. 16, 2010] abstract, p. 4014, right-hand column—p. 4015, figures 2, 3.

Brunet-Bruneau A. et al., "Microstructural characterization of ion assisted Sio2 thin films by visible and infrared ellipsometry", Journal of Vacuum Science and Technology: Part A, AVS/AIP, Melville, NY, US, vol. 16, No. 4, Jul. 1, 1998 (Jul. 1, 1998), pp. 2281-2286, XPO12004127, ISSN: 0734-2101, DOI: 10.1116/1.581341, p. 2283, right-hand column—p. 2284, left-hand column, figures 2, 4.

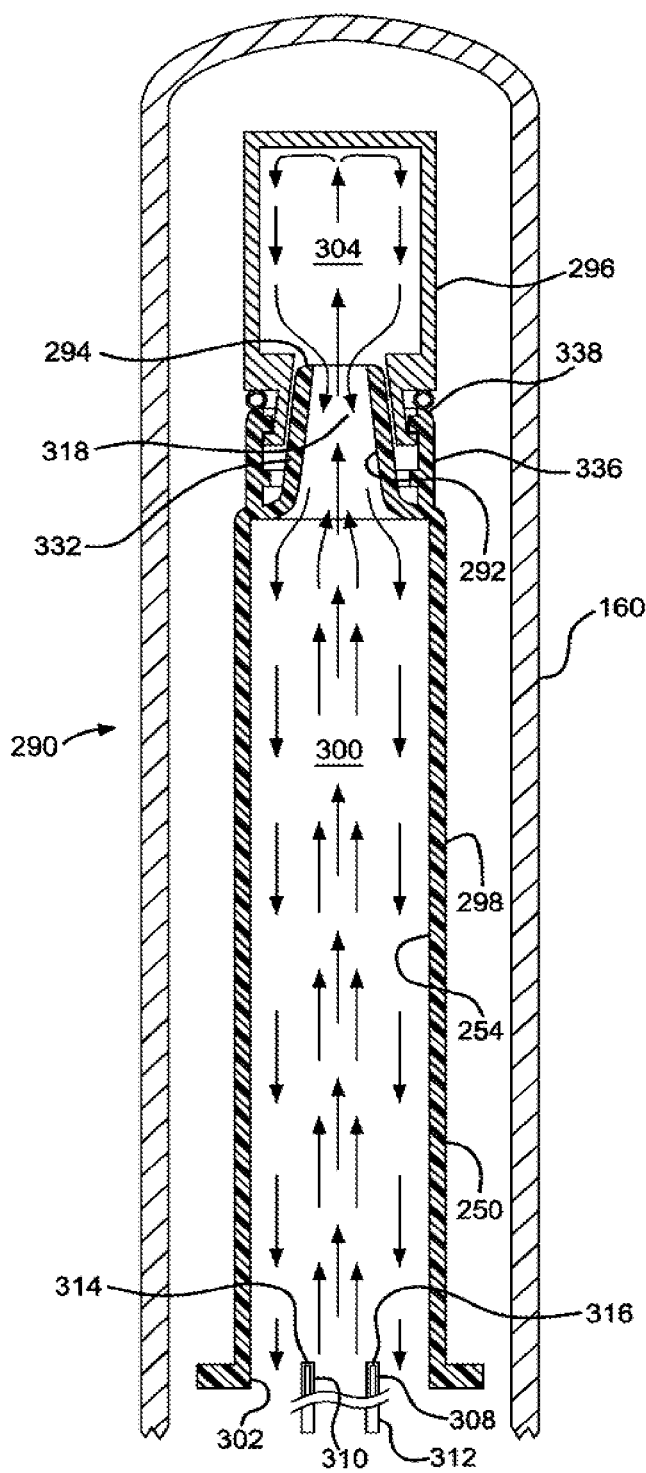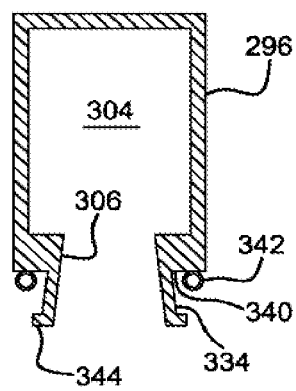
FIG. 3
FIG. 4

SiO$_x$ BARRIER FOR PHARMACEUTICAL PACKAGE AND COATING PROCESS

This application is a continuation of U.S. patent application Ser. No. 14/412,472, filed Jan. 2, 2015 as a national phase entry of PCT/US2013/048709, filed Jun. 28, 2013. Priority is claimed from U.S. Ser. Nos. 61/667,871, filed Jul. 3, 2012, and 61/800,746, filed Mar. 15, 2013, and this application is a continuation-in-part of U.S. Ser. No. 13/169,811, filed Jun. 27, 2011, now pending, which is a divisional of U.S. Ser. No. 12/779,007, filed May 12, 2010, now U.S. Pat. No. 7,985,188, which claims priority to U.S. Provisional Ser. Nos. 61/222,727, filed Jul. 2, 2009; 61/213,904, filed Jul. 24, 2009; 61/234,505, filed Aug. 17, 2009; 61/261,321, filed Nov. 14, 2009; 61/263,289, filed Nov. 20, 2009; 61/285,813, filed Dec. 11, 2009; 61/298,159, filed Jan. 25, 2010; 61/299,888, filed Jan. 29, 2010; 61/318,197, filed Mar. 26, 2010, and 61/333,625, filed May 11, 2010. The above patent and applications are incorporated here by reference in their entirety.

U.S. Pat. No. 7,985,188; International Application PCT/US11/36097, filed May 11, 2011; U.S. Ser. No. 61/558,885, filed Nov. 11, 2011; and U.S. Ser. No. 61/636,377, filed Apr. 20, 2012, are all incorporated here by reference in their entirety.

Also incorporated by reference in their entirety are the following European patent applications: EP10162755.2 filed May 12, 2010; EP10162760.2 filed May 12, 2010; EP10162756.0 filed May 12, 2010; EP10162758.6 filed May 12, 2010; EP10162761.0 filed May 12, 2010; and EP10162757.8 filed May 12, 2010. These European patent applications describe apparatus, vessels, precursors, coatings or layers and methods (in particular coating methods and test methods for examining the coatings or layers) which can generally be used in performing the present invention, unless stated otherwise herein.

FIELD OF THE INVENTION

The present invention relates to the technical field of coated surfaces, for example interior surfaces of pharmaceutical packages or other vessels for storing or other contact with fluids. Examples of suitable fluids include foods, biologically active compounds or body fluids, for example pharmaceutical materials, blood, and many others. The present invention also relates to a pharmaceutical package or other vessel and to a method for coating an inner or interior surface of a pharmaceutical package or other vessel. The present invention also relates more generally to medical devices, including devices other than packages or vessels, for example catheters.

The present disclosure also relates to improved methods for processing pharmaceutical packages or other vessels, for example multiple identical pharmaceutical packages or other vessels used for pharmaceutical preparation storage and delivery, venipuncture and other medical sample collection, and other purposes. Such pharmaceutical packages or other vessels are used in large numbers for these purposes, and must be relatively economical to manufacture and yet highly reliable in storage and use.

BACKGROUND OF THE INVENTION

One important consideration in manufacturing pharmaceutical packages or other vessels for storing or other contact with fluids, for example vials and pre-filled syringes, is that the contents of the pharmaceutical package or other vessel desirably will have a substantial shelf life. During this shelf life, it is important to isolate the material filling the pharmaceutical package or other vessel from atmospheric gases such as oxygen. It is also important to isolate such material from the vessel wall containing it, or from barrier layers or other functional layers applied to the pharmaceutical package or other vessel wall to avoid leaching material from the pharmaceutical package or other vessel wall, barrier layer, or other functional layers into the prefilled contents or vice versa.

Since many of these pharmaceutical packages or other vessels are inexpensive and used in large quantities, for certain applications it will be useful to reliably obtain the necessary shelf life without increasing the manufacturing cost to a prohibitive level.

For decades, most parenteral therapeutics have been delivered to end users in Type I medical grade borosilicate glass vessels such as vials or pre-filled syringes. The relatively strong, impermeable and inert surface of borosilicate glass has performed adequately for most drug products. However, the recent advent of costly, complex and sensitive biologics as well as such advanced delivery systems as auto injectors has exposed the physical and chemical shortcomings of glass pharmaceutical packages or other vessels, including possible contamination from metals, flaking, and breakage, among other problems. Moreover, glass contains several components which can leach out during storage and cause damage to the stored material. In more detail, borosilicate pharmaceutical packages or other vessels exhibit a number of drawbacks.

Glass is manufactured from sand containing a heterogeneous mixture of many elements (silicon, oxygen, boron, aluminum, sodium, calcium) with trace levels of other alkali metals and alkaline earth metals. Type I borosilicate glass consists of approximately 76% $SiO_2$, 10.5% $B_2O_3$, 5% $Al_2O_3$, 7% $Na_2O$ and 1.5% $CaO$ and often contains trace metals such as iron, magnesium, zinc, copper and others. The heterogeneous nature of borosilicate glass creates a non-uniform surface chemistry at the molecular level. Glass forming processes used to create glass vessels expose some portions of the vessels to temperatures as great as 1200° C. Under such high temperatures alkali ions migrate to the local surface and form oxides. The presence of ions extracted from borosilicate glass devices may be involved in degradation, aggregation and denaturation of some biologics. Many proteins and other biologics must be lyophilized (freeze dried), because they are not sufficiently stable in solution in glass vials or syringes.

Glass pharmaceutical packages or other vessels are prone to breakage or degradation during manufacture, filling operations, shipping and use, which means that glass particulates may enter the drug. The presence of glass particles has led to many FDA Warning Letters and to product recalls.

Glass-forming processes do not yield the tight dimensional tolerances required for some of the newer auto-injectors and delivery systems.

As a result, some companies have turned to plastic pharmaceutical packages or other vessels, which provide greater dimensional tolerance and less breakage than glass but lack its impermeability.

Although plastic is superior to glass with respect to breakage, dimensional tolerances and surface uniformity, its use for primary pharmaceutical packaging remains limited due to the following shortcomings:

Gas (oxygen) permeability: Plastic allows small molecule gases to permeate into (or out of) the device. The permeability of plastics to gases is significantly greater than that of glass and, in many cases (as with oxygen-sensitive drugs such as epinephrine), plastics have been unacceptable for that reason.

Water vapor transmission: Plastics allow water vapors to pass through devices to a greater degree than glass. This can be detrimental to the shelf life of a solid (lyophilized) drug. Alternatively, a liquid product may lose water in an arid environment.

Leachables and extractables: Plastic pharmaceutical packages or other vessels contain organic compounds that can leach out or be extracted into the drug product. These compounds can contaminate the drug and/or negatively impact the drug's stability.

Clearly, while plastic and glass pharmaceutical packages or other vessels each offer certain advantages in pharmaceutical primary packaging, neither is optimal for all drugs, biologics or other therapeutics. Thus, there is a desire for plastic pharmaceutical packages or other vessels, for example vials, sample collection tubes, and syringes, with gas and solute barrier properties which approach the properties of glass.

A non-exhaustive list of documents of possible relevance includes U.S. Pat. Nos. 7,488,683; 7,901,783; 6,068,884; 4,844,986; and 8,067,070 and U.S. Publ. Appl. Nos. 2008/0090039, 2011/0152820, 2006/0046006 and 2004/0267194. These documents are all incorporated by reference.

SUMMARY OF THE INVENTION

A non-limiting aspect of the invention is a vessel including a thermoplastic wall enclosing a lumen. The wall supports an $SiO_x$ composite barrier coating or layer, for which x is from 1.8 to 2.4, between the wall and the lumen. The $SiO_x$ composite barrier coating or layer is formed by PECVD from an organosilicon monomer and an oxidizing gas. The $SiO_x$ composite barrier coating or layer is formed in at least bonding and build-up stages, under the following conditions. During the bonding stage, the feed ratio of organosilicon monomer to oxidizing gas, in sccm, is from 2.5 to 10. During the build-up stage, the feed ratio of organosilicon monomer to oxidizing gas is from 0.1 to 0.05.

A non-limiting aspect of the invention is a vessel including a thermoplastic wall enclosing a lumen. The wall supports an $SiO_x$ composite barrier coating or layer, for which x is from 1.8 to 2.4, between the wall and the lumen. The $SiO_x$ composite barrier coating or layer is formed by PECVD from an organosilicon monomer and an oxidizing gas. The $SiO_x$ composite barrier coating or layer is formed at an initial RF power level from 20 to 4 W and a highest RF power level of from 300 to 30 W.

A non-limiting aspect of the invention is a vessel including a thermoplastic wall enclosing a lumen. The wall supports an $SiO_x$ composite barrier coating or layer, for which x is from 1.8 to 2.4, between the wall and the lumen. The degree of retention of the composite barrier coating or layer on the substrate is at least 95% by the Article Deformation/Tape Test Method described in this specification.

A non-limiting aspect of the invention is a vessel including a thermoplastic wall enclosing a lumen. The wall supports an $SiO_x$ composite barrier coating or layer, for which x is from 1.8 to 2.4, between the wall and the lumen. The degree of retention of the composite barrier coating or layer on the substrate is at least 90% by the Coated Article Cross-Scratch Tape Test Method.

A non-limiting aspect of the invention is a vessel including a thermoplastic wall enclosing a lumen. The wall supports an $SiO_x$ composite barrier coating or layer, for which x is from 1.8 to 2.4, between the wall and the lumen. High Resolution X-ray Photoelectron Spectroscopy (XPS) shows the presence of an interface between the composite barrier coating or layer and the wall or substrate. The interface has at least 1 mol. % $O_3$—Si—C covalent bonding, as a proportion of the $O_3$—Si—C covalent bonding plus $SiO_4$ bonding.

A non-limiting aspect of the invention is a vessel including a thermoplastic wall enclosing a lumen. The wall supports an $SiO_x$ composite barrier coating or layer, for which x is from 1.8 to 2.4, between the wall and the lumen. High Resolution X-ray Photoelectron Spectroscopy (XPS) shows the presence of an interface between the composite barrier coating or layer and the wall or substrate. The interface has an Si 2p chemical shift to lower binding energy (eV), compared to the binding energy of $SiO_4$ bonding.

A non-limiting aspect of the invention is a method of making a vessel. A thermoplastic wall enclosing a lumen is provided. An $SiO_x$ composite barrier coating or layer, for which x is from 1.8 to 2.4, is applied to the thermoplastic wall. The composite barrier coating or layer is supported by the wall between the wall and the lumen. The composite barrier coating or layer is applied by PECVD from an organosilicon monomer and oxidizing gas. The composite barrier coating or layer is applied in at least bonding and build-up stages, under the following conditions. During the bonding stage, the feed ratio of organosilicon monomer to oxidizing gas, in sccm, is from 2.5 to 10. During the build-up stage, the feed ratio of organosilicon monomer to oxidizing gas is from 0.1 to 0.05.

A non-limiting aspect of the invention is a method of making a vessel. A thermoplastic wall enclosing a lumen is provided. An $SiO_x$ composite barrier coating or layer, for which x is from 1.8 to 2.4, is applied to the thermoplastic wall. The composite barrier coating or layer is supported by the wall between the wall and the lumen. The composite barrier coating or layer is applied by PECVD from an organosilicon monomer and oxidizing gas. The composite barrier coating or layer is applied at an initial RF power level from 20 to 4 W and a highest RF power level of from 300 to 30 W.

A non-limiting aspect of the invention is a method of making a vessel. A thermoplastic wall enclosing a lumen is provided. An $SiO_x$ composite barrier coating or layer, for which x is from 1.8 to 2.4, is applied to the thermoplastic wall. The composite barrier coating or layer is supported by the wall between the wall and the lumen. The composite barrier coating or layer is applied by PECVD from an organosilicon monomer and oxidizing gas. The composite barrier coating or layer is applied in at least bonding and build-up stages. The degree of retention of the composite barrier coating or layer on the substrate is at least 95% by the Article Deformation/Tape Test Method.

A non-limiting aspect of the invention is a method of making a vessel. A thermoplastic wall enclosing a lumen is provided. An $SiO_x$ composite barrier coating or layer, for which x is from 1.8 to 2.4, is applied to the thermoplastic wall. The composite barrier coating or layer is supported by the wall between the wall and the lumen. The composite barrier coating or layer is applied by PECVD from an organosilicon monomer and oxidizing gas. The composite barrier coating or layer is applied in at least bonding and build-up stages. The degree of retention of the composite barrier coating or layer on the substrate is at least 90% by the Coated Article Cross-Scratch Tape Test Method.

A non-limiting aspect of the invention is a method of making a vessel. A thermoplastic wall enclosing a lumen is provided. An SiO$_x$ composite barrier coating or layer, for which x is from 1.8 to 2.4, is applied to the thermoplastic wall. The composite barrier coating or layer is supported by the wall between the wall and the lumen. The composite barrier coating or layer is applied by PECVD from an organosilicon monomer and oxidizing gas. The composite barrier coating or layer is applied in at least bonding and build-up stages. High Resolution X-ray Photoelectron Spectroscopy (XPS) shows the presence of an interface between the composite barrier coating or layer and the substrate having at least 1 mol. % O$_3$—Si—C covalent bonding, as a proportion of the O$_3$—Si—C covalent bonding plus SiO$_4$ bonding.

A non-limiting aspect of the invention is a method of making a vessel. A thermoplastic wall enclosing a lumen is provided. An SiO$_x$ composite barrier coating or layer, for which x is from 1.8 to 2.4, is applied to the thermoplastic wall. The composite barrier coating or layer is supported by the wall between the wall and the lumen. The composite barrier coating or layer is applied by PECVD from an organosilicon monomer and oxidizing gas. The composite barrier coating or layer is applied in at least bonding and build-up stages. High Resolution X-ray Photoelectron Spectroscopy (XPS) shows the presence of an Si 2p chemical shift to lower binding energy (eV), compared to the binding energy of SiO$_4$ bonding.

A non-limiting aspect of the invention is a filled package comprising a vessel having a lumen defined at least in part by a wall. The wall has an interior surface facing the lumen, an outer surface, and a coating set on the interior surface comprising a tie coating or layer, a barrier coating or layer, and a pH protective coating or layer. Optionally in any embodiment, the tie coating or layer and the barrier coating or layer together are provided in the form of a composite barrier as previously defined.

The tie coating or layer comprises SiO$_x$C$_y$ or SiN$_x$C$_y$ wherein x is from about 0.5 to about 2.4 and y is from about 0.6 to about 3. The tie coating or layer has an interior surface facing the lumen and an outer surface facing the wall interior surface.

The barrier coating or layer comprises SiO$_x$, wherein x is from 1.5 to 2.9, from 2 to 1000 nm thick, the barrier coating or layer of SiO$_x$ having an interior surface facing the lumen and an outer surface facing the interior surface of the tie coating or layer, the barrier coating or layer being effective to reduce the ingress of atmospheric gas into the lumen compared to an vessel without a barrier coating or layer;

The pH protective coating or layer comprises SiO$_x$C$_y$ or SiN$_x$C$_y$, wherein x is from about 0.5 to about 2.4 and y is from about 0.6 to about 3, the pH protective coating or layer having an interior surface facing the lumen and an outer surface facing the interior surface of the composite barrier coating or layer, The combination of the tie coating or layer and the pH protective coating or layer is effective to increase the calculated shelf life of the package (total Si/Si dissolution rate).

The package also includes a fluid composition contained in the lumen and having a pH between 5 and 9. The calculated shelf life of the package is more than six months at a storage temperature of 4° C.

A non-limiting aspect of the invention is an article including a wall having a surface and a coating set on the surface comprising a tie coating or layer, a barrier coating or layer, and a pH protective coating or layer.

The tie coating or layer comprises SiO$_x$C$_y$ or SiN$_x$C$_y$ wherein x is from about 0.5 to about 2.4 and y is from about 0.6 to about 3. The tie coating or layer has an outer surface facing the wall surface and an interior surface;

The barrier coating or layer comprises SiO$_x$, wherein x is from 1.5 to 2.9, from 2 to 1000 nm thick. The composite barrier coating or layer of SiO$_x$ has an outer surface facing the interior surface of the tie coating or layer and the composite barrier coating or layer of SiO$_x$ has an interior surface. The composite barrier coating or layer is effective to reduce the ingress of atmospheric gas through the wall compared to an uncoated wall.

Optionally in any embodiment, the tie coating or layer and the barrier coating or layer together are provided in the form of a composite barrier coating or layer as previously defined.

The pH protective coating or layer comprises SiO$_x$C$_y$ or SiN$_x$C$_y$ wherein x is from about 0.5 to about 2.4 and y is from about 0.6 to about 3. The pH protective coating or layer is deposited on the composite barrier coating or layer. The pH protective coating or layer is formed by chemical vapor deposition of a precursor selected from an acyclic siloxane, a monocyclic siloxane, a polycyclic siloxane, a polysilsesquioxane, a monocyclic silazane, a polycyclic silazane, a polysilsesquiazane, a silatrane, a silquasilatrane, a silproatrane, an azasilatrane, an azasilquasiatrane, an azasilproatrane, or a combination of any two or more of these precursors; and The rate of erosion of the pH protective coating or layer, if directly contacted by a fluid composition having a pH at some point between 5 and 9, is less than the rate of erosion of the composite barrier coating or layer, if directly contacted by the fluid composition.

A non-limiting aspect of the invention is a vessel comprising a thermoplastic wall having an interior surface enclosing a lumen. The interior surface has a tie coating or layer, a barrier coating or layer, and a pH protective coating or layer. A fluid is contained in the lumen having a pH greater than 5.

The tie coating or layer comprises SiO$_x$C$_y$ or SiN$_x$C$_y$ wherein x is from about 0.5 to about 2.4 and y is from about 0.6 to about 3, the tie coating or layer having an outer surface facing the wall surface and the tie coating or layer having an interior surface.

The barrier coating or layer comprises SiO$_x$, in which x is between 1.5 and 2.9. The barrier coating or layer is applied by PECVD, is positioned between the interior surface of the tie coating or layer and the fluid, and is supported by the thermoplastic wall. The barrier coating or layer has the characteristic of being subject to being measurably diminished in barrier improvement factor in less than six months as a result of attack by the fluid.

Optionally in any embodiment, the tie coating or layer and the barrier coating or layer together are provided in the form of a composite barrier as previously defined.

The vessel has a pH protective coating or layer of SiO$_x$C$_y$, in which x is between 0.5 and 2.4 and y is between 0.6 and 3. The pH protective coating or layer is applied by PECVD, is positioned between the composite barrier coating or layer and the fluid and is supported by the thermoplastic wall. The pH protective coating or layer and tie coating or layer together are effective to keep the composite barrier coating or layer at least substantially undissolved as a result of attack by the fluid for a period of at least six months.

BRIEF DESCRIPTION OF THE DRAWINGS

FIG. 3 is a view similar to FIG. 1 of another embodiment for processing syringe barrels and other pharmaceutical packages or other vessels.

FIG. 4 is an enlarged detail view of the processing vessel of FIG. 3.

Figure 1:
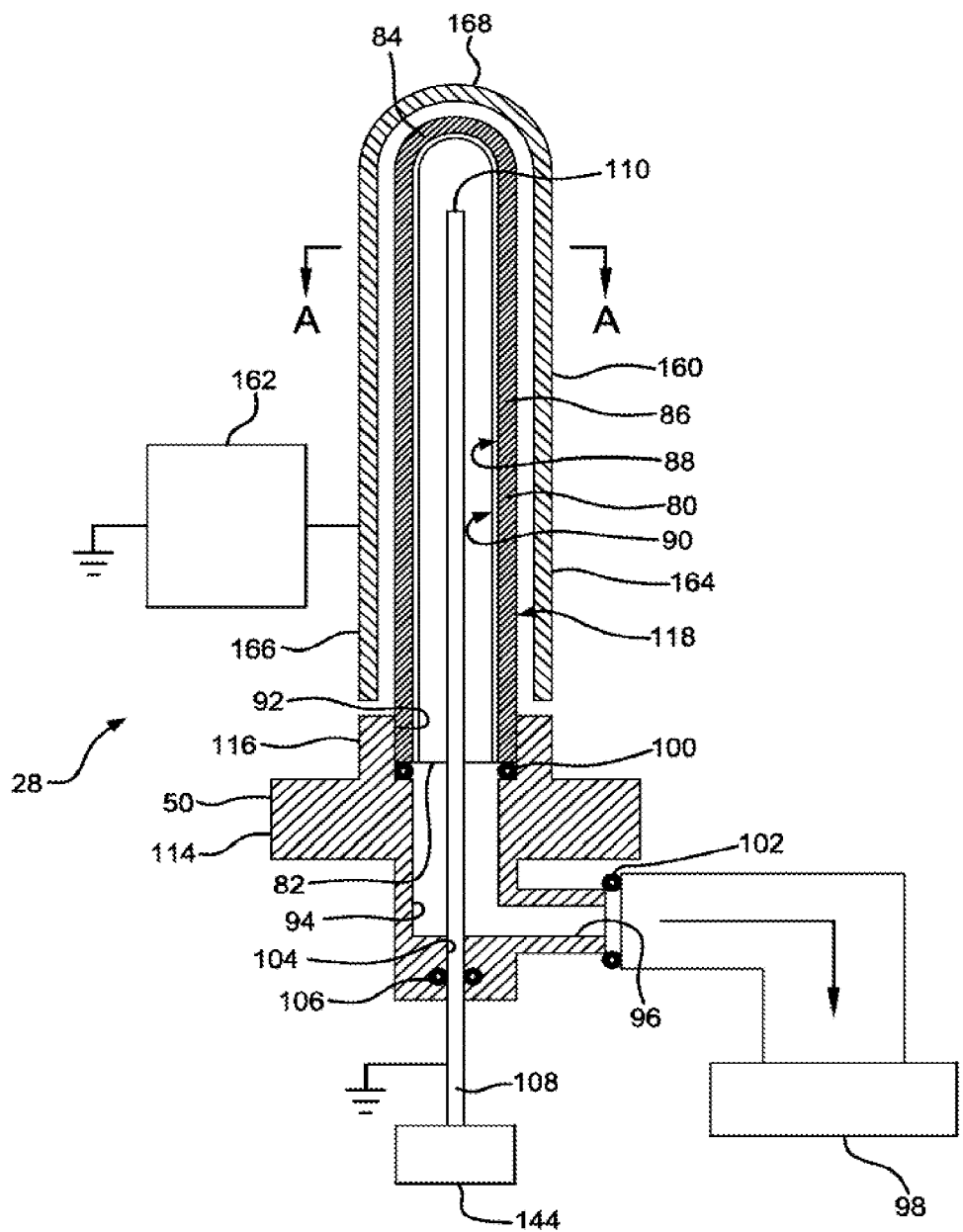
FIG. 1 is a schematic sectional view of a vessel holder in a coating station according to an embodiment of the disclosure.

The following reference characters are used in the drawing figures:

| | |
|---|---|
| 28 | coating station |
| 38 | Vessel holder |
| 50 | Vessel holder |
| 80 | Vessel |
| 82 | Opening |
| 84 | Closed end |
| 86 | Wall |
| 88 | Inner or interior surface |
| 90 | Composite barrier layer |
| 92 | Vessel port |
| 94 | Vacuum duct |
| 96 | Vacuum port |
| 98 | Vacuum source |
| 100 | O-ring (of 92) |
| 102 | O-ring (of 96) |
| 104 | Gas inlet port |
| 106 | O-ring (of 100) |
| 108 | Probe (counter electrode) |
| 110 | Gas delivery port (of 108) |
| 114 | Housing (of 50 or 112) |
| 116 | Collar |
| 118 | Exterior surface (of 80) |
| 144 | PECVD gas source |
| 152 | Pressure gauge |
| 160 | Electrode |
| 162 | Power supply |
| 164 | Sidewall (of 160) |
| 166 | Sidewall (of 160) |
| 168 | Closed end (of 160) |
| 210 | Pharmaceutical package |
| 212 | Lumen |
| 214 | Wall |
| 216 | Outer surface |
| 218 | Fluid composition |
| 220 | Interior surface (of 288) |
| 222 | Outer surface (of 288) |
| 224 | Interior surface (of 286) |
| 226 | Outer surface (of 286) |
| 250 | Syringe barrel |
| 254 | Inner or interior surface (of 250) |
| 256 | Back end (of 250) |
| 258 | Plunger (of 252) (relatively sliding part) |
| 260 | Front end (of 250) |
| 262 | Cap |
| 286 | pH protective coating |
| 287 | Lubricity layer (FIGS. 8-9) |
| 288 | Composite barrier layer |
| 290 | Apparatus for coating, for example, 250 |
| 292 | Inner or interior surface (of 294) |
| 294 | Restricted opening (of 250) |
| 296 | Processing vessel |
| 298 | Outer surface (of 250) |
| 300 | Lumen (of 250) |
| 302 | Larger opening (of 250) |
| 304 | Processing vessel lumen |
| 306 | Processing vessel opening |
| 308 | Inner electrode |
| 310 | Interior passage (of 308) |
| 312 | Proximal end (of 308) |
| 314 | Distal end (of 308) |
| 316 | Distal opening (of 308) |
| 318 | Plasma |
| 332 | First fitting (male Luer taper) |
| 334 | Second fitting (female Luer taper) |
| 336 | Locking collar (of 332) |
| 338 | First abutment (of 332) |
| 340 | Second abutment (of 332) |
| 342 | O-ring |
| 344 | Dog |
| 404 | Vent (FIG. 5) |
| 574 | Main vacuum valve |
| 576 | Vacuum line |
| 578 | Manual bypass valve |
| 580 | Bypass line |
| 582 | Vent valve |
| 584 | Main reactant gas valve |
| 586 | Main reactant feed line |
| 588 | Organosilicon liquid reservoir |
| 590 | Organosilicon feed line (capillary) |
| 592 | Organosilicon shut-off valve |
| 594 | Oxygen tank |
| 596 | Oxygen feed line |
| 598 | Mass flow controller |
| 600 | Oxygen shut-off valve |
| 602 | Source of carrier gas (FIG. 5) |
| 604 | Conduit (FIG. 5) |
| 606 | Carrier gas shut-off valve (FIG. 5) |
| 614 | Headspace |
| 616 | Pressure source |
| 618 | Pressure line |
| 620 | Capillary connection |

DETAILED DESCRIPTION

The present invention will now be described more fully, with reference to the accompanying drawings, in which several embodiments are shown. This invention can, however, be embodied in many different forms and should not be construed as limited to the embodiments set forth here. Rather, these embodiments are examples of the invention, which has the full scope indicated by the language of the claims. Like numbers refer to like or corresponding elements throughout. The following disclosure relates to all embodiments unless specifically limited to a certain embodiment.

Definition Section

In the context of the present invention, the following definitions and abbreviations are used:

RF is radio frequency.

The term "at least" in the context of the present invention means "equal or more" than the integer following the term. The word "comprising" does not exclude other elements or steps, and the indefinite article "a" or "an" does not exclude a plurality unless indicated otherwise. Whenever a parameter range is indicated, it is intended to disclose the parameter values given as limits of the range and all values of the parameter falling within said range.

"First" and "second" or similar references to, for example, processing stations or processing devices refer to the minimum number of processing stations or devices that are present, but do not necessarily represent the order or total number of processing stations and devices. These terms do not limit the number of processing stations or the particular processing carried out at the respective stations.

For purposes of the present invention, an "organosilicon precursor" is a compound having at least one of the linkages:

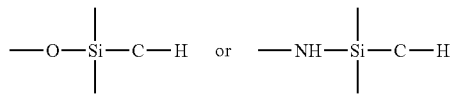

which is a tetravalent silicon atom connected to an oxygen or nitrogen atom and an organic carbon atom (an organic carbon atom being a carbon atom bonded to at least one hydrogen atom). A volatile organosilicon precursor, defined as such a precursor that can be supplied as a vapor in a PECVD apparatus, is an optional organosilicon precursor. Optionally, the organosilicon precursor is selected from the group consisting of a linear siloxane, a monocyclic siloxane, a polycyclic siloxane, a polysilsesquioxane, an alkyl trimethoxysilane, a linear silazane, a monocyclic silazane, a polycyclic silazane, a polysilsesquiazane, and a combination of any two or more of these precursors.

The feed amounts of PECVD precursors, gaseous reactant or process gases, and carrier gas are sometimes expressed in "standard volumes" in the specification and claims. The standard volume of a charge or other fixed amount of gas is the volume the fixed amount of the gas would occupy at a standard temperature and pressure (without regard to the actual temperature and pressure of delivery). Standard volumes can be measured using different units of volume, and still be within the scope of the present disclosure and claims. For example, the same fixed amount of gas could be expressed as the number of standard cubic centimeters, the number of standard cubic meters, or the number of standard cubic feet. Standard volumes can also be defined using different standard temperatures and pressures, and still be within the scope of the present disclosure and claims. For example, the standard temperature might be 0° C. and the standard pressure might be 760 Torr (as is conventional), or the standard temperature might be 20° C. and the standard pressure might be 1 Torr. But whatever standard is used in a given case, when comparing relative amounts of two or more different gases without specifying particular parameters, the same units of volume, standard temperature, and standard pressure are to be used relative to each gas, unless otherwise indicated.

The corresponding feed rates of PECVD precursors, gaseous reactant or process gases, and carrier gas are expressed in standard volumes per unit of time in the specification. For example, in the working examples the flow rates are expressed as standard cubic centimeters per minute, abbreviated as sccm. As with the other parameters, other units of time can be used, such as seconds or hours, but consistent parameters are to be used when comparing the flow rates of two or more gases, unless otherwise indicated.

A "vessel" in the context of the present invention can be any type of vessel with at least one opening and a wall defining an inner or interior surface. The substrate can be the inside wall of a vessel having a lumen. Though the invention is not necessarily limited to pharmaceutical packages or other vessels of a particular volume, pharmaceutical packages or other vessels are contemplated in which the lumen has a void volume of from 0.5 to 50 mL, optionally from 1 to 10 mL, optionally from 0.5 to 5 mL, optionally from 1 to 3 mL. The substrate surface can be part or all of the inner or interior surface of a vessel having at least one opening and an inner or interior surface.

The term "at least" in the context of the present invention means "equal or more" than the integer following the term. Thus, a vessel in the context of the present invention has one or more openings. One or two openings, like the openings of a sample tube (one opening) or a syringe barrel (two openings) are preferred. If the vessel has two openings, they can be of same or different size. If there is more than one opening, one opening can be used for the gas inlet for a PECVD coating method according to the present invention, while the other openings are either capped or open. A vessel according to the present invention can be a sample tube, for example for collecting or storing biological fluids like blood or urine, a syringe (or a part thereof, for example a syringe barrel) for storing or delivering a biologically active compound or composition, for example a medicament or pharmaceutical composition, a vial for storing biological materials or biologically active compounds or compositions, a pipe, for example a catheter for transporting biological materials or biologically active compounds or compositions, or a cuvette for holding fluids, for example for holding biological materials or biologically active compounds or compositions.

A vessel can be of any shape, a vessel having a substantially cylindrical wall adjacent to at least one of its open ends being preferred. Generally, the interior wall of the vessel is cylindrically shaped, like, for example in a sample tube or a syringe barrel. Sample tubes and syringes or their parts (for example syringe barrels) are contemplated.

A "hydrophobic layer" in the context of the present invention means that the coating or layer lowers the wetting tension of a surface coated with the coating or layer, compared to the corresponding uncoated surface. Hydrophobicity is thus a function of both the uncoated substrate and the coating or layer. The same applies with appropriate alterations for other contexts wherein the term "hydrophobic" is used. The term "hydrophilic" means the opposite, i.e. that the wetting tension is increased compared to reference sample. The present hydrophobic layers are primarily defined by their hydrophobicity and the process conditions providing hydrophobicity The values of w, x, y, and z used throughout this specification, as in the formula $Si_wO_xC_yH_z$ or its equivalent in this specification, $SiO_xC_y$, should be understood as ratios or an empirical formula (for example for a coating or layer), rather than as a limit on the number or type of atoms in a molecule. For example, octamethylcyclotetrasiloxane, which has the molecular composition $Si_4O_4C_8H_{24}$, can be described by the following empirical formula, arrived at by dividing each of w, x, y, and z in the molecular formula by 4, the largest common factor: $Si_1O_1C_2H_6$. The values of w, x, y, and z are also not limited to integers. For example, (acyclic) octamethyltrisiloxane, molecular composition $Si_3O_2C_8H_{24}$, is reducible to $Si_1O_{0.67}C_{2.67}H_8$. Also, in this specification $SiO_xC_yH_z$ is equivalent to $SiO_xC_y$ (i.e. w is set equal to 1 and the amount of hydrogen, if any, is not reported). It is not necessary to show the presence of hydrogen in any proportion to show the presence of $SiO_xC_y$.

"Wetting tension" is a specific measure for the hydrophobicity or hydrophilicity of a surface. An optional wetting tension measurement method in the context of the present invention is ASTM D 2578 or a modification of the method described in ASTM D 2578. This method uses standard wetting tension solutions (called dyne solutions) to determine the solution that comes nearest to wetting a plastic film surface for exactly two seconds. This is the film's wetting tension. The procedure utilized is varied herein from ASTM D 2578 in that the substrates are not flat plastic films, but are tubes made according to the Protocol for Forming PET Tube and (except for controls) coated according to the Protocol for coating Tube Interior with Hydrophobic Coating or Layer (see Example 9 of EP2251671 A2).

A "lubricity and/or pH protective coating" according to the present invention is a coating or layer which has a lower frictional resistance than the uncoated surface, which is a lubricity layer, and/or protects an underlying surface or layer from a fluid composition contacting the layer, which is a pH protective coating or layer (as more extensively defined elsewhere in this specification). In other words, respecting a lubricity layer, it reduces the frictional resistance of the coated surface in comparison to a reference surface that is uncoated. The present lubricity and/or pH protective coatings are primarily defined as lubricity layers by their lower frictional resistance than the uncoated surface and the process conditions providing lower frictional resistance than the uncoated surface, and optionally can have a composition according to the empirical composition $Si_wO_xC_yH_z$, (or its equivalent $SiO_xC_y$) as defined herein. It generally has an atomic ratio $Si_wO_xC_y$ (or its equivalent $SiO_xC_y$) wherein w is 1, x is from about 0.5 to about 2.4, y is from about 0.6 to about 3.

Typically, expressed as the formula $Si_wO_xC_y$, the atomic ratios of Si, O, and C in the "lubricity and/or pH protective coating" are, as several options:

Si 100: O 50-150: C 90-200 (i.e. w=1, x=0.5 to 1.5, y=0.9 to 2);

Si 100: O 70-130: C 90-200 (i.e. w=1, x=0.7 to 1.3, y=0.9 to 2)

Si 100: O 80-120: C 90-150 (i.e. w=1, x=0.8 to 1.2, y=0.9 to 1.5)

Si 100: O 90-120: C 90-140 (i.e. w=1, x=0.9 to 1.2, y=0.9 to 1.4), or

Si 100: O 92-107: C 116-133 (i.e. w=1, x=0.92 to 1.07, y=1.16 to 1.33)

The atomic ratio can be determined by XPS (X-ray photoelectron spectroscopy). Taking into account the H atoms, which are not measured by XPS, the coating or layer may thus in one aspect have the formula $Si_wO_xC_yH_z$ (or its equivalent $SiO_xC_y$), for example where w is 1, x is from about 0.5 to about 2.4, y is from about 0.6 to about 3, and z is from about 2 to about 9. Typically, such coating or layer would hence contain 36% to 41% carbon normalized to 100% carbon plus oxygen plus silicon.

"Frictional resistance" can be static frictional resistance and/or kinetic frictional resistance.

One of the optional embodiments of the present invention is a syringe part, for example a syringe barrel or plunger, coated with a lubricity and/or pH protective coating. In this contemplated embodiment, the relevant static frictional resistance in the context of the present invention is the breakout force as defined herein, and the relevant kinetic frictional resistance in the context of the present invention is the plunger sliding force as defined herein. For example, the plunger sliding force as defined and determined herein is suitable to determine the presence or absence and the lubricity and/or pH protective characteristics of a lubricity and/or pH protective coating or layer in the context of the present invention whenever the coating or layer is applied to any syringe or syringe part, for example to the inner wall of a syringe barrel. The breakout force is of particular relevance for evaluation of the coating or layer effect on a prefilled syringe, i.e. a syringe which is filled after coating and can be stored for some time, for example several months or even years, before the plunger is moved again (has to be "broken out").

The "plunger sliding force" (synonym to "glide force," "maintenance force", or Fm, also used in this description) in the context of the present invention is the force required to maintain movement of a plunger in a syringe barrel, for example during aspiration or dispense. It can advantageously be determined using the ISO 7886-1:1993 test described herein and known in the art. A synonym for "plunger sliding force" often used in the art is "plunger force" or "pushing force".

The "plunger breakout force" (synonym to "breakout force", "break loose force", "initiation force", Fi, also used in this description) in the context of the present invention is the initial force required to move the plunger in a syringe, for example in a prefilled syringe.

Both "plunger sliding force" and "plunger breakout force" and methods for their measurement are described in more detail in subsequent parts of this description. These two forces can be expressed in N, lbs or kg and all three units are used herein. These units correlate as follows: 1N=0.102 kg=0.2248 lbs (pounds).

Sliding force and breakout force are sometimes used herein to describe the forces required to advance a stopper or other closure into a pharmaceutical package or other vessel, such as a medical sample tube or a vial, to seat the stopper in a vessel to close the vessel. Its use is analogous to use in the context of a syringe and its plunger, and the measurement of these forces for a vessel and its closure are contemplated to be analogous to the measurement of these forces for a syringe, except that at least in most cases no liquid is ejected from a vessel when advancing the closure to a seated position.

"Slidably" means that the plunger, closure, or other removable part is permitted to slide in a syringe barrel or other vessel.

Coatings of $SiO_x$ are deposited by plasma enhanced chemical vapor deposition (PECVD) or other chemical vapor deposition processes on the vessel of a pharmaceutical package, in particular a thermoplastic package, to serve as a composite barrier coating or layer preventing oxygen, carbon dioxide, or other gases from entering the vessel and/or to prevent leaching of the pharmaceutical material into or through the package wall.

Referring to the Figures, in any embodiment of the vessel or method, the vessel can be provided in any configuration, for example a tube 80, a vial 228, a blister package 230, a syringe 252, a syringe barrel 250, a prefilled syringe (FIG. 8), a cartridge, a sample tube 80, or an evacuated blood sample tube, as several non-limiting examples. Any of these types of vessels is alternatively 288 referred to as a vessel 80 in this disclosure.

In any embodiment of the vessel 80 or method, the vessel 80 optionally can have a rated volume (the maximum volume of fluid it is routinely used to contain and deliver, as reported by the manufacturer) between 0.2 and 50 ml., optionally between 2 and 50 ml., optionally between 2 and 20 ml., optionally between 2 and 6 ml., optionally between 3 and 5 ml., optionally between 0.25 and 20 ml., optionally between 0.5 and 5 ml., optionally between 1 and 2 ml.

In any embodiment of the vessel 80 or method, the vessel 80 optionally has a fill volume (the entire volume of the stoppered vessel 80, including headspace) between 0.3 and 75 ml., optionally between 3 and 75 ml., optionally between 3 and 30 ml., optionally between 4 and 9 ml., optionally between 4 and 8 ml., optionally between 0.4 and 35 ml., optionally between 0.8 and 9 ml., optionally between 1.7 and 3.5 ml.

In any embodiment of the vessel 80 or method, the vessel 80 optionally includes a thermoplastic wall 214 enclosing a lumen 212. "Thermoplastic" is explicitly defined to include glass or quartz materials, one example of which is borosilicate glass, as well as organic thermoplastic resins and resin compositions. The wall supports an $SiO_x$ composite barrier coating or layer 288, for which x is from 1.8 to 2.4, between the wall and the lumen. The $SiO_x$ composite barrier coating or layer 288 is formed by PECVD from an organosilicon monomer and an oxidizing gas.

In any embodiment of the vessel 80, the $SiO_x$ composite barrier coating or layer 288 can optionally be formed in at least bonding and build-up stages.

In any embodiment of the vessel 80 or method, the substrate optionally is ablated by the plasma before the $SiO_x$ bonding and build-up stages. Ablation roughens the substrate surface and introduces organic material into the plasma which participates in coating formation, adding to the carbon and hydrogen in the plasma. The ablation is contemplated to subside as the composite barrier coating or layer 288 begins to bond and build up, leaving a surface that is not as readily ablated under deposition conditions.

In any embodiment of the vessel 80 or method, the $SiO_x$ composite barrier coating or layer 288 can be formed by PECVD from a gas feed including an organosilicon monomer, an oxidizing gas, and a carrier gas. (As used in this specification, "carrier gas" is also inclusive of a diluent gas.)

In any embodiment of the vessel 80 or method, the organosilicon monomer, also known as a precursor feed, can include an organosiloxane, an organosilane, an organosiloxazane, an organosilazane, or a combination of two or more of these. In any embodiment of the vessel 80 or method, gas feed optionally can contain a linear or branched siloxane having from 1 to 6 silicon atoms, a monocyclic siloxane, a polycyclic siloxane, a polysilsesquioxane, a monocyclic silazane, a polycyclic silazane, a polysilsesquiazane, a silatrane, a silquasilatrane, a silproatrane, an azasilatrane, an azasilquasiatrane, an azasilproatrane, or a combination of any two or more of these precursors. The composite barrier coating or layer 288 optionally can be applied by PECVD of a precursor feed comprising a monocyclic siloxane, a polycyclic siloxane, a polysilsesquioxane, a silatrane, a silquasilatrane, a silproatrane, or a combination of any two or more of these precursors.

In any embodiment of the vessel 80 or method, the oxidizing gas can include diatomic oxygen, $O_2$. Optionally, the oxidizing gas comprises hydrogen peroxide, $H_2O_2$. Optionally, the oxidizing gas comprises ozone, $O_3$. Optionally, the oxidizing gas comprises water, $H_2O$.

In any embodiment of the vessel 80 or method, a carrier gas can either be used or not. If used, the carrier gas optionally includes an inert gas under the PECVD conditions employed. In any embodiment of the vessel 80 or method, the carrier gas optionally comprises a noble gas. In any embodiment of the vessel 80 or method, the carrier gas optionally comprises helium. In any embodiment of the vessel 80 or method, the carrier gas optionally comprises neon. In any embodiment of the vessel 80 or method, the carrier gas optionally comprises argon. In any embodiment of the vessel 80 or method, the carrier gas optionally comprises krypton. In any embodiment of the vessel 80 or method, the carrier gas optionally comprises xenon. Mixtures of any two or more of these gases can also be employed.

In any embodiment of the vessel 80 or method, during the bonding stage the feed ratio of organosilicon monomer to oxidizing gas, in sccm, can be from 2.5 to 10. During the build-up stage, the feed ratio of organosilicon monomer to oxidizing gas can be from 0.1 to 0.05.

The plasma used in PECVD according to the present disclosure can be generated conventionally, as by using radio frequency (RF) energy or microwave energy. The $SiO_x$ composite barrier coating or layer 288 optionally can be formed at an initial power level (for example, an RF power level) from 20 to 4 W and a highest RF power level of from 300 to 30 W. In any embodiment of the vessel 80 or method, the power density at the initial RF power level optionally can be from 3 to 1 W/ml. In any embodiment of the vessel 80 or method, the power density at the highest RF power level is from 30 to 4 W/ml.

In any embodiment of the vessel such as a tube 80, a vial 228, a blister package 230, a syringe 252, a syringe barrel 250 or a cartridge, the degree of retention of the composite barrier coating or layer 288 on the substrate optionally can be at least 95% by the Article Deformation/Tape Test Method described in this specification.

In any embodiment of the vessel 80 such as a tube 80, a vial 228, a blister package 230, a syringe 252, a syringe barrel 250 or a cartridge, the degree of retention of the composite barrier coating or layer 288 on the substrate optionally can be at least 90% by the Coated Article Cross-Scratch Tape Test Method described in this specification.

In any embodiment of the vessel such as a tube 80, a vial 228, a blister package 230, a syringe 252, a syringe barrel 250 or a cartridge, High Resolution X-ray Photoelectron Spectroscopy (XPS) optionally shows the presence of an interface between the composite barrier coating or layer 288 and the wall or substrate. The interface optionally has at least 1 mol. % $O_3$—Si—C covalent bonding, as a proportion of the $O_3$—Si—C covalent bonding plus $SiO_4$ bonding.

In any embodiment of the vessel 80 such as a tube 80, a vial 228, a blister package 230, a syringe 252, a syringe barrel 250 or a cartridge, the interface optionally has an Si 2p chemical shift to lower binding energy (eV), compared to the binding energy of $SiO_4$ bonding.

Another embodiment is a method of making a vessel 80. In any embodiment of the method, a thermoplastic wall enclosing a lumen can be provided. An $SiO_x$ composite barrier coating or layer 288, for which x is from 1.8 to 2.4, is applied to the thermoplastic wall. The composite barrier coating or layer 288 is supported by the wall between the wall and the lumen. The composite barrier coating or layer 288 is applied by PECVD from an organosilicon monomer and oxidizing gas.

In any embodiment of the method, the composite barrier coating or layer 288 optionally can be applied in at least bonding and build-up stages, under the following conditions. During the bonding stage, the feed ratio of organosilicon monomer to oxidizing gas, in sccm, optionally can be from 2.5 to 10. During the build-up stage, the feed ratio of organosilicon monomer to oxidizing gas optionally can be from 0.1 to 0.05.

In any embodiment of the method, the composite barrier coating or layer 288 optionally can be applied at an initial RF power level from 20 to 4 W and a highest RF power level of from 300 to 30 W. In any embodiment of the vessel 80 or method, the RF power level optionally can be increased uniformly from the initial RF power level to the highest RF power level. Optionally, the RF power level can be increased in one or more steps from the initial RF power level to the highest RF power level.

In any embodiment of the vessel 80 or method, the RF power level optionally is not pulsed, meaning that it is applied without interruption from the beginning to the end of the deposition. As another option, however, the RF power level can be pulsed or turned on and off periodically during the deposition of a single composite barrier coating or layer 288 on a single vessel 80. This type of deposition using a pulsed RF power level is sometimes known as plasma impulse chemical vapor deposition.

In any embodiment of the method, the composite barrier coating or layer 288 optionally can have a degree of retention on the substrate of at least 95% by volume, as measured by the Article Deformation/Tape Test Method. In any embodiment of the vessel 80 or method, the degree of retention of the composite barrier coating or layer 288 on the substrate optionally is at least 96% by volume, optionally at least 97% by volume, optionally at least 98% by volume, optionally at least 99% by volume, optionally 100% by volume, according to the Article Deformation/Tape Test Method. In any embodiment of the vessel 80 or method, the Article Deformation/Tape Test Method optionally is carried out using axial deformation, but optionally can be carried out using diametric deformation instead.

In any embodiment of the method, the composite barrier coating or layer 288 optionally can have a degree of retention on the substrate of at least 90% by the Coated Article Cross-Scratch Tape Test Method. The degree of retention of the composite barrier coating or layer 288 on the substrate optionally is at least 91% by volume, optionally at least 92% by volume, optionally at least 93% by volume, optionally at least 94% by volume, optionally at least 95% by volume, optionally at least 96% by volume, optionally at least 97% by volume, optionally at least 98% by volume, optionally at least 99% by volume, optionally 100% by volume, according to the Coated Article Cross-Scratch Tape Test Method. As one option in any embodiment, the Coated Article Cross-Scratch Tape Test Method can be carried out using an X scratch pattern. As another option in any embodiment, the Coated Article Cross-Scratch Tape Test Method can be carried out using a rectangular scratch pattern.

In any embodiment of the method, the composite barrier coating or layer 288 optionally can have an interface between the composite barrier coating or layer 288 and the substrate having at least 1 mol. % $O_3$—Si—C covalent bonding, as a proportion of the $O_3$—Si—C covalent bonding plus $SiO_4$ bonding.

High Resolution X-ray Photoelectron Spectroscopy (XPS) optionally shows the presence of an interface between the composite barrier coating or layer 288 and the substrate having at least 2 mol. % $O_3$—Si—C covalent bonding, optionally at least 3 mol. % $O_3$—Si—C covalent bonding, optionally at least 4 mol. % $O_3$—Si—C covalent bonding, optionally at least 5 mol. % $O_3$—Si—C covalent bonding, optionally at least 6 mol. % $O_3$—Si—C covalent bonding, optionally at least 7 mol. % $O_3$—Si—C covalent bonding, optionally at least 8 mol. % $O_3$—Si—C covalent bonding, optionally at least 9 mol. % $O_3$—Si—C covalent bonding, optionally at least 10 mol. % $O_3$—Si—C covalent bonding, optionally at least 11 mol. % $O_3$—Si—C covalent bonding, optionally at least at least 12 mol. % $O_3$—Si—C covalent bonding, optionally at least 13 mol. % $O_3$—Si—C covalent bonding, optionally at least 14 mol. % $O_3$—Si—C covalent bonding, optionally at least 15 mol. % $O_3$—Si—C covalent bonding, optionally at least 16 mol. % $O_3$—Si—C covalent bonding, optionally at least 17 mol. % $O_3$—Si—C covalent bonding, optionally at least 18 mol. % $O_3$—Si—C covalent bonding, optionally at least 19 mol. % $O_3$—Si—C covalent bonding, optionally at least 20 mol. % $O_3$—Si—C covalent bonding, as a proportion of the $O_3$—Si—C covalent bonding plus $SiO_4$ bonding. The interface for any embodiment of the vessel 80 or method optionally has at most 25 mol. % $O_3$—Si—C covalent bonding, alternatively at most 20 mol. % $O_3$—Si—C covalent bonding, alternatively at most 15 mol. % $O_3$—Si—C covalent bonding, alternatively at most 10 mol. % $O_3$—Si—C covalent bonding, as a proportion of the $O_3$—Si—C covalent bonding plus $SiO_4$ bonding.

In any embodiment of the method, the composite barrier coating or layer 288 optionally can have an Si 2p chemical shift to lower binding energy (eV), compared to the binding energy of $SiO_4$ bonding, when studied using High Resolution X-ray Photoelectron Spectroscopy (XPS). In any embodiment of the vessel 80 or method, High Resolution X-ray Photoelectron Spectroscopy (XPS) optionally shows the presence of an interface between the composite barrier coating or layer 288 and the substrate having Si 2p peak broadening of at least 0.2 eV, compared to the binding energy of $SiO_4$ bonding.

In any embodiment of the vessel 80 or method, the lumen optionally can contain a pharmaceutical agent. The pharmaceutical agent optionally can have a pH between 5 and 9. An opening optionally can be provided in the vessel 80 between the lumen and the exterior of the vessel 80. A closure optionally can be seated in the opening.

Tie Coating or Layer

As an alternative to the above description of a composite barrier coating or layer having bonding and build-up portions, in other aspects of the invention a separate tie coating or layer and composite barrier coating or layer can be described, in which the properties of the respective layers are separately defined. The tie coating or layer can be defined as follows.

The tie coating or layer 289 has at least two functions. One function of the tie coating or layer 289 is to improve adhesion of a composite barrier coating or layer to a substrate, in particular a thermoplastic substrate, although a tie layer can be used to improve adhesion to a glass substrate or to another coating or layer. For example, a tie coating or layer, also referred to as an adhesion layer or coating can be applied to the substrate and the barrier layer can be applied to the adhesion layer to improve adhesion of the barrier layer or coating to the substrate.

Another function of the tie coating or layer 289 has been discovered: a tie coating or layer 289 applied under a composite barrier coating or layer 288 can improve the function of a pH protective coating or layer 286 applied over the composite barrier coating or layer 288.

The tie coating or layer 289 can be composed of, comprise, or consist essentially of $SiO_xC_y$, in which x is between 0.5 and 2.4 and y is between 0.6 and 3. Alternatively, the atomic ratio can be expressed as the formula $Si_wO_xC_y$. The atomic ratios of Si, O, and C in the tie coating or layer 289 are, as several options:

Si 100: O 50-150: C 90-200 (i.e. w=1, x=0.5 to 1.5, y=0.9 to 2);

Si 100: O 70-130: C 90-200 (i.e. w=1, x=0.7 to 1.3, y=0.9 to 2)

Si 100: O 80-120: C 90-150 (i.e. w=1, x=0.8 to 1.2, y=0.9 to 1.5)

Si 100: O 90-120: C 90-140 (i.e. w=1, x=0.9 to 1.2, y=0.9 to 1.4), or

Si 100: O 92-107: C 116-133 (i.e. w=1, x=0.92 to 1.07, y=1.16 to 1.33)

The atomic ratio can be determined by XPS. Taking into account the H atoms, which are not measured by XPS, the tie coating or layer 289 may thus in one aspect have the formula $Si_wO_xC_yH_z$ (or its equivalent $SiO_xC_y$), for example where w is 1, x is from about 0.5 to about 2.4, y is from about 0.6 to about 3, and z is from about 2 to about 9. Typically, tie coating or layer 289 would hence contain 36% to 41% carbon normalized to 100% carbon plus oxygen plus silicon.

Optionally, the tie coating or layer can be similar or identical in composition with the pH protective coating or layer 286 described elsewhere in this specification, although this is not a requirement.

The tie coating or layer 289 is contemplated generally to be from 5 nm to 100 nm thick, preferably from 5 to 20 nm thick, particularly if applied by chemical vapor deposition. These thicknesses are not critical. Commonly but not necessarily, the tie coating or layer 289 will be relatively thin, since its function is to change the surface properties of the substrate.

Barrier Coating or Layer

In the instance in which a separate tie coating or layer and composite barrier coating or layer are described, the composite barrier coating or layer can be described as follows.

A composite barrier coating or layer 288 optionally can be deposited by plasma enhanced chemical vapor deposition (PECVD) or other chemical vapor deposition processes on the vessel of a pharmaceutical package, in particular a thermoplastic package, to prevent oxygen, carbon dioxide, or other gases from entering the vessel and/or to prevent leaching of the pharmaceutical material into or through the package wall.

The composite barrier coating or layer for any embodiment defined in this specification (unless otherwise specified in a particular instance) is a coating or layer, optionally applied by PECVD as indicated in U.S. Pat. No. 7,985,188. The barrier layer optionally is characterized as an "$SiO_x$" coating, and contains silicon, oxygen, and optionally other elements, in which x, the ratio of oxygen to silicon atoms, is from about 1.5 to about 2.4, or 1.5 to about 2.3, or about 2. These alternative definitions of x apply to any use of the term $SiO_x$ in this specification to define a composite barrier coating or layer (though a composite barrier coating or layer has a different definition of x). The composite barrier coating or layer is applied, for example to the interior of a pharmaceutical package or other vessel, for example a sample collection tube, a syringe barrel, a vial, or another type of vessel.

The composite barrier coating or layer 288 comprises or consists essentially of $SiO_x$, wherein x is from 1.5 to 2.4, from 2 to 1000 nm thick, the composite barrier coating or layer 288 of $SiO_x$ having an interior surface 220 facing the lumen 212 and an outer surface 222 facing the wall 214 article surface 254, the composite barrier coating or layer 288 being effective to reduce the ingress of atmospheric gas into the lumen 212 compared to an uncoated vessel 250. One suitable barrier composition is one where x is 2.3, for example. For example, the composite barrier coating or layer such as 288 of any embodiment can be applied at a thickness of at least 2 nm, or at least 4 nm, or at least 7 nm, or at least 10 nm, or at least 20 nm, or at least 30 nm, or at least 40 nm, or at least 50 nm, or at least 100 nm, or at least 150 nm, or at least 200 nm, or at least 300 nm, or at least 400 nm, or at least 500 nm, or at least 600 nm, or at least 700 nm, or at least 800 nm, or at least 900 nm. The composite barrier coating or layer can be up to 1000 nm, or at most 900 nm, or at most 800 nm, or at most 700 nm, or at most 600 nm, or at most 500 nm, or at most 400 nm, or at most 300 nm, or at most 200 nm, or at most 100 nm, or at most 90 nm, or at most 80 nm, or at most 70 nm, or at most 60 nm, or at most 50 nm, or at most 40 nm, or at most 30 nm, or at most 20 nm, or at most 10 nm, or at most 5 nm thick. Ranges of 20-200 nm, optionally 20-30 nm, are contemplated. Specific thickness ranges composed of any one of the minimum thicknesses expressed above, plus any equal or greater one of the maximum thicknesses expressed above, are expressly contemplated.

The thickness of the $SiO_x$ or other composite barrier coating or layer can be measured, for example, by transmission electron microscopy (TEM), and its composition can be measured by X-ray photoelectron spectroscopy (XPS). The primer coating or layer described herein can be applied to a variety of pharmaceutical packages or other vessels made from plastic or glass, for example to plastic tubes, vials, and syringes.

A composite barrier coating or layer 288 of $SiO_x$, in which x is between 1.5 and 2.9, is applied by plasma enhanced chemical vapor deposition (PECVD) directly or indirectly to the thermoplastic wall 214 so that in the filled pharmaceutical package or other vessel 210 the composite barrier coating or layer 286 is located between the inner or interior surface 220 of the thermoplastic wall 214 and the fluid 218.

The composite barrier coating or layer 286 of $SiO_x$ is supported by the thermoplastic wall 214. The composite barrier coating or layer 286 as described elsewhere in this specification, or in U.S. Pat. No. 7,985,188, can be used in any embodiment.

Certain barrier coatings or layers such as $SiO_x$ as defined here have been found to have the characteristic of being subject to being measurably diminished in barrier improvement factor in less than six months as a result of attack by certain relatively high pH contents of the coated vessel as described elsewhere in this specification, particularly where the composite barrier coating or layer directly contacts the contents. This issue can be addressed using a pH protective coating or layer as discussed in this specification.

pH Protective Coating or Layer

The inventors have found that some barrier layers or coatings of $SiO_x$ are eroded or dissolved by some fluid compositions, for example aqueous compositions having a pH above about 5. Since coatings applied by chemical vapor deposition can be very thin—tens to hundreds of nanometers thick—even a relatively slow rate of erosion can remove or reduce the effectiveness of the barrier layer in less time than the desired shelf life of a product package. This is particularly a problem for fluid pharmaceutical compositions, since many of them have a pH of roughly 7, or more broadly in the range of 5 to 9, similar to the pH of blood and other human or animal fluids. The higher the pH of the pharmaceutical preparation, the more quickly it erodes or dissolves the $SiO_x$ coating.

The inventors have further found that certain pH protective coatings of $SiO_xC_y$ or $SiN_xC_y$ formed from cyclic or acyclic siloxane precursors, which pH protective coatings have a substantial organic component, do not erode quickly when exposed to fluid compositions, and in fact erode or dissolve more slowly when the fluid compositions have higher pHs within the range of 5 to 9. For example, at pH 8, the dissolution rate of a pH protective coating made from the precursor octamethylcyclotetrasiloxane, or OMCTS, is quite slow. These pH protective coatings of $SiO_xC_y$ or $SiN_xC_y$ can therefore be used to cover a barrier layer of $SiO_x$, retaining the benefits of the barrier layer by protecting it from the fluid composition in the pharmaceutical package.

Although the present invention does not depend upon the accuracy of the following theory, it is believed that the material properties of an effective $SiO_xC_y$ pH protective coating and those of an effective lubricity layer as described in U.S. Pat. No. 7,985,188 and in International Application PCT/US11/36097 are similar in some instances, such that a coating having the characteristics of a lubricity layer as described in certain working examples of this specification, U.S. Pat. No. 7,985,188, or International Application PCT/US11/36097 will also in certain cases serve as well as a pH protective coating to protect the barrier layer of the package and vice versa.

One specific type of lubricity and/or pH protective coatings contemplated here is made from one or more cyclic siloxanes and silazanes as described in this disclosure. Although the present invention does not depend upon the accuracy of the following theory, $SiO_xC_y$ or $SiN_xC_y$ coatings deposited from linear siloxane or linear silazane precursors, for example hexamethyldisiloxane (HMDSO), are believed to contain fragments of the original precursor to a large degree and low organic content. Such $SiO_xC_y$ or $SiN_xC_y$ coatings have a degree of water miscibility or swellability, allowing them to be attacked by aqueous solutions. $SiO_xC_y$ or $SiN_xC_y$ coatings deposited from cyclic siloxane or linear silazane precursors, for example octamethylcyclotetrasiloxane (OMCTS), are believed to include more intact cyclic siloxane rings and longer series of repeating units of the precursor structure. These coatings are believed to be nanoporous but structured and hydrophobic, and these properties are believed to contribute to their success as pH protective coatings. This is shown, for example, in U.S. Pat. No. 7,901,783.

Optionally, the pH protective coating or layer 286 can be composed of, comprise, or consist essentially of $Si_wO_xC_yH_z$ (or its equivalent $SiO_xC_y$) or $Si_wN_xC_yH_z$ or its equivalent $SiN_xC_y$), each as defined previously. The atomic ratio of Si:O:C or Si:N:C can be determined by XPS (X-ray photoelectron spectroscopy). Taking into account the H atoms, the pH protective coating or layer may thus in one aspect have the formula $Si_wO_xC_yH_z$, or its equivalent $SiO_xC_y$, for example where w is 1, x is from about 0.5 to about 2.4, y is from about 0.6 to about 3, and z is from about 2 to about 9.

Typically, expressed as the formula $Si_wO_xC_y$, the atomic ratios of Si, O, and C are, as several options:
Si 100: O 50-150: C 90-200 (i.e. w=1, x=0.5 to 1.5, y=0.9 to 2);
Si 100: O 70-130: C 90-200 (i.e. w=1, x=0.7 to 1.3, y=0.9 to 2)
Si 100: O 80-120: C 90-150 (i.e. w=1, x=0.8 to 1.2, y=0.9 to 1.5)
Si 100: O 90-120: C 90-140 (i.e. w=1, x=0.9 to 1.2, y=0.9 to 1.4)
Si 100: O 92-107: C 116-133 (i.e. w=1, x=0.92 to 1.07, y=1.16 to 1.33), or
Si 100: O 80-130: C 90-150.

Alternatively, the pH protective coating or layer can have atomic concentrations normalized to 100% carbon, oxygen, and silicon, as determined by X-ray photoelectron spectroscopy (XPS) of less than 50% carbon and more than 25% silicon. Alternatively, the atomic concentrations are from 25 to 45% carbon, 25 to 65% silicon, and 10 to 35% oxygen. Alternatively, the atomic concentrations are from 30 to 40% carbon, 32 to 52% silicon, and 20 to 27% oxygen. Alternatively, the atomic concentrations are from 33 to 37% carbon, 37 to 47% silicon, and 22 to 26% oxygen.

The thickness of the pH protective coating or layer can be, for example:
from 10 nm to 1000 nm;
alternatively from 10 nm to 1000 nm;
alternatively from 10 nm to 900 nm;
alternatively from 10 nm to 800 nm;
alternatively from 10 nm to 700 nm;
alternatively from 10 nm to 600 nm;
alternatively from 10 nm to 500 nm;
alternatively from 10 nm to 400 nm;
alternatively from 10 nm to 300 nm;
alternatively from 10 nm to 200 nm;
alternatively from 10 nm to 100 nm;
alternatively from 10 nm to 50 nm;
alternatively from 20 nm to 1000 nm;
alternatively from 50 nm to 1000 nm;
alternatively from 10 nm to 1000 nm;
alternatively from 50 nm to 800 nm;
alternatively from 100 nm to 700 nm;
alternatively from 300 to 600 nm.

Optionally, the atomic concentration of carbon in the pH protective layer, normalized to 100% of carbon, oxygen, and silicon, as determined by X-ray photoelectron spectroscopy (XPS), can be greater than the atomic concentration of carbon in the atomic formula for the organosilicon precursor. For example, embodiments are contemplated in which the atomic concentration of carbon increases by from 1 to 80 atomic percent, alternatively from 10 to 70 atomic percent, alternatively from 20 to 60 atomic percent, alternatively from 30 to 50 atomic percent, alternatively from 35 to 45 atomic percent, alternatively from 37 to 41 atomic percent.

Optionally, the atomic ratio of carbon to oxygen in the pH protective coating or layer can be increased in comparison to the organosilicon precursor, and/or the atomic ratio of oxygen to silicon can be decreased in comparison to the organosilicon precursor.

Optionally, the pH protective coating or layer can have an atomic concentration of silicon, normalized to 100% of carbon, oxygen, and silicon, as determined by X-ray photoelectron spectroscopy (XPS), less than the atomic concentration of silicon in the atomic formula for the feed gas. For example, embodiments are contemplated in which the atomic concentration of silicon decreases by from 1 to 80 atomic percent, alternatively by from 10 to 70 atomic percent, alternatively by from 20 to 60 atomic percent, alternatively by from 30 to 55 atomic percent, alternatively by from 40 to 50 atomic percent, alternatively by from 42 to 46 atomic percent.

As another option, a pH protective coating or layer is contemplated that can be characterized by a sum formula wherein the atomic ratio C:O can be increased and/or the atomic ratio Si:O can be decreased in comparison to the sum formula of the organosilicon precursor.

The pH protective coating or layer 286 commonly is located between the composite barrier coating or layer 288 and the fluid 218 in the finished article. The pH protective coating or layer 286 is supported by the thermoplastic wall 214.

The pH protective coating or layer 286 optionally is effective to keep the composite barrier coating or layer 288 at least substantially undissolved as a result of attack by the fluid 218 for a period of at least six months.

The pH protective coating or layer can have a density between 1.25 and 1.65 g/cm$^3$, alternatively between 1.35 and 1.55 g/cm$^3$, alternatively between 1.4 and 1.5 g/cm$^3$, alternatively between 1.4 and 1.5 g/cm$^3$, alternatively between 1.44 and 1.48 g/cm$^3$, as determined by X-ray reflectivity (XRR). Optionally, the organosilicon compound can be octamethylcyclotetrasiloxane and the pH protective coating or layer can have a density which can be higher than the density of a pH protective coating or layer made from HMDSO as the organosilicon compound under the same PECVD reaction conditions.

The pH protective coating or layer optionally can prevent or reduce the precipitation of a compound or component of a composition in contact with the pH protective coating or layer, in particular can prevent or reduce insulin precipitation or blood clotting, in comparison to the uncoated surface and/or to a barrier coated surface using HMDSO as precursor.

The pH protective coating or layer optionally can have an RMS surface roughness value (measured by AFM) of from about 5 to about 9, optionally from about 6 to about 8, optionally from about 6.4 to about 7.8. The Ra surface roughness value of the pH protective coating or layer, measured by AFM, can be from about 4 to about 6, optionally from about 4.6 to about 5.8. The Rmax surface roughness value of the pH protective coating or layer, measured by AFM, can be from about 70 to about 160, optionally from about 84 to about 142, optionally from about 90 to about 130.

The interior surface of the pH protective optionally can have a contact angle (with distilled water) of from 90° to 110°, optionally from 80° to 120°, optionally from 70° to 130°, as measured by Goniometer Angle measurement of a water droplet on the pH protective surface, per ASTM D7334-08 "Standard Practice for Surface Wettability of Coatings, Substrates and Pigments by Advancing Contact Angle Measurement."

The passivation layer or pH protective coating or layer 286 optionally shows an O-Parameter measured with attenuated total reflection (ATR) of less than 0.4, measured as:

$$O\text{-Parameter} = \frac{\text{Intensity at 1253 cm}^{-1}}{\text{Maximum intensity in the range 1000 to 1100 cm}^{-1}}$$

The O-Parameter is defined in U.S. Pat. No. 8,067,070, which claims an O-parameter value of most broadly from 0.4 to 0.9. It can be measured from physical analysis of an FTIR amplitude versus wave number plot to find the numerator and denominator of the above expression, as shown in FIG. 22, which is the same as FIG. 5 of U.S. Pat. No. 8,067,070, except annotated to show interpolation of the wave number and absorbance scales to arrive at an absorbance at 1253 cm$^{-1}$ of 0.0424 and a maximum absorbance at 1000 to 1100 cm$^{-1}$ of 0.08, resulting in a calculated O-parameter of 0.53. The O-Parameter can also be measured from digital wave number versus absorbance data.

U.S. Pat. No. 8,067,070 asserts that the claimed O-parameter range provides a superior pH protective coating or layer, relying on experiments only with HMDSO and HMDSN, which are both non-cyclic siloxanes. Surprisingly, it has been found by the present inventors that if the PECVD precursor is a cyclic siloxane, for example OMCTS, O-parameters outside the ranges claimed in U.S. Pat. No. 8,067,070, using OMCTS, provide even better results than are obtained in U.S. Pat. No. 8,067,070 with HMDSO.

Alternatively in the embodiment of FIGS. 19-21, the O-parameter has a value of from 0.1 to 0.39, or from 0.15 to 0.37, or from 0.17 to 0.35.

Even another aspect of the invention is a composite material as just described, exemplified in FIGS. 19-21, wherein the passivation layer shows an N-Parameter measured with attenuated total reflection (ATR) of less than 0.7, measured as:

$$N\text{-Parameter} = \frac{\text{Intensity at 840 cm}^{-1}}{\text{Intensity at 799 cm}^{-1}}$$

The N-Parameter is is also described in U.S. Pat. No. 8,067,070, and is measured analogously to the O-Parameter except that intensities at two specific wave numbers are used—neither of these wave numbers is a range. U.S. Pat. No. 8,067,070 claims a passivation layer with an N-Parameter of 0.7 to 1.6. Again, the present inventors have made better coatings employing a pH protective coating or layer 286 having an N-Parameter lower than 0.7, as described above. Alternatively, the N-parameter has a value of at least 0.3, or from 0.4 to 0.6, or at least 0.53.

The rate of erosion, dissolution, or leaching (different names for related concepts) of the pH protective coating or layer 286, if directly contacted by the fluid 218, is less than the rate of erosion of the composite barrier coating or layer 288, if directly contacted by the fluid 218.

The thickness of the pH protective coating or layer is contemplated to be from 50-500 nm, with a preferred range of 100-200 nm.

The pH protective coating or layer 286 is effective to isolate the fluid 218 from the composite barrier coating or layer 288, at least for sufficient time to allow the barrier coating to act as a barrier during the shelf life of the pharmaceutical package or other vessel 210.

The inventors have further found that certain pH protective coatings or layers of $SiO_xC_y$ or $SiN_xC_y$ formed from cyclic polysiloxane precursors, which pH protective coatings or layers have a substantial organic component, do not erode quickly when exposed to fluids, and in fact erode or dissolve more slowly when the fluids have higher pHs within the range of 5 to 9. For example, at pH 8, the dissolution rate of a pH protective coating or layer made from the precursor octamethylcyclotetrasiloxane, or OMCTS, is quite slow. These pH protective coatings or layers of $SiO_xC_y$ or $SiN_xC_y$ can therefore be used to cover a barrier layer of $SiO_x$, retaining the benefits of the barrier layer by protecting it from the fluid in the pharmaceutical package. The pH protective layer is applied over at least a portion of the $SiO_x$ layer to protect the $SiO_x$ layer from contents stored in a vessel, where the contents otherwise would be in contact with the $SiO_x$ layer.

Although the present invention does not depend upon the accuracy of the following theory, it is further believed that effective pH protective coatings or layers for avoiding erosion can be made from cyclic siloxanes and silazanes as described in this disclosure. $SiO_xC_y$ or $SiN_xC_y$ coatings deposited from cyclic siloxane or linear silazane precursors, for example octamethylcyclotetrasiloxane (OMCTS), are believed to include intact cyclic siloxane rings and longer series of repeating units of the precursor structure. These coatings are believed to be nanoporous but structured and hydrophobic, and these properties are believed to contribute to their success as pH protective coatings or layers. This is shown, for example, in U.S. Pat. No. 7,901,783.

$SiO_xC_y$ or $SiN_xC_y$ coatings also can be deposited from linear siloxane or linear silazane precursors, for example hexamethyldisiloxane (HMDSO) or tetramethyldisiloxane (TMDSO).

Optionally an FTIR absorbance spectrum of the pH protective coating or layer 286 of any embodiment has a ratio greater than 0.75 between the maximum amplitude of the Si—O—Si symmetrical stretch peak normally located between about 1000 and 1040 $cm^{-1}$, and the maximum amplitude of the Si—O—Si asymmetric stretch peak normally located between about 1060 and about 1100 $cm^{-1}$. Alternatively in any embodiment, this ratio can be at least 0.8, or at least 0.9, or at least 1.0, or at least 1.1, or at least 1.2. Alternatively in any embodiment, this ratio can be at most 1.7, or at most 1.6, or at most 1.5, or at most 1.4, or at most 1.3. Any minimum ratio stated here can be combined with any maximum ratio stated here, as an alternative embodiment of the invention of FIGS. 19-21.

Optionally, in any embodiment the pH protective coating or layer 286, in the absence of the medicament, has a non-oily appearance. This appearance has been observed in some instances to distinguish an effective pH protective coating or layer from a lubricity layer, which in some instances has been observed to have an oily (i.e. shiny) appearance.

Optionally, for the pH protective coating or layer 286 in any embodiment, the silicon dissolution rate by a 50 mM potassium phosphate buffer diluted in water for injection, adjusted to pH 8 with concentrated nitric acid, and containing 0.2 wt. % polysorbate-80 surfactant, (measured in the absence of the medicament, to avoid changing the dissolution reagent), at 40° C., is less than 170 ppb/day. (Polysorbate-80 is a common ingredient of pharmaceutical preparations, available for example as Tween®-80 from Uniqema Americas LLC, Wilmington Delaware)

Optionally, for the pH protective coating or layer 286 in any embodiment, the silicon dissolution rate is less than 160 ppb/day, or less than 140 ppb/day, or less than 120 ppb/day, or less than 100 ppb/day, or less than 90 ppb/day, or less than 80 ppb/day. Optionally, in any embodiment of FIGS. 24-26 the silicon dissolution rate is more than 10 ppb/day, or more than 20 ppb/day, or more than 30 ppb/day, or more than 40 ppb/day, or more than 50 ppb/day, or more than 60 ppb/day. Any minimum rate stated here can be combined with any maximum rate stated here for the pH protective coating or layer 286 in any embodiment.

Optionally, for the pH protective coating or layer 286 in any embodiment the total silicon content of the pH protective coating or layer and barrier coating, upon dissolution into a test composition with a pH of 8 from the vessel, is less than 66 ppm, or less than 60 ppm, or less than 50 ppm, or less than 40 ppm, or less than 30 ppm, or less than 20 ppm.

The inventors offer the following theory of operation of the pH protective coating or layer described here. The invention is not limited by the accuracy of this theory or to the embodiments predictable by use of this theory.

The dissolution rate of the $SiO_x$ barrier layer is believed to be dependent on SiO bonding within the layer. Oxygen bonding sites (silanols) are believed to increase the dissolution rate.

It is believed that the OMCTS-based pH protective coating or layer bonds with the silanol sites on the $SiO_x$ barrier layer to "heal" or passivate the $SiO_x$ surface and thus dramatically reduces the dissolution rate. In this hypothesis, the thickness of the OMCTS layer is not the primary means of protection—the primary means is passivation of the $SiO_x$ surface. It is contemplated that a pH protective coating or layer as described in this specification can be improved by increasing the crosslink density of the pH protective coating or layer.

Hydrophobic Layer

The pH protective or lubricity coating or layer of $SiO_xC_y$ also can have utility as a hydrophobic layer, independent of whether it also functions as a pH protective coating or layer. Suitable hydrophobic coatings or layers and their application, properties, and use are described in U.S. Pat. No. 7,985,188. Dual functional pH protective/hydrophobic coatings or layers having the properties of both types of coatings or layers can be provided for any embodiment of the present invention.

An embodiment can be carried out under conditions effective to form a hydrophobic pH protective coating or layer on the substrate. Optionally, the hydrophobic characteristics of the pH protective coating or layer can be set by setting the ratio of the $O_2$ to the organosilicon precursor in the gaseous reactant, and/or by setting the electric power used for generating the plasma. Optionally, the pH protective coating or layer can have a lower wetting tension than the uncoated surface, optionally a wetting tension of from 20 to 72 dyne/cm, optionally from 30 to 60 dynes/cm, optionally from 30 to 40 dynes/cm, optionally 34 dyne/cm. Optionally, the pH protective coating or layer can be more hydrophobic than the uncoated surface.

Use of a coating or layer according to any described embodiment is contemplated as (i) a lubricity coating having a lower frictional resistance than the uncoated surface; and/or (ii) a pH protective coating or layer preventing dissolution of the barrier coating in contact with a fluid, and/or (iii) a hydrophobic layer that is more hydrophobic than the uncoated surface.

Pharmaceutical Packages

Figure 8:
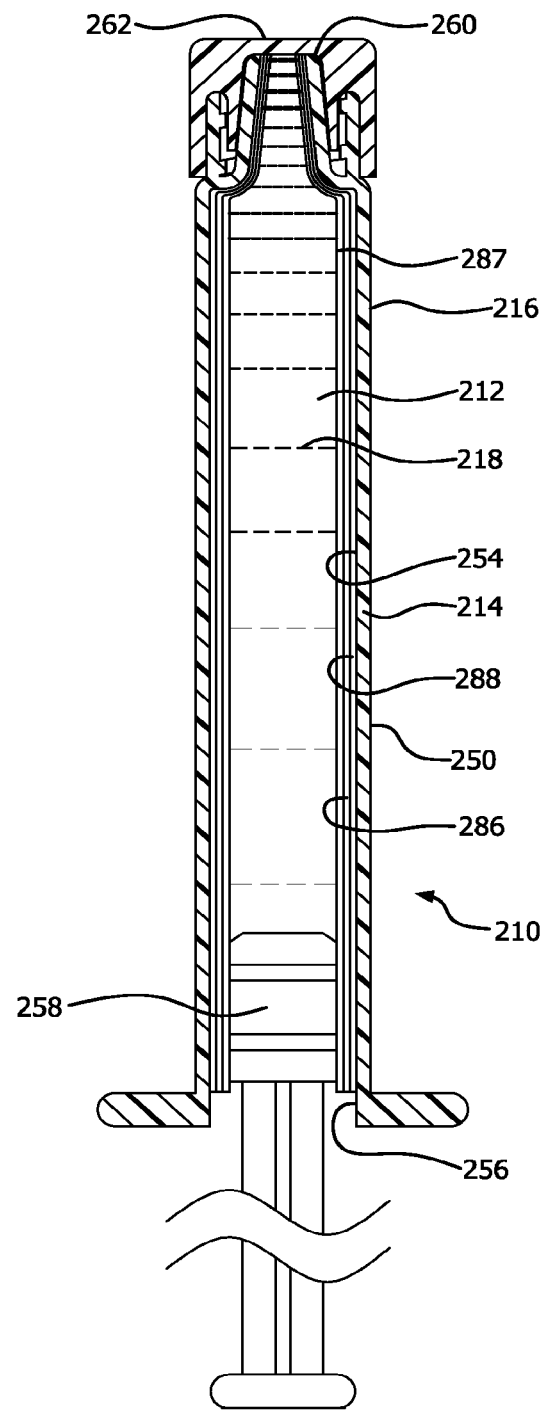
FIG. 8 is an assembly view of a prefilled syringe provided with a composite barrier layer, a pH protective coating or layer, and a lubricity layer and filled and closed to provide a pharmaceutical package.
Figure 9:
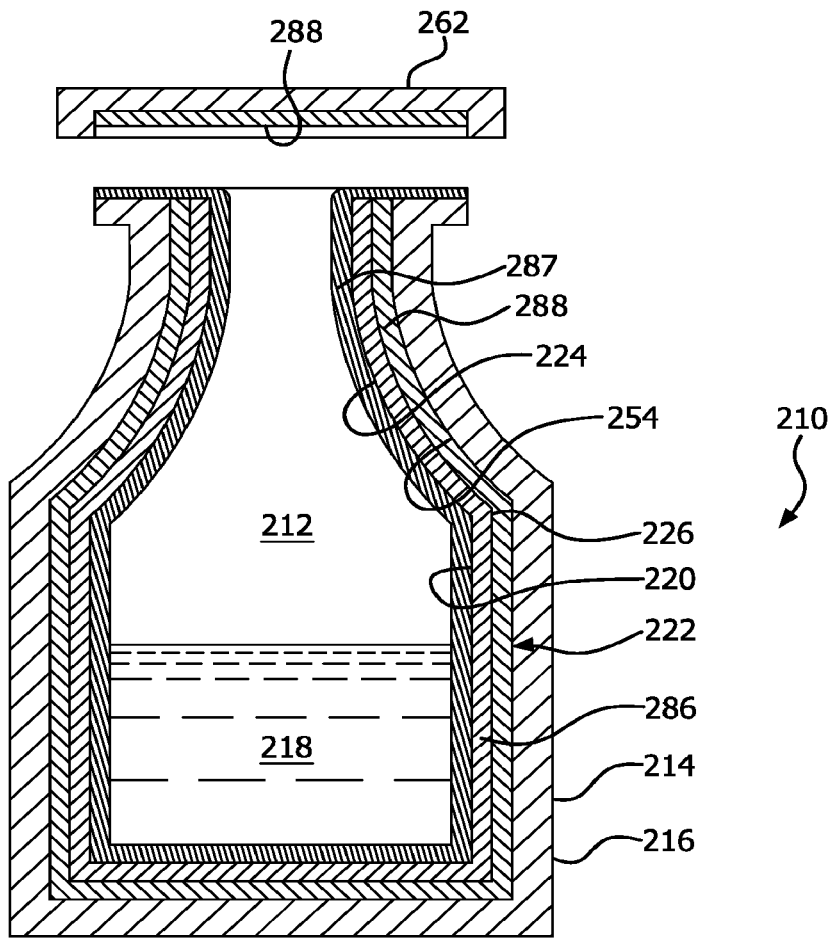
FIG. 9 is a schematic view of a pharmaceutical package in the form of a vial provided with a composite barrier layer, a pH protective coating or layer, and optionally a lubricity layer.
Figure 10:
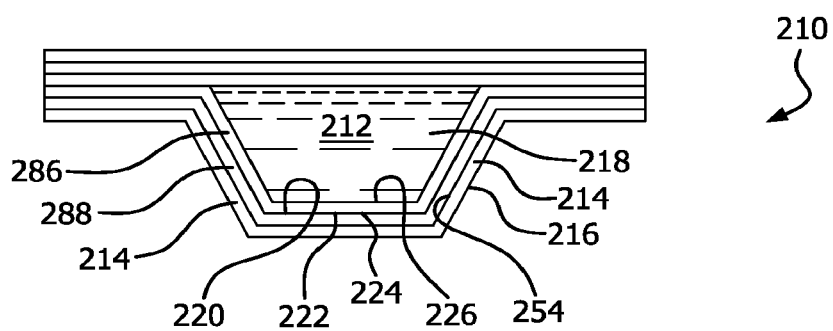
FIG. 10 is a schematic view of a pharmaceutical package in the form of a blister package provided with a composite barrier layer and a pH protective coating or layer.
Figure 11:
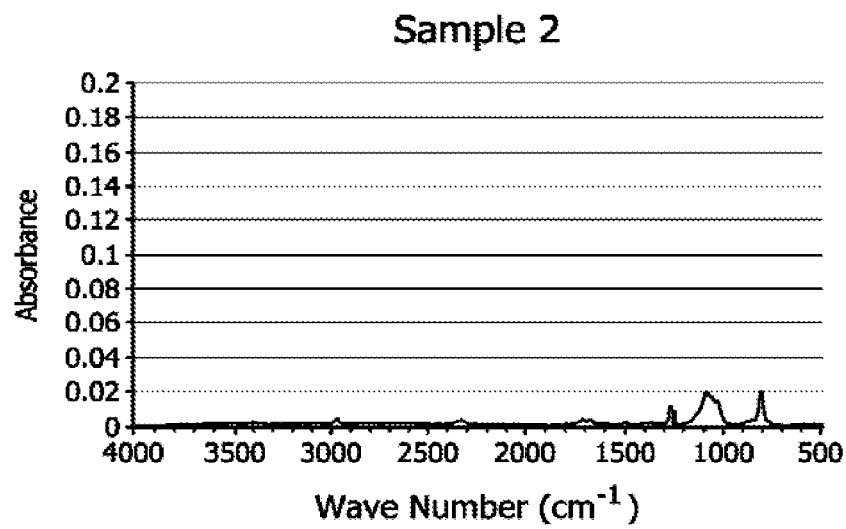
FIGS. 11-14 are FTIR absorbance spectra showing absorbance at the symmetric stretching mode (1000-1040 cm$^{-1}$) and the asymmetric stretching mode (1060-1100 cm$^{-1}$) of the Si—O—Si bond.
Figure 12:
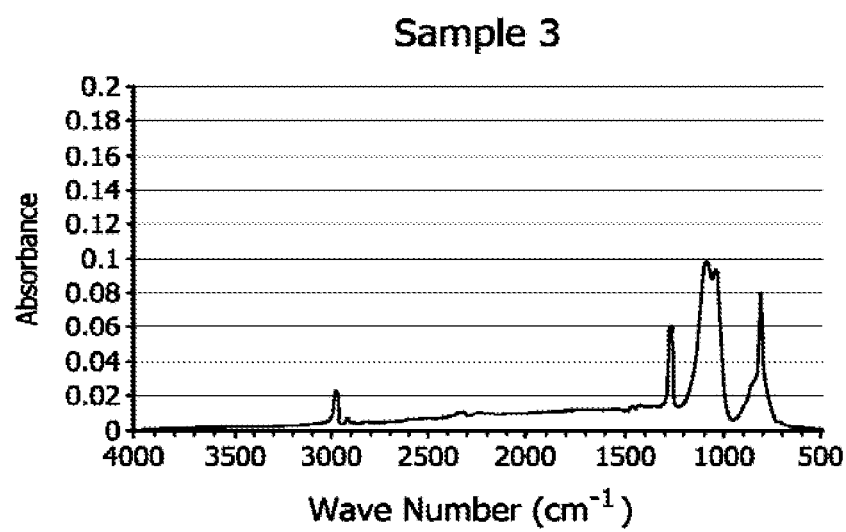
Figure 13:
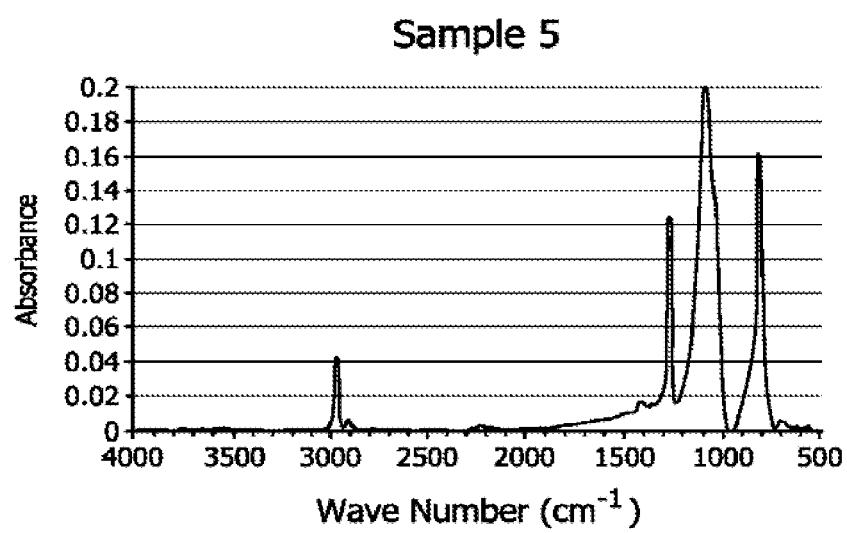

Three embodiments of the invention having many common features are those of FIGS. 8-10. Some of their common features are the following, indicated in many cases by common reference characters or names. The nature of the features of each embodiment can be as described later in the specification.

The pharmaceutical packages 210 of FIGS. 8-10 each include a vessel, a fluid composition 218, a composite barrier coating or layer 288 (alternatively described as a tie coating or layer plus a composite barrier coating or layer), and a pH protective coating 286. The vessel 250 has a lumen 212 defined at least in part by a wall 214 made of thermoplastic material.

The wall 214 has an interior surface 254 facing the lumen 212 and an outer surface 216.

The fluid composition 218 is contained in the lumen 212 and has a pH between 5 and 9.

The composite barrier coating or layer 288 comprises or consists essentially of $SiO_x$, wherein x is from 1.5 to 2.4, from 2 to 1000 nm thick, the composite barrier coating or layer 288 of $SiO_x$ having an interior surface 220 facing the lumen 212 and an outer surface 222 facing the wall 214 interior surface 254, the composite barrier coating or layer 288 being effective to reduce the ingress of atmospheric gas into the lumen 212 compared to an uncoated vessel 250. One suitable barrier composition is one where x is 2.3, for example.

The pH protective coating 286 is made of $SiO_xC_y$ or $SiN_xC_y$, wherein x is from about 0.5 to about 2.4 and y is from about 0.6 to about 3. The pH protective coating 286 has an interior surface 224 facing the lumen 212 and an outer surface 226 facing the interior surface 220 of the composite barrier coating or layer 288. The pH protective coating 286 is formed by chemical vapor deposition of a precursor selected from a monocyclic siloxane, a polycyclic siloxane, a polysilsesquioxane, a monocyclic silazane, a polycyclic silazane, a polysilsesquiazane, a Silatrane, a Silquasilatrane, a Silproatrane, an azasilatrane, an azasilquasiatrane, an azasilproatrane, or a combination of any two or more of these precursors. This process is described in more detail throughout this specification.

The rate of erosion of the pH protective coating 286, if directly contacted by the fluid composition 218, is less than the rate of erosion of the composite barrier coating or layer 288, if directly contacted by the fluid composition 218.

The pH protective coating 286 is effective to isolate the fluid composition 218 from the composite barrier coating or layer 288.

The embodiments of FIGS. 8-9 also share as a common feature a lubricity layer 287, which serves in the syringe of FIG. 8 to reduce the friction of the plunger 258 sliding in the syringe barrel 250 and in the vial of FIG. 9 to ease the insertion of a stopper cap (not shown) into the mouth of the vial to close it.

Optionally any of the embodiments of FIGS. 8-10 have as a common feature that at least a portion of the wall 214 of the vessel 250 comprises or consists essentially of a polymer, for example a polyolefin (for example a cyclic olefin polymer, a cyclic olefin copolymer, or polypropylene), a polyester, for example polyethylene terephthalate, a polycarbonate, or any combination or copolymer of any of these. Optionally for any of the embodiments of FIGS. 8-10, at least a portion of the wall 214 of the vessel 250 comprises or consists essentially of glass, for example borosilicate glass. A combination of any two or more of the materials in this paragraph can also be used.

Optionally for the embodiments of FIG. 8, the vessel 250 comprises a syringe barrel 250.

Optionally for the embodiments of FIG. 9, the vessel 250 comprises a vial.

Optionally for the embodiments of FIG. 10, the vessel 250 comprises a blister package.

Optionally for any of the embodiments of FIGS. 8-10, the fluid composition 218 has a pH between 5 and 6, optionally between 6 and 7, optionally between 7 and 8, optionally between 8 and 9, optionally between 6.5 and 7.5, optionally between 7.5 and 8.5, optionally between 8.5 and 9.

Optionally for any of the embodiments of FIGS. 8-10, the fluid composition 218 is a liquid at 20° C. and ambient pressure at sea level, which is defined as a pressure of 760 mm Hg.

Optionally for any of the embodiments of FIGS. 8-10, the fluid composition 218 is an aqueous liquid.

Optionally for any of the embodiments of FIGS. 8-10, the composite barrier coating or layer 288 is from 4 nm to 500 nm thick, optionally from 7 nm to 400 nm thick, optionally from 10 nm to 300 nm thick, optionally from 20 nm to 200 nm thick, optionally from 30 nm to 100 nm thick.

Optionally for any of the embodiments of FIGS. 8-10, the pH protective coating 286 comprises or consists essentially of $SiO_xC_y$. Optionally for any of the embodiments of FIGS. 8-10, the pH protective coating 286 comprises or consists essentially of $SiN_xC_y$.

Optionally for any of the embodiments of FIGS. 8-10, the precursor comprises a monocyclic siloxane, a polycyclic siloxane, a polysilsesquioxane, a monocyclic silazane, a polycyclic silazane, a polysilsesquiazane, a silatrane, a silquasilatrane, a silproatrane, an azasilatrane, an azasilquasiatrane, an azasilproatrane, or a combination of any two or more of these precursors.

Optionally for any of the embodiments of FIGS. 8-10, the precursor comprises a monocyclic siloxane, a polycyclic siloxane, a polysilsesquioxane, a Silatrane, a Silquasilatrane, a Silproatrane, or a combination of any two or more of these precursors. Optionally for any of the embodiments of FIGS. 8-10, the precursor comprises octamethylcyclotetrasiloxane (OMCTS) or consists essentially of OMCTS. Other precursors described elsewhere in this specification or known in the art are also contemplated for use according to the invention.

Optionally for any of the embodiments of FIGS. 8-10, the precursor comprises a monocyclic silazane, a polycyclic silazane, a polysilsesquiazane, an azasilatrane, an azasilquasiatrane, an azasilproatrane, or a combination of any two or more of these precursors.

Optionally for any of the embodiments of FIGS. 8-10, the pH protective coating 286 as applied is between 10 and 1000 nm thick, optionally between 50 and 800 nm thick, optionally between 100 and 700 nm thick, optionally between 300 and 600 nm thick. The thickness does not need to be uniform throughout the vessel, and will typically vary from the preferred values in portions of a vessel.

Optionally for any of the embodiments of FIGS. 8-10, the pH protective coating 286 contacting the fluid composition 218 is between 10 and 1000 nm thick, optionally between 50 and 500 nm thick, optionally between 100 and 400 nm thick, optionally between 150 and 300 nm thick two years after the pharmaceutical package 210 is assembled.

Optionally for any of the embodiments of FIGS. 8-10, the rate of erosion of the pH protective coating 286, if directly contacted by a fluid composition 218 having a pH of 8, is less than 20%, optionally less than 15%, optionally less than 10%, optionally less than 7%, optionally from 5% to 20%, optionally 5% to 15%, optionally 5% to 10%, optionally 5% to 7%, of the rate of erosion of the composite barrier coating or layer 288, if directly contacted by the same fluid composition 218 under the same conditions.

Optionally for any of the embodiments of FIGS. 8-10, the pH protective coating 286 is at least coextensive with the composite barrier coating or layer 288. The pH protective coating 286 alternatively can be less extensive than the barrier coating, as when the fluid composition does not contact or seldom is in contact with certain parts of the barrier coating absent the pH protective coating. The pH protective coating 286 alternatively can be more extensive than the barrier coating, as it can cover areas that are not provided with a barrier coating.

Optionally for any of the embodiments of FIGS. 8-10, the pharmaceutical package 210 can have a shelf life, after the pharmaceutical package 210 is assembled, of at least one year, alternatively at least two years.

Optionally for any of the embodiments of FIGS. 8-10, the shelf life is measured at 3° C., alternatively at 4° C. or higher, alternatively at 20° C. or higher, alternatively at 23° C., alternatively at 40° C.

Optionally for any of the embodiments of FIGS. 8-10, the pH of the fluid composition 218 is between 5 and 6 and the thickness by TEM of the pH protective coating 286 is at least 80 nm at the end of the shelf life. Alternatively, the pH of the fluid composition 218 is between 6 and 7 and the thickness by TEM of the pH protective coating 286 is at least 80 nm at the end of the shelf life. Alternatively, the pH of the fluid composition 218 is between 7 and 8 and the thickness by TEM of the pH protective coating 286 is at least 80 nm at the end of the shelf life. Alternatively, the pH of the fluid composition 218 is between 8 and 9 and the thickness by TEM of the pH protective coating 286 is at least 80 nm at the end of the shelf life. Alternatively, the pH of the fluid composition 218 is between 5 and 6 and the thickness by TEM of the pH protective coating 286 is at least 150 nm at the end of the shelf life. Alternatively, the pH of the fluid composition 218 is between 6 and 7 and the thickness by TEM of the pH protective coating 286 is at least 150 nm at the end of the shelf life. Alternatively, the pH of the fluid composition 218 is between 7 and 8 and the thickness by TEM of the pH protective coating 286 is at least 150 nm at the end of the shelf life. Alternatively, the pH of the fluid composition 218 is between 8 and 9 and the thickness by TEM of the pH protective coating 286 is at least 150 nm at the end of the shelf life.

Optionally for any of the embodiments of FIGS. 8-10, the fluid composition 218 removes the pH protective coating 286 at a rate of 1 nm or less of lubricity and/or pH protective coating thickness per 44 hours of contact with the fluid composition 218 (200 nm per year), alternatively 1 nm or less of lubricity and/or pH protective coating thickness per 88 hours of contact with the fluid composition 218 (100 nm per year), alternatively 1 nm or less of lubricity and/or pH protective coating thickness per 175 hours of contact with the fluid composition 218 (50 nm per year), alternatively 1 nm or less of lubricity and/or pH protective coating thickness per 250 hours of contact with the fluid composition 218 (35 nm per year), alternatively 1 nm or less of lubricity and/or pH protective coating thickness per 350 hours of contact with the fluid composition 218 (25 nm per year). The rate of removing the pH protective coating can be determined by TEM from samples exposed to the fluid composition for known periods.

Optionally for any of the embodiments of FIGS. 8-10, the pH protective coating 286 is effective to provide a lower frictional resistance than the uncoated interior surface 254. Preferably the frictional resistance is reduced by at least 25%, more preferably by at least 45%, even more preferably by at least 60% in comparison to the uncoated interior surface 254. For example, the pH protective coating 286 preferably is effective to reduce the frictional resistance between a portion of the wall 214 contacted by the fluid composition 218 and a relatively sliding part 258 after the pharmaceutical package 210 is assembled. Preferably, the pH protective coating 286 is effective to reduce the frictional resistance between the wall 214 and a relatively sliding part 258 at least two years after the pharmaceutical package 210 is assembled.

Fluid Composition

Optionally for any of the embodiments of FIGS. 8-10, the fluid composition 218 comprises a member or a combination of two or more members selected from the group consisting of:

Inhalation Anesthetics
    Aliflurane
    Chloroform
    Cyclopropane
    Desflurane (Suprane)
    Diethyl Ether
    Enflurane (Ethrane)
    Ethyl Chloride
    Ethylene
    Halothane (Fluothane)
    Isoflurane (Forane, Isoflo)
    Isopropenyl vinyl ether
    Methoxyflurane
    methoxyflurane,
    Methoxypropane
    Nitrous Oxide
    Roflurane
    Sevoflurane (Sevorane, Ultane, Sevoflo)
    Teflurane
    Trichloroethylene
    Vinyl Ether
    Xenon Injectable Drugs
    Ablavar (Gadofosveset Trisodium Injection)
    Abarelix Depot
    Abobotulinumtoxin A Injection (Dysport)
    ABT-263
    ABT-869
    ABX-EFG
    Accretropin (Somatropin Injection)
    Acetadote (Acetylcysteine Injection)
    Acetazolamide Injection (Acetazolamide Injection)
    Acetylcysteine Injection (Acetadote)
    Actemra (Tocilizumab Injection)
    Acthrel (Corticorelin Ovine Triflutate for Injection)
    Actummune
    Activase
    Acyclovir for Injection (Zovirax Injection)
    Adacel
    Adalimumab
    Adenoscan (Adenosine Injection)
    Adenosine Injection (Adenoscan)
    Adrenaclick
    AdreView (Iobenguane I 123 Injection for Intravenous Use)
    Afluria
    Ak-Fluor (Fluorescein Injection)
    Aldurazyme (Laronidase)
    Alglucerase Injection (Ceredase)
    Alkeran Injection (Melphalan Hcl Injection)
    Allopurinol Sodium for Injection (Aloprim)
    Aloprim (Allopurinol Sodium for Injection)
    Alprostadil
    Alsuma (Sumatriptan Injection)
    ALTU-238
    Amino Acid Injections
    Aminosyn
    Apidra
    Apremilast
    Alprostadil Dual Chamber System for Injection (Caverject Impulse)
    AMG 009
    AMG 076
    AMG 102
    AMG 108
    AMG 114
    AMG 162
    AMG 220
    AMG 221
    AMG 222
    AMG 223

AMG 317
AMG 379
AMG 386
AMG 403
AMG 477
AMG 479
AMG 517
AMG 531
AMG 557
AMG 623
AMG 655
AMG 706
AMG 714
AMG 745
AMG 785
AMG 811
AMG 827
AMG 837
AMG 853
AMG 951
Amiodarone HCl Injection (Amiodarone HCl Injection)
Amobarbital Sodium Injection (Amytal Sodium)
Amytal Sodium (Amobarbital Sodium Injection)
Anakinra
Anti-Abeta
Anti-Beta7
Anti-Beta20
Anti-CD4
Anti-CD20
Anti-CD40
Anti-IFNalpha
Anti-IL13
Anti-OX40L
Anti-oxLDS
Anti-NGF
Anti-NRP1
Arixtra
Amphadase (Hyaluronidase Inj)
Ammonul (Sodium Phenylacetate and Sodium Benzoate Injection)
Anaprox
Anzemet Injection (Dolasetron Mesylate Injection)
Apidra (Insulin Glulisine [rDNA origin] Inj)
Apomab
Aranesp (darbepoetin alfa)
Argatroban (Argatroban Injection)
Arginine Hydrochloride Injection (R-Gene 10
Aristocort
Aristospan
Arsenic Trioxide Injection (Trisenox)
Articane HCl and Epinephrine Injection (Septocaine)
Arzerra (Ofatumumab Injection)
Asclera (Polidocanol Injection)
Ataluren
Ataluren-DMD
Atenolol Inj (Tenormin I.V. Injection)
Atracurium Besylate Injection (Atracurium Besylate Injection)
Avastin
Azactam Injection (Aztreonam Injection)
Azithromycin (Zithromax Injection)
Aztreonam Injection (Azactam Injection)
Baclofen Injection (Lioresal Intrathecal)
Bacteriostatic Water (Bacteriostatic Water for Injection)
Baclofen Injection (Lioresal Intrathecal)
Bal in Oil Ampules (Dimercarprol Injection)
BayHepB
BayTet
Benadryl
Bendamustine Hydrochloride Injection (Treanda)
Benztropine Mesylate Injection (Cogentin)
Betamethasone Injectable Suspension (Celestone Soluspan)
Bexxar
Bicillin C-R 900/300 (Penicillin G Benzathine and Penicillin G Procaine Injection)
Blenoxane (Bleomycin Sulfate Injection)
Bleomycin Sulfate Injection (Blenoxane)
Boniva Injection (Ibandronate Sodium Injection)
Botox Cosmetic (OnabotulinumtoxinA for Injection)
BR3-FC
Bravelle (Urofollitropin Injection)
Bretylium (Bretylium Tosylate Injection)
Brevital Sodium (Methohexital Sodium for Injection)
Brethine
Briobacept
BTT-1023
Bupivacaine HCl
Byetta
Ca-DTPA (Pentetate Calcium Trisodium Inj)
Cabazitaxel Injection (Jevtana)
Caffeine Alkaloid (Caffeine and Sodium Benzoate Injection)
Calcijex Injection (Calcitrol)
Calcitrol (Calcijex Injection)
Calcium Chloride (Calcium Chloride Injection 10%)
Calcium Disodium Versenate (Edetate Calcium Disodium Injection)
Campath (Altemtuzumab)
Camptosar Injection (Irinotecan Hydrochloride)
Canakinumab Injection (Ilaris)
Capastat Sulfate (Capreomycin for Injection)
Capreomycin for Injection (Capastat Sulfate)
Cardiolite (Prep kit for Technetium Tc99 Sestamibi for Injection)
Carticel
Cathflo
Cefazolin and Dextrose for Injection (Cefazolin Injection)
Cefepime Hydrochloride
Cefotaxime
Ceftriaxone
Cerezyme
Carnitor Injection
Caverject
Celestone Soluspan
Celsior
Cerebyx (Fosphenytoin Sodium Injection)
Ceredase (Alglucerase Injection)
Ceretec (Technetium Tc99m Exametazime Injection)
Certolizumab
CF-101
Chloramphenicol Sodium Succinate (Chloramphenicol Sodium Succinate Injection)
Chloramphenicol Sodium Succinate Injection (Chloramphenicol Sodium Succinate)
Cholestagel (Colesevelam HCL)
Choriogonadotropin Alfa Injection (Ovidrel)
Cimzia
Cisplatin (Cisplatin Injection)
Clolar (Clofarabine Injection)
Clomiphine Citrate
Clonidine Injection (Duraclon)
Cogentin (Benztropine Mesylate Injection)
Colistimethate Injection (Coly-Mycin M)

Coly-Mycin M (Colistimethate Injection)
Compath
Conivaptan Hcl Injection (Vaprisol)
Conjugated Estrogens for Injection (Premarin Injection)
Copaxone
Corticorelin Ovine Triflutate for Injection (Acthrel)
Corvert (Ibutilide Fumarate Injection)
Cubicin (Daptomycin Injection)
CF-101
Cyanokit (Hydroxocobalamin for Injection)
Cytarabine Liposome Injection (DepoCyt)
Cyanocobalamin
Cytovene (ganciclovir)
D.H.E. 45
Dacetuzumab
Dacogen (Decitabine Injection)
Dalteparin
Dantrium IV (Dantrolene Sodium for Injection)
Dantrolene Sodium for Injection (Dantrium IV)
Daptomycin Injection (Cubicin)
Darbepoietin Alfa
DDAVP Injection (Desmopressin Acetate Injection)
Decavax
Decitabine Injection (Dacogen)
Dehydrated Alcohol (Dehydrated Alcohol Injection)
Denosumab Injection (Prolia)
Delatestryl
Delestrogen
Delteparin Sodium
Depacon (Valproate Sodium Injection)
Depo Medrol (Methylprednisolone Acetate Injectable Suspension)
DepoCyt (Cytarabine Liposome Injection)
DepoDur (Morphine Sulfate XR Liposome Injection)
Desmopressin Acetate Injection (DDAVP Injection)
Depo-Estradiol
Depo-Provera 104 mg/ml
Depo-Provera 150 mg/ml
Depo-Testosterone
Dexrazoxane for Injection, Intravenous Infusion Only (Totect)
Dextrose/Electrolytes
Dextrose and Sodium Chloride Inj (Dextrose 5% in 0.9% Sodium Chloride)
Dextrose
Diazepam Injection (Diazepam Injection)
Digoxin Injection (Lanoxin Injection)
Dilaudid-HP (Hydromorphone Hydrochloride Injection)
Dimercarprol Injection (Bal in Oil Ampules)
Diphenhydramine Injection (Benadryl Injection)
Dipyridamole Injection (Dipyridamole Injection)
DMOAD
Docetaxel for Injection (Taxotere)
Dolasetron Mesylate Injection (Anzemet Injection)
Doribax (Doripenem for Injection)
Doripenem for Injection (Doribax)
Doxercalciferol Injection (Hectorol Injection)
Doxil (Doxorubicin Hcl Liposome Injection)
Doxorubicin Hcl Liposome Injection (Doxil)
Duraclon (Clonidine Injection)
Duramorph (Morphine Injection)
Dysport (Abobotulinumtoxin A Injection)
Ecallantide Injection (Kalbitor)
EC-Naprosyn (naproxen)
Edetate Calcium Disodium Injection (Calcium Disodium Versenate)
Edex (Alprostadil for Injection)
Engerix
Edrophonium Injection (Enlon)
Eliglustat Tartate
Eloxatin (Oxaliplatin Injection)
Emend Injection (Fosaprepitant Dimeglumine Injection)
Enalaprilat Injection (Enalaprilat Injection)
Enlon (Edrophonium Injection)
Enoxaparin Sodium Injection (Lovenox)
Eovist (Gadoxetate Disodium Injection)
Enbrel (etanercept)
Enoxaparin
Epicel
Epinepherine
Epipen
Epipen Jr.
Epratuzumab
Erbitux
Ertapenem Injection (Invanz)
Erythropoieten
Essential Amino Acid Injection (Nephramine)
Estradiol Cypionate
Estradiol Valerate
Etanercept
Exenatide Injection (Byetta)
Evlotra
Fabrazyme (Adalsidase beta)
Famotidine Injection
FDG (Fludeoxyglucose F 18 Injection)
Feraheme (Ferumoxytol Injection)
Feridex I.V. (Ferumoxides Injectable Solution)
Fertinex
Ferumoxides Injectable Solution (Feridex I.V.)
Ferumoxytol Injection (Feraheme)
Flagyl Injection (Metronidazole Injection)
Fluarix
Fludara (Fludarabine Phosphate)
Fludeoxyglucose F 18 Injection (FDG)
Fluorescein Injection (Ak-Fluor)
Follistim AQ Cartridge (Follitropin Beta Injection)
Follitropin Alfa Injection (Gonal-f RFF)
Follitropin Beta Injection (Follistim AQ Cartridge)
Folotyn (Pralatrexate Solution for Intravenous Injection)
Fondaparinux
Forteo (Teriparatide (rDNA origin) Injection)
Fostamatinib
Fosaprepitant Dimeglumine Injection (Emend Injection)
Foscarnet Sodium Injection (Foscavir)
Foscavir (Foscarnet Sodium Injection)
Fosphenytoin Sodium Injection (Cerebyx)
Fospropofol Disodium Injection (Lusedra)
Fragmin
Fuzeon (enfuvirtide)
GA101
Gadobenate Dimeglumine Injection (Multihance)
Gadofosveset Trisodium Injection (Ablavar)
Gadoteridol Injection Solution (ProHance)
Gadoversetamide Injection (OptiMARK)
Gadoxetate Disodium Injection (Eovist)
Ganirelix (Ganirelix Acetate Injection)
Gardasil
GC1008
GDFD
Gemtuzumab Ozogamicin for Injection (Mylotarg)
Genotropin
Gentamicin Injection
GENZ-112638
Golimumab Injection (Simponi Injection)

Gonal-f RFF (Follitropin Alfa Injection)
Granisetron Hydrochloride (Kytril Injection)
Gentamicin Sulfate
Glatiramer Acetate
Glucagen
Glucagon
HAE1
Haldol (Haloperidol Injection)
Havrix
Hectorol Injection (Doxercalciferol Injection)
Hedgehog Pathway Inhibitor
Heparin
Herceptin
hG-CSF
Humalog
Human Growth Hormone
Humatrope
HuMax
Humegon
Humira
Humulin
Ibandronate Sodium Injection (Boniva Injection)
Ibuprofen Lysine Injection (NeoProfen)
Ibutilide Fumarate Injection (Corvert)
Idamycin PFS (Idarubicin Hydrochloride Injection)
Idarubicin Hydrochloride Injection (Idamycin PFS)
Ilaris (Canakinumab Injection)
Imipenem and Cilastatin for Injection (Primaxin I.V.)
Imitrex
Incobotulinumtoxin A for Injection (Xeomin)
Increlex (Mecasermin [rDNA origin] Injection)
Indocin IV (Indomethacin Inj)
Indomethacin Inj (Indocin IV)
Infanrix
Innohep
Insulin
Insulin Aspart [rDNA origin] Inj (NovoLog)
Insulin Glargine [rDNA origin] Injection (Lantus)
Insulin Glulisine [rDNA origin] Inj (Apidra)
Interferon alfa-2b, Recombinant for Injection (Intron A)
Intron A (Interferon alfa-2b, Recombinant for Injection)
Invanz (Ertapenem Injection)
Invega Sustenna (Paliperidone Palmitate Extended-Release Injectable Suspension)
Invirase (saquinavir mesylate)
Iobenguane I123 Injection for Intravenous Use (AdreView)
Iopromide Injection (Ultravist)
Ioversol Injection (Optiray Injection)
Iplex (Mecasermin Rinfabate [rDNA origin] Injection)
Iprivask
Irinotecan Hydrochloride (Camptosar Injection)
Iron Sucrose Injection (Venofer)
Istodax (Romidepsin for Injection)
Itraconazole Injection (Sporanox Injection)
Jevtana (Cabazitaxel Injection)
Jonexa
Kalbitor (Ecallantide Injection)
KCL in DSNS (Potassium Chloride in 5% Dextrose and Sodium Chloride Injection)
KCL in D5 W
KCL in NS
Kenalog 10 Injection (Triamcinolone Acetonide Injectable Suspension)
Kepivance (Palifermin)
Keppra Injection (Levetiracetam)
Keratinocyte
KFG
Kinase Inhibitor
Kineret (Anakinra)
Kinlytic (Urokinase Injection)
Kinrix
Klonopin (clonazepam)
Kytril Injection (Granisetron Hydrochloride)
lacosamide Tablet and Injection (Vimpat)
Lactated Ringer's
Lanoxin Injection (Digoxin Injection)
Lansoprazole for Injection (Prevacid I.V.)
Lantus
Leucovorin Calcium (Leucovorin Calcium Injection)
Lente (L)
Leptin
Levemir
Leukine Sargramostim
Leuprolide Acetate
Levothyroxine
Levetiracetam (Keppra Injection)
Lovenox
Levocarnitine Injection (Carnitor Injection)
Lexiscan (Regadenoson Injection)
Lioresal Intrathecal (Baclofen Injection)
Liraglutide [rDNA] Injection (Victoza)
Lovenox (Enoxaparin Sodium Injection)
Lucentis (Ranibizumab Injection)
Lumizyme
Lupron (Leuprolide Acetate Injection)
Lusedra (Fospropofol Disodium Injection)
Maci
Magnesium Sulfate (Magnesium Sulfate Injection)
Mannitol Injection (Mannitol IV)
Marcaine (Bupivacaine Hydrochloride and Epinephrine Injection)
Maxipime (Cefepime Hydrochloride for Injection)
MDP Multidose Kit of Technetium Injection (Technetium Tc99m Medronate Injection)
Mecasermin [rDNA origin] Injection (Increlex)
Mecasermin Rinfabate [rDNA origin] Injection (Iplex)
Melphalan Hcl Injection (Alkeran Injection)
Methotrexate
Menactra
Menopur (Menotropins Injection)
Menotropins for Injection (Repronex)
Methohexital Sodium for Injection (Brevital Sodium)
Methyldopate Hydrochloride Injection, Solution (Methyldopate Hcl)
Methylene Blue (Methylene Blue Injection)
Methylprednisolone Acetate Injectable Suspension (Depo Medrol)
MetMab
Metoclopramide Injection (Reglan Injection)
Metrodin (Urofollitropin for Injection)
Metronidazole Injection (Flagyl Injection)
Miacalcin
Midazolam (Midazolam Injection)
Mimpara (Cinacalet)
Minocin Injection (Minocycline Inj)
Minocycline Inj (Minocin Injection)
Mipomersen
Mitoxantrone for Injection Concentrate (Novantrone)
Morphine Injection (Duramorph)
Morphine Sulfate XR Liposome Injection (DepoDur)
Morrhuate Sodium (Morrhuate Sodium Injection)
Motesanib
Mozobil (Plerixafor Injection)

Multihance (Gadobenate Dimeglumine Injection)
Multiple Electrolytes and Dextrose Injection
Multiple Electrolytes Injection
Mylotarg (Gemtuzumab Ozogamicin for Injection)
Myozyme (Alglucosidase alfa)
Nafcillin Injection (Nafcillin Sodium)
Nafcillin Sodium (Nafcillin Injection)
Naltrexone XR Inj (Vivitrol)
Naprosyn (naproxen)
NeoProfen (Ibuprofen Lysine Injection)
Nandrol Decanoate
Neostigmine Methylsulfate (Neostigmine Methylsulfate Injection)
NEO-GAA
NeoTect (Technetium Tc 99m Depreotide Injection)
Nephramine (Essential Amino Acid Injection)
Neulasta (pegfilgrastim)
Neupogen (Filgrastim)
Novolin
Novolog
NeoRecormon
Neutrexin (Trimetrexate Glucuronate Inj)
NPH (N)
Nexterone (Amiodarone HCl Injection)
Norditropin (Somatropin Injection)
Normal Saline (Sodium Chloride Injection)
Novantrone (Mitoxantrone for Injection Concentrate)
Novolin 70/30 Innolet (70% NPH, Human Insulin Isophane Suspension and 30%
Regular, Human Insulin Injection)
NovoLog (Insulin Aspart [rDNA origin] Inj)
Nplate (romiplostim)
Nutropin (Somatropin (rDNA origin) for Inj)
Nutropin AQ
Nutropin Depot (Somatropin (rDNA origin) for Inj)
Octreotide Acetate Injection (Sandostatin LAR)
Ocrelizumab
Ofatumumab Injection (Arzerra)
Olanzapine Extended Release Injectable Suspension (Zyprexa Relprevv)
Omnitarg
Omnitrope (Somatropin [rDNA origin] Injection)
Ondansetron Hydrochloride Injection (Zofran Injection)
OptiMARK (Gadoversetamide Injection)
Optiray Injection (Ioversol Injection)
Orencia
Osmitrol Injection in Aviva (Mannitol Injection in Aviva Plastic Vessel 250)
Osmitrol Injection in Viaflex (Mannitol Injection in Viaflex Plastic Vessel 250)
Osteoprotegrin
Ovidrel (Choriogonadotropin Alfa Injection)
Oxacillin (Oxacillin for Injection)
Oxaliplatin Injection (Eloxatin)
Oxytocin Injection (Pitocin)
Paliperidone Palmitate Extended-Release Injectable Suspension (Invega Sustenna)
Pamidronate Disodium Injection (Pamidronate Disodium Injection)
Panitumumab Injection for Intravenous Use (Vectibix)
Papaverine Hydrochloride Injection (Papaverine Injection)
Papaverine Injection (Papaverine Hydrochloride Injection)
Parathyroid Hormone
Paricalcitol Injection Fliptop Vial (Zemplar Injection)
PARP Inhibitor
Pediarix
PEGIntron
Peginterferon
Pegfilgrastim
Penicillin G Benzathine and Penicillin G Procaine
Pentetate Calcium Trisodium Inj (Ca-DTPA)
Pentetate Zinc Trisodium Injection (Zn-DTPA)
Pepcid Injection (Famotidine Injection)
Pergonal
Pertuzumab
Phentolamine Mesylate (Phentolamine Mesylate for Injection)
Physostigmine Salicylate (Physostigmine Salicylate (injection))
Physostigmine Salicylate (injection) (Physostigmine Salicylate)
Piperacillin and Tazobactam Injection (Zosyn)
Pitocin (Oxytocin Injection)
Plasma-Lyte 148 (Multiple Electrolytes Inj)
Plasma-Lyte 56 and Dextrose (Multiple Electrolytes and Dextrose Injection in Viaflex
Plastic Vessel 250)
PlasmaLyte
Plerixafor Injection (Mozobil)
Polidocanol Injection (Asclera)
Potassium Chloride
Pralatrexate Solution for Intravenous Injection (Folotyn)
Pramlintide Acetate Injection (Symlin)
Premarin Injection (Conjugated Estrogens for Injection)
Prep kit for Technetium Tc99 Sestamibi for Injection (Cardiolite)
Prevacid I.V. (Lansoprazole for Injection)
Primaxin I.V. (Imipenem and Cilastatin for Injection)
Prochymal
Procrit
Progesterone
ProHance (Gadoteridol Injection Solution)
Prolia (Denosumab Injection)
Promethazine HCl Injection (Promethazine Hydrochloride Injection)
Propranolol Hydrochloride Injection (Propranolol Hydrochloride Injection)
Quinidine Gluconate Injection (Quinidine Injection)
Quinidine Injection (Quinidine Gluconate Injection)
R-Gene 10 (Arginine Hydrochloride Injection)
Ranibizumab Injection (Lucentis)
Ranitidine Hydrochloride Injection (Zantac Injection)
Raptiva
Reclast (Zoledronic Acid Injection)
Recombivarix HB
Regadenoson Injection (Lexiscan)
Reglan Injection (Metoclopramide Injection)
Remicade
Renagel
Renvela (Sevelamer Carbonate)
Repronex (Menotropins for Injection)
Retrovir IV (Zidovudine Injection)
rhApo2L/TRAIL
Ringer's and 5% Dextrose Injection (Ringers in Dextrose)
Ringer's Injection (Ringers Injection)
Rituxan
Rituximab
Rocephin (ceftriaxone)
Rocuronium Bromide Injection (Zemuron)
Roferon-A (interferon alfa-2a)
Romazicon (flumazenil)
Romidepsin for Injection (Istodax)

Saizen (Somatropin Injection)
Sandostatin LAR (Octreotide Acetate Injection)
Sclerostin Ab
Sensipar (cinacalcet)
Sensorcaine (Bupivacaine HCl Injections)
Septocaine (Articane HCl and Epinephrine Injection)
Serostim LQ (Somatropin (rDNA origin) Injection)
Simponi Injection (Golimumab Injection)
Sodium Acetate (Sodium Acetate Injection)
Sodium Bicarbonate (Sodium Bicarbonate 5% Injection)
Sodium Lactate (Sodium Lactate Injection in AVIVA)
Sodium Phenylacetate and Sodium Benzoate Injection (Ammonul)
Somatropin (rDNA origin) for Inj (Nutropin)
Sporanox Injection (Itraconazole Injection)
Stelara Injection (Ustekinumab)
Stemgen
Sufenta (Sufentanil Citrate Injection)
Sufentanil Citrate Injection (Sufenta)
Sumavel
Sumatriptan Injection (Alsuma)
Symlin
Symlin Pen
Systemic Hedgehog Antagonist
Synvisc-One (Hylan G-F 20 Single Intra-articular Injection)
Tarceva
Taxotere (Docetaxel for Injection)
Technetium Tc 99m
Telavancin for Injection (Vibativ)
Temsirolimus Injection (Torisel)
Tenormin I.V. Injection (Atenolol Inj)
Teriparatide (rDNA origin) Injection (Forteo)
Testosterone Cypionate
Testosterone Enanthate
Testosterone Propionate
Tev-Tropin (Somatropin, rDNA Origin, for Injection)
tgAAC94
Thallous Chloride
Theophylline
Thiotepa (Thiotepa Injection)
Thymoglobulin (Anti-Thymocyte Globulin (Rabbit)
Thyrogen (Thyrotropin Alfa for Injection)
Ticarcillin Disodium and Clavulanate Potassium Galaxy (Timentin Injection)
Tigan Injection (Trimethobenzamide Hydrochloride Injectable)
Timentin Injection (Ticarcillin Disodium and Clavulanate Potassium Galaxy)
TNKase
Tobramycin Injection (Tobramycin Injection)
Tocilizumab Injection (Actemra)
Torisel (Temsirolimus Injection)
Totect (Dexrazoxane for Injection, Intravenous Infusion Only)
Trastuzumab-DM1
Travasol (Amino Acids (Injection))
Treanda (Bendamustine Hydrochloride Injection)
Trelstar (Triptorelin Pamoate for Injectable Suspension)
Triamcinolone Acetonide
Triamcinolone Diacetate
Triamcinolone Hexacetonide Injectable Suspension (Aristospan Injection 20 mg)
Triesence (Triamcinolone Acetonide Injectable Suspension)
Trimethobenzamide Hydrochloride Injectable (Tigan Injection)
Trimetrexate Glucuronate Inj (Neutrexin)
Triptorelin Pamoate for Injectable Suspension (Trelstar)
Twinject
Trivaris (Triamcinolone Acetonide Injectable Suspension)
Trisenox (Arsenic Trioxide Injection)
Twinrix
Typhoid Vi
Ultravist (Iopromide Injection)
Urofollitropin for Injection (Metrodin)
Urokinase Injection (Kinlytic)
Ustekinumab (Stelara Injection)
Ultralente (U)
Valium (diazepam)
Valproate Sodium Injection (Depacon)
Valtropin (Somatropin Injection)
Vancomycin Hydrochloride (Vancomycin Hydrochloride Injection)
Vancomycin Hydrochloride Injection (Vancomycin Hydrochloride)
Vaprisol (Conivaptan Hcl Injection)
VAQTA
Vasovist (Gadofosveset Trisodium Injection for Intravenous Use)
Vectibix (Panitumumab Injection for Intravenous Use)
Venofer (Iron Sucrose Injection)
Verteporfin Inj (Visudyne)
Vibativ (Telavancin for Injection)
Victoza (Liraglutide [rDNA] Injection)
Vimpat (lacosamide Tablet and Injection)
Vinblastine Sulfate (Vinblastine Sulfate Injection)
Vincasar PFS (Vincristine Sulfate Injection)
Victoza
Vincristine Sulfate (Vincristine Sulfate Injection)
Visudyne (Verteporfin Inj)
Vitamin B-12
Vivitrol (Naltrexone XR Inj)
Voluven (Hydroxyethyl Starch in Sodium Chloride Injection)
Xeloda
Xenical (orlistat)
Xeomin (Incobotulinumtoxin A for Injection)
Xolair
Zantac Injection (Ranitidine Hydrochloride Injection)
Zemplar Injection (Paricalcitol Injection Fliptop Vial)
Zemuron (Rocuronium Bromide Injection)
Zenapax (daclizumab)
Zevalin
Zidovudine Injection (Retrovir IV)
Zithromax Injection (Azithromycin)
Zn-DTPA (Pentetate Zinc Trisodium Injection)
Zofran Injection (Ondansetron Hydrochloride Injection)
Zingo
Zoledronic Acid for Inj (Zometa)
Zoledronic Acid Injection (Reclast)
Zometa (Zoledronic Acid for Inj)
Zosyn (Piperacillin and Tazobactam Injection)
Zyprexa Relprevv (Olanzapine Extended Release Injectable Suspension)
Liquid Drugs (Non-Injectable)
Abilify
AccuNeb (Albuterol Sulfate Inhalation Solution)
Actidose Aqua (Activated Charcoal Suspension)
Activated Charcoal Suspension (Actidose Aqua)
Advair
Agenerase Oral Solution (Amprenavir Oral Solution)
Akten (Lidocaine Hydrochloride Ophthalmic Gel)
Alamast (Pemirolast Potassium Ophthalmic Solution)

Albumin (Human) 5% Solution (Buminate 5%)
Albuterol Sulfate Inhalation Solution
Alinia
Alocril
Alphagan
Alrex
Alvesco
Amprenavir Oral Solution
Analpram-HC
Arformoterol Tartrate Inhalation Solution (Brovana)
Aristospan Injection 20 mg (Triamcinolone Hexacetonide Injectable Suspension)
Asacol
Asmanex
Astepro
Astepro (Azelastine Hydrochloride Nasal Spray)
Atrovent Nasal Spray (Ipratropium Bromide Nasal Spray)
Atrovent Nasal Spray 0.06
Augmentin ES-600
Azasite (Azithromycin Ophthalmic Solution)
Azelaic Acid (Finacea Gel)
Azelastine Hydrochloride Nasal Spray (Astepro)
Azelex (Azelaic Acid Cream)
Azopt (Brinzolamide Ophthalmic Suspension)
Bacteriostatic Saline
Balanced Salt
Bepotastine
Bactroban Nasal
Bactroban
Beclovent
Benzac W
Betimol
Betoptic S
Bepreve
Bimatoprost Ophthalmic Solution
Bleph 10 (Sulfacetamide Sodium Ophthalmic Solution 10%)
Brinzolamide Ophthalmic Suspension (Azopt)
Bromfenac Ophthalmic Solution (Xibrom)
Bromhist
Brovana (Arformoterol Tartrate Inhalation Solution)
Budesonide Inhalation Suspension (Pulmicort Respules)
Cambia (Diclofenac Potassium for Oral Solution)
Capex
Carac
Carboxine-PSE
Carnitor
Cayston (Aztreonam for Inhalation Solution)
Cellcept
Centany
Cerumenex
Ciloxan Ophthalmic Solution (Ciprofloxacin HCL Ophthalmic Solution)
Ciprodex
Ciprofloxacin HCL Ophthalmic Solution (Ciloxan Ophthalmic Solution)
Clemastine Fumarate Syrup (Clemastine Fumarate Syrup)
CoLyte (PEG Electrolytes Solution)
Combiven
Comtan
Condylox
Cordran
Cortisporin Ophthalmic Suspension
Cortisporin Otic Suspension
Cromolyn Sodium Inhalation Solution (Intal Nebulizer Solution)
Cromolyn Sodium Ophthalmic Solution (Opticrom)
Crystalline Amino Acid Solution with Electrolytes (Aminosyn Electrolytes)
Cutivate
Cuvposa (Glycopyrrolate Oral Solution)
Cyanocobalamin (CaloMist Nasal Spray)
Cyclosporine Oral Solution (Gengraf Oral Solution)
Cyclogyl
Cysview (Hexaminolevulinate Hydrochloride Intravesical Solution)
DermOtic Oil (Fluocinolone Acetonide Oil Ear Drops)
Desmopressin Acetate Nasal Spray
DDAVP
Derma-Smoothe/FS
Dexamethasone Intensol
Dianeal Low Calcium
Dianeal PD
Diclofenac Potassium for Oral Solution (Cambia)
Didanosine Pediatric Powder for Oral Solution (Videx)
Differin
Dilantin 125 (Phenytoin Oral Suspension)
Ditropan
Dorzolamide Hydrochloride Ophthalmic Solution (Trusopt)
Dorzolamide Hydrochloride-Timolol Maleate Ophthalmic Solution (Cosopt)
Dovonex Scalp (Calcipotriene Solution)
Doxycycline Calcium Oral Suspension (Vibramycin Oral)
Efudex
Elaprase (Idursulfase Solution)
Elestat (Epinastine HCl Ophthalmic Solution)
Elocon
Epinastine HCl Ophthalmic Solution (Elestat)
Epivir HBV
Epogen (Epoetin alfa)
Erythromycin Topical Solution 1.5% (Staticin)
Ethiodol (Ethiodized Oil)
Ethosuximide Oral Solution (Zarontin Oral Solution)
Eurax
Extraneal (Icodextrin Peritoneal Dialysis Solution)
Felbatol
Feridex I.V. (Ferumoxides Injectable Solution)
Flovent
Floxin Otic (Ofloxacin Otic Solution)
Flo-Pred (Prednisolone Acetate Oral Suspension)
Fluoroplex
Flunisolide Nasal Solution (Flunisolide Nasal Spray 0.025%)
Fluorometholone Ophthalmic Suspension (FML)
Flurbiprofen Sodium Ophthalmic Solution (Ocufen)
FML
Foradil
Formoterol Fumarate Inhalation Solution (Perforomist)
Fosamax
Furadantin (Nitrofurantoin Oral Suspension)
Furoxone
Gammagard Liquid (Immune Globulin Intravenous (Human) 10%)
Gantrisin (Acetyl Sulfisoxazole Pediatric Suspension)
Gatifloxacin Ophthalmic Solution (Zymar)
Gengraf Oral Solution (Cyclosporine Oral Solution)
Glycopyrrolate Oral Solution (Cuvposa)
Halcinonide Topical Solution (Halog Solution)
Halog Solution (Halcinonide Topical Solution)
HEP-LOCK U/P (Preservative-Free Heparin Lock Flush Solution)
Heparin Lock Flush Solution (Hepflush 10

Hexaminolevulinate Hydrochloride Intravesical Solution (Cysview)
Hydrocodone Bitartrate and Acetaminophen Oral Solution (Lortab Elixir)
Hydroquinone 3% Topical Solution (Melquin-3 Topical Solution)
IAP Antagonist
Isopto
Ipratropium Bromide Nasal Spray (Atrovent Nasal Spray)
Itraconazole Oral Solution (Sporanox Oral Solution)
Ketorolac Tromethamine Ophthalmic Solution (Acular LS)
Kaletra
Lanoxin
Lexiva
Leuprolide Acetate for Depot Suspension (Lupron Depot 11.25 mg)
Levobetaxolol Hydrochloride Ophthalmic Suspension (Betaxon)
Levocarnitine Tablets, Oral Solution, Sugar-Free (Carnitor)
Levofloxacin Ophthalmic Solution 0.5% (Quixin)
Lidocaine HCl Sterile Solution (Xylocaine MPF Sterile Solution)
Lok Pak (Heparin Lock Flush Solution)
Lorazepam Intensol
Lortab Elixir (Hydrocodone Bitartrate and Acetaminophen Oral Solution)
Lotemax (Loteprednol Etabonate Ophthalmic Suspension)
Loteprednol Etabonate Ophthalmic Suspension (Alrex)
Low Calcium Peritoneal Dialysis Solutions (Dianeal Low Calcium)
Lumigan (Bimatoprost Ophthalmic Solution 0.03% for Glaucoma)
Lupron Depot 11.25 mg (Leuprolide Acetate for Depot Suspension)
Megestrol Acetate Oral Suspension (Megestrol Acetate Oral Suspension)
MEK Inhibitor
Mepron
Mesnex
Mestinon
Mesalamine Rectal Suspension Enema (Rowasa)
Melquin-3 Topical Solution (Hydroquinone 3% Topical Solution)
MetMab
Methyldopate Hcl (Methyldopate Hydrochloride Injection, Solution)
Methylin Oral Solution (Methylphenidate HCl Oral Solution 5 mg/5 mL and 10 mg/5 mL)
Methylprednisolone Acetate Injectable Suspension (Depo Medrol)
Methylphenidate HCl Oral Solution 5 mg/5 mL and 10 mg/5 mL (Methylin Oral Solution)
Methylprednisolone sodium succinate (Solu Medrol)
Metipranolol Ophthalmic Solution (Optipranolol)
Migranal
Miochol-E (Acetylcholine Chloride Intraocular Solution)
Micro-K for Liquid Suspension (Potassium Chloride Extended Release Formulation for Liquid Suspension)
Minocin (Minocycline Hydrochloride Oral Suspension)
Nasacort
Neomycin and Polymyxin B Sulfates and Hydrocortisone
Nepafenac Ophthalmic Suspension (Nevanac)
Nevanac (Nepafenac Ophthalmic Suspension)
Nitrofurantoin Oral Suspension (Furadantin)
Noxafil (Posaconazole Oral Suspension)
Nystatin (oral) (Nystatin Oral Suspension)
Nystatin Oral Suspension (Nystatin (oral))
Ocufen (Flurbiprofen Sodium Ophthalmic Solution)
Ofloxacin Ophthalmic Solution (Ofloxacin Ophthalmic Solution)
Ofloxacin Otic Solution (Floxin Otic)
Olopatadine Hydrochloride Ophthalmic Solution (Pataday)
Opticrom (Cromolyn Sodium Ophthalmic Solution)
Optipranolol (Metipranolol Ophthalmic Solution)
Patanol
Pediapred
PerioGard
Phenytoin Oral Suspension (Dilantin 125)
Phisohex
Posaconazole Oral Suspension (Noxafil)
Potassium Chloride Extended Release Formulation for Liquid Suspension (Micro-K for Liquid Suspension)
Pataday (Olopatadine Hydrochloride Ophthalmic Solution)
Patanase Nasal Spray (Olopatadine Hydrochloride Nasal Spray)
PEG Electrolytes Solution (CoLyte)
Pemirolast Potassium Ophthalmic Solution (Alamast)
Penlac (Ciclopirox Topical Solution)
PENNSAID (Diclofenac Sodium Topical Solution)
Perforomist (Formoterol Fumarate Inhalation Solution)
Peritoneal Dialysis Solution
Phenylephrine Hydrochloride Ophthalmic Solution (Neo-Synephrine)
Phospholine Iodide (Echothiophate Iodide for Ophthalmic Solution)
Podofilox (Podofilox Topical Solution)
Pred Forte (Prednisolone Acetate Ophthalmic Suspension)
Pralatrexate Solution for Intravenous Injection (Folotyn)
Pred Mild
Prednisone Intensol
Prednisolone Acetate Ophthalmic Suspension (Pred Forte)
Prevacid
PrismaSol Solution (Sterile Hemofiltration Hemodiafiltration Solution)
ProAir
Proglycem
ProHance (Gadoteridol Injection Solution)
Proparacaine Hydrochloride Ophthalmic Solution (Alcaine)
Propine
Pulmicort
Pulmozyme
Quixin (Levofloxacin Ophthalmic Solution 0.5%)
QVAR
Rapamune
Rebetol
Relacon-HC
Rotarix (Rotavirus Vaccine, Live, Oral Suspension)
Rotavirus Vaccine, Live, Oral Suspension (Rotarix)
Rowasa (Mesalamine Rectal Suspension Enema)
Sabril (Vigabatrin Oral Solution)
Sacrosidase Oral Solution (Sucraid)
Sandimmune
Sepra
Serevent Diskus
Solu Cortef (Hydrocortisone Sodium Succinate)

Solu Medrol (Methylprednisolone sodium succinate)
Spiriva
Sporanox Oral Solution (Itraconazole Oral Solution)
Staticin (Erythromycin Topical Solution 1.5%)
Stalevo
Starlix
Sterile Hemofiltration Hemodiafiltration Solution (PrismaSol Solution)
Stimate
Sucralfate (Carafate Suspension)
Sulfacetamide Sodium Ophthalmic Solution 10% (Bleph 10
Synarel Nasal Solution (Nafarelin Acetate Nasal Solution for Endometriosis)
Taclonex Scalp (Calcipotriene and Betamethasone Dipropionate Topical Suspension)
Tamiflu
Tobi
TobraDex
Tobradex ST (Tobramycin/Dexamethasone Ophthalmic Suspension 0.3%/0.05%)
Tobramycin/Dexamethasone Ophthalmic Suspension 0.3%/0.05% (Tobradex ST)
Timolol
Timoptic
Travatan Z
Treprostinil Inhalation Solution (Tyvaso)
Trusopt (Dorzolamide Hydrochloride Ophthalmic Solution)
Tyvaso (Treprostinil Inhalation Solution)
Ventolin
Vfend
Vibramycin Oral (Doxycycline Calcium Oral Suspension)
Videx (Didanosine Pediatric Powder for Oral Solution)
Vigabatrin Oral Solution (Sabril)
Viokase
Viracept
Viramune
Vitamin K1 (Fluid Colloidal Solution of Vitamin K1)
Voltaren Ophthalmic (Diclofenac Sodium Ophthalmic Solution)
Zarontin Oral Solution (Ethosuximide Oral Solution)
Ziagen
Zyvox
Zymar (Gatifloxacin Ophthalmic Solution)
Zymaxid (Gatifloxacin Ophthalmic Solution)
Drug Classes
  5-alpha-reductase inhibitors
  5-aminosalicylates
  5HT3 receptor antagonists
  adamantane antivirals
  adrenal cortical steroids
  adrenal corticosteroid inhibitors
  adrenergic bronchodilators
  agents for hypertensive emergencies
  agents for pulmonary hypertension
  aldosterone receptor antagonists
  alkylating agents
  alpha-adrenoreceptor antagonists
  alpha-glucosidase inhibitors
  alternative medicines
  amebicides
  aminoglycosides
  aminopenicillins
  aminosalicylates
  amylin analogs
  Analgesic Combinations
  Analgesics
  androgens and anabolic steroids
  angiotensin converting enzyme inhibitors
  angiotensin II inhibitors
  anorectal preparations
  anorexiants
  antacids
  anthelmintics
  anti-angiogenic ophthalmic agents
  anti-CTLA-4 monoclonal antibodies
  anti-infectives
  antiadrenergic agents, centrally acting
  antiadrenergic agents, peripherally acting
  antiandrogens
  antianginal agents
  antiarrhythmic agents
  antiasthmatic combinations
  antibiotics/antineoplastics
  anticholinergic antiemetics
  anticholinergic antiparkinson agents
  anticholinergic bronchodilators
  anticholinergic chronotropic agents
  anticholinergics/antispasmodics
  anticoagulants
  anticonvulsants
  antidepressants
  antidiabetic agents
  antidiabetic combinations
  antidiarrheals
  antidiuretic hormones
  antidotes
  antiemetic/antivertigo agents
  antifungals
  antigonadotropic agents
  antigout agents
  antihistamines
  antihyperlipidemic agents
  antihyperlipidemic combinations
  antihypertensive combinations
  antihyperuricemic agents
  antimalarial agents
  antimalarial combinations
  antimalarial quinolines
  antimetabolites
  antimigraine agents
  antineoplastic detoxifying agents
  antineoplastic interferons
  antineoplastic monoclonal antibodies
  antineoplastics
  antiparkinson agents
  antiplatelet agents
  antipseudomonal penicillins
  antipsoriatics
  antipsychotics
  antirheumatics
  antiseptic and germicides
  antithyroid agents
  antitoxins and antivenins
  antituberculosis agents
  antituberculosis combinations
  antitussives
  antiviral agents
  antiviral combinations
  antiviral interferons
  anxiolytics, sedatives, and hypnotics
  aromatase inhibitors
  atypical antipsychotics azole antifungals
bacterial vaccines
barbiturate anticonvulsants
barbiturates
BCR-ABL tyrosine kinase inhibitors
benzodiazepine anticonvulsants
benzodiazepines
beta-adrenergic blocking agents
beta-lactamase inhibitors
bile acid sequestrants
biologicals
bisphosphonates
bone resorption inhibitors
bronchodilator combinations
bronchodilators
calcitonin
calcium channel blocking agents
carbamate anticonvulsants
carbapenems
carbonic anhydrase inhibitor anticonvulsants
carbonic anhydrase inhibitors
cardiac stressing agents
cardioselective beta blockers
cardiovascular agents
catecholamines
CD20 monoclonal antibodies
CD33 monoclonal antibodies
CD52 monoclonal antibodies
central nervous system agents
cephalosporins
cerumenolytics
chelating agents
chemokine receptor antagonist
chloride channel activators
cholesterol absorption inhibitors
cholinergic agonists
cholinergic muscle stimulants
cholinesterase inhibitors
CNS stimulants
coagulation modifiers
colony stimulating factors
contraceptives
corticotropin
coumarins and indandiones
cox-2 inhibitors
decongestants
dermatological agents
diagnostic radiopharmaceuticals
dibenzazepine anticonvulsants
digestive enzymes
dipeptidyl peptidase 4 inhibitors
diuretics
dopaminergic antiparkinsonism agents
drugs used in alcohol dependence
echinocandins
EGFR inhibitors
estrogen receptor antagonists
estrogens
expectorants
factor Xa inhibitors
fatty acid derivative anticonvulsants
fibric acid derivatives
first generation cephalosporins
fourth generation cephalosporins
functional bowel disorder agents
gallstone solubilizing agents
gamma-aminobutyric acid analogs gamma-aminobutyric acid reuptake inhibitors
gamma-aminobutyric acid transaminase inhibitors
gastrointestinal agents
general anesthetics
genitourinary tract agents
GI stimulants
glucocorticoids
glucose elevating agents
glycopeptide antibiotics
glycoprotein platelet inhibitors
glycylcyclines
gonadotropin releasing hormones
gonadotropin-releasing hormone antagonists
gonadotropins
group I antiarrhythmics
group II antiarrhythmics
group III antiarrhythmics
group IV antiarrhythmics
group V antiarrhythmics
growth hormone receptor blockers
growth hormones
*H. pylori* eradication agents
H2 antagonists
hematopoietic stem cell mobilizer
heparin antagonists
heparins
HER2 inhibitors
herbal products
histone deacetylase inhibitors
hormone replacement therapy
hormones
hormones/antineoplastics
hydantoin anticonvulsants
illicit (street) drugs
immune globulins
immunologic agents
immunosuppressive agents
impotence agents
in vivo diagnostic biologicals
incretin mimetics
inhaled anti-infectives
inhaled corticosteroids
inotropic agents
insulin
insulin-like growth factor
integrase strand transfer inhibitor
interferons
intravenous nutritional products
iodinated contrast media
ionic iodinated contrast media
iron products
ketolides
laxatives
leprostatics
leukotriene modifiers
lincomycin derivatives
lipoglycopeptides
local injectable anesthetics
loop diuretics
lung surfactants
lymphatic staining agents
lysosomal enzymes
macrolide derivatives
macrolides
magnetic resonance imaging contrast media
mast cell stabilizers
medical gas meglitinides
metabolic agents
methylxanthines
mineralocorticoids
minerals and electrolytes
miscellaneous agents
miscellaneous analgesics
miscellaneous antibiotics
miscellaneous anticonvulsants
miscellaneous antidepressants
miscellaneous antidiabetic agents
miscellaneous antiemetics
miscellaneous antifungals
miscellaneous antihyperlipidemic agents
miscellaneous antimalarials
miscellaneous antineoplastics
miscellaneous antiparkinson agents
miscellaneous antipsychotic agents
miscellaneous antituberculosis agents
miscellaneous antivirals
miscellaneous anxiolytics, sedatives and hypnotics
miscellaneous biologicals
miscellaneous bone resorption inhibitors
miscellaneous cardiovascular agents
miscellaneous central nervous system agents
miscellaneous coagulation modifiers
miscellaneous diuretics
miscellaneous genitourinary tract agents
miscellaneous GI agents
miscellaneous hormones
miscellaneous metabolic agents
miscellaneous ophthalmic agents
miscellaneous otic agents
miscellaneous respiratory agents
miscellaneous sex hormones
miscellaneous topical agents
miscellaneous uncategorized agents
miscellaneous vaginal agents
mitotic inhibitors
monoamine oxidase inhibitors
monoclonal antibodies
mouth and throat products
mTOR inhibitors
mTOR kinase inhibitors
mucolytics
multikinase inhibitors
muscle relaxants
mydriatics
narcotic analgesic combinations
narcotic analgesics
nasal anti-infectives
nasal antihistamines and decongestants
nasal lubricants and irrigations
nasal preparations
nasal steroids
natural penicillins
neuraminidase inhibitors
neuromuscular blocking agents
next generation cephalosporins
nicotinic acid derivatives
nitrates
NNRTIs
non-cardioselective beta blockers
non-iodinated contrast media
non-ionic iodinated contrast media
non-sulfonylureas
nonsteroidal anti-inflammatory agents
norepinephrine reuptake inhibitors
norepinephrine-dopamine reuptake inhibitors
nucleoside reverse transcriptase inhibitors (NRTIs)
nutraceutical products
nutritional products
ophthalmic anesthetics
ophthalmic anti-infectives
ophthalmic anti-inflammatory agents
ophthalmic antihistamines and decongestants
ophthalmic diagnostic agents
ophthalmic glaucoma agents
ophthalmic lubricants and irrigations
ophthalmic preparations
ophthalmic steroids
ophthalmic steroids with anti-infectives
ophthalmic surgical agents
oral nutritional supplements
otic anesthetics
otic anti-infectives
otic preparations
otic steroids
otic steroids with anti-infectives
oxazolidinedione anticonvulsants
parathyroid hormone and analogs
penicillinase resistant penicillins
penicillins
peripheral opioid receptor antagonists
peripheral vasodilators
peripherally acting antiobesity agents
phenothiazine antiemetics
phenothiazine antipsychotics
phenylpiperazine antidepressants
plasma expanders
platelet aggregation inhibitors
platelet-stimulating agents
polyenes
potassium-sparing diuretics
probiotics
progesterone receptor modulators
progestins
prolactin inhibitors
prostaglandin D2 antagonists
protease inhibitors
proton pump inhibitors
psoralens
psychotherapeutic agents
psychotherapeutic combinations
purine nucleosides
pyrrolidine anticonvulsants
quinolones
radiocontrast agents
radiologic adjuncts
radiologic agents
radiologic conjugating agents
radiopharmaceuticals
RANK ligand inhibitors
recombinant human erythropoietins
renin inhibitors
respiratory agents
respiratory inhalant products
rifamycin derivatives
salicylates
sclerosing agents
second generation cephalosporins
selective estrogen receptor modulators
selective serotonin reuptake inhibitors
serotonin-norepinephrine reuptake inhibitors serotoninergic neuroenteric modulators
sex hormone combinations
sex hormones
skeletal muscle relaxant combinations
skeletal muscle relaxants
smoking cessation agents
somatostatin and somatostatin analogs
spermicides
statins
sterile irrigating solutions
streptomyces derivatives
succinimide anticonvulsants
sulfonamides
sulfonylureas
synthetic ovulation stimulants
tetracyclic antidepressants
tetracyclines
therapeutic radiopharmaceuticals
thiazide diuretics
thiazolidinediones
thioxanthenes
third generation cephalosporins
thrombin inhibitors
thrombolytics
thyroid drugs
tocolytic agents
topical acne agents
topical agents
topical anesthetics
topical anti-infectives
topical antibiotics
topical antifungals
topical antihistamines
topical antipsoriatics
topical antivirals
topical astringents
topical debriding agents
topical depigmenting agents
topical emollients
topical keratolytics
topical steroids
topical steroids with anti-infectives
toxoids
triazine anticonvulsants
tricyclic antidepressants
trifunctional monoclonal antibodies
tumor necrosis factor (TNF) inhibitors
tyrosine kinase inhibitors
ultrasound contrast media
upper respiratory combinations
urea anticonvulsants
urinary anti-infectives
urinary antispasmodics
urinary pH modifiers
uterotonic agents
vaccine
vaccine combinations
vaginal anti-infectives
vaginal preparations
vasodilators
vasopressin antagonists
vasopressors
VEGF/VEGFR inhibitors
viral vaccines
viscosupplementation agents
vitamin and mineral combinations
vitamins Diagnostic Tests
17-Hydroxyprogesterone
ACE (Angiotensin I converting enzyme)
Acetaminophen
Acid phosphatase
ACTH
Activated clotting time
Activated protein C resistance
Adrenocorticotropic hormone (ACTH)
Alanine aminotransferase (ALT)
Albumin
Aldolase
Aldosterone
Alkaline phosphatase
Alkaline phosphatase (ALP)
Alpha1-antitrypsin
Alpha-fetoprotein
Alpha-fetoprotien
Ammonia levels
Amylase
ANA (antinuclear antbodies)
ANA (antinuclear antibodies)
Angiotensin-converting enzyme (ACE)
Anion gap
Anticardiolipin antibody
Anticardiolipin antivbodies (ACA)
Anti-centromere antibody
Antidiuretic hormone
Anti-DNA
Anti-Dnase-B
Anti-Gliadin antibody
Anti-glomerular basement membrane antibody
Anti-HBc (Hepatitis B core antibodies
Anti-HBs (Hepatitis B surface antibody
Antiphospholipid antibody
Anti-RNA polymerase
Anti-Smith (Sm) antibodies
Anti-Smooth Muscle antibody
Antistreptolysin O (ASO)
Antithrombin III
Anti-Xa activity
Anti-Xa assay
Apolipoproteins
Arsenic
Aspartate aminotransferase (AST)
B12
Basophil
Beta-2-Microglobulin
Beta-hydroxybutyrate
B-HCG
Bilirubin
Bilirubin, direct
Bilirubin, indirect
Bilirubin, total
Bleeding time
Blood gases (arterial)
Blood urea nitrogen (BUN)
BUN
BUN (blood urea nitrogen)
CA 125
CA 15-3
CA 19-9
Calcitonin
Calcium
Calcium (ionized)
Carbon monoxide (CO)
Carcinoembryonic antigen (CEA)

CBC
CEA
CEA (carcinoembryonic antigen)
Ceruloplasmin
CH50Chloride
Cholesterol
Cholesterol, HDL
Clot lysis time
Clot retraction time
CMP
$CO_2$
Cold agglutinins
Complement C3
Copper
Corticotrophin releasing hormone (CRH) stimulation test
Cortisol
Cortrosyn stimulation test
C-peptide
CPK (Total)
CPK-MB
C-reactive protein
Creatinine
Creatinine kinase (CK)
Cryoglobulins
DAT (Direct antiglobulin test)
D-Dimer
Dexamethasone suppression test
DHEA-S
Dilute Russell viper venom
Elliptocytes
Eosinophil
Erythrocyte sedimentation rate (ESR)
Estradiol
Estriol
Ethanol
Ethylene glycol
Euglobulin lysis
Factor V Leiden
Factor VIII inhibitor
Factor VIII level
Ferritin
Fibrin split products
Fibrinogen
Folate
Folate (serum
Fractional excretion of sodium (FENA)
FSH (follicle stimulating factor)
FTA-ABS
Gamma glutamyl transferase (GGT)
Gastrin
GGTP (Gamma glutamyl transferase)
Glucose
Growth hormone
Haptoglobin
HBeAg (Hepatitis Be antigen)
HBs-Ag (Hepatitis B surface antigen)
*Helicobacter pylori*
Hematocrit
Hematocrit (HCT)
Hemoglobin
Hemoglobin A1C
Hemoglobin electrophoresis
Hepatitis A antibodies
Hepatitis C antibodies
IAT (Indirect antiglobulin test)
Immunofixation (IFE)
Iron
Lactate dehydrogenase (LDH)
Lactic acid (lactate)
LDH
LH (Leutinizing hormone
Lipase
Lupus anticoagulant
Lymphocyte
Magnesium
MCH (mean corpuscular hemoglobin
MCHC (mean corpuscular hemoglobin concentration)
MCV (mean corpuscular volume)
Methylmalonate
Monocyte
MPV (mean platelet volume)
Myoglobin
Neutrophil
Parathyroid hormone (PTH)
Phosphorus
Platelets (plt)
Potassium
Prealbumin
Prolactin
Prostate specific antigen (PSA)
Protein C
Protein S
PSA (prostate specific antigen)
PT (Prothrombin time)
PTT (Partial thromboplastin time)
RDW (red cell distribution width)
Renin
Rennin
Reticulocyte count
reticulocytes
Rheumatoid factor (RF)
Sed Rate
Serum glutamic-pyruvic transaminase (SGPT
Serum protein electrophoresis (SPEP)
Sodium
T3-resin uptake (T3RU)
T4, Free
Thrombin time
Thyroid stimulating hormone (TSH)
Thyroxine (T4
Total iron binding capacity (TIBC)
Total protein
Transferrin
Transferrin saturation
Triglyceride (TG)
Troponin
Uric acid
Vitamin B12
White blood cells (WBC)
Widal test As several examples, the fluid composition 218 can be an inhalation anesthetic, a drug, or a diagnostic test material. Any of these fluid compositions 218 can be an injectable material, a volatile material capable of being inhaled, or otherwise capable of being introduced into a subject.

In the embodiment of FIG. 8 in particular, the pharmaceutical package 210 is a syringe. The syringe can comprise a syringe barrel 250 and a plunger 258. The wall 214 can define at least a portion of the syringe barrel 250. The plunger 258 can be a relatively sliding part of the syringe, with respect to the syringe barrel 250. The term "syringe," however, is broadly defined to include cartridges, injection "pens," and other types of barrels or reservoirs adapted to be assembled with one or more other components to provide a functional syringe. "Syringe" is also broadly defined to include related articles such as auto-injectors, which provide a mechanism for dispensing the contents.

Another aspect of the invention illustrated by FIGS. 8-10 is an article such as any of the pharmaceutical packages or other vessels 210 including a wall 214, a fluid composition 218, a composite barrier coating or layer 288, and a pH protective coating 286.

The wall 214 has an inner or interior surface 254.

The fluid composition 218 is contained in the lumen 212 and has a pH between 5 and 9.

The composite barrier coating or layer 288 is made at least in part of $SiO_x$, wherein x is from 1.5 to 2.4, from 2 to 1000 nm thick. The composite barrier coating or layer 288 of $SiO_x$ has an interior surface 220 facing the lumen 212 and an outer surface 222 facing the wall inner or interior surface 254. The composite barrier coating or layer 288 is effective to reduce the ingress of atmospheric gas into the lumen 212, compared to an uncoated container otherwise the same as the pharmaceutical package or other vessel 210.

The pH protective coating 286 is made at least in part of $SiO_xC_y$ or $SiN_xC_y$ where x is from about 0.5 to about 2.4 and y is from about 0.6 to about 3. The pH protective coating 286 has an interior surface 224 facing the lumen 212 and an outer surface 226 facing the interior surface 254 of the composite barrier coating or layer 288. The pH protective coating 286 is formed by chemical vapor deposition of a precursor selected from a monocyclic siloxane, a polycyclic siloxane, a polysilsesquioxane, a monocyclic silazane, a polycyclic silazane, a polysilsesquiazane, a silatrane, a silquasilatrane, a silproatrane, an azasilatrane, an azasilquasiatrane, an azasilproatrane, or a combination of any two or more of these precursors. One specific example of a suitable pH protective coating precursor of this type is octamethylcyclotetrasiloxane or OMCTS. Other specific examples of precursors within this broad definition are provided elsewhere in this specification.

The rate of erosion, dissolution, or leaching (different names for related concepts) of the pH protective coating 286, if directly contacted by the fluid composition 218, is less than the rate of erosion of the composite barrier coating or layer 288, if directly contacted by the fluid composition 218.

The pH protective coating 286 is effective to isolate the fluid composition 218 from the composite barrier coating or layer 288, at least for sufficient time to allow the barrier coating to act as a barrier during the shelf life of the pharmaceutical package or other vessel 210.

Still another aspect of the invention, again illustrated by FIGS. 8-10, is a pharmaceutical package or other vessel 210 including a thermoplastic wall 214 having an inner or interior surface 220 enclosing a lumen 212. A fluid composition 218 contained in the lumen 212 has a pH greater than 5.

A composite barrier coating or layer 286 of $SiO_x$, in which x is between 1.5 and 2.4, is applied by plasma enhanced chemical vapor deposition (PECVD) directly or indirectly to the thermoplastic wall 214 so that in the filled pharmaceutical package or other vessel 210 the composite barrier coating or layer 286 is located between the inner or interior surface 220 of the thermoplastic wall 214 and the fluid composition 218. The composite barrier coating or layer 286 of $SiO_x$ is supported by the thermoplastic wall 214. The composite barrier coating or layer 286 has the characteristic of being subject to being measurably diminished in barrier improvement factor in less than six months as a result of attack by the fluid composition 218. The composite barrier coating or layer 286 as described elsewhere in this specification, or in U.S. Pat. No. 7,985,188, can be used in any embodiment.

The barrier improvement factor (BIF) of the barrier layer can be determined by providing two groups of identical containers, adding a barrier layer to one group of containers, testing a barrier property (such as the rate of outgassing in micrograms per minute or another suitable measure) on containers having a barrier, doing the same test on containers lacking a barrier, and taking a ratio of the properties of the materials with versus without a barrier. For example, if the rate of outgassing through the barrier is one-third the rate of outgassing without a barrier, the barrier has a BIF of 3.

A pH protective coating 286 of $SiO_xC_y$, in which x is between 0.5 and 2.4 and y is between 0.6 and 3, is applied by PECVD directly or indirectly to the composite barrier coating or layer 288 so it is located between the composite barrier coating or layer 288 and the fluid composition 218 in the finished article. The pH protective coating 286 is supported by the thermoplastic wall 214. The pH protective coating 286 is effective to keep the composite barrier coating or layer 288 at least substantially undissolved as a result of attack by the fluid composition 218 for a period of at least six months.

Any embodiment of FIGS. 8-10 can further optionally include a lubricity layer 287. The lubricity layer 287 can be applied between the pH protective coating and the lumen. Lubricity layers 287 as described elsewhere in this specification, or in U.S. Pat. No. 7,985,188, can be used in any embodiment.

Any embodiment of FIGS. 8-10 can further optionally include a further coating applied adjacent to the inner surface of the pH protective coating, the further coating having an outer surface facing the interior surface of the thermoplastic wall and an inner surface facing the lumen.

Optionally, any embodiment of FIGS. 8-10 can further include a fluid composition 218 in contact with the pH protective coating The pH protective and lubricity layers 286 and 287 of any embodiment of FIGS. 8-10 can be either separate layers with a sharp transition or a single, graduated layer that transitions between the pH protective coating 286 and the lubricity layer 287, without a sharp interface between them.

Optionally an FTIR absorbance spectrum of the pH protective coating 286 of any embodiment of FIGS. 8-10 has a ratio greater than 0.75 between the maximum amplitude of the Si—O—Si symmetrical stretch peak normally located between about 1000 and 1040 $cm^{-1}$, and the maximum amplitude of the Si—O—Si asymmetric stretch peak normally located between about 1060 and about 1100 $cm^{-1}$. Alternatively in any embodiment, this ratio can be at least 0.8, or at least 0.9, or at least 1.0, or at least 1.1, or at least 1.2. Alternatively in any embodiment, this ratio can be at most 1.7, or at most 1.6, or at most 1.5, or at most 1.4, or at most 1.3. Any minimum ratio stated here can be combined with any maximum ratio stated here, as an alternative embodiment of the invention of FIGS. 8-10.

Optionally, in any embodiment of FIGS. 8-10 the pH protective coating, in the absence of the medicament, has a non-oily appearance. This appearance has been observed in some instances to distinguish an effective pH protective coating from a lubricity layer, which in some instances has been observed to have an oily (i.e. shiny) appearance.

Optionally, in any embodiment of FIGS. 8-10 the silicon dissolution rate by a 50 mM potassium phosphate buffer diluted in water for injection, adjusted to pH 8 with concentrated nitric acid, and containing 0.2 wt. % polysorbate- 80 surfactant, (measured in the absence of the medicament, to avoid changing the dissolution reagent), at 40° C., is less than 170 ppb/day. (Polysorbate-80 is a common ingredient of pharmaceutical preparations, available for example as Tween®-80 from Uniqema Americas LLC, Wilmington Delaware) As will be seen from the working examples, the silicon dissolution rate is measured by determining the total silicon leached from the vessel into its contents, and does not distinguish between the silicon derived from the pH protective coating 286, the lubricity layer 287, the composite barrier coating or layer 288, or other materials present.

Optionally, in any embodiment of FIGS. 8-10 the silicon dissolution rate is less than 160 ppb/day, or less than 140 ppb/day, or less than 120 ppb/day, or less than 100 ppb/day, or less than 90 ppb/day, or less than 80 ppb/day. Optionally, in any embodiment of FIGS. 8-10 the silicon dissolution rate is more than 10 ppb/day, or more than 20 ppb/day, or more than 30 ppb/day, or more than 40 ppb/day, or more than 50 ppb/day, or more than 60 ppb/day. Any minimum rate stated here can be combined with any maximum rate stated here, as an alternative embodiment of the invention of FIGS. 8-10.

Optionally, in any embodiment of FIGS. 8-10 the total silicon content of the pH protective coating and barrier coating, upon dissolution into a test composition with a pH of 8 from the vessel, is less than 66 ppm, or less than 60 ppm, or less than 50 ppm, or less than 40 ppm, or less than 30 ppm, or less than 20 ppm.

Optionally, in any embodiment of FIGS. 8-10 the calculated shelf life of the package (total Si/Si dissolution rate) is more than six months, or more than 1 year, or more than 18 months, or more than 2 years, or more than 2½ years, or more than 3 years, or more than 4 years, or more than 5 years, or more than 10 years, or more than 20 years. Optionally, in any embodiment of FIGS. 8-10 the calculated shelf life of the package (total Si/Si dissolution rate) is less than 60 years.

Any minimum time stated here can be combined with any maximum time stated here, as an alternative embodiment of the invention of FIGS. 8-10.

Optionally, in any embodiment of FIGS. 8-10 the pH protective coating is applied by PECVD at a power level per of more than 22,000 kJ/kg of mass of precursor, or more than 30,000 kJ/kg of mass of precursor, or more than 40,000 kJ/kg of mass of precursor, or more than 50,000 kJ/kg of mass of precursor, or more than 60,000 kJ/kg of mass of precursor, or more than 62,000 kJ/kg of mass of precursor, or more than 70,000 kJ/kg of mass of precursor, or more than 80,000 kJ/kg of mass of precursor, or more than 100,000 kJ/kg of mass of precursor, or more than 200,000 kJ/kg of mass of precursor, or more than 300,000 kJ/kg of mass of precursor, or more than 400,000 kJ/kg of mass of precursor, or more than 500,000 kJ/kg of mass of precursor.

Optionally, in any embodiment of FIGS. 8-10 the pH protective coating is applied by PECVD at a power level per of less than 2,000,000 kJ/kg of mass of precursor, or less than 1,000,000 kJ/kg of mass of precursor, or less than 700,000 kJ/kg of mass of precursor, or less than 500,000 kJ/kg of mass of precursor, or less than 100,000 kJ/kg of mass of precursor, or less than 90,000 kJ/kg of mass of precursor, or less than 81,000 kJ/kg of mass of precursor.

Optionally, in any embodiment of FIGS. 8-10, the thermoplastic wall is a syringe barrel. A plunger is positioned for sliding in the barrel and a lubricity coating or layer is present on at least a portion of the plunger.

Optionally, in any embodiment of FIGS. 8-10, the lubricity coating or layer is configured to provide a lower piston sliding force or breakout force than the uncoated substrate.

Optionally, in any embodiment of FIGS. 8-10, the lubricity layer has one of the atomic ratios previously defined for the lubricity and/or pH protective coating, measured by X-ray photoelectron spectroscopy (XPS). The lubricity layer has a thickness by transmission electron microscopy (TEM) between 10 and 500 nm; the lubricity layer deposited by plasma enhanced chemical vapor deposition (PECVD) under conditions effective to form a coating from a precursor selected from a linear siloxane, a monocyclic siloxane, a polycyclic siloxane, a polysilsesquioxane, a linear silazane, a monocyclic silazane, a polycyclic silazane, a polysilsesquiazane, a silatrane, a silquasilatrane, a silproatrane, an azasilatrane, an azasilquasiatrane, an azasilproatrane, or a combination of any two or more of these precursors.

Even another aspect of the invention, exemplified in FIGS. 8-10, is a composite material including a substrate such as a wall 214, a composite barrier coating or layer 288 disposed on the substrate or wall 214, and a passivation layer or pH protective coating 286 on the barrier layer or coating 288. Several examples of articles made from such a composite material are a syringe barrel, a vial, and a medical device of any kind. The passivation layer or pH protective coating 286 is deposited by PECVD using a source material comprising a monocyclic siloxane, a polycyclic siloxane, a polysilsesquioxane, a monocyclic silazane, a polycyclic silazane, a polysilsesquiazane, a silatrane, a silquasilatrane, a silproatrane, an azasilatrane, an azasilquasiatrane, an azasilproatrane, or a combination of any two or more of these precursors.

The passivation layer or pH protective coating, taking into account the H atoms, may thus in one aspect have the formula $Si_wO_xC_yH_z$, for example where w is 1, x is from about 0.5 to about 2.4, y is from about 0.6 to about 3, and z is from about 2 to about 9. Typically, expressed as the formula $Si_wO_xC_y$, the atomic ratios of Si, O, and C are, as several options:

Si 100: O 80-130: C 90-150,
Si 100: O 90-120: C 90-140, or
Si 100: O 92-107: C 116-133.

The passivation layer or pH protective coating 286 shows an O-Parameter measured with attenuated total reflection (ATR) of less than 0.4, measured as:

$$O\text{-Parameter} = \frac{\text{Intensity at } 1253 \text{ cm}^{-1}}{\text{Maximum intensity in the range } 1000 \text{ to } 1100 \text{ cm}^{-1}}$$

Figure 15:
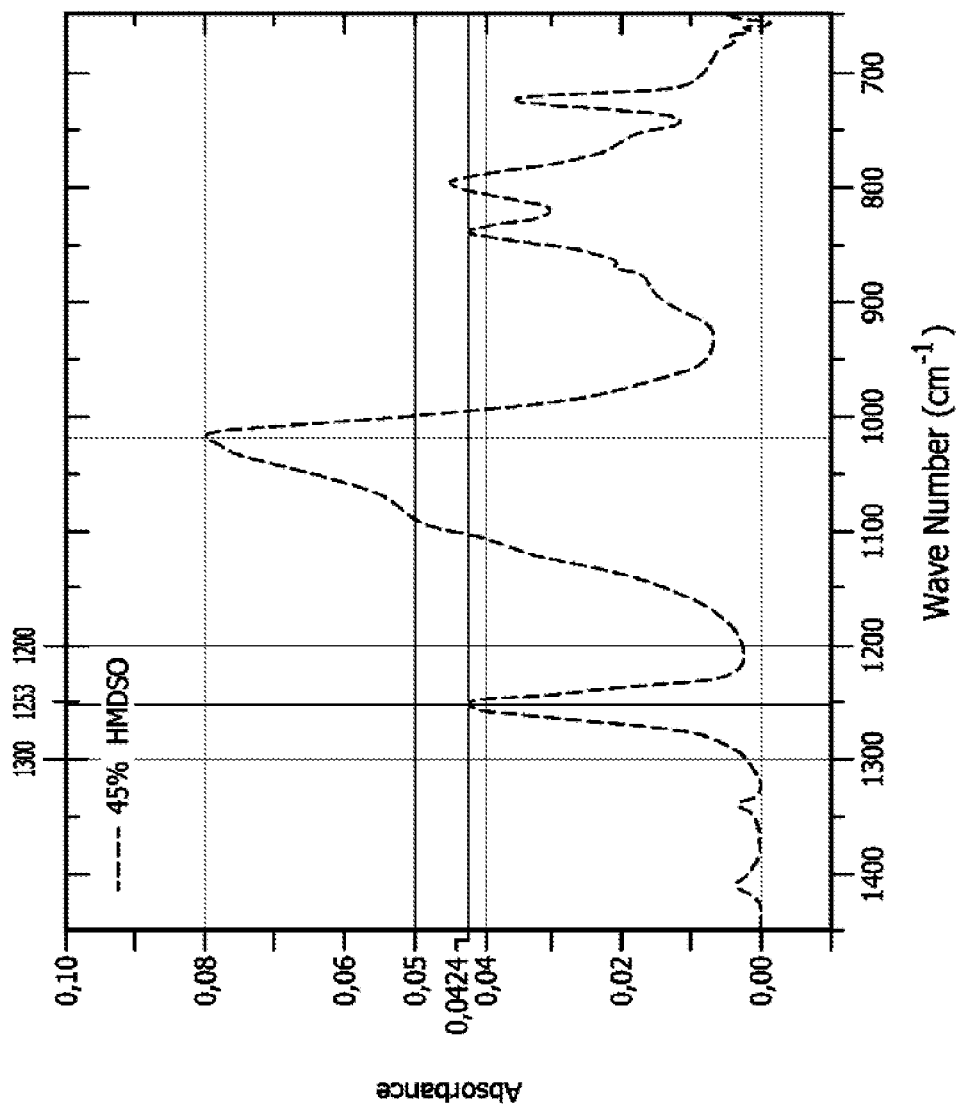
FIG. 15 is a FTIR amplitude versus wave number plot marked up from FIG. 5 of U.S. Pat. No. 8,067,070.

The O-Parameter is defined in U.S. Pat. No. 8,067,070, which claims an O-parameter value of most broadly from 0.4 to 0.9. It can be measured from physical analysis of an FTIR amplitude versus wave number plot to find the numerator and denominator of the above expression, as shown in FIG. 15, which is the same as FIG. 5 of U.S. Pat. No. 8,067,070, except annotated to show interpolation of the wave number and absorbance scales to arrive at an absorbance at 1253 cm$^{-1}$ of 0.0424 and a maximum absorbance at 1000 to 1100 cm$^{-1}$ of 0.08, resulting in a calculated O-parameter of 0.53. The O-Parameter can also be measured from digital wave number versus absorbance data.

U.S. Pat. No. 8,067,070 asserts that the claimed O-parameter range provides a superior pH protective coating or layer, relying on experiments only with HMDSO and HMDSN, which are both non-cyclic siloxanes. Surprisingly, it has been found by the present inventors that if the PECVD precursor is a cyclic siloxane, for example OMCTS, O-parameters outside the ranges claimed in U.S. Pat. No. 8,067, 070, using OMCTS, provide even better results than are obtained in U.S. Pat. No. 8,067,070 with HMDSO.

Alternatively in the embodiment of FIGS. 8-10, the O-parameter has a value of from 0.1 to 0.39, or from 0.15 to 0.37, or from 0.17 to 0.35.

Even another aspect of the invention is a composite material as just described, exemplified in FIGS. 8-10, wherein the passivation layer shows an N-Parameter measured with attenuated total reflection (ATR) of less than 0.7, measured as:

$$N\text{-Parameter} = \frac{\text{Intensity at 840 cm}^{-1}}{\text{Intensity at 799 cm}^{-1}}.$$

The N-Parameter is also described in U.S. Pat. No. 8,067,070, and is measured analogously to the O-Parameter except that intensities at two specific wave numbers are used—neither of these wave numbers is a range. U.S. Pat. No. 8,067,070 claims a passivation layer with an N-Parameter of 0.7 to 1.6. Again, the present inventors have made better coatings employing a pH protective coating 286 having an N-Parameter lower than 0.7, as described above. Alternatively, the N-parameter has a value of at least 0.3, or from 0.4 to 0.6, or at least 0.53.

Theory of Operation

The inventors offer the following theory of operation of the pH protective coating or layer described here. The invention is not limited by the accuracy of this theory or to the embodiments predictable by use of this theory.

The dissolution rate of the $SiO_x$ barrier layer is believed to be dependent on SiO bonding within the layer. Oxygen bonding sites (silanols) are believed to increase the dissolution rate.

It is believed that the OMCTS-based pH protective coating or layer bonds with the silanol sites on the $SiO_x$ barrier layer to "heal" or passivate the $SiO_x$ surface and thus dramatically reduces the dissolution rate. In this hypothesis, the thickness of the OMCTS layer is not the primary means of protection—the primary means is passivation of the $SiO_x$ surface. It is contemplated that a pH protective coating as described in this specification can be improved by increasing the crosslink density of the pH protective coating or layer.

Additional Embodiments

The pH protective coating described in this specification can be applied in many different ways. For one example, the low-pressure PECVD process described in U.S. Pat. No. 7,985,188 can be used. For another example, instead of using low-pressure PECVD, atmospheric PECVD can be employed to deposit the pH protective coating. For another example, the coating can be simply evaporated and allowed to deposit on the $SiO_x$ layer to be protected. For another example, the coating can be sputtered on the $SiO_x$ layer to be protected. For still another example, the pH protective coating or layer can be applied from a liquid medium used to rinse or wash the $SiO_x$ layer.

Other precursors and methods can be used to apply the pH protective coating or passivating treatment. For example, hexamethylene disilazane (HMDZ) can be used as the precursor. HMDZ has the advantage of containing no oxygen in its molecular structure. This passivation treatment is contemplated to be a surface treatment of the $SiO_x$ barrier layer with HMDZ. To slow down and/or eliminate the decomposition of the silicon dioxide coatings at silanol bonding sites, the coating must be passivated. It is contemplated that passivation of the surface with HMDZ (and optionally application of a few mono layers of the HMDZ-derived coating) will result in a toughening of the surface against dissolution, resulting in reduced decomposition. It is contemplated that HMDZ will react with the —OH sites that are present in the silicon dioxide coating, resulting in the evolution of $NH_3$ and bonding of S—$(CH_3)_3$ to the silicon (it is contemplated that hydrogen atoms will be evolved and bond with nitrogen from the HMDZ to produce $NH_3$).

It is contemplated that this HMDZ passivation can be accomplished through several possible paths.

One contemplated path is dehydration/vaporization of the HMDZ at ambient temperature. First, an $SiO_x$ surface is deposited, for example using hexamethylene disiloxane (HMDSO). The as-coated silicon dioxide surface is then reacted with HMDZ vapor. In an embodiment, as soon as the $SiO_x$ surface is deposited onto the article of interest, the vacuum is maintained. The HMDSO and oxygen are pumped away and a base vacuum is achieved. Once base vacuum is achieved, HMDZ vapor is flowed over the surface of the silicon dioxide (as coated on the part of interest) at pressures from the mTorr range to many Torr. The HMDZ is then pumped away (with the resulting $NH_3$ that is a byproduct of the reaction). The amount of $NH_3$ in the gas stream can be monitored (with a residual gas analyzer—RGA—as an example) and when there is no more $NH_3$ detected, the reaction is complete. The part is then vented to atmosphere (with a clean dry gas or nitrogen). The resulting surface is then found to have been passivated. It is contemplated that this method optionally can be accomplished without forming a plasma.

Alternatively, after formation of the $SiO_x$ composite barrier coating or layer, the vacuum can be broken before dehydration/vaporization of the HMDZ.

Dehydration/vaporization of the HMDZ can then be carried out in either the same apparatus used for formation of the $SiO_x$ composite barrier coating or layer or different apparatus.

Dehydration/vaporization of HMDZ at an elevated temperature is also contemplated. The above process can alternatively be carried out at an elevated temperature exceeding room temperature up to about 150° C. The maximum temperature is determined by the material from which the coated part is constructed. An upper temperature should be selected that will not distort or otherwise damage the part being coated.

Dehydration/vaporization of HMDZ with a plasma assist is also contemplated. After carrying out any of the above embodiments of dehydration/vaporization, once the HMDZ vapor is admitted into the part, a plasma is generated. The plasma power can range from a few watts to 100+ watts (similar powers as used to deposit the $SiO_x$). The above is not limited to HMDZ and could be applicable to any molecule that will react with hydrogen, for example any of the nitrogen-containing precursors described in this specification.

Another way of applying the pH protective coating is to apply as the pH protective coating an amorphous carbon or fluorocarbon coating, or a combination of the two.

Amorphous carbon coatings can be formed by PECVD using a saturated hydrocarbon, (e.g. methane or propane) or an unsaturated hydrocarbon (e.g. ethylene, acetylene) as a precursor for plasma polymerization. Fluorocarbon coatings can be derived from fluorocarbons (for example, hexafluoroethylene or tetrafluoroethylene). Either type of coating, or a combination of both, can be deposited by vacuum PECVD or atmospheric pressure PECVD. It is contemplated that that an amorphous carbon and/or fluorocarbon coating will provide better passivation of an $SiO_x$ barrier layer than a siloxane coating since an amorphous carbon and/or fluorocarbon coating will not contain silanol bonds.

It is further contemplated that fluorosilicon precursors can be used to provide a pH protective coating or layer over an $SiO_x$ barrier layer. This can be carried out by using as a precursor a fluorinated silane precursor such as hexafluorosilane and a PECVD process. The resulting coating would also be expected to be a non-wetting coating.

It is further contemplated that any embodiment of the pH protective coating processes described in this specification can also be carried out without using the article to be coated to contain the plasma. For example, external surfaces of medical devices, for example catheters, surgical instruments, closures, and others can be protected or passivated by sputtering the coating, employing a radio frequency target.

Yet another coating modality contemplated for protecting or passivating an $SiO_x$ barrier layer is coating the barrier layer using a polyamidoamine epichlorohydrin resin. For example, the barrier coated part can be dip coated in a fluid polyamidoamine epichlorohydrin resin melt, solution or dispersion and cured by autoclaving or other heating at a temperature between 60 and 100° C. It is contemplated that a coating of polyamidoamine epichlorohydrin resin can be preferentially used in aqueous environments between pH 5-8, as such resins are known to provide high wet strength in paper in that pH range. Wet strength is the ability to maintain mechanical strength of paper subjected to complete water soaking for extended periods of time, so it is contemplated that a coating of polyamidoamine epichlorohydrin resin on an $SiO_x$ barrier layer will have similar resistance to dissolution in aqueous media. It is also contemplated that, because polyamidoamine epichlorohydrin resin imparts a lubricity improvement to paper, it will also provide lubricity in the form of a coating on a thermoplastic surface made of, for example, COC or COP.

Even another approach for protecting an $SiO_x$ layer is to apply as a pH protective coating or layer a liquid-applied coating of a polyfluoroalkyl ether, followed by atmospheric plasma curing the pH protective coating. For example, it is contemplated that the process practiced under the trademark TriboGlide®, described in this specification, can be used to provide a pH protective coating or layer that is also a lubricity layer, as TriboGlide® is conventionally used to provide lubricity.

PECVD Apparatus and Methods for pH Protective Coating

Suitable methods and apparatus for applying a barrier or lubricity coating or layer such as 90 of $SiO_x$, $SiO_xC_y$, or $SiN_xC_y$ to a substrate such as the vessel 80 (FIG. 1) or a vial are described, for example, in U.S. Pat. No. 7,985,188 or the EP applications cited in paragraph [002], under conditions effective to form a coating or layer.

For depositing a pH protective coating, a precursor feed or process gas can be employed having a standard volume ratio of, for example:

from 0.5 to 10 standard volumes, optionally from 1 to 6 standard volumes, optionally from 2 to 4 standard volumes, optionally equal to or less than 6 standard volumes, optionally equal to or less than 2.5 standard volumes, optionally equal to or less than 1.5 standard volumes, optionally equal to or less than 1.25 standard volumes of the precursor, for example OMCTS or one of the other precursors of any embodiment;

from 0 to 100 standard volumes, optionally from 1 to 80 standard volumes, optionally from 5 to 100 standard volumes, optionally from 10 to 70 standard volumes, of a carrier gas of any embodiment;

from 0.1 to 10 standard volumes, optionally from 0.1 to 2 standard volumes, optionally from 0.2 to 1.5 standard volumes, optionally from 0.2 to 1 standard volumes, optionally from 0.5 to 1.5 standard volumes, optionally from 0.8 to 1.2 standard volumes of an oxidizing agent.

Another embodiment is a pH protective coating or layer of the type made by the above process.

Another embodiment is a vessel such as the vessel 80 (FIG. 1) including a lumen defined by a surface defining a substrate. A pH protective coating or layer is present on at least a portion of the substrate, typically deposited over an $SiO_x$ barrier layer to protect the barrier layer from dissolution. The pH protective coating or layer is made by the previously defined process.

Figure 5:
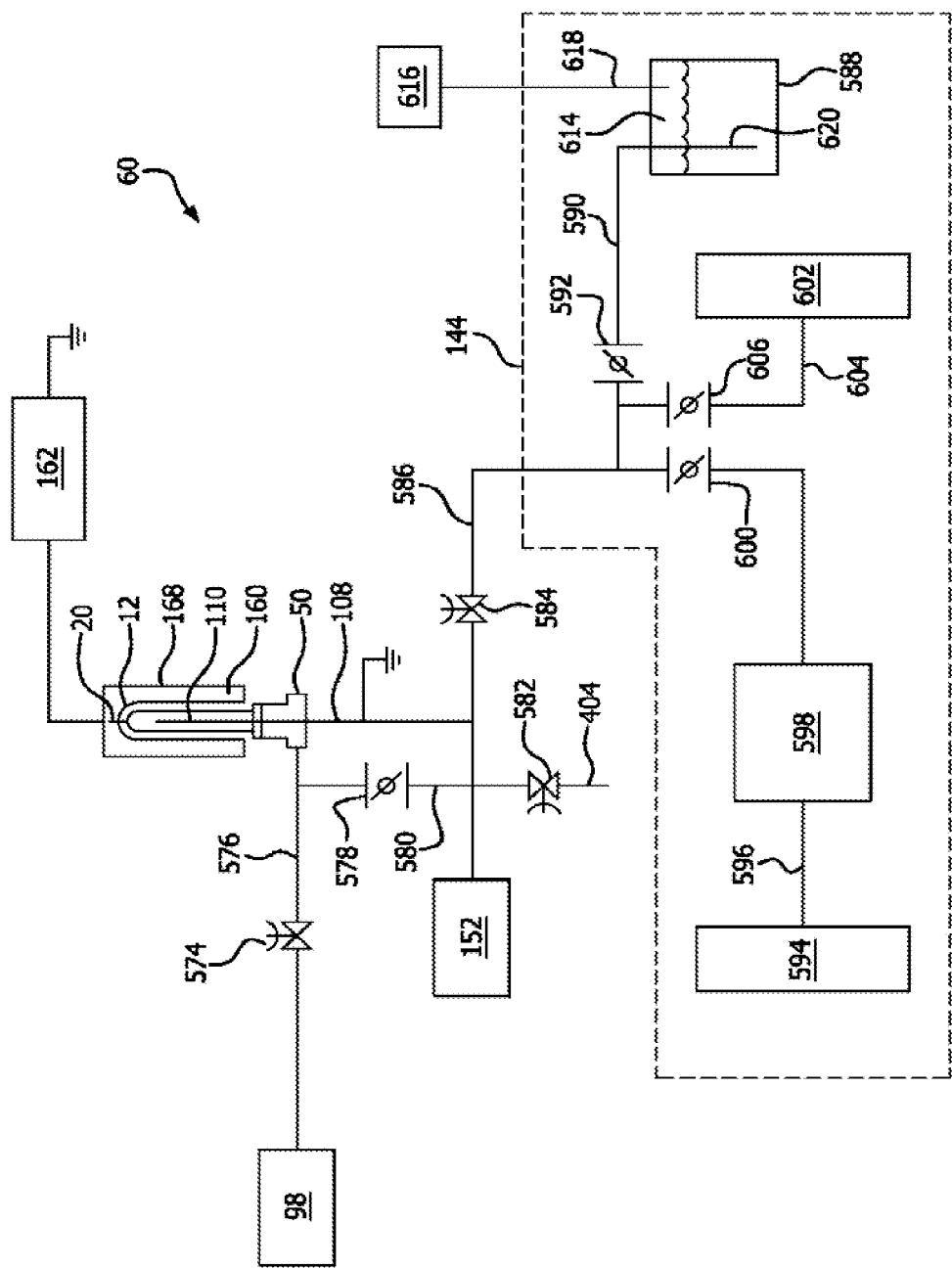
FIG. 5 is a schematic view of an assembly for treating pharmaceutical packages or other vessels. The assembly is usable with the apparatus in any of the preceding figures.

Still another embodiment is a chemical vapor deposition apparatus such as the apparatus 28 illustrated in FIG. 5 (or any other illustrated coating apparatus, such as the apparatus illustrated in FIGS. 1-4), for applying a pH protective coating or layer to a substrate.

Referring now to FIG. 5, suitable chemical vapor deposition apparatus is shown.

Referring to FIG. 8, yet another embodiment is a syringe such as 252 comprising a plunger 258, a barrel 250, and a pH protective coating or layer on the inner or interior surface 264. The barrel 250 is a vessel and has an inner or interior surface 264 defining the vessel lumen 274 and receiving the plunger 258 for sliding. The vessel inner or interior surface 264 is a substrate. A pH protective coating or layer can be applied on the substrate 264, the plunger 258, or both, by chemical vapor deposition. In addition to this pH protective coating or layer, the syringe may contain one or more other coatings or layers, for example an $SiO_x$ composite barrier coating or layer. Said additional coating(s) or layer(s) may be located under the lubricity and/or composite barrier coating or layer, i.e. nearer to the barrel of the syringe.

For any embodiment of a syringe such as 252, in particular a syringe that is stored or intended to be stored for an extended time while prefilled, the plunger 258 optionally is provided with a lubricity layer, at least on its surface in contact with the barrel interior surface 264, and the barrel interior surface 264 is provided with an $SiO_x$ barrier layer protected by a pH protective coating or layer wherever it is in contact or likely to be in contact with a fluid pharmaceutical composition contained in the syringe. An advantage of this construction is that the pH protective coating or layer, which is in contact with the fluid pharmaceutical composition when the syringe is stored prefilled, can be optimized for protection of the $SiO_x$ barrier layer, while the lubricity layer, which is located where the plunger typically contacts the inner surface 264 at a fixed location during storage, can be optimized for lubricity. The lubricity coating or layer on the plunger is in the right position to prevent "stiction" during storage and to continue to lower the friction between the plunger and barrel when the plunger is advanced, and if applied by CVD is contemplated to be less subject to displacement by the force exerted by the plunger on the barrel than traditional silicon oil coatings or layers and more uniformly applied as a uniform coating rather than as isolated droplets of liquid. As a further option, an adhesion layer or coating of $SiO_xC_y$ can be applied to the substrate and the barrier layer can be applied to the adhesion layer to improve adhesion of the $SiO_x$ barrier layer or coating to the substrate.

A concern of converting from glass to plastic syringes centers around the potential for leachable materials from plastics. With plasma coating technology, the coatings or layers derived from non-metal gaseous precursors, for example HMDSO or OMCTS or other organosilicon compounds, will itself contain no trace metals and function as a barrier to inorganic, metals and organic solutes, preventing leaching of these species from the coated substrate into syringe fluids. In addition to leaching control of plastic syringes, the same plasma pH protective coating or layer technology offers potential to provide a solute barrier to the plunger tip, typically made of elastomeric plastic compositions containing even higher levels of leachable organic oligomers and catalysts.

Moreover, certain syringes prefilled with synthetic and biological pharmaceutical formulations are very oxygen and moisture sensitive. A critical factor in the conversion from glass to plastic syringe barrels will be the improvement of plastic oxygen and moisture barrier performance. The plasma pH protective coating or layer technology is suitable to maintain the $SiO_x$ composite barrier coating or layer for protection against oxygen and moisture over an extended shelf life.

Even another embodiment is a plunger 258 for a syringe 252, comprising a piston or tip, a pH protective coating or layer, and a push rod. The piston or tip has a front face, a generally cylindrical side face that slides within the barrel 250, comprising a substrate, and a back portion. The side face is configured to movably seat within a syringe barrel. The pH protective coating or layer is on the substrate and is a lubricity and/or pH protective coating interfacing with the side face. The lubricity and/or pH protective coating is produced from a chemical vapor deposition (CVD) process employing the previously defined precursor feed or process gas. The push rod engages the back portion of the piston and is configured for advancing the piston in a syringe barrel.

Even another embodiment is a medical or diagnostic kit including a vessel having a coating or layer as defined in any embodiment herein on a substrate as defined in any embodiment above. Optionally, the kit additionally includes a medicament or diagnostic agent which is contained in the vessel with a pH protective coating in contact with the coating or layer; and/or a hypodermic needle, double-ended needle, or other delivery conduit; and/or an instruction sheet.

Other aspects of the invention include any one or more of the following:
  Use of the pH protective coating or layer according to any embodiment described above for treating a surface and thereby preventing or reducing mechanical and/or chemical effects of the surface on a compound or composition in contact with the pH protective coating or layer;
  Use of the coating or layer according to any described embodiment as a lubricity and/or pH protective coating;
  Use of the coating or layer according to any described embodiment for protecting a compound or composition contacting the pH protective coating or layer against mechanical and/or chemical effects of the surface of the vessel material without a pH protective coating;
  Use of the coating or layer according to any described embodiment for preventing or reducing precipitation and/or clotting or platelet activation of a compound or a component of the composition in contact with the coating or layer.

As one option, the compound or a component of the composition is insulin, and precipitation of the insulin is prevented or reduced. As another option, the compound or a component of the composition is blood or a blood fraction, and blood clotting or platelet activation is prevented or reduced. As still another option, the vessel with a pH protective coating is a blood collection tube. Optionally, the blood collection tube can contain an agent for preventing blood clotting or platelet activation, for example ethylenediamineteetraacetic acid (EDTA), a sodium salt thereof, or heparin.

Additional options for use of the invention include any one or more of the following:
  Use of a coated substrate according to any described embodiment, for example a vessel such as a sample collection tube, for example a blood collection tube and/or a closed-ended sample collection tube; a vial; a conduit; a cuvette; or a vessel part, for example a stopper; or a syringe, or a syringe part, for example a barrel or piston for reception and/or storage and/or delivery of a compound or composition.

The use of a coated substrate according to any described embodiment is contemplated for storing insulin.

The use of a coated substrate according to any described embodiment is contemplated for storing blood. Optionally, the stored blood is viable for return to the vascular system of a patient.

Use of a coating or layer according to any described embodiment is contemplated as (i) a lubricity coating having a lower frictional resistance than the uncoated surface; and/or (ii) a pH protective coating preventing dissolution of the barrier coating in contact with a fluid, and/or (iii) a hydrophobic layer that is more hydrophobic than the uncoated surface.

Other aspects of the invention include any of the uses defined above in the summary section.

Precursors for PECVD pH Protective Coating or Layer

The organosilicon precursor for the composite barrier coating or layer and the pH protective layer can include any of the following precursors useful for PECVD. The precursor for the PECVD pH protective coating or layer of the present invention is broadly defined as an organometallic precursor. An organometallic precursor is defined in this specification as comprehending compounds of metal elements from Group III and/or Group IV of the Periodic Table having organic residues, for example hydrocarbon, aminocarbon or oxycarbon residues. Organometallic compounds as presently defined include any precursor having organic moieties bonded to silicon or other Group III/IV metal atoms directly, or optionally bonded through oxygen or nitrogen atoms. The relevant elements of Group III of the Periodic Table are Boron, Aluminum, Gallium, Indium, Thallium, Scandium, Yttrium, and Lanthanum, Aluminum and Boron being preferred. The relevant elements of Group IV of the Periodic Table are Silicon, Germanium, Tin, Lead, Titanium, Zirconium, Hafnium, and Thorium, with Silicon and Tin being preferred. Other volatile organic compounds can also be contemplated. However, organosilicon compounds are preferred for performing present invention.

An organosilicon precursor is contemplated, where an "organosilicon precursor" is defined throughout this specification most broadly as a compound having at least one of the linkages:

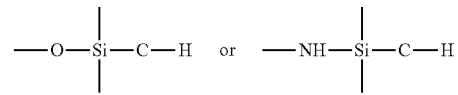

The first structure immediately above is a tetravalent silicon atom connected to an oxygen atom and an organic carbon atom (an organic carbon atom being a carbon atom bonded to at least one hydrogen atom). The second structure immediately above is a tetravalent silicon atom connected to an —NH— linkage and an organic carbon atom (an organic carbon atom being a carbon atom bonded to at least one hydrogen atom). Optionally, the organosilicon precursor is selected from the group consisting of a linear siloxane, a monocyclic siloxane, a polycyclic siloxane, a polysilsesquioxane, a linear silazane, a monocyclic silazane, a polycyclic silazane, a polysilsesquiazane, and a combination of any two or more of these precursors. Also contemplated as a precursor, though not within the two formulas immediately above, is an alkyl trimethoxysilane.

If an oxygen-containing precursor (for example a Siloxane) is used, a representative predicted empirical composition resulting from PECVD under conditions forming a hydrophobic or lubricating pH protective coating or layer would be $Si_wO_xC_yH_z$ or its equivalent $SiO_xC_y$, as defined in the Definition Section, while a representative predicted empirical composition resulting from PECVD under conditions forming a composite barrier coating or layer would be $SiO_x$, where x in this formula is from about 1.5 to about 2.4. If a nitrogen-containing precursor (for example a silazane) is used, the predicted composition would be $Si_{w*}N_{x*}C_{y*}H_{z*}$, i.e. in $Si_wO_xC_yH_z$ or its equivalent $SiO_xC_y$ as specified in the Definition Section, O is replaced by N and the indices for H are adapted to the higher valency of N as compared to O (3 instead of 2. The latter adaptation will generally follow the ratio of w, x, y and z in a Siloxane to the corresponding indices in its aza counterpart. In a particular aspect of the invention, $Si_{w*}N_{x*}C_{y*}H_{z*}$ (or its equivalent $SiN_{x*}C_{y*}$) in which w*, x*, y*, and z* are defined the same as w, x, y, and z for the siloxane counterparts, but for an optional deviation in the number of hydrogen atoms.

One type of precursor starting material having the above empirical formula is a linear siloxane, for example a material having the following formula:

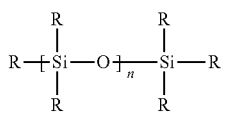

in which each R is independently selected from alkyl, for example methyl, ethyl, propyl, isopropyl, butyl, isobutyl, t-butyl, vinyl, alkyne, or others, and n is 1, 2, 3, 4, or greater, optionally two or greater. Several examples of contemplated linear siloxanes are
hexamethyldisiloxane (HMDSO),
octamethyltrisiloxane,
decamethyltetrasiloxane,
dodecamethylpentasiloxane,
or combinations of two or more of these. The analogous silazanes in which —NH— is substituted for the oxygen atom in the above structure are also useful for making analogous pH protective coatings or layers. Several examples of contemplated linear silazanes are octamethyltrisilazane, decamethyltetrasilazane, or combinations of two or more of these.

Another type of precursor starting material, among the preferred starting materials in the present context, is a monocyclic siloxane, for example a material having the following structural formula:

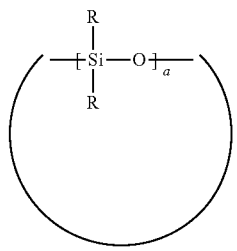

in which R is defined as for the linear structure and "a" is from 3 to about 10, or the analogous monocyclic silazanes. Several examples of contemplated hetero-substituted and unsubstituted monocyclic siloxanes and silazanes include 1,3,5-trimethyl-1,3,5-tris(3,3,3-trifluoropropyl)methyl]cyclotrisiloxane 2,4,6,8-tetramethyl-2,4,6,8-tetravinylcyclotetrasiloxane, pentamethylcyclopentasiloxane, pentavinylpentamethylcyclopentasiloxane, hexamethylcyclotrisiloxane, hexaphenylcyclotrisiloxane, octamethylcyclotetrasiloxane (OMCTS), octaphenylcyclotetrasiloxane, decamethylcyclopentasiloxane dodecamethylcyclohexasiloxane, methyl(3,3,3-trifluoropropl)cyclosiloxane, Cyclic organosilazanes are also contemplated, such as Octamethylcyclotetrasilazane, 1,3,5,7-tetravinyl-1,3,5,7-tetramethylcyclotetrasilazane hexamethylcyclotrisilazane, octamethylcyclotetrasilazane, decamethylcyclopentasilazane, dodecamethylcyclohexasilazane, or combinations of any two or more of these.

Another type of precursor starting material, among the preferred starting materials in the present context, is a polycyclic siloxane, for example a material having one of the following structural formulas:

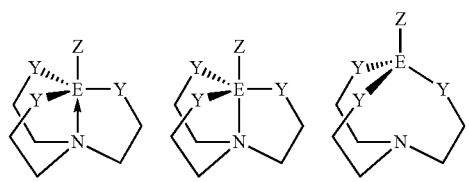

in which Y can be oxygen or nitrogen, E is silicon, and Z is a hydrogen atom or an organic substituent, for example alkyl such as methyl, ethyl, propyl, isopropyl, butyl, isobutyl, t-butyl, vinyl, alkyne, or others. When each Y is oxygen, the respective structures, from left to right, are a Silatrane, a Silquasilatrane, and a Silproatrane. When Y is nitrogen, the respective structures are an azasilatrane, an azasilquasiatrane, and an azasilproatrane.

Another type of polycyclic siloxane precursor starting material, among the preferred starting materials in the present context, is a polysilsesquioxane, with the empirical formula $RSiO_{1.5}$ and the structural formula:

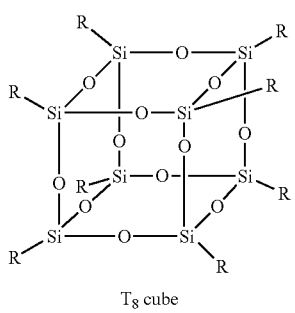

T8 cube in which each R is a hydrogen atom or an organic substituent, for example alkyl such as methyl, ethyl, propyl, isopropyl, butyl, isobutyl, t-butyl, vinyl, alkyne, or others. Two commercial materials of this sort are SST-eM01 poly(methylsilsesquioxane), in which each R is methyl, and SST-3MH1.1 poly(Methyl-Hydridosilsesquioxane), in which 90% of the R groups are methyl, 10% are hydrogen atoms. This material is available in a 10% solution in tetrahydrofuran, for example. Combinations of two or more of these are also contemplated. Other examples of a contemplated precursor are methylsilatrane, CAS No. 2288-13-3, in which each Y is oxygen and Z is methyl, methylazasilatrane, poly(methylsilsesquioxane) (for example SST-eM01 poly(methylsilsesquioxane)), in which each R optionally can be methyl, SST-3MH1.1 poly(Methyl-Hydridosilsesquioxane) (for example SST-3MH1.1 poly(Methyl-Hydridosilsesquioxane)), in which 90% of the R groups are methyl and 10% are hydrogen atoms, or a combination of any two or more of these.

The analogous polysilsesquiazanes in which —NH— is substituted for the oxygen atom in the above structure are also useful for making analogous pH protective coating or layer. Examples of contemplated polysilsesquiazanes are a poly(methylsilsesquiazane), in which each R is methyl, and a poly(Methyl-Hydridosilsesquiazane, in which 90% of the R groups are methyl, 10% are hydrogen atoms. Combinations of two or more of these are also contemplated.

One particularly contemplated precursor for the composite barrier coating or layer according to the present invention is a linear siloxane, for example is HMDSO. One particularly contemplated precursor for the lubricity coating or layer and the pH protective coating or layer according to the present invention is a cyclic siloxane, for example octamethylcyclotetrasiloxane (OMCTS).

It is believed that the OMCTS or other cyclic siloxane molecule provides several advantages over other siloxane materials. First, its ring structure results in a less dense pH protective coating or layer (as compared to pH protective coating or layer prepared from HMDSO). The molecule also allows selective ionization so that the final structure and chemical composition of the pH protective coating or layer can be directly controlled through the application of the plasma power. Other organosilicon molecules are readily ionized (fractured) so that it is more difficult to retain the original structure of the molecule.

In any of the PECVD methods according to the present invention, the applying step optionally can be carried out by vaporizing the precursor and providing it in the vicinity of the substrate. For example, OMCTS is usually vaporized by heating it to about 50° C. before applying it to the PECVD apparatus.

Cyclic organosilicon precursors, in particular monocyclic organosilicon precursors (like the monocyclic precursors listed elsewhere in present description), and specifically OMCTS, are particularly suitable to achieve a pH protective coating or layer.

Other Components of PECVD Reaction Mixture and Ratios of Components for pH Protective Coating or Layer Generally, for a pH protective coating or layer, $O_2$ can be present in an amount (which can, for example be expressed by the flow rate in sccm) which is less than one order of magnitude greater than the organosilicon amount. In contrast, in order to achieve a composite barrier coating or layer, the amount of $O_2$ typically is at least one order of magnitude higher than the amount of organosilicon precursor. In particular, the volume ratio (in sccm) of organosilicon precursor to $O_2$ for a pH protective coating or layer can be in the range from 0.1:1 to 10:1, optionally in the range from 0.3:1 to 8:1, optionally in the range from 0.5:1 to 5:1, optionally from 1:1 to 3:1. The presence of the precursor and $O_2$ in the volume ratios as given in Tables 1 to 3 is specifically suitable to achieve a pH protective coating or layer.

In one aspect of the invention, a carrier gas is absent in the reaction mixture, in another aspect of the invention, it is present. Suitable carrier gases include Argon, Helium and other noble gases such as Neon and Xenon. When the carrier gas is present in the reaction mixture, it is typically present in a volume (in sccm) exceeding the volume of the organosilicon precursor. For example, the ratio of the organosilicon precursor to carrier gas can be from 1:1 to 1:50, optionally from 1:5 to 1:40, optionally from 1:10 to 1:30. One function of the carrier gas is to dilute the reactants in the plasma, encouraging the formation of a coating on the substrate instead of powdered reaction products that do not adhere to the substrate and are largely removed with the exhaust gases.

Since the addition of Argon gas improves the lubricity and/or pH protective performance (see the working examples below), it is believed that additional ionization of the molecule in the presence of Argon contributes to providing lubricity. The Si—O—Si bonds of the molecule have a high bond energy followed by the Si—C, with the C—H bonds being the weakest. Lubricity and/or pH protective appears to be achieved when a portion of the C—H bonds are broken. This allows the connecting (cross-linking) of the structure as it grows. Addition of oxygen (with the Argon) is understood to enhance this process. A small amount of oxygen can also provide C—O bonding to which other molecules can bond. The combination of breaking C—H bonds and adding oxygen all at low pressure and power leads to a chemical structure that is solid while providing lubricity.

In any of embodiments, one preferred combination of process gases includes octamethylcyclotetrasiloxane (OMCTS) or another cyclic siloxane as the precursor, in the presence of oxygen as an oxidizing gas and argon as a carrier gas. Without being bound to the accuracy of this theory, the inventors believe this particular combination is effective for the following reasons. The presence of $O_2$, $N_2O$, or another oxidizing gas and/or of a carrier gas, in particular of a carrier gas, for example a noble gas, for example Argon (Ar), is contemplated to improve the resulting pH protective coating or layer.

Some non-exhaustive alternative selections and suitable proportions of the precursor gas, oxygen, and a carrier gas are provided below.

OMCTS: 0.5-5.0 sccm
Oxygen: 0.1-5.0 sccm
Argon: 1.0-20 sccm

PECVD Apparatus for Forming pH Protective Coating or Layer

The low-pressure PECVD process described in U.S. Pat. No. 7,985,188 can be used to provide the barrier, lubricity, and pH protective layers described in this specification. A brief synopsis of that process follows.

A PECVD apparatus suitable for performing the present invention includes a vessel holder, an inner electrode, an outer electrode, and a power supply. A vessel seated on the vessel holder defines a plasma reaction chamber, which optionally can be a vacuum chamber. Optionally, a source of vacuum, a reactant gas source, a gas feed or a combination of two or more of these can be supplied. Optionally, a gas drain, not necessarily including a source of vacuum, is provided to transfer gas to or from the interior of a vessel seated on the port to define a closed chamber.

The PECVD apparatus can be used for atmospheric-pressure PECVD, in which case the plasma reaction chamber does not need to function as a vacuum chamber.

Figure 2:
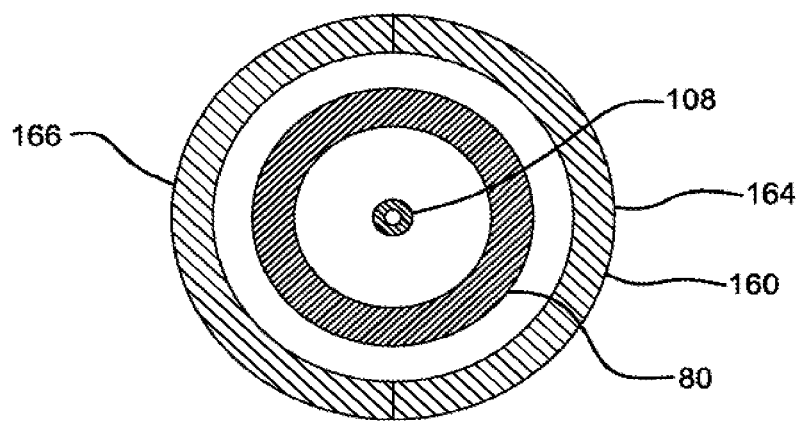
FIG. 2 is a section taken along section lines A-A of FIG. 1.

Referring to FIGS. 1 and 2, the vessel holder 50 comprises a gas inlet port 104 for conveying a gas into a vessel seated on the vessel port. The gas inlet port 104 has a sliding seal provided by at least one O-ring 106, or two O-rings in series, or three O-rings in series, which can seat against a cylindrical probe 108 when the probe 108 is inserted through the gas inlet port 104. The probe 108 can be a gas inlet conduit that extends to a gas delivery port at its distal end 110. The distal end 110 of the illustrated embodiment can be inserted deep into the vessel 80 for providing one or more PECVD reactants and other precursor feed or process gases.

FIG. 5 shows additional optional details of the coating or layer station 28 that are usable, for example, with all the illustrated embodiments. The coating or layer station 28 can also have a main vacuum valve 574 in its vacuum line 576 leading to the pressure sensor 152. A manual bypass valve 578 is provided in the bypass line 580. A vent valve 582 controls flow at the vent 404.

Flow out of the PECVD gas or precursor source 144 is controlled by a main reactant gas valve 584 regulating flow through the main reactant feed line 586. One component of the gas source 144 is the organosilicon liquid reservoir 588. The contents of the reservoir 588 are drawn through the organosilicon capillary line 590, which is provided at a suitable length to provide the desired flow rate. Flow of organosilicon vapor is controlled by the organosilicon shut-off valve 592. Pressure is applied to the headspace 614 of the liquid reservoir 588, for example a pressure in the range of 0-15 psi (0 to 78 cm. Hg), from a pressure source 616 such as pressurized air connected to the headspace 614 by a pressure line 618 to establish repeatable organosilicon liquid delivery that is not dependent on atmospheric pressure (and the fluctuations therein). The reservoir 588 is sealed and the capillary connection 620 is at the bottom of the reservoir 588 to ensure that only neat organosilicon liquid (not the pressurized gas from the headspace 614 flows through the capillary tube 590. The organosilicon liquid optionally can be heated above ambient temperature, if necessary or desirable to cause the organosilicon liquid to evaporate, forming an organosilicon vapor. To accomplish this heating, the pH protective coating or layer apparatus can advantageously include heated delivery lines from the exit of the precursor reservoir to as close as possible to the gas inlet into the syringe. Preheating is useful, for example, when feeding OMCTS.

Oxygen is provided from the oxygen tank 594 via an oxygen feed line 596 controlled by a mass flow controller 598 and provided with an oxygen shut-off valve 600.

For instances in which a carrier gas is used, the carrier gas is obtained from a source of carrier gas 602 and passes via a conduit 604, controlled by a carrier gas shut-off valve 606, to the main reactant feed line 586 where it is combined with the other components of the PECVD gas feed.

Referring especially to FIG. 1, the processing station 28 can include an electrode 160 fed by a radio frequency power supply 162 for providing an electric field for generating plasma within the vessel 80 during processing. In this embodiment, the probe 108 is also electrically conductive and is grounded, thus providing a counter-electrode within the vessel 80. Alternatively, in any embodiment the outer electrode 160 can be grounded and the probe 108 directly connected to the power supply 162.

In the embodiment of FIG. 1, the outer electrode 160 can either be generally cylindrical as illustrated in FIGS. 1 and 2 or a generally U-shaped elongated channel as illustrated in FIG. 1 (FIG. 2 being an embodiment of the section taken along section line A-A of FIG. 1). Each illustrated embodiment has one or more sidewalls, such as 164 and 166, and optionally a top end 168, disposed about the vessel 80 in close proximity.

Referring to FIGS. 3 and 4, a specific adaptation of the PECVD process is described for applying PECVD coatings to a vessel such as a syringe barrel that is open at both ends.

FIGS. 3 and 4 show a method and apparatus generally indicated at 290 for coating or layer an inner or interior surface 292 of a restricted opening 294 of a generally tubular vessel 250 to be processed, for example the restricted front opening 294 of a syringe barrel 250, by PECVD. The previously described process is modified by connecting the restricted opening 294 to a processing vessel 296 and optionally making certain other modifications.

The generally tubular vessel 250 to be processed includes an outer surface 298, an inner or inner or interior surface 254 defining a lumen 300, a larger opening 302 having an inner diameter, and a restricted opening 294 that is defined by an inner or interior surface 292 and has an inner diameter smaller than the inner diameter of the larger opening 302.

The processing vessel 296 has a lumen 304 and a processing vessel opening 306, which optionally is the only opening, although in other embodiments a second opening can be provided that optionally is closed off during processing. The processing vessel opening 306 is connected with the restricted opening 294 of the vessel 250 to be processed to establish communication between the lumen 300 of the vessel 250 to be processed and the processing vessel lumen via the restricted opening 294.

At least a partial vacuum is drawn within the lumen 300 of the vessel 250 to be processed and lumen 304 of the processing vessel 296. A PECVD reactant is flowed from the gas source 144 through the first opening 302, then through the lumen 300 of the vessel 250 to be processed, then through the restricted opening 294, then into the lumen 304 of the processing vessel 296.

The PECVD reactant can be introduced through the larger opening 302 of the vessel 250 by providing a generally tubular inner electrode 308 having an interior passage 310, a proximal end 312, a distal end 314, and a distal opening 316, in an alternative embodiment multiple distal openings can be provided adjacent to the distal end 314 and communicating with the interior passage 310. The distal end of the electrode 308 can be placed adjacent to or into the larger opening 302 of the vessel 250 to be processed. A reactant gas can be fed through the distal opening 316 of the electrode 308 into the lumen 300 of the vessel 250 to be processed. The reactant will flow through the restricted opening 294, then into the lumen 304, to the extent the PECVD reactant is provided at a higher pressure than the vacuum initially drawn before introducing the PECVD reactant.

Plasma 318 is generated adjacent to the restricted opening 294 under conditions effective to deposit a coating or layer of a PECVD reaction product on the inner or interior surface 292 of the restricted opening 294.

More details concerning adapting the PECVD process to syringe processing are provided, for example, in U.S. Pat. No. 7,985,188.

Specific PECVD conditions for application of a pH protective coating or layer are provided below.

Plasma Conditions for pH protective Coating or Layer

Typically, the plasma in the PECVD process is generated at RF frequency. For providing a pH protective layer on the interior of a vessel by a plasma reaction carried out within the vessel, the plasma of any embodiment can be generated with an electric power of from 0.1 to 500 W, optionally from 0.1 to 400 W, optionally from 0.1 to 300 W, optionally from 1 to 250 W, optionally from 1 to 200 W, even optionally from 10 to 150 W, optionally from 20 to 150 W, for example of 40 W, optionally from 40 to 150 W, even optionally from 60 to 150 W. The ratio of the electrode power to the plasma volume can be less than 100 W/ml, optionally is from 5 W/ml to 75 W/ml, optionally is from 6 W/ml to 60 W/ml, optionally is from 10 W/ml to 50 W/ml, optionally from 20 W/ml to 40 W/ml. These power levels are suitable for applying pH protective coatings or layers to syringes and sample tubes and pharmaceutical packages or other vessels of similar geometry having a void volume of 5 mL in which PECVD plasma is generated. It is contemplated that for larger or smaller objects the power applied, in Watts, should be increased or reduced accordingly to scale the process to the size of the substrate.

Exemplary reaction conditions for preparing a pH protective coating or layer according to the present invention in a 3 ml sample size syringe with a ⅛" diameter tube (open at the end) are as follows:

Flow Rate Ranges:
  OMCTS: 0.5-10 sccm
  Oxygen: 0.1-10 sccm
  Argon: 1.0-200 sccm
  Power: 0.1-500 watts
Specific Flow Rates:
  OMCTS: 2.0 sccm
  Oxygen: 0.7 sccm
  Argon: 7.0 sccm
  Power: 3.5 watts The pH protective coating or layer and its application are described in more detail below. A method for applying the coating includes several steps. A vessel wall is provided, as is a reaction mixture comprising plasma forming gas, i.e. an organosilicon compound gas, optionally an oxidizing gas, and optionally a hydrocarbon gas.

Plasma is formed in the reaction mixture that is substantially free of hollow cathode plasma. The vessel wall is contacted with the reaction mixture, and the pH protective coating or layer of $SiO_x$ is deposited on at least a portion of the vessel wall.

In certain embodiments, the generation of a uniform plasma throughout the portion of the vessel to be coated is contemplated, as it has been found in certain instances to generate a better pH protective coating or layer. Uniform plasma means regular plasma that does not include a substantial amount of hollow cathode plasma (which has a higher emission intensity than regular plasma and is manifested as a localized area of higher intensity interrupting the more uniform intensity of the regular plasma).

Method of Applying a Lubricity Coating or Layer

A method of applying an optional lubricity coating or layer derived from an organosilicon precursor, and the resulting pH protective coating or layer and coated item are described for example in U.S. Pat. No. 7,985,188. A "lubricity coating" or any similar term is generally defined as a coating or layer that reduces the frictional resistance of the coated surface, relative to the uncoated surface. If the coated object is a syringe (or syringe part, for example syringe barrel) or any other item generally containing a plunger or movable part in sliding contact with the coated surface, the frictional resistance has two main aspects—breakout force and plunger sliding force.

It should be understood that a coating optionally can be both a lubricity coating or layer and a pH protective coating or layer, respectively as explained in this description.

Hydrophobic Layer

The pH protective or lubricity coating or layer of $Si_wO_xC_y$, or its equivalent $SiO_xC_y$, also can have utility as a hydrophobic layer. A coating or layer of this kind is contemplated to be hydrophobic, independent of whether it also functions as a lubricity and/or pH protective coating. A coating or layer or treatment is defined as "hydrophobic" if it lowers the wetting tension of a surface, compared to the corresponding uncoated or untreated surface. Hydrophobicity is thus a function of both the untreated substrate and the treatment.

Suitable hydrophobic coatings or layers and their application, properties, and use are described in U.S. Pat. No. 7,985,188. Dual functional pH protective/hydrophobic coatings or layers having the properties of both types of coatings or layers can be provided for any embodiment of the present invention.

Measurement of Coating Thickness

Figure 6:
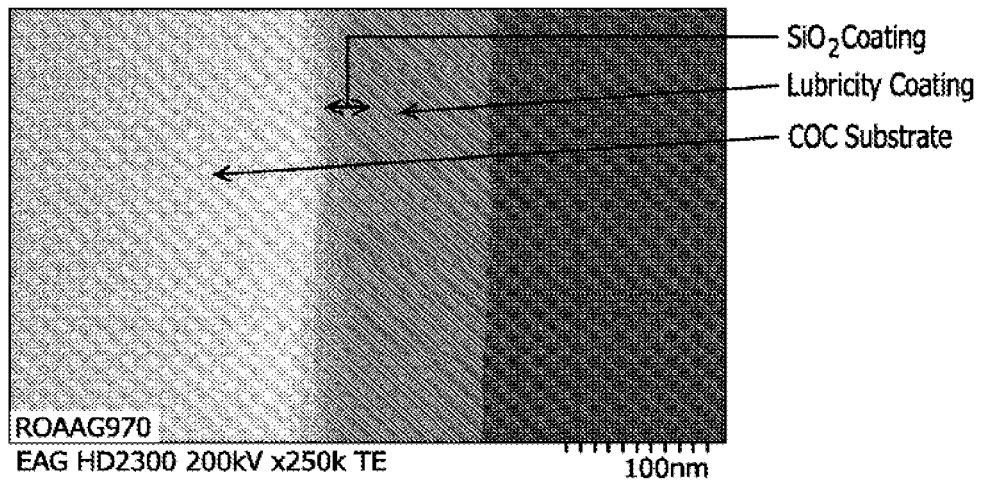
FIG. 6 shows a TEM image of a lubricity and/or pH protective coating or layer according to the invention coated on a composite barrier coating or layer, which in turn is coated on a COC substrate.
Figure 7:
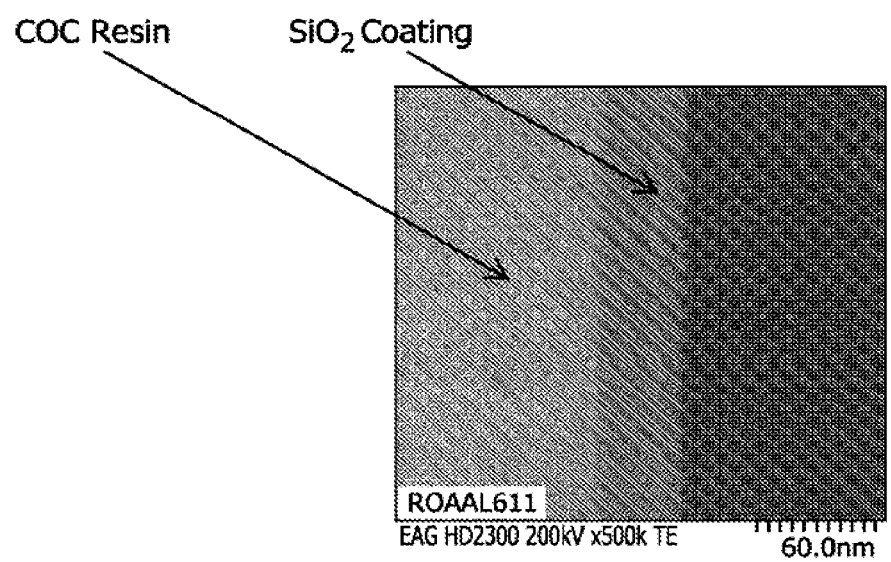
FIG. 7 shows a TEM image of a composite barrier coating or layer which is coated on a COC substrate.

The thickness of a PECVD coating or layer such as the pH protective coating or layer, the composite barrier coating or layer, the lubricity coating or layer, and/or a composite of any two or more of these layers can be measured, for example, by transmission electron microscopy (TEM). An exemplary TEM image for a lubricity and/or pH protective coating or layer is shown in FIG. 6. An exemplary TEM image for an $SiO_2$ composite barrier coating or layer is shown in FIG. 7.

The TEM can be carried out, for example, as follows. Samples can be prepared for Focused Ion Beam (FIB) cross-sectioning in two ways. Either the samples can be first coated with a thin layer of carbon (50-100 nm thick) and then coated with a sputtered coating or layer of platinum (50-100 nm thick) using a K575X Emitech pH protective coating or layer system, or the samples can be coated directly with the pH protective sputtered Pt layer. The coated samples can be placed in an FEI FIB200 FIB system. An additional coating or layer of platinum can be FIB-deposited by injection of an organometallic gas while rastering the 30 kV gallium ion beam over the area of interest. The area of interest for each sample can be chosen to be a location half way down the length of the syringe barrel. Thin cross sections measuring approximately 15 μm ("micrometers") long, 2 μm wide and 15 μm deep can be extracted from the die surface using an in-situ FIB lift-out technique. The cross sections can be attached to a 200 mesh copper TEM grid using FIB-deposited platinum. One or two windows in each section, measuring about 8 μm wide, can be thinned to electron transparency using the gallium ion beam of the FEI FIB.

Cross-sectional image analysis of the prepared samples can be performed utilizing either a Transmission Electron Microscope (TEM), or a Scanning Transmission Electron Microscope (STEM), or both. All imaging data can be recorded digitally. For STEM imaging, the grid with the thinned foils can be transferred to a Hitachi HD2300 dedicated STEM. Scanning transmitted electron images can be acquired at appropriate magnifications in atomic number contrast mode (ZC) and transmitted electron mode (TE). The following instrument settings can be used.

| Instrument | Scanning Transmission Electron Microscope |
|---|---|
| Manufacturer/Model | Hitachi HD2300 |
| Accelerating Voltage | 200 kV |
| Objective Aperture | #2 |
| Condenser Lens 1 Setting | 1.672 |
| Condenser Lens 2 Setting | 1.747 |
| Approximate Objective Lens Setting | 5.86 |
| ZC Mode Projector Lens | 1.149 |
| TE Mode Projector Lens | 0.7 |
| Image Acquisition | |
| Pixel Resolution | 1280 × 960 |
| Acquisition Time | 20 sec. (×4 |

For TEM analysis the sample grids can be transferred to a Hitachi HF2000 transmission electron microscope. Transmitted electron images can be acquired at appropriate magnifications. The relevant instrument settings used during image acquisition can be those given below.

| Instrument | Transmission Electron Microscope |
|---|---|
| Manufacturer/Model | Hitachi HF2000 |
| Accelerating Voltage | 200 kV |
| Condenser Lens 1 | 0.78 |
| Condenser Lens 2 | 0 |
| Objective Lens | 6.34 |
| Condenser Lens Aperture | #1 |
| Objective Lens Aperture for imaging | #3 |
| Selective Area Aperture for SAD | N/A |

Measurement of Adhesion

The following methods can be used to measure the degree of adhesion of the composite barrier coating or layer to a substrate. Key references are:
(1) ASTM D3359-09 "Standard Test Methods for Measuring Adhesion by Tape Test"
(2) B905-00 "Standard Test Methods for Assessing the Adhesion of Metallic and Inorganic Coatings by the Mechanized Tape Test."
(A1) Coated Article Deformation/Tape Test Method
(Sections of References 1 and 2 followed whenever relevant)
General In this method as used in this specification, a deformation force is applied to an $SiO_x$ coated article to stress the coating, after which the extent of removal of the coating with adhesive tape is assessed.
Sample Preparation:

A coated vial, syringe barrel, cartridge or other article having a cylindrical section is cut at each end of the article resulting in a uniform constant inner diameter (ID) open-ended cylinder. The non-cylindrical or differing ID sections are discarded. Cutting is performed with a hot wire cutter. If appropriate, careful removal of any particles that may be present is achieved with clean, dry compressed air (no physical contact should be made with the coated interior of the cylinder).
Sample Deformation:

The uniform coated cylinder derived from the vial, syringe barrel, cartridge, or other article is placed in an Instron® stress-strain material testing machine, either (a) in an axial deformation orientation, with open ends vertical; the stainless Instron® plates contacting the circular open edges (also known as "top down deformation") or (b) in a diametric deformation orientation with its open ends horizontal; the stainless Instron® plates contacting two parallel opposed lengths of the cylinder (also known as "side deformation"). Unless otherwise stated, axial deformation is employed in the test methods specified in the claims.

Depending on the plastic composition, mold conditions, and cylinder thickness, compression deformation forces are applied; forces should not exceed levels which would result in any irreversible physical deformation or failure of the cylinder. For axial testing of thermoplastic containers as recited in the claims, a compression force of 350 lb. (158 Kg) is employed. For diametric deformation in alternative testing, the same compression force is applied. If side compression or diametric deformation is selected, reproducible contact location of the cylinder on the stainless plates relative to mold lines should be established.
Tape Application: Half Cylinder Approach The cylinder is cut longitudinally in half using the same cutting methods applied in the Sample Preparation Section.

The curved nature of the cylinders requires a narrow tape strip to facilitate uniform, bubble-free tape adhesion to the coated inner wall surface. A one-sided Scotch Brand adhesive tape is cut to a width of three millimeters and length about six millimeters longer than the overall cylinder length. The adhesive tape section is clamped from about three millimeters from each end of the tape with long handled needle-nose tweezers or micro-hemostats, without touching the walls. Once the tape extends axially and its ends are equally positioned beyond each open end of the cylinder, the tape is contacted with the curved coated inner wall. A small pencil eraser head or hemispherical-rounded end three millimeter stainless rod is then moved up and down the tape surface between the clamps, removing any bubbles under the tape. It is important to apply a uniform force on the tape.

Once the tape is uniformly adhered to the inner wall, the clamps can be removed, but making sure the previously clamped ends do not adhere to the wall.
Tape Removal:

(See Reference 2-p3 (Section 7.4) for details of Tape Pull Time, Rate, and Angle). For the tests carried out in this specification, a 90° tape pull was used as described below.
90° Tape Pull A single needle-nose tweezer or micro-hemostat used previously in the Tape Application Section is clamped on the opposite free end of the wall surface affixed tape, followed by uniform pulling at a 90° angle (perpendicular to the adhered tape) on the clamped tape end with removal of the tape. Clamps attached to an Instron® vertical motion bar can be utilized to provide a uniform rate of tape pull removal.
Adhesion Assessment:
Coating Thickness Determination (Line Scanning)

Using a Layer Explorer UT Instrument (www.rap-id.com) or equivalent interferometric thickness measurement device, the coating thickness before and after tape application is measured along an axial line bisecting the location of the adherent tape. The reduction of area (coating thickness× length of scan) of the difference after tape pull versus before tape adhesion is a measure of the degree of coating adhesion. This is represented as a percent of original coating retained after tape pull.

(A2) Coated Article Cross-Scratch/Tape Test Method (Sections of References 1 and 2 Followed Whenever Relevant)

General

In this method as used in this specification, the coating of an $SiO_x$ coated article is scratched to stress the coating, after which the extent of removal of the coating with adhesive tape is assessed.

Sample Preparation:

A coated vial, syringe barrel, or cartridge is cut at each end of the article and cut in half along an axial plane as described above, resulting in a uniform constant inner diameter (ID) half cylinder.

X Scratch Pattern:

If an X scratch pattern is selected, as specified in certain claims, an "X" is scribed onto the inner coated wall surface of the half cylinder, using a stainless pointed dental pick. The shape of the X is a uniformly shaped and positioned pair of scratches forming an axially elongated pattern. The smaller angle between the two scratches is a uniform value between 30° and 40°.

Half Cylinder Cross-Cut

If a rectangular scratch pattern is selected, as specified in certain claims or described in Reference 2, Section 10 (p3), an "square cross-cut" is scribed onto the inner coated wall surface of the cylinder, using a sharp razor blade, scalpel, knife or other cutting device.

Tape Application:

Half Cylinder Approach

The tape is applied as described above, but is positioned to overlie the scratches. If an X scratch pattern is employed, the tape is positioned to extend axially with the center of the X centered circumferentially on the tape. If a rectangular scratch pattern is employed, the tape is positioned to extend axially with the tape centered circumferentially on the scratch pattern.

Tape Removal:

(See Reference 2-p3 (Section 7.4) for details of Tape Pull Time, Rate, and Angle)

90° Tape Pull

A single clamp is clamped on the opposite free end of the wall surface affixed tape, followed by uniform pulling at a 90° angle (perpendicular to the adhered tape) on the clamped tape end with removal of the tape. The clamp is attached to an Instron® vertical motion bar to provide a uniform rate of tape pull removal.

Adhesion Assessment:

Coating Thickness Determination (Line Scanning)

Using a Layer Explorer UT Instrument (www.rap-id.com) or equivalent interferometric thickness measurement device, the coating thickness before and after tape application (but both after X-cut or Cross-cut) along a line bisecting the location of the adherent tape is measured. The reduction of area (coating thickness×length of scan) of the difference after tape pull versus before tape adhesion is a measure of the degree of coating adhesion. This can be represented as a percent of original coating retained after tape pull.

(B1) Inventive Adhesion performance of $SiO_x$ barrier coating on a COP 5 milliliter vial versus comparative borosilicate glass vial using A1 and A2 Adhesion Assessment Methods.

Using established $SiO_x$ coating procedures discussed in the Protocol for Coating Syringe Barrel Interior with $SiO_x$ in this specification, 5 milliliter injection blow-molded vials ($SiO_2$ Medical Products) and borosilicate glass 5 milliliter vials (Schott) are coated with a composite barrier coating or layer.

Utilizing A1 and A2 Adhesion assessment methods, adhesion results (Table 4) are obtained.

(B2) Inventive Adhesion performance of Bilayer Coated ($SiO_x$ barrier and p-OMCTS pH protective) coating on a COP 5 milliliter vial versus comparative borosilicate glass vial using A1 and A2 Adhesion Assessment Methods.

Using established $SiO_x$ coating procedures discussed previously in Protocol for Coating Syringe Barrel Interior with $SiO_x$ in this specification, 5 milliliter injection blow-molded vials ($SiO_2$ Medical Products) and borosilicate glass 5 milliliter vials (Schott) were coated with a standard $SiO_x$ composite barrier coating or layer and a standard pH protective coating or layer.

Utilizing A1 and A2 Adhesion assessment methods, adhesion results (Table 4) are obtained.

(B3) Inventive Adhesion performance of $SiO_x$ barrier coating on a COP 1 milliliter long staked needle syringe barrel versus comparative borosilicate glass syringe barrel using A1 and A2 Adhesion Assessment Methods.

Using the Protocol for Coating Syringe Barrel Interior with $SiO_x$ in this specification, one milliliter injection blow-molded staked needle syringe barrel ($SiO_2$ Medical Products) and borosilicate glass syringe barrel (Becton-Dickenson, silicone oil previously removed with hexane) were coated under standard $SiO_x$ coating procedures.

Utilizing A1 and A2 Adhesion assessment methods, adhesion results (Table 4) are obtained.

(B4) Inventive Adhesion performance of Bilayer Coated ($SiO_x$ composite barrier coating or layer and p-OMCTS pH protective coating or layer) coating on a thermoplastic vial versus comparative borosilicate glass vial using A1 and A2 Adhesion Assessment Methods.

Using the Protocol for Coating Syringe Barrel Interior with $SiO_x$ in this specification, one mL (milliliter) injection blow-molded staked needle syringe barrel ($SiO_2$ Medical Products) and borosilicate glass syringe barrel (Becton-Dickenson, silicone oil previously removed with hexane) are coated under $SiO_x$ composite barrier coating or layer and pH protective coating or layer protocols as shown in this specification.

Utilizing A1 and A2 Adhesion assessment methods, adhesion results (Table 5) are predicted.

PECVD Treated Pharmaceutical Packages or Other Vessels Coated Pharmaceutical Packages or Other Vessels Pharmaceutical packages or other vessels, such as a prefilled syringe (schematically shown in FIG. 8) or a vial or blister pack (schematically shown in FIGS. 9 and 10) are contemplated having a composite barrier coating or layer such as 288 at least partially covered by a pH protective coating or layer such as 286.

The pharmaceutical package 210 as shown in any embodiment, for example FIGS. 8-10, comprises a vessel or vessel part such as 250; optionally a composite barrier coating or layer such as 288 on the vessel or vessel part; a pH protective coating or layer such as 286 on the vessel, vessel part, or composite barrier coating or layer; and a pharmaceutical composition or preparation such as 218 contained within the vessel.

The composite barrier coating or layer such as 288 can be an $SiO_x$ composite barrier coating or layer applied as described in any embodiment of this specification. For example, the composite barrier coating or layer such as 288 of any embodiment can be applied at a thickness of at least 2 nm, or at least 4 nm, or at least 7 nm, or at least 10 nm, or at least 20 nm, or at least 30 nm, or at least 40 nm, or at least 50 nm, or at least 100 nm, or at least 150 nm, or at least 200 nm, or at least 300 nm, or at least 400 nm, or at least 500 nm, or at least 600 nm, or at least 700 nm, or at least 800 nm, or at least 900 nm. The composite barrier coating or layer can be up to 1000 nm, or at most 900 nm, or at most 800 nm, or at most 700 nm, or at most 600 nm, or at most 500 nm, or at most 400 nm, or at most 300 nm, or at most 200 nm, or at most 100 nm, or at most 90 nm, or at most 80 nm, or at most 70 nm, or at most 60 nm, or at most 50 nm, or at most 40 nm, or at most 30 nm, or at most 20 nm, or at most 10 nm, or at most 5 nm thick. Specific thickness ranges composed of any one of the minimum thicknesses expressed above, plus any equal or greater one of the maximum thicknesses expressed above, are expressly contemplated. The thickness of the $SiO_x$ or other composite barrier coating or layer can be measured, for example, by transmission electron microscopy (TEM), and its composition can be measured by X-ray photoelectron spectroscopy (XPS). The pH protective coating or layer described herein can be applied to a variety of pharmaceutical packages or other vessels made from plastic or glass, for example to plastic tubes, vials, and syringes.

The pH protective coating or layer such as 286 can be an $SiO_xC_y$ pH protective coating or layer applied as described in any embodiment of this specification. For example, the pH protective coating or layer such as 286 of any embodiment comprises or consists essentially of a coating or layer of $SiO_xC_y$ applied over the composite barrier coating or layer 288 to protect at least a portion of the composite barrier coating or layer from the pharmaceutical preparation such as 218 in FIGS. 8-10. The pH protective coating or layer such as 286 is provided, for example, by applying one of the described precursors on or in the vicinity of a substrate in a PECVD process, providing a pH protective coating. The coating can be applied, for example, at a thickness of 1 to 5000 nm, or 10 to 1000 nm, or 10 to 500 nm, or 10 to 200 nm, or 20 to 100 nm, or 30 to 1000 nm, or 30 to 500 nm thick, or 30 to 1000 nm, or 20 to 100 nm, or 80 to 150 nm, and crosslinking or polymerizing (or both) the pH protective layer, optionally in a PECVD process, to provide a protected surface.

Although not intending to be bound according to the accuracy of the following theory, the inventors contemplate that the pH protective coating or layer, applied over an $SiO_x$ barrier layer on a vessel wall, functions at least in part by passivating the $SiO_x$ barrier layer surface against attack by the contents of the vessel, as well as providing a more resistant or sacrificial independent layer to isolate the $SiO_x$ barrier layer from the contents of the vessel. It is thus contemplated that the pH protective coating or layer can be very thin, and even so improve the shelf life of the pharmaceutical package.

A lubricity coating or layer can be applied after applying an $SiO_x$ barrier layer and/or a pH protective coating or layer to the inner or interior surface or to other parts of the pharmaceutical package, as described in U.S. Pat. No. 7,985,188.

Thus, the coating or layer 90 can comprise a composite barrier coating or layer of $SiO_x$ and a pH protective layer of $Si_wO_xC_y$ (which for all embodiments in this specification is equivalent to $SiO_xC_y$, since w=1) and optionally in any embodiment further including a lubricity coating or layer, each characterized as defined in this specification. As another option, the composite barrier coating or layer of $SiO_x$ can be deposited at a location more remote from the pH protective coating or layer, with at least one intervening coating or layer of another material.

Another expedient contemplated here, for adjacent layers of $SiO_x$ and a lubricity and/or pH protective coating or layer, is a graded composite of $SiO_x$ and $Si_wO_xC_y$, or its equivalent $SiO_xC_y$, as defined in the Definition Section. A graded composite can be separate layers of a lubricity and/or pH protective and/or barrier layer or coating with a transition or interface of intermediate composition between them, or separate layers of a lubricity and/or pH protective and/or hydrophobic layer and $SiO_x$ with an intermediate distinct pH protective coating or layer of intermediate composition between them, or a single coating or layer that changes continuously or in steps from a composition of a lubricity and/or pH protective and/or hydrophobic layer to a composition more like $SiO_x$, going through the pH protective coating or layer in a normal direction.

The grade in the graded composite can go in either direction. For example, the composition of $SiO_x$ can be applied directly to the substrate and graduate to a composition further from the surface of a pH protective coating or layer, and optionally can further graduate to another type of coating or layer, such as a hydrophobic coating or layer or a lubricity coating or layer. Additionally, in any embodiment an adhesion coating or layer, for example $Si_wO_xC_y$, or its equivalent $SiO_xC_y$, optionally can be applied directly to the substrate before applying the barrier layer. A graduated pH protective coating or layer is particularly contemplated if a layer of one composition is better for adhering to the substrate than another, in which case the better-adhering composition can, for example, be applied directly to the substrate. It is contemplated that the more distant portions of the graded pH protective coating or layer can be less compatible with the substrate than the adjacent portions of the graded pH protective coating or layer, since at any point the pH protective coating or layer is changing gradually in properties, so adjacent portions at nearly the same depth of the pH protective coating or layer have nearly identical composition, and more widely physically separated portions at substantially different depths can have more diverse properties. It is also contemplated that a pH protective coating or layer portion that forms a better barrier against transfer of material to or from the substrate can be directly against the substrate, to prevent the more remote pH protective coating or layer portion that forms a poorer barrier from being contaminated with the material intended to be barred or impeded by the barrier.

The applied coatings or layers, instead of being graded, optionally can have sharp transitions between one layer and the next, without a substantial gradient of composition. Such pH protective coating or layer can be made, for example, by providing the gases to produce a layer as a steady state flow in a non-plasma state, then energizing the system with a brief plasma discharge to form a coating or layer on the substrate. If a subsequent pH protective coating or layer is to be applied, the gases for the previous pH protective coating or layer are cleared out and the gases for the next pH protective coating or layer are applied in a steady-state fashion before energizing the plasma and again forming a distinct layer on the surface of the substrate or its outermost previous pH protective coating or layer, with little if any gradual transition at the interface.

Vessel Made of Glass

Another embodiment is a pharmaceutical package 210 as shown in any embodiment, for example FIGS. 8-10, comprising a vessel or vessel part such as 214 or 250 made of glass; optionally a composite barrier coating or layer such as 288 on the vessel or vessel part; a pH protective coating or layer such as 286 on the vessel, vessel part, or composite barrier coating or layer; and a pharmaceutical composition or preparation such as 218 contained within the vessel. In this embodiment the composite barrier coating or layer is optional because a glass vessel wall in itself is an extremely good barrier layer. It is contemplated to optionally provide a barrier layer primarily to provide isolation: in other words, to prevent contact and interchange of material of any kind, such as ions of the glass or constituents of the pharmaceutical composition or preparation between the vessel wall and the contents of the vessel. The pH protective layer as defined in this specification is contemplated to perform the isolation function independently, at least to a degree. This protection layer is contemplated to provide a useful function on glass in contact with the pharmaceutical composition or preparation, as the present working examples show that borosilicate glass, commonly used today for pharmaceutical packaging, is dissolved by a fluid composition having a pH exceeding 5. Particularly in applications where such dissolution is disadvantageous or perceived to be disadvantageous, the present pH protective coatings or layers will find utility.

The vessel can be made, for example of glass of any type used in medical or laboratory applications, such as soda-lime glass, borosilicate glass, or other glass formulations. One function of a pH protective coating or layer on a glass vessel can be to reduce the ingress of ions in the glass, either intentionally or as impurities, for example sodium, calcium, or others, from the glass to the contents of the pharmaceutical package or other vessel, such as a reagent or blood in an evacuated blood collection tube. Alternatively, a dual functional pH protective/lubricity coating or layer can be used on a glass vessel in whole or in part, such as selectively at surfaces contacted in sliding relation to other parts, to provide lubricity, for example to ease the insertion or removal of a stopper or passage of a sliding element such as a piston in a syringe, as well as to provide the isolation of a pH protective coating or layer. Still another reason to coat a glass vessel, for example with a dual functional hydrophobic and pH protective coating or layer, is to prevent a reagent or intended sample for the pharmaceutical package or other vessel, such as blood, from sticking to the wall of the vessel or an increase in the rate of coagulation of the blood in contact with the wall of the vessel, as well as to provide the isolation of a pH protective coating or layer.

A related embodiment is a vessel as described in the previous paragraphs, in which the composite barrier coating or layer is made of soda lime glass, borosilicate glass, or another type of glass coating or layer on a substrate.

Vessels Generally

A vessel with a pH protective coating as described herein and/or prepared according to a method described herein can be used for reception and/or storage and/or delivery of a compound or composition. The compound or composition can be sensitive, for example air-sensitive, oxygen-sensitive, sensitive to humidity and/or sensitive to mechanical influences. It can be a biologically active compound or composition, for example a pharmaceutical preparation or medicament like insulin or a composition comprising insulin. In another aspect, it can be a biological fluid, optionally a bodily fluid, for example blood or a blood fraction. In certain aspects of the present invention, the compound or composition can be a product to be administered to a subject in need thereof, for example a product to be injected, like blood (as in transfusion of blood from a donor to a recipient or reintroduction of blood from a patient back to the patient) or insulin.

A vessel with a pH protective coating as described herein and/or prepared according to a method described herein can further be used for protecting a compound or composition contained in its interior space against mechanical and/or chemical effects of the surface of the vessel material. For example, it can be used for preventing or reducing precipitation and/or clotting or platelet activation of the compound or a component of the composition, for example insulin precipitation or blood clotting or platelet activation.

It can further be used for protecting a compound or composition contained in its interior against the environment outside of the pharmaceutical package or other vessel, for example by preventing or reducing the entry of one or more compounds from the environment surrounding the vessel into the interior space of the vessel. Such environmental compound can be a gas or liquid, for example an atmospheric gas or liquid containing oxygen, air, and/or water vapor.

A vessel with a pH protective coating as described herein can also be evacuated and stored in an evacuated state. For example, the pH protective coating or layer allows better maintenance of the vacuum in comparison to a corresponding vessel without a pH protective coating. In one aspect of this embodiment, the vessel with a pH protective coating is a blood collection tube. The tube can also contain an agent for preventing blood clotting or platelet activation, for example EDTA or heparin.

Any of the above-described embodiments can be made, for example, by providing as the vessel a length of tubing from about 1 cm to about 200 cm, optionally from about 1 cm to about 150 cm, optionally from about 1 cm to about 120 cm, optionally from about 1 cm to about 100 cm, optionally from about 1 cm to about 80 cm, optionally from about 1 cm to about 60 cm, optionally from about 1 cm to about 40 cm, optionally from about 1 cm to about 30 cm long, and processing it with a probe electrode as described below. Particularly for the longer lengths in the above ranges, it is contemplated that relative motion between the probe and the vessel can be useful during pH protective coating or layer formation. This can be done, for example, by moving the vessel with respect to the probe or moving the probe with respect to the vessel.

In these embodiments, it is contemplated that the composite barrier coating or layer can be thinner or less complete than would be preferred to provide the high gas barrier integrity needed in an evacuated blood collection tube. In these embodiments, it is contemplated that the pH protective coating or layer can be thinner or less complete than would be preferred to provide the long shelf life needed to store a liquid material in contact with the barrier layer for an extended period.

As an optional feature of any of the foregoing embodiments the vessel has a central axis.

As an optional feature of any of the foregoing embodiments the vessel wall is sufficiently flexible to be flexed at least once at 20° C., without breaking the wall, over a range from at least substantially straight to a bending radius at the central axis of not more than 100 times as great as the outer diameter of the vessel.

As an optional feature of any of the foregoing embodiments the bending radius at the central axis is not more than 90 times as great as, or not more than 80 times as great as, or not more than 70 times as great as, or not more than 60 times as great as, or not more than 50 times as great as, or not more than 40 times as great as, or not more than 30 times as great as, or not more than 20 times as great as, or not more than 10 times as great as, or not more than 9 times as great as, or not more than 8 times as great as, or not more than 7 times as great as, or not more than 6 times as great as, or not more than 5 times as great as, or not more than 4 times as great as, or not more than 3 times as great as, or not more than 2 times as great as, or not more than, the outer diameter of the vessel.

As an optional feature of any of the foregoing embodiments the vessel wall can be a fluid-contacting surface made of flexible material.

As an optional feature of any of the foregoing embodiments the vessel lumen can be the fluid flow passage of a pump.

As an optional feature of any of the foregoing embodiments the vessel can be a blood bag adapted to maintain blood in good condition for medical use.

As an optional feature of any of the foregoing embodiments the polymeric material can be a silicone elastomer or a thermoplastic polyurethane, as two examples, or any material suitable for contact with blood, or with insulin.

In an optional embodiment, the vessel has an inner diameter of at least 2 mm, or at least 4 mm.

As an optional feature of any of the foregoing embodiments the vessel is a tube.

As an optional feature of any of the foregoing embodiments the lumen has at least two open ends.

Vessel Containing Viable Blood, Having a pH protective Coating or Layer Deposited from an Organosilicon Precursor Even another embodiment is a blood containing vessel. Several non-limiting examples of such a vessel are a blood transfusion bag, a blood sample collection vessel in which a sample has been collected, the tubing of a heart-lung machine, a flexible-walled blood collection bag, or tubing used to collect a patient's blood during surgery and reintroduce the blood into the patient's vasculature. If the vessel includes a pump for pumping blood, a particularly suitable pump is a centrifugal pump or a peristaltic pump. The vessel has a wall; the wall has an inner or interior surface defining a lumen. The inner or interior surface of the wall has an at least partial pH protective coating or layer of a pH protective layer, which optionally also presents a hydrophobic surface. The pH protective coating or layer can be as thin as monomolecular thickness or as thick as about 1000 nm. The vessel contains blood viable for return to the vascular system of a patient disposed within the lumen in contact with the hydrophobic layer.

An embodiment is a blood containing vessel including a wall and having an inner or interior surface defining a lumen. The inner or interior surface has an at least partial pH protective coating or layer that optionally also presents a hydrophobic surface. The pH protective coating or layer can also comprise or consist essentially of $SiO_xC_y$, where x and y are as defined in this specification. The thickness of the hydrophobic coating or layer is within the range from monomolecular thickness to about 1000 nm thick on the inner or interior surface. The vessel contains blood viable for return to the vascular system of a patient disposed within the lumen in contact with the hydrophobic coating or layer.

pH Protective Coating or Layer Deposited from an Organosilicon Precursor Reduces Clotting or Platelet Activation of Blood in the Vessel Another embodiment is a vessel having a wall. The wall has an inner or interior surface defining a lumen and has an at least partial pH protective coating or layer that presents a hydrophobic surface, where optionally x and y are as previously defined. The thickness of the pH protective coating or layer is from monomolecular thickness to about 1000 nm thick on the inner or interior surface. The pH protective coating or layer is effective to reduce the clotting or platelet activation of blood exposed to the inner or interior surface, compared to the same type of wall uncoated with a hydrophobic layer.

It is contemplated that the incorporation of a hydrophobic layer will reduce the adhesion or clot forming tendency of the blood, as compared to its properties in contact with an unmodified polymeric or $SiO_x$ surface. This property is contemplated to reduce or potentially eliminate the need for treating the blood with heparin, as by reducing the necessary blood concentration of heparin in a patient undergoing surgery of a type requiring blood to be removed from the patient and then returned to the patient, as when using a heart-lung machine during cardiac surgery. It is contemplated that this will reduce the complications of surgery involving the passage of blood through such a pharmaceutical package or other vessel, by reducing the bleeding complications resulting from the use of heparin.

Another embodiment is a vessel including a wall and having an inner or interior surface defining a lumen. The inner or interior surface has an at least partial pH protective coating or layer that presents a hydrophobic surface, the thickness of the pH protective coating or layer being from monomolecular thickness to about 1000 nm thick on the inner or interior surface, the pH protective coating or layer being effective to reduce the clotting or platelet activation of blood exposed to the inner or interior surface.

Vessel Containing Viable Blood, Having a pH protective Coating or Layer of Group III or IV Element Another embodiment is a blood containing vessel having a wall having an inner or interior surface defining a lumen. The inner or interior surface has an at least partial pH protective coating or layer of a composition comprising one or more elements of Group III, one or more elements of Group IV, or a combination of two or more of these. The thickness of the pH protective coating or layer is between monomolecular thickness and about 1000 nm thick, inclusive, on the inner or interior surface. The vessel contains blood viable for return to the vascular system of a patient disposed within the lumen in contact with the pH protective coating or layer.

pH protective Coating or Layer of Group III or IV Element Reduces Clotting or Platelet Activation of Blood in the Vessel Optionally, in the vessel of the preceding paragraph, the pH protective coating or layer of the Group III or IV Element is effective to reduce the clotting or platelet activation of blood exposed to the inner or interior surface of the vessel wall.

Pharmaceutical Delivery Vessels

A vessel with a pH protective coating or vessel as described herein can be used for preventing or reducing the escape of a compound or composition contained in the vessel into the environment surrounding the vessel.

Further uses of the pH protective coating or layer and vessel as described herein, which are apparent from any part of the description and claims, are also contemplated.

Common Conditions for All Embodiments

In any embodiment contemplated here, many common conditions can be used, for example any of the following, in any combination. Alternatively, any different conditions described elsewhere in this specification or claims can be employed.

I. Coating Receiver of any Embodiment
Vessel of any Embodiment

The vessel can be a sample collection tube, for example a blood collection tube, or a syringe, or a syringe part, for example a barrel or piston or plunger; a vial; a conduit; or a cuvette. The substrate can be a closed-ended tube, for example a medical sample collection tube. The substrate can be the inside wall of a vessel having a lumen, the lumen having a void volume of from 0.5 to 50 mL, optionally from 1 to 10 mL, optionally from 0.5 to 5 mL, optionally from 1 to 3 mL. The substrate surface can be part or all of the inner or interior surface of a vessel having at least one opening and an inner or interior surface, and wherein the gaseous reactant, also known in any embodiment as a precursor feed, fills the interior lumen of the vessel and the plasma can be generated in part or all of the interior lumen of the vessel.

Syringe and Parts

The substrate can be a syringe barrel. The syringe barrel can have a plunger sliding surface and the pH protective coating or layer can be disposed on at least a portion of the plunger sliding surface. The pH protective coating or layer can be a lubricity and/or pH protective coating. The lubricity and/or pH protective coating or layer can be on the barrel inner or interior surface. The lubricity and/or pH protective coating or layer can be on the plunger. In a particular aspect, the substrate is a staked needle syringe or part of a staked needle syringe.

Vessel to Receive Stopper

The substrate can be a stopper receiving surface in the mouth of a vessel. The substrate can be a generally conical or cylindrical inner or interior surface of an opening of a vessel adapted to receive a stopper.

Stopper

The substrate can be a sliding surface of a stopper. The substrates can be coated by providing a multiplicity of the stoppers located in a single substantially evacuated vessel. The chemical vapor deposition can be plasma-enhanced chemical vapor deposition and the stopper can be contacted with the plasma. The chemical vapor deposition can be plasma-enhanced chemical vapor deposition. The plasma can be formed upstream of the stopper, producing plasma product, and the plasma product can be contacted with the stopper.

A closure can define a substrate coated with a pH protective coating or layer, optionally a stopper coated with a lubricity and/or pH protective coating. The substrate can be a closure seated in a vessel defining a lumen and a surface of the closure facing the lumen can be coated with the pH protective coating or layer.

The pH protective coating or layer can be effective to reduce the transmission of a metal ion constituent of the stopper into the lumen of the vessel.

Substrate of any Embodiment

The substrate can be a vessel wall. A portion of the vessel wall in contact with a wall-contacting surface of a closure can be coated with the pH protective coating or layer. The pH protective coating or layer can be a composite of material having first and second layers. The first coating or layer can interface with the elastomeric stopper. The first layer of the pH protective coating or layer can be effective to reduce the transmission of one or more constituents of the stopper into the vessel lumen. The second pH protective coating or layer can interface with the inner wall of the vessel. The second layer can be effective to reduce friction between the stopper and the inner wall of the vessel when the stopper is seated on the vessel.

Alternatively, the first and second layers of any embodiment can be defined by a pH protective coating or layer of graduated properties containing carbon and hydrogen, in which the proportions of carbon and hydrogen are less in the first coating or layer (applied to the substrate) than in the second coating or layer (exposed to the contents of the vessel).

The pH protective coating or layer of any embodiment can be applied by plasma enhanced chemical vapor deposition.

The substrate of any embodiment can comprise glass, alternatively a polymer, alternatively a polycarbonate polymer, alternatively an olefin polymer, alternatively a cyclic olefin copolymer, alternatively a polypropylene polymer, alternatively a polyester polymer, alternatively a polyethylene terephthalate polymer, alternatively a polyethylene naphthalate polymer, alternatively a combination, composite or blend of any two or more of the above materials.

II. Gaseous Reactant or Process Gas Limitations of any Embodiment

Deposition Conditions of any Embodiment

The plasma for PECVD, if used, can be generated at reduced pressure and the reduced pressure can be less than 300 mTorr, optionally less than 200 mTorr, even optionally less than 100 mTorr. The physical and chemical properties of the pH protective coating or layer can be set by setting the ratio of $O_2$ to the organosilicon precursor in the gaseous reactant, and/or by setting the electric power used for generating the plasma.

Relative Proportions of Gases of any Embodiment

The process gas can contain this ratio of gases for preparing a lubricity and/or pH protective coating or layer:
    from 0.5 to 10 standard volumes of the precursor;
    from 1 to 100 standard volumes of a carrier gas,
    from 0.1 to 10 standard volumes of an oxidizing agent.
alternatively this ratio:
    from 1 to 6 standard volumes of the precursor;
    from 1 to 80 standard volumes of a carrier gas,
    from 0.1 to 2 standard volumes of an oxidizing agent.
alternatively this ratio:
    from 2 to 4 standard volumes, of the precursor;
    from 1 to 100 standard volumes of a carrier gas,
    from 0.1 to 2 standard volumes of an oxidizing agent.
alternatively this ratio:
    from 1 to 6 standard volumes of the precursor;
    from 3 to 70 standard volumes, of a carrier gas,
    from 0.1 to 2 standard volumes of an oxidizing agent.
alternatively this ratio:
    from 2 to 4 standard volumes, of the precursor;
    from 3 to 70 standard volumes of a carrier gas,
    from 0.1 to 2 standard volumes of an oxidizing agent.
alternatively this ratio:
    from 1 to 6 standard volumes of the precursor;
    from 1 to 100 standard volumes of a carrier gas,
    from 0.2 to 1.5 standard volumes of an oxidizing agent.
alternatively this ratio:
    zfrom 2 to 4 standard volumes, of the precursor;
    from 1 to 100 standard volumes of a carrier gas,
    from 0.2 to 1.5 standard volumes of an oxidizing agent.
alternatively this ratio:
    from 1 to 6 standard volumes of the precursor;
    from 3 to 70 standard volumes of a carrier gas,
    from 0.2 to 1.5 standard volumes of an oxidizing agent.
alternatively this ratio:
    from 2 to 4 standard volumes of the precursor;
    from 3 to 70 standard volumes of a carrier gas,
    from 0.2 to 1.5 standard volumes of an oxidizing agent.

alternatively this ratio:
    from 1 to 6 standard volumes of the precursor;
    from 1 to 100 standard volumes of a carrier gas,
    from 0.2 to 1 standard volumes of an oxidizing agent.
alternatively this ratio:
    from 2 to 4 standard volumes of the precursor;
    from 1 to 100 standard volumes of a carrier gas,
    from 0.2 to 1 standard volumes of an oxidizing agent.
alternatively this ratio:
    from 1 to 6 standard volumes of the precursor;
    from 3 to 70 standard volumes of a carrier gas,
    from 0.2 to 1 standard volumes of an oxidizing agent.
alternatively this ratio:
    2 to 4 standard volumes, of the precursor;
    from 3 to 70 standard volumes of a carrier gas,
    from 0.2 to 1 standard volumes of an oxidizing agent.
alternatively this ratio:
    from 1 to 6 standard volumes of the precursor;
    from 5 to 100 standard volumes of a carrier gas,
    from 0.1 to 2 standard volumes of an oxidizing agent.
alternatively this ratio:
    from 2 to 4 standard volumes, of the precursor;
    from 5 to 100 standard volumes of a carrier gas,
    from 0.1 to 2 standard volumes
    of an oxidizing agent.
alternatively this ratio:
    from 1 to 6 standard volumes of the precursor;
    from 10 to 70 standard volumes, of a carrier gas,
    from 0.1 to 2 standard volumes of an oxidizing agent.
alternatively this ratio:
    from 2 to 4 standard volumes, of the precursor;
    from 10 to 70 standard volumes of a carrier gas,
    from 0.1 to 2 standard volumes of an oxidizing agent.
alternatively this ratio:
    from 1 to 6 standard volumes of the precursor;
    from 5 to 100 standard volumes of a carrier gas,
    from 0.5 to 1.5 standard volumes of an oxidizing agent.
alternatively this ratio:
    from 2 to 4 standard volumes, of the precursor;
    from 5 to 100 standard volumes of a carrier gas,
    from 0.5 to 1.5 standard volumes of an oxidizing agent.
alternatively this ratio:
    from 1 to 6 standard volumes of the precursor;
    from 10 to 70 standard volumes, of a carrier gas,
    from 0.5 to 1.5 standard volumes of an oxidizing agent.
alternatively this ratio:
    from 2 to 4 standard volumes of the precursor;
    from 10 to 70 standard volumes of a carrier gas,
    from 0.5 to 1.5 standard volumes of an oxidizing agent.
alternatively this ratio:
    from 1 to 6 standard volumes of the precursor;
    from 5 to 100 standard volumes of a carrier gas,
    from 0.8 to 1.2 standard volumes of an oxidizing agent.
alternatively this ratio:
    from 2 to 4 standard volumes of the precursor;
    from 5 to 100 standard volumes of a carrier gas,
    from 0.8 to 1.2 standard volumes of an oxidizing agent.
alternatively this ratio:
    from 1 to 6 standard volumes of the precursor;
    from 10 to 70 standard volumes of a carrier gas,
    from 0.8 to 1.2 standard volumes of an oxidizing agent.
alternatively this ratio:
    2 to 4 standard volumes, of the precursor;
    from 10 to 70 standard volumes of a carrier gas,
    from 0.8 to 1.2 standard volumes of an oxidizing agent.

Precursor of any Embodiment

The organosilicon precursor has been described elsewhere in this description.

The organosilicon compound can in certain aspects, particularly when a lubricity and/or pH protective coating or layer is formed, comprise octamethylcyclotetrasiloxane (OMCTS). The organosilicon compound for any embodiment of said certain aspects can consist essentially of octamethylcyclotetrasiloxane (OMCTS). The organosilicon compound can in certain aspects, particularly when a barrier coating or layer is formed, be or comprise hexamethyldisiloxane.

The reaction gas can also include a hydrocarbon. The hydrocarbon can comprise methane, ethane, ethylene, propane, acetylene, or a combination of two or more of these.

The organosilicon precursor can be delivered at a rate of equal to or less than 10 sccm, optionally equal to or less than 6 sccm, optionally equal to or less than 2.5 sccm, optionally equal to or less than 1.5 sccm, optionally equal to or less than 1.25 sccm. Larger pharmaceutical packages or other vessels or other changes in conditions or scale may require more or less of the precursor. The precursor can be provided at less than 1 Torr absolute pressure.

Carrier Gas of any Embodiment

The carrier gas can comprise or consist of an inert gas, for example argon, helium, xenon, neon, another gas that is inert to the other constituents of the process gas under the deposition conditions, or any combination of two or more of these.

Oxidizing Gas of any Embodiment

The oxidizing gas can comprise or consist of oxygen ($O_2$ and/or $O_3$ (commonly known as ozone)), nitrous oxide, or any other gas that oxidizes the precursor during PECVD at the conditions employed. The oxidizing gas comprises about 1 standard volume of oxygen. The gaseous reactant or process gas can be at least substantially free of nitrogen.

III. Plasma of any Embodiment

The plasma of any PECVD embodiment can be formed in the vicinity of the substrate. The plasma can in certain cases, especially when preparing a composite barrier coating or layer, be a non-hollow-cathode plasma. In other certain cases, especially when preparing a lubricity coating or layer, a non-hollow-cathode plasma is not desired. The plasma can be formed from the gaseous reactant at reduced pressure. Sufficient plasma generation power input can be provided to induce pH protective coating or layer formation on the substrate.

IV. RF Power of any Embodiment

The precursor can be contacted with a plasma made by energizing the vicinity of the precursor with electrodes powered at a frequency of 10 kHz to 2.45 GHz, alternatively from about 13 to about 14 MHz.

The precursor can be contacted with a plasma made by energizing the vicinity of the precursor with electrodes powered at radio frequency, optionally at a frequency of from 10 kHz to less than 300 MHz, optionally from 1 to 50 MHz, even optionally from 10 to 15 MHz, optionally at 13.56 MHz.

The precursor can be contacted with a plasma made by energizing the vicinity of the precursor with electrodes supplied with electric power at from 0.1 to 25 W, optionally from 1 to 22 W, optionally from 1 to 10 W, even optionally from 1 to 5 W, optionally from 2 to 4 W, for example of 3 W, optionally from 3 to 17 W, even optionally from 5 to 14 W, for example 6 or 7.5 W, optionally from 7 to 11 W, for example of 8 W, from 0.1 to 500 W, optionally from 0.1 to 400 W, optionally from 0.1 to 300 W, optionally from 1 to 250 W, optionally from 1 to 200 W, even optionally from 10 to 150 W, optionally from 20 to 150 W, for example of 40 W, optionally from 40 to 150 W, even optionally from 60 to 150 W.

The precursor can be contacted with a plasma made by energizing the vicinity of the precursor with electrodes supplied with electric power density at less than 10 W/ml of plasma volume, alternatively from 6 W/ml to 0.1 W/ml of plasma volume, alternatively from 5 W/ml to 0.1 W/ml of plasma volume, alternatively from 4 W/ml to 0.1 W/ml of plasma volume, alternatively from 2 W/ml to 0.2 W/ml of plasma volume, alternatively from 10 W/ml to 50 W/ml, optionally from 20 W/ml to 40 W/ml.

The plasma can be formed by exciting the reaction mixture with electromagnetic energy, alternatively microwave energy.

V. Other Process Options of any Embodiment

The applying step for applying a pH protective coating or layer to the substrate can be carried out by vaporizing the precursor and providing it in the vicinity of the substrate.

The chemical vapor deposition employed can be PECVD and the deposition time can be from 1 to 30 sec, alternatively from 2 to 10 sec, alternatively from 3 to 9 sec. The purposes for optionally limiting deposition time can be to avoid overheating the substrate, to increase the rate of production, and to reduce the use of process gas and its constituents. The purposes for optionally extending deposition time can be to provide a thicker pH protective coating or layer for particular deposition conditions.

VI. pH Protective Coating or Layer Properties of any Embodiment

Hydrophobicity Properties of any Embodiment

An embodiment can be carried out under conditions effective to form a hydrophobic pH protective coating or layer on the substrate. Optionally, the hydrophobic characteristics of the pH protective coating or layer can be set by setting the ratio of the $O_2$ to the organosilicon precursor in the gaseous reactant, and/or by setting the electric power used for generating the plasma. Optionally, the pH protective coating or layer can have a lower wetting tension than the uncoated surface, optionally a wetting tension of from 20 to 72 dyne/cm, optionally from 30 to 60 dynes/cm, optionally from 30 to 40 dynes/cm, optionally 34 dyne/cm. Optionally, the pH protective coating or layer can be more hydrophobic than the uncoated surface.

Thickness of any Embodiment

Optionally, the pH protective coating or layer can have a thickness determined by transmission electron microscopy (TEM), of any amount stated in this disclosure.

Composition of any Embodiment

Optionally, the lubricity and/or pH protective coating or layer can be composed of $Si_wO_xC_yH_z$ (or its equivalent $SiO_xC_y$) or $Si_wN_xC_yH_z$ or its equivalent $SiN_xC_y$), each as defined previously. The atomic ratio of Si:O:C can be determined by XPS (X-ray photoelectron spectroscopy). Taking into account the H atoms, the pH protective coating or layer may thus in one aspect have the formula $Si_wO_xC_yH_z$, or its equivalent $SiO_xC_y$, for example where w is 1, x is from about 0.5 to about 2.4, y is from about 0.6 to about 3, and z is from about 2 to about 9.

Typically, expressed as the formula $Si_wO_xC_y$, the atomic ratios of Si, O, and C are, as several options:

Si 100: O 50-150: C 90-200 (i.e. w=1, x=0.5 to 1.5, y=0.9 to 2);

Si 100: O 70-130: C 90-200 (i.e. w=1, x=0.7 to 1.3, y=0.9 to 2)

Si 100: O 80-120: C 90-150 (i.e. w=1, x=0.8 to 1.2, y=0.9 to 1.5)

Si 100: O 90-120: C 90-140 (i.e. w=1, x=0.9 to 1.2, y=0.9 to 1.4), or

Si 100: O 92-107: C 116-133 (i.e. w=1, x=0.92 to 1.07, y=1.16 to 1.33).

Alternatively, the pH protective coating or layer can have atomic concentrations normalized to 100% carbon, oxygen, and silicon, as determined by X-ray photoelectron spectroscopy (XPS) of less than 50% carbon and more than 25% silicon. Alternatively, the atomic concentrations are from 25 to 45% carbon, 25 to 65% silicon, and 10 to 35% oxygen. Alternatively, the atomic concentrations are from 30 to 40% carbon, 32 to 52% silicon, and 20 to 27% oxygen. Alternatively, the atomic concentrations are from 33 to 37% carbon, 37 to 47% silicon, and 22 to 26% oxygen.

Optionally, the atomic concentration of carbon in the pH protective layer, normalized to 100% of carbon, oxygen, and silicon, as determined by X-ray photoelectron spectroscopy (XPS), can be greater than the atomic concentration of carbon in the atomic formula for the organosilicon precursor. For example, embodiments are contemplated in which the atomic concentration of carbon increases by from 1 to 80 atomic percent, alternatively from 10 to 70 atomic percent, alternatively from 20 to 60 atomic percent, alternatively from 30 to 50 atomic percent, alternatively from 35 to 45 atomic percent, alternatively from 37 to 41 atomic percent.

Optionally, the atomic ratio of carbon to oxygen in the pH protective coating or layer can be increased in comparison to the organosilicon precursor, and/or the atomic ratio of oxygen to silicon can be decreased in comparison to the organosilicon precursor.

Optionally, the pH protective coating or layer can have an atomic concentration of silicon, normalized to 100% of carbon, oxygen, and silicon, as determined by X-ray photoelectron spectroscopy (XPS), less than the atomic concentration of silicon in the atomic formula for the feed gas. For example, embodiments are contemplated in which the atomic concentration of silicon decreases by from 1 to 80 atomic percent, alternatively by from 10 to 70 atomic percent, alternatively by from 20 to 60 atomic percent, alternatively by from 30 to 55 atomic percent, alternatively by from 40 to 50 atomic percent, alternatively by from 42 to 46 atomic percent.

As another option, a pH protective coating or layer is contemplated that can be characterized by a sum formula wherein the atomic ratio C:O can be increased and/or the atomic ratio Si:O can be decreased in comparison to the sum formula of the organosilicon precursor.

Other pH Protective Coating or Layer Properties of any Embodiment

The pH protective coating or layer can have a density between 1.25 and 1.65 $g/cm^3$, alternatively between 1.35 and 1.55 $g/cm^3$, alternatively between 1.4 and 1.5 $g/cm^3$, alternatively between 1.4 and 1.5 $g/cm^3$, alternatively between 1.44 and 1.48 $g/cm^3$, as determined by X-ray reflectivity (XRR). Optionally, the organosilicon compound can be octamethylcyclotetrasiloxane and the pH protective coating or layer can have a density which can be higher than the density of a pH protective coating or layer made from HMDSO as the organosilicon compound under the same PECVD reaction conditions.

The pH protective coating or layer optionally can prevent or reduce the precipitation of a compound or component of a composition in contact with the pH protective coating or layer, in particular can prevent or reduce insulin precipitation or blood clotting, in comparison to the uncoated surface and/or to a barrier coated surface using HMDSO as precursor.

The substrate can be a pharmaceutical package or other vessel, for protecting a compound or composition contained or received in the vessel with a pH protective coating against mechanical and/or chemical effects of the surface of the uncoated substrate.

The substrate can be a pharmaceutical package or other vessel, for preventing or reducing precipitation and/or clotting of a compound or a component of the composition in contact with the inner or interior surface of the vessel. The compound or composition can be a biologically active compound or composition, for example a medicament, for example the compound or composition can comprise insulin, wherein insulin precipitation can be reduced or prevented. Alternatively, the compound or composition can be a biological fluid, for example a bodily fluid, for example blood or a blood fraction wherein blood clotting can be reduced or prevented.

The pH protective coating or layer optionally can have an RMS surface roughness value (measured by AFM) of from about 5 to about 9, optionally from about 6 to about 8, optionally from about 6.4 to about 7.8. The $R_a$ surface roughness value of the pH protective coating or layer, measured by AFM, can be from about 4 to about 6, optionally from about 4.6 to about 5.8. The $R_{max}$ surface roughness value of the pH protective coating or layer, measured by AFM, can be from about 70 to about 160, optionally from about 84 to about 142, optionally from about 90 to about 130.

VII. Product Made of Vessel Plus Contents, Optional for any Embodiment

In any embodiment, the substrate can be a vessel having an inner or interior surface defining a lumen and an exterior surface, the pH protective coating or layer can be on the inner or interior surface of the pharmaceutical package or other vessel, and the vessel can contain a compound or composition in its lumen, for example citrate or a citrate containing composition, or for example insulin or an insulin containing composition. A prefilled syringe is especially considered which contains injectable or other liquid drugs like insulin.

EXAMPLES

The following Examples are in part already disclosed in EP 2 251 455. In order to avoid unnecessary repetition, not all of the Examples in EP 2 251 455 A2 are repeated here, but explicit reference is herewith made to them.

Basic Protocols for Forming and Coating Syringe Barrels

The pharmaceutical packages or other vessels tested in the subsequent working examples were formed and coated according to the following exemplary protocols, except as otherwise indicated in individual examples. Particular parameter values given in the following basic protocols, for example the electric power and gaseous reactant or process gas flow, are typical values. When parameter values were changed in comparison to these typical values, this will be indicated in the subsequent working examples. The same applies to the type and composition of the gaseous reactant or process gas.

In some instances, the reference characters and Figures mentioned in the following protocols and additional details can be found in U.S. Pat. No. 7,985,188.

Protocol for Coating Syringe Barrel Interior with $SiO_x$

The apparatus and protocol generally as found in U.S. Pat. No. 7,985,188 can be used for coating syringe barrel interiors with an $SiO_x$ composite barrier coating or layer, varied as follows. 5 ml vials are provided for barrier coating. The feed gas is a mixture of 1.56 sccm of HMDSO (hexamethylenedisiloxane) and 20 sccm of $O_2$, with no carrier gas. The RF power profile is as follows. The initial power level is 20 W, and the final power level is 140 W. The power level is increased linearly from 20 W to 140 W over a period of two seconds. The power level is then maintained at 140 W for 13 seconds, the remainder of the coating sequence. The resulting $SiO_x$ composite barrier coating or layer is a minimum of 40 nm and a maximum of 65 nm thick. High Resolution X-ray Photoelectron Spectroscopy (XPS) typically shows the presence of an interface, typically not more than 3 nm thick, between the composite barrier coating or layer and the substrate having at least 2 mol. % $O_3$—Si—C covalent bonding, as a proportion of the $O_3$—Si—C covalent bonding plus $SiO_4$ bonding. High Resolution X-ray Photoelectron Spectroscopy (XPS) also shows the interface between the composite barrier coating or layer and the substrate has Si 2p peak broadening of at least 0.2 eV, compared to the binding energy of $SiO_4$ bonding.

Protocol for Coating Syringe Barrel Interior with OMCTS pH protective Coating

Syringe barrels already coated with a composite barrier coating or layer of $SiO_x$, as previously identified, are further interior coated with a pH protective coating as previously identified, generally following the protocols of U.S. Pat. No. 7,985,188 for applying the lubricity coating or layer, except with modified conditions in certain instances as noted in the working examples. The conditions given here are for a COC syringe barrel, and can be modified as appropriate for syringe barrels made of other materials. The apparatus as generally shown in FIGS. 3 and 4 is used to hold a syringe barrel with butt sealing at the base of the syringe barrel. Additionally a cap is provided that seals the end of the syringe barrel (illustrated in FIG. 3).

The syringe barrel is carefully moved into the sealing position over the extended probe or counter electrode 108 and pushed against a plasma screen. The plasma screen is fit snugly around the probe or counter electrode 108 insuring good electrical contact. The probe or counter electrode 108 is grounded to the casing of the RF matching network.

The gas delivery port 110 is connected to a manual ball valve or similar apparatus for venting, a thermocouple pressure gauge and a bypass valve connected to the vacuum pumping line. In addition, the gas system is connected to the gas delivery port 110 allowing the gaseous reactant or process gas, octamethylcyclotetrasiloxane (OMCTS) (or the specific gaseous reactant or process gas reported for a particular example) to be flowed through the gas delivery port 110 (under process pressures) into the interior of the syringe barrel.

The gas system is comprised of a commercially available heated mass flow vaporization system that heats the OMCTS to about 100° C. The heated mass flow vaporization system is connected to liquid octamethylcyclotetrasiloxane (Alfa Aesar® Part Number A12540, 98%). The OMCTS flow rate is set to the specific organosilicon precursor flow reported for a particular example. To ensure no condensation of the vaporized OMCTS flow past this point, the gas stream is diverted to the pumping line when it is not flowing into the interior of the COC syringe barrel for processing.

Once the syringe barrel is installed, the vacuum pump valve is opened to the vessel holder 50 and the interior of the COC syringe barrel. A vacuum pump and blower comprise the vacuum pump system. The pumping system allows the interior of the COC syringe barrel to be reduced to pressure(s) of less than 100 mTorr while the gaseous reactant or process gases is flowing at the indicated rates.

Once the base vacuum level is achieved, the vessel holder 50 assembly is moved into the electrode 160 assembly. The gas stream (OMCTS vapor) is flowed into the gas delivery port 110 (by adjusting the 3-way valve from the pumping line to the gas delivery port 110. Pressure inside the COC syringe barrel is approximately 140 mTorr as measured by a capacitance manometer (MKS) installed on the pumping line near the valve that controls the vacuum. In addition to the COC syringe barrel pressure, the pressure inside the gas delivery port 110 and gas system is also measured with the thermocouple vacuum gauge that is connected to the gas system. This pressure is typically less than 6 Torr.

Once the gas is flowing to the interior of the COC syringe barrel, the RF power supply is turned on to its fixed power level. A 600 Watt RF power supply is used (at 13.56 MHz) at a fixed power level indicated in a specific example. The RF power supply is connected to an auto match which matches the complex impedance of the plasma (to be created in the vessel) to the output impedance of the RF power supply. The forward power is as stated and the reflected power is 0 Watts so that the stated power is delivered to the interior of the vessel. The RF power supply is controlled by a laboratory timer and the power on time set to 10 seconds (or a different time stated in a given example).

Upon initiation of the RF power, a uniform plasma is established inside the interior of the vessel. The plasma is maintained for the entire pH protective coating or layer time, until the RF power is terminated by the timer. The plasma produces a pH protective coating or layer on the interior of the vessel.

After pH protective coating, the gas flow is diverted back to the vacuum line and the vacuum valve is closed. The vent valve is then opened, returning the interior of the COC syringe barrel to atmospheric pressure (approximately 760 Torr). The treated vessel is then carefully removed from the vessel holder 50 assembly (after moving the vessel holder 50 assembly out of the electrode 160 assembly).

A similar protocol is used, except using apparatus generally like that of FIG. 1, for applying a pH protective coating or layer to vials.

Protocol for Total Silicon Measurement

This protocol is used to determine the total amount of silicon coatings present on the entire vessel wall. A supply of 0.1 N potassium hydroxide (KOH) aqueous solution is prepared, taking care to avoid contact between the solution or ingredients and glass. The water used is purified water, 18 MΩ quality. A Perkin Elmer Optima Model 7300DV ICP-OES instrument is used for the measurement except as otherwise indicated.

Each device (vial, syringe, tube, or the like) to be tested and its cap and crimp (in the case of a vial) or other closure are weighed empty to 0.001 g, then filled completely with the KOH solution (with no headspace), capped, crimped, and reweighed to 0.001 g. In a digestion step, each vial is placed in a sonicating water bath at 40° C. for a minimum of 8-10 hours. The digestion step is carried out to quantitatively remove the silicon coatings from the vessel wall into the KOH solution. After this digestion step, the vials are removed from the sonicating water bath and allowed to cool to room temperature. The contents of the vials are transferred into 15 ml ICP tubes. The total Si concentration is run on each solution by ICP/OES following the operating procedure for the ICP/OES.

The total Si concentration is reported as parts per billion of Si in the KOH solution. This concentration represents the total amount of silicon coatings that were on the vessel wall before the digestion step was used to remove it.

The total Si concentration can also be determined for fewer than all the silicon layers on the vessel, as when an $SiO_x$ barrier layer is applied, an $SiO_xC_y$ second layer (for example, a lubricity layer or a pH protective coating or layer) is then applied, and it is desired to know the total silicon concentration of just the $SiO_xC_y$ layer. This determination is made by preparing two sets of vessels, one set to which only the $SiO_x$ layer is applied and the other set to which the same $SiO_x$ layer is applied, followed by the $SiO_xC_y$ layer or other layers of interest. The total Si concentration for each set of vessels is determined in the same manner as described above. The difference between the two Si concentrations is the total Si concentration of the $SiO_xC_y$ second layer.

Protocol for Measuring Dissolved Silicon in a Vessel

In some of the working examples, the amount of silicon dissolved from the wall of the vessel by a test solution is determined, in parts per billion (ppb), for example to evaluate the dissolution rate of the test solution. This determination of dissolved silicon is made by storing the test solution in a vessel provided with an $SiO_x$ and/or $SiO_xC_y$ coating or layer under test conditions, then removing a sample of the solution from the vessel and testing the Si concentration of the sample. The test is done in the same manner as the Protocol for Total Silicon Measurement, except that the digestion step of that protocol is replaced by storage of the test solution in the vessel as described in this protocol. The total Si concentration is reported as parts per billion of Si in the test solution Protocol for Determining Average Dissolution Rate The average dissolution rates reported in the working examples are determined as follows. A series of test vessels having a known total total silicon measurement are filled with the desired test solution analogous to the manner of filling the vials with the KOH solution in the Protocol for Total Silicon Measurement. (The test solution can be a physiologically inactive test solution as employed in the present working examples or a physiologically active pharmaceutical preparation intended to be stored in the vessels to form a pharmaceutical package). The test solution is stored in respective vessels for several different amounts of time, then analyzed for the Si concentration in parts per billion in the test solution for each storage time. The respective storage times and Si concentrations are then plotted. The plots are studied to find a series of substantially linear points having the steepest slope.

The plot of dissolution amount (ppb Si) versus days decreases in slope with time. It is believed that the dissolution rate is not flattening out because the Si layer has been fully digested by the test solution.

For the PC194 test data in Table 2, linear plots of dissolution versus time data are prepared by using a least squares linear regression program to find a linear plot corresponding to the first five data points of each of the experimental plots. The slope of each linear plot is then determined and reported as representing the average dissolution rate applicable to the test, measured in parts per billion of Si dissolved in the test solution per unit of time.

Protocol for Determining Calculated Shelf Life

The calculated shelf life values reported in the working examples below are determined by extrapolation of the total silicon measurements and average dissolution rates, respectively determined as described in the Protocol for Total Silicon Measurement and the Protocol for Determining Average Dissolution Rate. The assumption is made that under the indicated storage conditions the $SiO_xC_y$ pH protective coating will be removed at the average dissolution rate until the coating is entirely removed. Thus, the total silicon measurement for the vessel, divided by the dissolution rate, gives the period of time required for the test solution to totally dissolve the $SiO_xC_y$ coating. This period of time is reported as the calculated shelf life. Unlike commercial shelf life calculations, no safety factor is calculated. Instead, the calculated shelf life is the calculated time to failure.

It should be understood that because the plot of ppb Si versus hours decreases in slope with time, an extrapolation from relatively short measurement times to relatively long calculated shelf lives is believed to be a "worst case" test that tends to underestimate the calculated shelf life actually obtainable.

Examples 1-4

Syringe samples were produced as follows. A COC 8007 extended barrel syringe was produced according to the Protocol for Forming COC Syringe Barrel. An $SiO_x$ barrier coating or layer is applied to some of the syringes according to the Protocol for coating COC Syringe Barrel Interior with $SiO_x$. A lubricity and/or pH protective coating or layer is applied to the $SiO_x$ coated syringes according to the Protocol for Coating COC Syringe Barrel Interior with OMCTS Lubricity Coating, modified as follows. The OMCTS was supplied from a vaporizer, due to its low volatility. Argon carrier gas was used. The process conditions were set to the following:
  OMCTS—3 sccm
  Argon gas—65 sccm
  Power—6 watts
  Time—10 seconds Several syringes are then tested for lubricity using a Genesis Packaging Plunger Force Tester (Model SFT-01 Syringe Force Tester, manufactured by Genesis Machinery, Lionville, PA) according to the Protocol for Lubricity Testing. Both the initiation force and maintenance forces (in Newtons) were noted relative to an uncoated sample, and expected data based on similar experiments are reported in Table 4.

Syringes coated with silicon oil are included as a reference since this is the current industry standard.

The lubricity coatings produced according to these working examples also function as pH protective coatings or layers to increase the shelf life of the vessels, compared to similar vessels provided with a composite barrier coating or layer but no lubricity coating or layer.

Examples 5-8

Syringe samples are produced as follows. A COC 8007 extended barrel syringe was produced according to the Protocol for Forming COC Syringe Barrel. An $SiO_x$ pH protective coating or layer is applied to the syringe barrels according to the Protocol for Coating COC Syringe Barrel Interior with $SiO_x$. A lubricity and/or pH protective coating or layer is applied to the $SiO_x$ coated syringes according to the Protocol for Coating COC Syringe Barrel Interior with OMCTS, modified as follows. Argon carrier gas and oxygen are used where noted in Table 6. The process conditions are set to the following, or as indicated in Table 6:
  OMCTS—3 sccm (when used)
  Argon gas—7.8 sccm (when used)
  Oxygen 0.38 sccm (when used)
  Power—3 watts
  Power on time—10 seconds The syringes of Examples 5 and 6 prepared under these conditions. The syringes of Example are 7 prepared under these conditions except without a lubricity and/or pH protective coating or layer, and the syringes of Example 8 (a commercial syringe coated with silicon oil) are then tested for lubricity and/or pH protective coatings using a Genesis Packaging Plunger Force Tester according to the Protocol for Lubricity Testing. Both the initiation force and maintenance forces (in Newtons) are noted relative to an uncoated sample, and expected data based on similar experiments are reported in Table 6. Syringes coated with silicon oil were included as a reference since this is the current industry standard.

The lubricity results predicted in Table 6 (Initiation Force and Maintenance Force), illustrate under these test conditions as well that the lubricity and/or pH protective coating or layer on Syringes E and F are expected to markedly improve their lubricity compared to Syringes G which lack any lubricity and/or pH protective coating or layer. The lubricity and/or pH protective coating or layer on the syringes of Examples 5 and 6 also are expected to markedly improve their lubricity compared to the syringes of Example 8, which contain the standard lubricity coating or layer in the industry.

The syringes of Examples 5-7 are also tested to determine total extractable silicon levels (representing extraction of the organosilicon-based PECVD pH protective coating or layer) using the Protocol for Measuring Dissolved Silicon in a Vessel, modified and supplemented as shown in this example.

The silicon is extracted using saline water digestion. The tip of each syringe plunger is covered with PTFE tape to prevent extracting material from the elastomeric tip material, then inserted into the syringe barrel base. The syringe barrel is filled with two milliliters of 0.9% aqueous saline solution via a hypodermic needle inserted through the Luer tip of the syringe. This is an appropriate test for extractables because many prefilled syringes are used to contain and deliver saline solution. The Luer tip is plugged with a piece of PTFE beading of appropriate diameter. The syringe is set into a PTFE test stand with the Luer tip facing up and placed in an oven at 50° C. for 72 hours.

Then, either a static or a dynamic mode is used to remove the saline solution from the syringe barrel. According to the static mode indicated in Table 6, the syringe plunger is removed from the test stand, and the fluid in the syringe is decanted into a vessel. According to the dynamic mode indicated in Table 6, the Luer tip seal is removed and the plunger is depressed to push fluid through the syringe barrel and expel the contents into a vessel. In either case, the fluid obtained from each syringe barrel is brought to a volume of 50 ml using 18.2MΩ-cm deionized water and further diluted by a factor of 2 to minimize sodium background during analysis. The CVH barrels contain two milliliters and the commercial barrels contain 2.32 milliliters.

Next, the fluid recovered from each syringe is tested for extractable silicon using the Protocol for Measuring Dissolved Silicon in a Vessel. The instrument used is a Perkin Elmer Elan DRC II equipped with a Cetac ASX-520 autosampler. The following ICP-MS conditions are employed:
  Nebulizer: Quartz Meinhardt
  Spray Chamber: Cyclonic
  RF (radio frequency) power: 1550 Watts
  Argon (Ar) Flow: 15.0 L/min
  Auxiliary Ar Flow: 1.2 L/min
  Nebulizer Gas Flow: 0.88 L/min Integration time: 80 sec
Scanning mode: Peak hopping
RPq (The RPq is a rejection parameter) for Cerium as CeO (m/z 156: <2%

Aliquots from aqueous dilutions obtained from the syringes of Examples 5-7 are injected and analyzed for Si in concentration units of micrograms per liter. The expected results of this test, based on similar testing, are shown in Table 6. While the results are not quantitative, they do indicate that extractables from the lubricity and/or pH protective coating or layer are not clearly higher than the extractables for the $SiO_x$ barrier layer only. Also, the static mode produced far less extractables than the dynamic mode, which was expected.

Comparative Example 9: Dissolution of $SiO_x$ Coating Versus pH

The Protocol for Measuring Dissolved Silicon in a Vessel is followed, except as modified here. Test solutions—50 mM buffer solutions at pH 3, 6, 7, 8, 9, and 12 are prepared. Buffers are selected having appropriate pKa values to provide the pH values being studied. A potassium phosphate buffer is selected for pH 3, 7, 8 and 12, a sodium citrate buffer is utilized for pH 6 and tris buffer is selected for pH 9. 3 ml of each test solution is placed in borosilicate glass 5 ml pharmaceutical vials and $SiO_x$ coated 5 ml thermoplastic pharmaceutical vials. The vials are all closed with standard coated stoppers and crimped. The vials are placed in storage at 20-25° C. and pulled at various time points for inductively coupled plasma spectrometer (ICP) analysis of Si content in the solutions contained in the vials, in parts per billion (ppb) by weight, for different storage times.

The Protocol for Determining Average Dissolution Rate Si content is used to monitor the rate of glass dissolution, except as modified here. The data is plotted to determine an average rate of dissolution of borosilicate glass or $SiO_x$ coating at each pH condition.

The rate of Si dissolution in ppb is converted to a predicted thickness (nm) rate of Si dissolution by determining the total weight of Si removed, then using a surface area calculation of the amount of vial surface (11.65 cm²) exposed to the solution and a density of $SiO_x$ of 2.2 g/cm³ The predicted initial thickness of the coating is about 36 nm at pH 5, about 80 nm at pH 6, about 230 nm at pH 7, about 400 nm at pH 7.5, about 750 nm at pH 8, and about 2600 nm at pH 9.

The coating thicknesses represent atypically harsh case scenarios for pharma and biotech products. Most biotech products and many pharma products are stored at refrigerated conditions and none are typically recommended for storage above room temperature. As a general rule of thumb, storage at a lower temperature reduces the thickness required, all other conditions being equivalent.

The following conclusions are reached, based on this test. First, the amount of dissolved Si in the $SiO_x$ coating or glass increases exponentially with increasing pH. Second, the $SiO_x$ coating dissolves more slowly than borosilicate glass at a pH lower than 8. The $SiO_x$ coating shows a linear, monophasic dissolution over time, whereas borosilicate glass tends to show a more rapid dissolution in the early hours of exposure to solutions, followed by a slower linear dissolution. This may be due to surface accumulation of some salts and elements on borosilicate during the forming process relative to the uniform composition of the $SiO_x$ coating. This result incidentally suggests the utility of an $SiO_x$ coating on the wall of a borosilicate glass vial to reduce dissolution of the glass at a pH lower than 8. Third, PECVD applied barrier coatings for vials in which pharmaceutical preparations are stored will need to be adapted to the specific pharmaceutical preparation and proposed storage conditions (or vice versa), at least in some instances in which the pharmaceutical preparation interacts with the barrier coating significantly.

Example 10

An experiment is conducted with vessels coated with $SiO_x$ coating+OMCTS lubricity layer, to test the lubricity layer for its functionality as a pH protective coating. The vessels are 5 mL vials (the vials are normally filled with product to 5 mL; their capacity without headspace, when capped, is about 7.5 mL) composed of cyclic olefin co-polymer (COC, Topas® 6013M-07).

Sixty vessels are coated on their interior surfaces with an $SiO_x$ coating produced in a plasma enhanced chemical vapor deposition (PECVD) process using a HMDSO precursor gas according to the Protocol for Coating Tube Interior with $SiO_x$ set forth above, except that equipment suitable for coating a vial is used. The following conditions are used.
HMDSO flow rate: 0.47 sccm
Oxygen flow rate: 7.5 sccm
RF power: 70 Watts
Coating time: 12 seconds (includes a 2-sec RF power ramp-up time)

Next the $SiO_x$ coated vials are coated over the $SiO_x$ with an $SiO_xC_y$ coating produced in a PECVD process using an OMCTS precursor gas according to the Protocol for Coating COC Syringe Barrel Interior with OMCTS Lubricity Coating set forth above, except that the same coating equipment is used as for the $SiO_x$ coating. Thus, the special adaptations in the protocol for coating a syringe are not used. The following conditions are used.
OMCTS flow rate: 2.5 sccm
Argon flow rate: 10 sccm
Oxygen flow rate: 0.7 sccm
RF power: 3.4 Watts
Coating time: 5 seconds Eight vials are selected and the total deposited quantity of PECVD coating ($SiO_x+SiO_xC_y$) is determined with a Perkin Elmer Optima Model 7300DV ICP-OES instrument, using the Protocol for Total Silicon Measurement set forth above. This measurement determines the total amount of silicon in both coatings, and does not distinguish between the respective $SiO_x$ and $SiO_xC_y$ coatings. The results are shown in Table 7.

In the following work, except as indicated otherwise in this example, the Protocol for Determining Average Dissolution Rate is followed. Two buffered pH test solutions are used in the remainder of the experiment, respectively at pH 4 and pH 8 to test the effect of pH on dissolution rate. Both test solutions are 50 mM buffers using potassium phosphate as the buffer, diluted in water for injection (WFI) (0.1 um sterilized, filtered). The pH is adjusted to pH 4 or 8, respectively, with concentrated nitric acid.

25 vials are filled with 7.5 ml per vial of pH 4 buffered test solution and 25 other vials are filled with 7.5 ml per vial of pH 4 buffered test solution (note the fill level is to the top of the vial—no head space). The vials are closed using prewashed butyl stoppers and aluminum crimps. The vials at each pH are split into two groups. One group at each pH containing 12 vials is stored at 4° C. and the second group of 13 vials is stored at 23° C.

The vials are sampled at Days 1, 3, 6, and 8. The Protocol for Measuring Dissolved Silicon in a Vessel is used, except as otherwise indicated in this example. The analytical result is reported on the basis of parts per billion of silicon in the buffered test solutions of each vial. A dissolution rate is calculated in terms of parts per billion per day as described above in the Protocol for Determining Average Dissolution Rate. The results at the respective storage temperatures are shown in Table 8:

The observations of Si dissolution versus time for the OMCTS-based coating at pH 8 and pH 4 indicate the pH 4 rates are higher at ambient conditions. Thus, the pH 4 rates are used to determine how much material would need to be initially applied to leave a coating of adequate thickness at the end of the shelf life, taking account of the amount of the initial coating that would be dissolved. The results of this calculation are shown in Table 9:

Based on this calculation, the OMCTS lubricity layer needs to be about 2.5 times thicker—resulting in dissolution of 33945 ppb versus the 14,371 ppb representing the entire mass of coating tested—to achieve a 3-year calculated shelf life.

Example 11

The results of Comparative Example 9 and Example 10 above can be compared as shown in Table 10, where the "lubricity layer" is the coating of $SiO_xC_y$ referred to in Example 10.

This data shows that the silicon dissolution rate of $SiO_x$ alone is reduced by more than 2 orders of magnitude at pH 8 in vials also coated with $SiO_xC_y$ coatings.

Another comparison is shown by the data at Table 11 from several different experiments carried out under similar accelerated dissolution conditions.

Row A ($SiO_x$ with OMCTS coating) versus C ($SiO_x$ without OMCTS coating) show that the OMCTS lubricity layer is also an effective pH protective coating or layer to the $SiO_x$ coating at pH 8. The OMCTS coating reduced the one-day dissolution rate from 2504 ug/L ("u" or p or the Greek letter "mu" as used herein are identical, and are abbreviations for "micro") to 165 ug/L. This data also shows that an HMDSO-based $Si_wO_xC_y$ (or its equivalent $SiO_xC_y$) overcoat (Row D) provided a far higher dissolution rate than an OMCTS-based $Si_wO_xC_y$ (or its equivalent $SiO_xC_y$) overcoat (Row A). This data shows that a substantial benefit can be obtained by using a cyclic precursor versus a linear one.

Example 12

Samples 1-6 as listed in Table 1 are prepared as described in Example 9, with further details as follows.

A cyclic olefin copolymer (COC) resin is injection molded to form a batch of 5 ml vials. Silicon chips are adhered with double-sided adhesive tape to the internal walls of the vials. The vials and chips are coated with a two layer coating by plasma enhanced chemical vapor deposition (PECVD). The first layer is composed of $SiO_x$ with barrier properties as defined in the present disclosure, and the second layer is an $SiO_xC_y$ pH protective coating or layer.

A precursor gas mixture comprising OMCTS, argon, and oxygen is introduced inside each vial. The gas inside the vial is excited between capacitively coupled electrodes by a radio-frequency (13.56 MHz) power source i. The monomer flow rate ($F_m$) in units of sccm, oxygen flow rate ($F_o$) in units of sccm, argon flowrate in sccm, and power (W) in units of watts are shown in Table 1.

A composite parameter, W/FM in units of kJ/kg, is calculated from process parameters W, $F_m$, $F_o$ and the molecular weight, M in g/mol, of the individual gas species. W/FM is defined as the energy input per unit mass of polymerizing gases. Polymerizing gases are defined as those species that are incorporated into the growing coating such as, but not limited to, the monomer and oxygen. Non-polymerizing gases, by contrast, are those species that are not incorporated into the growing coating, such as but not limited to argon, helium and neon.

In this test, PECVD processing at high W/FM is believed to cause higher monomer fragmentation, producing organosiloxane coatings with higher cross-link density. PECVD processing at low W/FM, by comparison, is believed to result in lower monomer fragmentation producing organosiloxane coatings with a relatively lower cross-link density.

The relative cross-link density of samples 2, 3, 5, and 6 is compared between different coatings by measuring FTIR absorbance spectra. The spectra of samples 2, 3, 5, and 6 are provided in FIGS. 11-14. In each spectrum, the ratio of the peak absorbance at the symmetric stretching mode (1000-1040 $cm^{-1}$) versus the peak absorbance at the asymmetric stretching mode (1060-1100 $cm^{-1}$) of the Si—O—Si bond is measured, and the ratio of these two measurements is calculated, all as shown in Table 1. The respective ratios are found to have a linear correlation to the composite parameter W/FM.

A qualitative relation—whether the coating appeared oily (shiny, often with irridescence) or non-oily (non-shiny) when applied on the silicon chips—is also found to correlate with the W/FM values in Table 1. Oily appearing coatings deposited at lower W/FM values, as confirmed by Table 1, are believed to have a lower crosslink density, as determined by their lower sym/asym ratio, relative to the non-oily coatings that were deposited at higher W/FM and a higher cross-link density. The only exception to this general rule of thumb is sample 2 in Table 1. It is believed that the coating of sample 2 exhibits a non-oily appearance because it is was too thin to see. Thus, an oilyness observation is not reported in Table 1 for sample 2. The chips were analyzed by FTIR in transmission mode, with the infrared spectrum transmitted through the chip and sample coating, and the transmission through an uncoated null chip subtracted.

Non-oily organosiloxane layers produced at higher W/FM values, which protect the underlying $SiO_x$ coating from aqueous solutions at elevated pH and temperature, are preferred because they provide lower Si dissolution and a longer shelf life, as predicted by Table 1 based on similar experiments. For example, the calculated silicon dissolution by contents of the vial at a pH of 8 and 40° C. is reduced for the non-oily coatings, and the resulting shelf life was 1381 days in one case and 1147 days in another, as opposed to the much shorter shelf lives and higher rates of dissolution for oily coatings. Calculated shelf life is determined as shown for Example 9. The calculated shelf life also correlates linearly to the ratio of symmetric to asymmetric stretching modes of the Si—O—Si bond in organosiloxane pH protective coatings.

Figure 14:
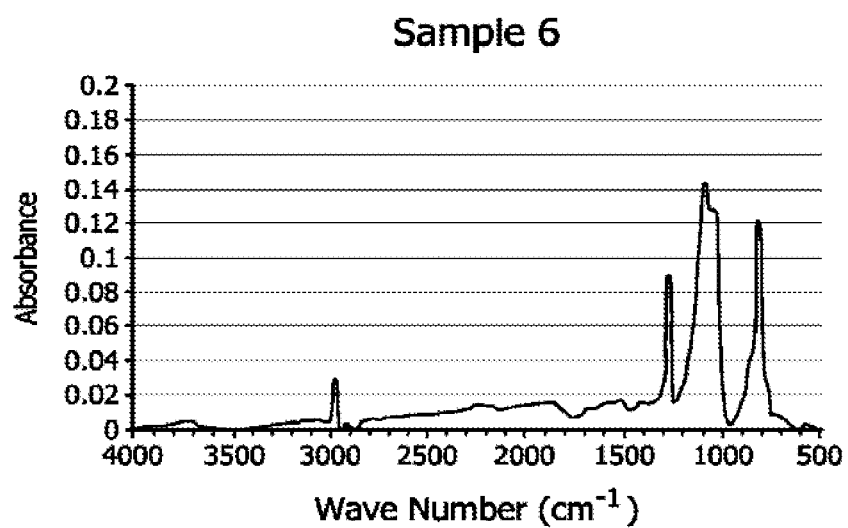

Sample 6 can be particularly compared to Sample 5. An organosiloxane, pH protective coating is deposited according to the process conditions of sample 6 in Table 1. The coating is deposited at a high W/FM. This results in a non-oily coating with a high expected Si—O—Si sym/asym ratio of 0.958, which results in a low rate of dissolution of 84.1 ppb/day (measured by the Protocol for Determining Average Dissolution Rate) and long shelf life of 1147 days (measured by the Protocol for Determining Calculated Shelf Life). The FTIR spectra of this coating is shown in FIG. 14, which exhibits a relatively similar asymmetric Si—O—Si peak absorbance compared to the symmetric Si—O—Si peak absorbance. This is an indication of a higher cross-link density coating, which is a preferred characteristic for pH protection and long shelf life.

An organosiloxane pH protective coating was deposited according to the process conditions of sample 5 in Table 1. The coating was deposited at a moderate W/FM. This resulted in an oily coating with a low Si—O—Si sym/asym ratio of 0.673, which is expected to result in a high rate of dissolution of 236.7 ppb/day (following the Protocol for Determining Average Dissolution Rate) and shorter shelf life of 271 days (following the Protocol for Determining Calculated Shelf Life). The FTIR spectrum of this coating exhibits a relatively high asymmetric Si—O—Si peak absorbance compared to the symmetric Si—O—Si peak absorbance. This is an indication of a lower cross-link density coating, which is contemplated to be an unfavorable characteristic for pH protection and long shelf life.

Sample 2 can be particularly compared to Sample 3. A pH protective coating is deposited according to the process conditions of sample 2 in Table 1. The coating is deposited at a low W/FM. This is expected to result in a coating that exhibits a low Si—O—Si sym/asym ratio of 0.582, which results in a high rate of dissolution of 174 ppb/day and short shelf life of 107 days. The FTIR spectrum of this coating exhibits a relatively high asymmetric Si—O—Si peak absorbance compared to the symmetric Si—O—Si peak absorbance. This is an indication of a lower cross-link density coating, which is an unfavorable characteristic for pH protection and long shelf life.

An organosiloxane, pH protective coating is deposited according to the process conditions of sample 3 in Table 1. The coating is deposited at a high W/FM. This results in a non-oily coating with a high Si—O—Si sym/asym ratio of 0.947, which results in a predicted low rate of Si dissolution of 79.5 ppb/day (following the Protocol for Determining Average Dissolution Rate) and long shelf life of 1381 days (following the Protocol for Determining Calculated Shelf Life). The FTIR spectrum of this coating exhibits a relatively similar asymmetric Si—O—Si peak absorbance compared to the symmetric Si—O—Si peak absorbance. This is an indication of a higher cross-link density coating, which is a preferred characteristic for pH protection and long shelf life.

Example 13

An experiment similar to Example 10 is carried out, modified as indicated in this example and in Table 2 (where the expected results, based on similar work with a different barrier coating or layer, are tabulated). 100 5 mL COP vials are made and coated with an $SiO_x$ barrier layer and an OMCTS-based pH protective coating or layer as described previously, except that for Sample PC194 only the pH protective coating or layer is applied. The coating quantity is again measured in parts per billion extracted from the surfaces of the vials to remove the entire pH protective coating, as reported in Table 2.

In this example, several different coating dissolution conditions are employed. The test solutions used for dissolution contain either 0.02 or 0.2 wt. % polysorbate-80 surfactant, as well as a buffer to maintain a pH of 8. Dissolution tests are carried out at either 23° C. or 40° C.

Multiple syringes are filled with each test solution, stored at the indicated temperature, and analyzed at several intervals to determine the extraction profile and the amount of silicon extracted. An average dissolution rate for protracted storage times is then calculated by extrapolating the data obtained according to the Protocol for Determining Average Dissolution Rate. The predicted results, based on similar experiments, are calculated as described previously and are shown in Table 2. Of particular note, as shown on Table 2, were the very long calculated shelf lives of the filled packages provided with a PC 194 pH protective coating or layer:

21045 days (over 57 years) based on storage at a pH of 8, 0.02 wt. % polysorbate-80 surfactant, at 23° C.;
38768 days (over 100 years) based on storage at a pH of 8, 0.2 wt. % polysorbate-80 surfactant, at 23° C.;
8184 days (over 22 years) based on storage at a pH of 8, 0.02 wt. % polysorbate-80 surfactant, at 40° C.; and
14732 days (over 40 years) based on storage at a pH of 8, 0.2 wt. % polysorbate-80 surfactant, at 40° C.

Referring to Table 2, the longest calculated shelf lives corresponded with the use of an RF power level of 150 Watts and a corresponding high W/FM value. It is believed that the use of a higher power level causes higher cross-link density of the pH protective coating or layer.

Example 14

Another series of experiments similar to those of Example 13 are run, showing the effect of progressively increasing the RF power level on the FTIR absorbance spectrum of the pH protective coating or layer. The results are tabulated in Table 3, which in each instance shows a symmetric/asymmetric ratio greater than 0.75 between the maximum amplitude of the Si—O—Si symmetrical stretch peak normally located between about 1000 and 1040 $cm^{-1}$, and the maximum amplitude of the Si—O—Si asymmetric stretch peak normally located between about 1060 and about 1100 $cm^{-1}$. Thus, the symmetric/asymmetric ratio is 0.79 at a power level of 20 W, 1.21 or 1.22 at power levels of 40, 60, or 80 W, and 1.26 at 100 Watts under otherwise comparable conditions.

The 150 Watt data in Table 3 is taken under somewhat different conditions than the other data, so it is not directly comparable with the 20-100 Watt data discussed above. The FTIR data of samples 6 and 8 of Table 3 is taken from the upper portion of the vial and the FTIR data of samples 7 and 9 of Table 3 is taken from the lower portion of the vial. Also, the amount of OMCTS is cut in half for samples 8 and 9 of Table 3, compared to samples 6 and 7. Reducing the oxygen level while maintaining a power level of 150 W is expected to raise the symmetric/asymmetric ratio still further, as shown by comparing samples 6 and 7 to samples 8 and 9 in Table 3.

It is believed that, other conditions being equal, increasing the symmetric/asymmetric ratio increases the shelf life of a vessel filled with a material having a pH exceeding 5.

Table 12 shows the calculated O-Parameters and N-Parameters (as defined in U.S. Pat. No. 8,067,070) for the experiments summarized in Table 3. As Table 12 shows, the O-Parameters ranged from 0.134 to 0.343, and the N-Parameters ranged from 0.408 to 0.623—all outside the ranges claimed in U.S. Pat. No. 8,067,070.

Examples 15-17

Syringe samples for examples 15-17, employing three different pH protective coatings or layers, were produced in the same manner as for Examples 5-8 except as indicated in Table 13:

Example 15 had a three-component pH protective coating or layer employing OMCTS, oxygen, and carrier gas. Example 16 had a two component pH protective coating or layer employing OMCTS and oxygen, but no carrier gas. Example 17 had a one-component pH protective coating or layer (OMCTS only). Syringes 15-17 were then tested for lubricity as described for Examples 5-8.

The pH protective coatings or layers produced according to these working examples are also contemplated to function as pH protective coatings or layers to increase the shelf life of the vessels, compared to similar vessels provided with a composite barrier coating or layer but no pH protective coating or layer.

Examples 18-20

Examples 15-17 using an OMCTS precursor gas were repeated in Examples 18-20, except that HMDSO was used as the precursor in Examples 18-20. The results are shown in Table 14. The coatings produced according to these working examples are contemplated to function as pH protective coatings or layers, and also as pH protective coatings or layers to increase the shelf life of the vessels, compared to similar vessels provided with a composite barrier coating or layer but no pH protective coating or layer.

Examples 21-32

In these examples the surface roughness of the pH protective coating or layer was determined.

OMCTS pH protective coatings or layers were applied with previously described equipment with the indicated specific process conditions (Table 15) onto one milliliter COC 6013 molded syringe barrels. Atomic force microscopy (AFM) Root Mean Square (RMS) and other roughness determinations (Tables 15 and 16) were made using the procedures indicated. Average RMS values are taken from three different RMS readings on the surface. The plunger force tests, AFM and SEM tests reported in Table 15 were performed on different samples due to the nature of the individual tests which prohibited a performance of all tests on one sample.

Further testing was carried out on sister samples Examples 29, 30, and 31, respectively made under conditions similar to Example 23, 26, and 28 to show the AFM roughness data.

The pH protective coatings or layers produced according to these working examples are also contemplated to function as pH protective coatings or layers to increase the shelf life of the vessels, compared to similar vessels provided with a composite barrier coating or layer but no pH protective coating or layer.

Example 32: pH Protective Coating or Layer Extractables

Silicon extractables from syringes were measured using ICP-MS analysis as described in the Protocol for Measuring Dissolved Silicon in a Vessel. The syringes were evaluated in both static and dynamic situations. The Protocol for Measuring Dissolved Silicon in a Vessel, modified as follows, describes the test procedure:
 Syringe filled with 2 ml of 0.9% saline solution
 Syringe placed in a stand—stored at 50° C. for 72 hours.
 After 72 hours saline solution test for dissolved silicon
 Dissolved silicon measured before and after saline solution expelled through syringe.

The extractable Silicon Levels from a silicon oil coated glass syringe and a pH protective coated and $SiO_x$ coated COC syringe are shown in Table 17. Precision of the ICP-MS total silicon measurement is +/−3%.

Summary of Lubricity and/or pH Protective Measurements

Table 18 shows a summary of the above OMCTS coatings or layers

Example 33

The purpose of this example was to evaluate the recoverability or drainage of a slightly viscous aqueous solution from glass, COP and coated vials, This study evaluated the recovery of a 30 cps (centipoise) carbohydrate solution in water-for-injection from (A) an uncoated COP vial, (B) an $SiO_x$+pH protective layer coated COP vial prepared according to the above Protocol for Coating Syringe Barrel Interior with $SiO_x$, followed by the Protocol for Coating Syringe Barrel Interior with OMCTS pH protective Coating or Layer, and (C) a glass vial.

2.0 ml of the carbohydrate solution was pipetted into 30 vials each of glass, COP and pH protective coated vials. The solution was aspirated from the vials with a 10 ml syringe, through a 23 gauge, 1.5" needle. The vials were tipped to one side as the solution was aspirated to maximize the amount recovered. The same technique and similar withdrawal time was used for all vials. The vials were weighed empty, after placing 2.0 ml of the solution to the vial and at the conclusion of aspirating the solution from the vial. The amount delivered to the vial (A) was determined by subtracting the weight of the empty vial from the weight of the vial with the 2.0 ml of solution. The weight of solution not recovered (B) was determined by subtracting the weight of the empty vial from the weight of the vials after aspirating the solution from the vial. The percent unrecovered was determined by dividing B by A and multiplying by 100.

It was observed during the aspiration of drug product that the glass vials remained wetted with the solution. The COP vial repelled the liquid and as the solution was aspirated from the vials. This helped with recovery but droplets were observed to bead on the sidewalls of the vials during the aspiration. The pH protective coated vials also repelled the liquid during aspiration but no beading of solution on the sidewalls was observed.

The conclusion was that pH protective coated vials do not wet with aqueous solutions as do glass vials, leading to superior recovery of drug product relative to glass. pH protective coated vials were not observed to cause beading of solution on sidewall during aspiration of aqueous products therefore coated vials performed better than uncoated COP vials in product recovery experiments.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art and practicing the claimed invention, from a study of the drawings, the disclosure, and the appended claims. In the claims, the word "comprising" does not exclude other elements or steps, and the indefinite article "a" or "an" does not exclude a plurality. The mere fact that certain measures are recited in mutually different dependent claims does not indicate that a combination of these measures cannot be used to advantage. Any reference signs in the claims should not be construed as limiting the scope.

TABLE 1

| | Process Parameters | | | | Si Dissolution @ pH8/40° C. | | | FTIR Absorbance | | | |
|---|---|---|---|---|---|---|---|---|---|---|---|
| Samples | Flow Rate OMCTS | Ar | O² Flow Rate | Power (W) | W/FM (kJ/kg) | Total Si (ppb) | Shelf life (days) | Rate of Dissolution (ppb/day) | Si—O—Si sym stretch (1000-1040 cm⁻¹) | Si—O—Si asym stretch (1060-1100 cm⁻¹) | Ratio Si—O—Si (sym/asym) | Oilyness |
| 1 | 3 | 10 | 0.5 | 14 | 21613 | 43464 | 385 | 293.18 | 0.153 | 0.219 | 0.700 | YES |
| 2 | 3 | 20 | 0.5 | 2 | 3088 | 7180 | 107 | 174.08 | 0.011 | 0.020 | 0.582 | NA |
| 3 | 1 | 20 | 0.5 | 14 | 62533 | 42252.17 | 1381 | 79.53 | 0.093 | 0.098 | 0.947 | NO |
| 4 | 2 | 15 | 0.5 | 8 | 18356 | 27398 | 380 | 187.63 | 0.106 | 0.141 | 0.748 | YES |
| 5 | 3 | 20 | 0.5 | 14 | 21613 | 24699 | 271 | 236.73 | 0.135 | 0.201 | 0.673 | YES |
| 6 | 1 | 10 | 0.5 | 14 | 62533 | 37094 | 1147 | 84.1 | 0.134 | 0.140 | 0.958 | NO |

TABLE 2

| Sample | OMCTS Flow Rate (sccm) | Argon Flow Rate (sccm) | O² Flow Rate (sccm) | Power (W) | Plasma Duration (sec) | W/FM (kJ/kg) | Total Si (ppb) (OMCTS) layer | Calculated Shelf-life (days) | Average Rate of Dissolution (ppb/day) |
|---|---|---|---|---|---|---|---|---|---|
| | Process Parameters | | | | | | Si Dissolution @ pH8/23° C./0.02% Tween ®-80 | | |
| PC194 018 | 0.5 | 20 | 0.5 | 150 | 20 | 1223335 | 73660 | 21045 | 3.5 |
| | 1.0 | 20 | 0.5 | 18 | 15 | 77157 | 42982 | 1330 | 32.3 |
| | Process Parameters | | | | | | Si Dissolution @ pH8/23° C./0.2% Tween ®-80 | | |
| PC194 018 048 | 0.5 | 20 | 0.5 | 150 | 20 | 1223335 | 73660 | 38768 | 1.9 |
| | 1.0 | 20 | 0.5 | 18 | 15 | 77157 | 42982 | 665 | 64.6 |
| | 4 | 80 | 2 | 35 | 20 | 37507 | 56520 | 1074 | 52.62 |
| | Process Parameters | | | | | | Si Dissolution @ pH8/40° C./0.02% Tween ®-80 | | |
| PC194 018 | 0.5 | 20 | 0.5 | 150 | 20 | 1223335 | 73660 | 8184 | 9 |
| | 1.0 | 20 | 0.5 | 18 | 15 | 77157 | 42982 | 511 | 84 |
| | Process Parameters | | | | | | Si Dissolution @ pH8/40° C./0.2% Tween ®-80 | | |
| PC194 018 | 0.5 | 20 | 0.5 | 150 | 20 | 1223335 | 73660 | 14732 | 5 |
| | 1.0 | 20 | 0.5 | 18 | 15 | 77157 | 42982 | 255 | 168 |

TABLE 3

| Samples ID | OMCTS Flow Rate (sccm) | Argon Flow Rate (sccm) | O² Flow Rate (sccm) | Power (W) | Plasma Duration (sec) | W/FM (kJ/kg) | Symmetric Stretch Peak at 1000-1040 cm⁻¹ | Assymetric Stretch Peak at (1060-1100 cm⁻¹ | Symmetric/ Assymetric Ratio |
|---|---|---|---|---|---|---|---|---|---|
| | Process Parameters | | | | | | FTIR Results | | |
| 1 | 1 | 20 | 0.5 | 20 | 20 | 85,730 | 0.0793 | 0.1007 | 0.79 |
| 2 | 1 | 20 | 0.5 | 40 | 20 | 171,460 | 0.0619 | 0.0507 | 1.22 |
| 3 | 1 | 20 | 0.5 | 60 | 20 | 257,190 | 0.1092 | 0.0904 | 1.21 |
| 4 | 1 | 20 | 0.5 | 80 | 20 | 342,919 | 0.1358 | 0.1116 | 1.22 |
| 5 | 1 | 20 | 0.5 | 100 | 20 | 428,649 | 0.209 | 0.1658 | 1.26 |
| 6 | 1 | 20 | 0.5 | 150 | 20 | 642,973 | 0.2312 | 0.1905 | 1.21 |
| 7 | 1 | 20 | 0.5 | 150 | 20 | 642,973 | 0.2324 | 0.1897 | 1.23 |
| 8 | 0.5 | 20 | 0.5 | 150 | 20 | 1,223,335 | 0.1713 | 0.1353 | 1.27 |
| 9 | 0.5 | 20 | 0.5 | 150 | 20 | 1,223,335 | 0.1475 | 0.1151 | 1.28 |

TABLE 4

PLUNGER SLIDING FORCE MEASUREMENTS OF OMCTS-BASED PLASMA pH protective COATING OR LAYER MADE WITH CARRIER GAS

| Example | pH protective coating or layer Type | lubricity Monomer | Lubricity and/or pH protective coating or layer Time (sec) | Lubricity and/or pH protective OMCTS Flow Rate (sccm) | Lubricity and/or pH protective $O_2$ Flow Rate (sccm) | Carrier Gas (Ar) Flow Rate (sccm) | pH protective coating or layer Power (Watts) | Initiation Force, $F_i$ (N, Kg.) | Maintenance Force, $F_m$ (N, Kg.) |
|---|---|---|---|---|---|---|---|---|---|
| 1 (Control) | Uncoated COC | n/a | n/a | n/a | n/a | n/a | n/a | >11 N >1.1 Kg. | >11N >1.1 Kg. |
| 2 (Industry Standard) | Silicon oil on COC | n/a | n/a | n/a | n/a | n/a | n/a | 8.2 N 0.84 Kg. | 6.3N 0.64 Kg. |
| 3 (without Oxygen) | L3 lubricity coating or layer over $SiO_x$ on COC | OMCTS | 10 sec | 3 | 0 | 65 | 6 | 4.6 N 0.47 Kg. | 4.6N 0.47 Kg. |
| 4 (with Oxygen) | L2 lubricity and/or pH protective coating or layer over $SiO_x$ on COC | OMCTS | 10 sec | 3 | 1 | 65 | 6 | 4.8 N 0.49 Kg. | 3.5N 0.36 Kg. |

TABLE 5

COATED VIAL AND STAKED NEEDLE SYRINGE BARREL ADHESION

| Experiment Number | Example (Inventive, I, or Comparative, C) | Sample | Method | Relative Retention (by Experiment number) |
|---|---|---|---|---|
| 1 | B1 ( I ) | SiOx Coated CO Vial Cylinder | A1 | 1 > 2 |
| 2 | B1 ( C ) | SiOx Coated glass Vial Cylinder | A1 | 2 < 1 |
| 3 | B1 ( I ) | SiOx Coated COP Vial Cylinder | A2 | 3 > 4 |
| 4 | B1 ( C ) | SiOx Coated glass Vial Cylinder | A2 | 4 < 3 |
| 5 | B2 ( I ) | Bilayer Coated COP Vial Cylinder | A1 | 5 > 6 |
| 6 | B2 ( C ) | Bilayer Coated glass Vial Cylinder | A1 | 6 < 5 |
| 7 | B2 ( I ) | Bilayer Coated COP Vial Cylinder | A2 | 7 > 8 |
| 8 | B2 ( C ) | Bilayer Coated glass Vial Cylinder | A2 | 8 < 7 |
| 9 | B3 ( I ) | SiOx Coated COP Syringe Barrel Cylinder | A1 | 9 > 10 |
| 10 | B3 ( C ) | SiOx Coated glass Syringe Barrel Cylinder | A1 | 10 < 9 |
| 11 | B3 ( I ) | SiOx Coated COP Syringe Barrel Cylinder | A2 | 11 > 12 |
| 12 | B3 ( C ) | SiOx Coated glass Syringe Barrel Cylinder | A2 | 12 < 11 |
| 13 | B4 ( I ) | Bilayer Coated COP Syringe Barrel Cylinder | A1 | 13 > 14 |
| 14 | B4 ( C ) | Bilayer Coated glass Syringe Barrel Cylinder | A1 | 14 < 13 |
| 15 | B4 ( I ) | Bilayer Coated COP Syringe Barrel Cylinder | A2 | 15 > 16 |
| 16 | B4 ( C ) | Bilayer Coated glass Syringe Barrel Cylinder | A2 | 16 < 15 |

* {[(Pretape length × coating height) − (Post tape length × coating height)]/(Pretape length × coating height)} * 100%

TABLE 6

OMCTS LUBRICITY AND/OR pH protective COATING OR LAYER (Examples 5 and 6)

| Example | OMCTS (sccm) | $O_2$ (sccm) | Ar (sccm) | Initiation Force, Fi (N) | Maintenance Force, Fm (N) | ICPMS (μg./liter) | ICPMS Mode |
|---|---|---|---|---|---|---|---|
| 5 | 3.0 | 0.38 | 7.8 | 4.8 | 3.5 | <5 | static |
| 6 | 3.0 | 0.38 | 7.8 | 5.4 | 4.3 | 38 | dynamic |
| 7 ($SiO_x$ only) | n/a | n/a | n/a | 13 | 11 | <5 | static |
| 8 (silicon oil) | n/a | n/a | n/a | 8.2 | 6.3 | | |

TABLE 7

Quantity of SiOx + Lubricity layer on Vials

| Vial | Total Silicon ug/L |
|---|---|
| 1 | 13844 |
| 2 | 14878 |
| 3 | 14387 |
| 4 | 13731 |
| 5 | 15260 |
| 6 | 15017 |
| 7 | 15118 |
| 8 | 12736 |
| Mean | 14371 |
| StdDev | 877 |

TABLE 8

Shelf Life Conditions 23° C.

| | Vial SiOx + Lubricity Coating at pH 4 | Vial SiOx + Lubricity Coating at pH 8 |
|---|---|---|
| Si Dissolution Rate (PPB/day) | 31 | 7 |

Shelf Life Conditions 4° C.

| | Vial SiOx + Lubricity Coating at pH 4 | Vial SiOx + Lubricity Coating at pH 8 |
|---|---|---|
| Si Dissolution Rate (PPB/day) | 7 | 11 |

TABLE 9

Shelf Life Calculation

| | Vial with SiOx + Lubricity Coating at pH 4 |
|---|---|
| Si Dissolution Rate (PPB/day) | 31 |
| Mass of Coating Tested (Total Si) | 14,371 |
| Shelf Life (days) at 23° C. | 464 |
| Shelf Life (years) at 23° C. | 1.3 |
| Required Mass of Coating (Total Si) -- 2-years | 22,630 |

TABLE 9-continued

Shelf Life Calculation

| | Vial with SiOx + Lubricity Coating at pH 4 |
|---|---|
| Required Mass of Coating (Total Si) -- 3-years | 33,945 |

TABLE 10

Shelf Life Conditions -- pH 8 and 23° C.

| | Vial with SiOx | Vial with SiOx + Lubricity Coating |
|---|---|---|
| Si Dissolution Rate (PPB/day) | 1,250 | 7 |

TABLE 11

SILICON DISSOLUTION WITH PH 8 AT 40° C. (ug/L)

| Vial Coating Description | 1 day | 2 days | 3 days | 4 days | 7 days | 10 days | 15 days |
|---|---|---|---|---|---|---|---|
| A. $SiO_x$ made with HMDSO Plasma + $Si_wO_xC_y$ or its equivalent $SiO_xC_y$ made with OMCTS Plasma | 165 | 211 | 226 | 252 | 435 | 850 | 1,364 |
| B. $Si_wO_xC_y$ or its equivalent $SiO_xC_y$ made with OMCTS Plasma | 109 | 107 | 76 | 69 | 74 | 158 | 198 |
| C. $SiO_x$ made with HMDSO Plasma | 2,504 | 4,228 | 5,226 | 5,650 | 9,292 | 10,177 | 9,551 |
| D. $SiO_x$ made with HMDSO Plasma + $Si_wO_xC_y$ or its equivalent $SiO_xC_y$ made with HMDSO Plasma | 1,607 | 1,341 | 3,927 | 10,182 | 18,148 | 20,446 | 21,889 |
| E. $Si_wO_xC_y$ or its equivalent $SiO_xC_y$ made with HMDSO Plasma | 1,515 | 1,731 | 1,813 | 1,743 | 2,890 | 3,241 | 3,812 |

TABLE 12

| Samples ID | OMCTS Flow Rate (sccm) | Argon Flow Rate (sccm) | $O_2$ Flow Rate (sccm) | Power (W) | Plasma Duration (sec) | W/FM (kJ/kg) | O-Parameter | N-Parameter |
|---|---|---|---|---|---|---|---|---|
| | | | | Process Parameters | | | | |
| 1 | 1 | 20 | 0.5 | 20 | 20 | 85,730 | 0.343 | 0.436 |
| 2 | 1 | 20 | 0.5 | 40 | 20 | 171,460 | 0.267 | 0.408 |
| 3 | 1 | 20 | 0.5 | 60 | 20 | 257,190 | 0.311 | 0.457 |
| 4 | 1 | 20 | 0.5 | 80 | 20 | 342,919 | 0.270 | 0.421 |
| 5 | 1 | 20 | 0.5 | 100 | 20 | 428,649 | 0.177 | 0.406 |
| 6 | 1 | 20 | 0.5 | 150 | 20 | 642,973 | 0.151 | 0.453 |
| 7 | 1 | 20 | 0.5 | 150 | 20 | 642,973 | 0.151 | 0.448 |
| 8 | 0.5 | 20 | 0.5 | 150 | 20 | 1,223,335 | 0.134 | 0.623 |
| 9 | 0.5 | 20 | 0.5 | 150 | 20 | 1,223,335 | 0.167 | 0.609 |

TABLE 13

OMCTS pH protective coating or layer

OMCTS-2.5 sccm
Argon gas-7.6 sccm (when used)
Oxygen 0.38 sccm (when used)
Power-3 watts
Power on time-10 seconds

TABLE 14

HMDSO pH protective coating or layer

| Example | HMDSO (sccm) | $O_2$ (sccm) | Ar (sccm) |
|---|---|---|---|
| 18 | 2.5 | 0.38 | 7.6 |
| 19 | 2.5 | 0.38 | — |
| 20 | 2.5 | — | — |

TABLE 15

| Example | OMCTS (sccm) | Ar/$O_2$ (sccm) | Power (Watts) | Dep. Time (sec) | SEM Micrograph (5 micronAF Vertical) | AFM RMS (nanometers) |
|---|---|---|---|---|---|---|
| 21 | 2.0 | 10/0.38 | 3.5 | 10 | FIG. 6 | |
| 22 | | | | | | |
| 23 | | | | | | 19.6, 9.9, 9.4 (Average = 13.0 FIGS. 8, 9, 10 |
| 24 | 2.0 | 10/0.38 | 4.5 | 10 | FIG. 7 | |
| 25 | | | | | | |
| 26 | | | | | | 12.5, 8.4, 6.1 (Average = 6.3) FIG. 11, 15, 16 |
| 27 | 2.0 | 10/0 | 3.4 | 10 | | |
| 28 | | | | | | 1.9, 2.6, 3.0 (Average = 2.3) Fig 14, 15,16 |

TABLE 16

|  | $SiO_x$/Lub | Coater | Mode | Siloxane Feed | Ar/$O_2$ | Power (W) | Dep. Time (Sec.) |
|---|---|---|---|---|---|---|---|
| Example 29 $SiO_x$/Baseline OMCTS Lub | $SiO_x$: | Auto-Tube | Auto | HMDSO 52.5 in, 133.4 cm. | 0 sccm Ar, 90 sccm $O_2$ | 37 | 7 |
| | Lubricity: | Auto-S | same | OMCTS, 2.0 sccm | 10 sccm Ar 0.38 sccm $O_2$ | 3,4 | 10 |
| Example 30 $SiO_x$/High Pwr OMCTS Lub | $SiO_x$: | same | same | same | same | 37 | 7 |
| | Lubricity: | same | same | same | same | 4,5 | 10 |
| Example 31 $SiO_x$/No $O_2$ OMCTS Lub | $SiO_x$: | Auto-Tube | same | same | 0 sccm Ar, 90 sccm $O_2$ | 37 | 7 |
| | Lubricity: | Auto-S | same | same | 10 sccm Ar 0 sccm $O_2$ | 3,4 | 10 |

TABLE 17

Silicon Extractables Comparison of Lubricity Coatings

| Package Type | Statis (ug/L) | Dynamic (ug/L) |
|---|---|---|
| Cyclic Olefin Syringe with CV Holdings SiOCH Lubricity Coating | 70 | 81 |
| Borocilicate Glass Syringe with Silicon Oil | 825 | 835 |

TABLE 18

Summary Table of OMCTS pH protective COATING OR LAYER from Tables 4, 6, 13 and 15

| Example | OMCTS (sccm) | $O_2$ (sccm) | Ar (sccm) | Power (Watt) | Dep Time (sec) |
|---|---|---|---|---|---|
| 3 | 3.0 | 0.00 | 65 | 6 | 10 |
| 4 | 3.0 | 1.00 | 65 | 6 | 10 |
| 5 | 3.0 | 0.38 | 7.8 | 6 | 10 |
| 6 | 3.0 | 0.38 | 7.8 | 6 | 10 |
| 15 | 2.5 | 0.38 | 7.6 | 6 | 10 |
| 16 | 2.5 | 0.38 | 0.0 | 6 | 10 |
| 17 | 2.5 | 0.00 | 0.0 | 6 | 10 |
| 21 | 2.0 | 0.38 | 10 | 3.5 | 10 |
| 24 | 2.0 | 0.38 | 10 | 4.5 | 10 |
| 27 | 2.0 | 0.00 | 10 | 3.4 | 10 |
| 29 | 2.0 | 0.38 | 10 | 3.4 | 10 |
| 30 | 2.0 | 0.38 | 10 | 4.5 | 10 |
| 31 | 2.0 | 0.00 | 10 | 3.4 | 10 |

What is claimed:

1. A vessel comprising a thermoplastic wall enclosing a lumen and an $SiO_x$ composite barrier coating or layer, for which x is from 1.8 to 2.4, supported by the wall between the wall and the lumen, an interior surface of the composite barrier coating or layer facing the lumen, and
   a pH protective coating or layer of $SiO_xC_y$ or $SiN_xC_y$ wherein x is from about 0.5 to about 2.4 and y is from about 0.6 and about 3, the pH protective coating or layer having an interior surface facing the lumen and an outer surface facing the interior surface of the composite barrier coating or layer,
   in which an FTIR absorbance spectrum of the pH protective coating or layer has a ratio greater than 0.75 and at most 1 between:

the maximum amplitude of the Si—O—Si symmetrical stretch peak between about 1000 and 1040 cm$^{-1}$, and
the maximum amplitude of the Si—O—Si asymmetric stretch peak between about 1060 and about 1100 cm$^{-1}$, the pH protective coating or layer being effective to increase the calculated shelf life of the vessel (total Si/Si dissolution rate).

2. The vessel of claim 1, in which the vessel has a rated volume between 0.5 and 5 ml and/or a fill volume between 0.8 and 9 ml.

3. The vessel of claim 1, in which the vessel is a vial, a syringe, a prefilled syringe, or a cartridge.

4. The vessel of claim 1, in which the the SiO$_x$ composite barrier coating or layer is formed at an initial RF power level of from 3 to 1 W/mL.

5. The vessel of claim 1, in which the SiO$_x$ composite barrier coating or layer is formed by PECVD from an organosilicon monomer and oxidizing gas, and the organosilicon monomer is an organosiloxane having from 2 to 6 silicon atoms per molecule.

6. The vessel of claim 1, in which at least a portion of the wall of the vessel comprises a cyclic olefin polymer, polypropylene, or a polyester.

7. The vessel of claim 1, in which the pH protective coating or layer comprises SiO$_x$C$_y$.

8. The vessel of claim 1, in which the pH protective coating or layer as applied is between 100 and 700 nm thick.

9. The vessel of claim 1, in which the rate of erosion of the pH protective coating or layer, if directly contacted by a fluid composition having a pH of 8, is from 5% to 20% of the rate of erosion of the composite barrier coating or layer, if directly contacted by the same fluid composition under the same conditions.

10. The vessel of claim 1, in which the silicon dissolution rate by a 50 mM potassium phosphate buffer diluted in water for injection, adjusted to pH 8 with concentrated nitric acid, and containing 0.2 wt. % polysorbate-80 surfactant from the vessel is less than 170 ppb/day.

11. The vessel of claim 1, in which the calculated shelf life (total Si/Si dissolution rate) is more than 1 year and less than 5 years.

12. The vessel of claim 1, in which the lumen contains a fluid composition comprising a member selected from the group consisting of:

INHALATION ANESTHETICS

Aliflurane; Chloroform; Cyclopropane; Desflurane (Suprane); Diethyl Ether; Enflurane (Ethrane); Ethyl Chloride; Ethylene; Halothane (Fluothane); Isoflurane (Forane, Isoflo); Isopropenyl vinyl ether; Methoxyflurane; Methoxypropane; Nitrous Oxide; Roflurane; Sevoflurane (Sevorane, Ultane, Sevoflo); Teflurane; Trichloroethylene; Vinyl Ether; Xenon;

INJECTABLE DRUGS

Ablavar (Gadofosveset Trisodium Injection); Abarelix Depot; Abobotulinumtoxin A Injection (Dysport); ABT-263; ABT-869; ABX-EFG; Accretropin (Somatropin Injection); Acetadote (Acetylcysteine Injection); Acetazolamide Injection (Acetazolamide Injection); Acetylcysteine Injection (Acetadote); Actemra (Tocilizumab Injection); Acthrel (Corticorelin Ovine Triflutate for Injection); Actummune; Activase; Acyclovir for Injection (Zovirax Injection); Adacel; Adalimumab; Adenoscan (Adenosine Injection); Adenosine Injection (Adenoscan); Adrenaclick; AdreView (Iobenguane I 123 Injection for Intravenous Use); Afluria; Ak-Fluor (Fluorescein Injection); Aldurazyme (Laronidase); Alglucerase Injection (Ceredase); Alkeran Injection (Melphalan Hcl Injection); Allopurinol Sodium for Injection (Aloprim); Aloprim (Allopurinol Sodium for Injection); Alprostadil; Alsuma (Sumatriptan Injection); ALTU-238; Amino Acid Injections; Aminosyn; Apidra; Apremilast; Alprostadil Dual Chamber System for Injection (Caverject Impulse); AMG 009; AMG 076; AMG 102; AMG 108; AMG 114; AMG 162; AMG 220; AMG 221; AMG 222; AMG 223; AMG 317; AMG 379; AMG 386; AMG 403; AMG 477; AMG 479; AMG 517; AMG 531; AMG 557; AMG 623; AMG 655; AMG 706; AMG 714; AMG 745; AMG 785; AMG 811; AMG 827; AMG 837; AMG 853; AMG 951; Amiodarone HCl Injection (Amiodarone HCl Injection); Amobarbital Sodium Injection (Amytal Sodium); Amytal Sodium (Amobarbital Sodium Injection); Anakinra; Anti-Abeta; Anti-Beta7; Anti-Beta20; Anti-CD4; Anti-CD20; Anti-CD40; Anti-IFNalpha; Anti-IL13; Anti-OX40L; Anti-oxLDS; Anti-NGF; Anti-NRP1; Arixtra; Amphadase (Hyaluronidase Inj); Ammonul (Sodium Phenylacetate and Sodium Benzoate Injection); Anaprox; Anzemet Injection (Dolasetron Mesylate Injection); Apidra (Insulin Glulisine [rDNA origin] Inj); Apomab; Aranesp (darbepoetin alfa); Argatroban (Argatroban Injection); Arginine Hydrochloride Injection (R-Gene 10); Aristocort; Aristospan; Arsenic Trioxide Injection (Trisenox); Articane HCl and Epinephrine Injection (Septocaine); Arzerra (Ofatumumab Injection); Asclera (Polidocanol Injection); Ataluren; Ataluren-DMD; Atenolol Inj (Tenormin I.V. Injection); Atracurium Besylate Injection (Atracurium Besylate Injection); Avastin; Azactam Injection (Aztreonam Injection); Azithromycin (Zithromax Injection); Aztreonam Injection (Azactam Injection); Baclofen Injection (Lioresal Intrathecal); Bacteriostatic Water (Bacteriostatic Water for Injection); Baclofen Injection (Lioresal Intrathecal); Bal in Oil Ampules (Dimercarprol Injection); BayHepB; BayTet; Benadryl; Bendamustine Hydrochloride Injection (Treanda); Benztropine Mesylate Injection (Cogentin); Betamethasone Injectable Suspension (Celestone Soluspan); Bexxar; Bicillin C-R 900/300 (Penicillin G Benzathine and Penicillin G Procaine Injection); Blenoxane (Bleomycin Sulfate Injection); Bleomycin Sulfate Injection (Blenoxane); Boniva Injection (Ibandronate Sodium Injection); Botox Cosmetic (OnabotulinumtoxinA for Injection); BR3-FC; Bravelle (Urofollitropin Injection); Bretylium (Bretylium Tosylate Injection); Brevital Sodium (Methohexital Sodium for Injection); Brethine; Briobacept; BTT-1023; Bupivacaine HCl; Byetta; Ca-DTPA (Pentetate Calcium Trisodium Inj); Cabazitaxel Injection (Jevtana); Caffeine Alkaloid (Caffeine and Sodium Benzoate Injection); Calcijex Injection (Calcitrol); Calcitrol (Calcijex Injection); Calcium Chloride (Calcium Chloride Injection 10%); Calcium Disodium Versenate (Edetate Calcium Disodium Injection); Campath (Altemtuzumab); Camptosar Injection (Irinotecan Hydrochloride); Canakinumab Injection (Ilaris); Capastat Sulfate (Capreomycin for Injection); Capreomycin for Injection (Capastat Sulfate); Cardiolite (Prep kit for Technetium Tc99 Sestamibi for Injection); Carticel; Cathflo; Cefazolin and Dextrose for Injection (Cefazolin Injection); Cefepime Hydrochloride; Cefotaxime; Ceftriaxone; Cerezyme; Carnitor Injection; Caverject; Celestone Soluspan; Celsior; Cerebyx (Fosphenytoin Sodium Injection); Ceredase (Alglucerase Injection);

Ceretec (Technetium Tc99m Exametazime Injection); Certolizumab; CF-101; Chloramphenicol Sodium Succinate (Chloramphenicol Sodium Succinate Injection); Chloramphenicol Sodium Succinate Injection (Chloramphenicol Sodium Succinate); Cholestagel (Colesevelam HCL); Choriogonadotropin Alfa Injection (Ovidrel); Cimzia; Cisplatin (Cisplatin Injection); Clolar (Clofarabine Injection); Clomiphine Citrate; Clonidine Injection (Duraclon); Cogentin (Benztropine Mesylate Injection); Colistimethate Injection (Coly-Mycin M); Coly-Mycin M (Colistimethate Injection); Compath; Conivaptan Hcl Injection (Vaprisol); Conjugated Estrogens for Injection (Premarin Injection); Copaxone; Corticorelin Ovine Triflutate for Injection (Acthrel); Corvert (Ibutilide Fumarate Injection); Cubicin (Daptomycin Injection); CF-101; Cyanokit (Hydroxocobalamin for Injection); Cytarabine Liposome Injection (DepoCyt); Cyanocobalamin; Cytovene (ganciclovir); D.H.E. 45; Dacetuzumab; Dacogen (Decitabine Injection); Dalteparin; Dantrium IV (Dantrolene Sodium for Injection); Dantrolene Sodium for Injection (Dantrium IV); Daptomycin Injection (Cubicin); Darbepoietin Alfa; DDAVP Injection (Desmopressin Acetate Injection); Decavax; Decitabine Injection (Dacogen) (Dehydrated Alcohol (Dehydrated Alcohol Injection); Denosumab Injection (Prolia); Delatestryl; Delestrogen; Delteparin Sodium; Depacon (Valproate Sodium Injection); Depo Medrol (Methylprednisolone Acetate Injectable Suspension); DepoCyt (Cytarabine Liposome Injection); DepoDur (Morphine Sulfate XR Liposome Injection); Desmopressin Acetate Injection (DDAVP Injection); Depo-Estradiol; Depo-Provera 104 mg/ml; Depo-Provera 150 mg/ml; Depo-Testosterone; Dexrazoxane for Injection, Intravenous Infusion Only (Totect); Dextrose/Electrolytes; Dextrose and Sodium Chloride Inj (Dextrose 5% in 0.9% Sodium Chloride); Dextrose; Diazepam Injection (Diazepam Injection); Digoxin Injection (Lanoxin Injection); Dilaudid-HP (Hydromorphone Hydrochloride Injection); Dimercarprol Injection (Bal in Oil Ampules); Diphenhydramine Injection (Benadryl Injection); Dipyridamole Injection (Dipyridamole Injection); DMOAD; Docetaxel for Injection (Taxotere); Dolasetron Mesylate Injection (Anzemet Injection); Doribax (Doripenem for Injection); Doripenem for Injection (Doribax); Doxercalciferol Injection (Hectorol Injection); Doxil (Doxorubicin Hcl Liposome Injection); Doxorubicin Hcl Liposome Injection (Doxil); Duraclon (Clonidine Injection); Duramorph (Morphine Injection); Dysport (Abobotulinumtoxin A Injection); Ecallantide Injection (Kalbitor); EC-Naprosyn (naproxen); Edetate Calcium Disodium Injection (Calcium Disodium Versenate); Edex (Alprostadil for Injection); Engerix; Edrophonium Injection (Enlon); Eliglustat Tartate; Eloxatin (Oxaliplatin Injection); Emend Injection (Fosaprepitant Dimeglumine Injection); Enalaprilat Injection (Enalaprilat Injection); Enlon (Edrophonium Injection); Enoxaparin Sodium Injection (Lovenox); Eovist (Gadoxetate Disodium Injection); Enbrel (etanercept); Enoxaparin Epicel; Epinephrine; Epipen; Epipen Jr.; Epratuzumab; Erbitux; Ertapenem Injection (Invanz); Erythropoieten; Essential Amino Acid Injection (Nephramine); Estradiol Cypionate; Estradiol Valerate; Etanercept; Exenatide Injection (Byetta); Evlotra; Fabrazyme (Adalsidase beta); Famotidine Injection; FDG (Fludeoxyglucose F 18 Injection); Feraheme (Ferumoxytol Injection); Feridex I.V. (Ferumoxides Injectable Solution); Fertinex; Ferumoxides Injectable Solution (Feridex I.V.); Ferumoxytol Injection (Feraheme); Flagyl Injection (Metronidazole Injection); Fluarix; Fludara (Fludarabine Phosphate); Fludeoxyglucose F 18 Injection (FDG); Fluorescein Injection (Ak-Fluor); Follistim AQ Cartridge (Follitropin Beta Injection); Follitropin Alfa Injection (Gonal-f RFF); Follitropin Beta Injection (Follistim AQ Cartridge); Folotyn (Pralatrexate Solution for Intravenous Injection); Fondaparinux; Forteo (Teriparatide (rDNA origin) Injection); Fostamatinib; Fosaprepitant Dimeglumine Injection (Emend Injection); Foscarnet Sodium Injection (Foscavir); Foscavir (Foscarnet Sodium Injection); Fosphenytoin Sodium Injection (Cerebyx); Fospropofol Disodium Injection (Lusedra); Fragmin; Fuzeon (enfuvirtide); GA101; Gadobenate Dimeglumine Injection (Multihance); Gadofosveset Trisodium Injection (Ablavar); Gadoteridol Injection Solution (ProHance); Gadoversetamide Injection (OptiMARK); Gadoxetate Disodium Injection (Eovist); Ganirelix (Ganirelix Acetate Injection); Gardasil; GC1008; GDFD; Gemtuzumab Ozogamicin for Injection (Mylotarg); Genotropin; Gentamicin Injection; GENZ-112638; Golimumab Injection (Simponi Injection); Gonal-f RFF (Follitropin Alfa Injection); Granisetron Hydrochloride (Kytril Injection); Gentamicin Sulfate; Glatiramer Acetate; Glucagen; Glucagon; HAE1; Haldol (Haloperidol Injection); Havrix; Hectorol Injection (Doxercalciferol Injection); Hedgehog Pathway Inhibitor; Heparin; Herceptin; hG-CSF; Humalog; Human Growth Hormone; Humatrope; HuMax; Humegon; Humira; Humulin; Ibandronate Sodium Injection (Boniva Injection); Ibuprofen Lysine Injection (NeoProfen); Ibutilide Fumarate Injection (Corvert); Idamycin PFS (Idarubicin Hydrochloride Injection); Idarubicin Hydrochloride Injection (Idamycin PFS); Ilaris (Canakinumab Injection); Imipenem and Cilastatin for Injection (Primaxin I.V.); Imitrex; Incobotulinumtoxin A for Injection (Xeomin); Increlex (Mecasermin [rDNA origin] Injection); Indocin IV (Indomethacin Inj); Indomethacin Inj (Indocin IV); Infanrix; Innohep; Insulin; Insulin Aspart [rDNA origin] Inj (NovoLog); Insulin Glargine [rDNA origin] Injection (Lantus); Insulin Glulisine [rDNA origin] Inj (Apidra); Interferon alfa-2b, Recombinant for Injection (Intron A); Intron A (Interferon alfa-2b, Recombinant for Injection); Invanz (Ertapenem Injection); Invega Sustenna (Paliperidone Palmitate Extended-Release Injectable Suspension); Invirase (saquinavir mesylate); Iobenguane I 123 Injection for Intravenous Use (AdreView); Iopromide Injection (Ultravist); Ioversol Injection (Optiray Injection); Iplex (Mecasermin Rinfabate [rDNA origin] Injection); Iprivask; Irinotecan Hydrochloride (Camptosar Injection); Iron Sucrose Injection (Venofer); Istodax (Romidepsin for Injection); Itraconazole Injection (Sporanox Injection); Jevtana (Cabazitaxel Injection); Jonexa; Kalbitor (Ecallantide Injection); KCL in D5NS (Potassium Chloride in 5% Dextrose and Sodium Chloride Injection); KCL in D5W; KCL in NS; Kenalog 10 Injection (Triamcinolone Acetonide Injectable Suspension); Kepivance (Palifermin); Keppra Injection (Levetiracetam); Keratinocyte; KFG; Kinase Inhibitor; Kineret (Anakinra); Kinlytic (Urokinase Injection); Kinrix; Klonopin (clonazepam); Kytril Injection (Granisetron Hydrochloride); lacosamide Tablet and Injection (Vimpat); Lactated Ringer's; Lanoxin Injection (Digoxin Injection); Lansoprazole for Injection (Prevacid I.V.); Lantus; Leucovorin Calcium (Leucovorin Calcium Injection); Lente (L); Leptin; Levemir; Leukine Sargramostim; Leuprolide Acetate; Levothyroxine; Levetiracetam (Keppra Injection); Lovenox; Levocarnitine Injection (Carnitor Injection); Lexiscan (Regadenoson Injection); Lioresal Intrathecal (Baclofen Injection); Liraglutide [rDNA] Injection (Victoza); Lovenox (Enoxaparin Sodium Injection); Lucentis (Ranibizumab Injection); Lumizyme; Lupron (Leuprolide Acetate Injection); Lusedra (Fospropofol Disodium Injection); Maci; Magnesium Sulfate (Magnesium Sulfate Injection); Mannitol Injection (Mannitol IV); Marcaine (Bupivacaine Hydrochloride and Epinephrine Injection); Maxipime (Cefepime Hydrochloride for Injection); MDP Multidose Kit of Technetium Injection (Technetium Tc99m Medronate Injection); Mecasermin [rDNA origin] Injection (Increlex); Mecasermin Rinfabate [rDNA origin] Injection (Iplex); Melphalan Hcl Injection (Alkeran Injection); Methotrexate; Menactra; Menopur (Menotropins Injection); Menotropins for Injection (Repronex); Methohexital Sodium for Injection (Brevital Sodium); Methyldopate Hydrochloride Injection, Solution (Methyldopate Hcl); Methylene Blue (Methylene Blue Injection); Methylprednisolone Acetate Injectable Suspension (Depo Medrol); MetMab; Metoclopramide Injection (Reglan Injection); Metrodin (Urofollitropin for Injection); Metronidazole Injection (Flagyl Injection); Miacalcin; Midazolam (Midazolam Injection); Mimpara (Cinacalet); Minocin Injection (Minocycline Inj); Minocycline Inj (Minocin Injection); Mipomersen; Mitoxantrone for Injection Concentrate (Novantrone); Morphine Injection (Duramorph); Morphine Sulfate XR Liposome Injection (DepoDur); Morrhuate Sodium (Morrhuate Sodium Injection); Motesanib; Mozobil (Plerixafor Injection); Multihance (Gadobenate Dimeglumine Injection); Multiple Electrolytes and Dextrose Injection; Multiple Electrolytes Injection; Mylotarg (Gemtuzumab Ozogamicin for Injection); Myozyme (Alglucosidase alfa); Nafcillin Injection (Nafcillin Sodium); Nafcillin Sodium (Nafcillin Injection); Naltrexone XR Inj (Vivitrol); Naprosyn (naproxen); NeoProfen (Ibuprofen Lysine Injection); Nandrol Decanoate; Neostigmine Methylsulfate (Neostigmine Methylsulfate Injection); NEO-GAA; NeoTect (Technetium Tc 99m Depreotide Injection); Nephramine (Essential Amino Acid Injection); Neulasta (pegfilgrastim); Neupogen (Filgrastim); Novolin; Novolog; NeoRecormon; Neutrexin (Trimetrexate Glucuronate Inj); NPH (N); Nexterone (Amiodarone HCl Injection); Norditropin (Somatropin Injection); Normal Saline (Sodium Chloride Injection); Novantrone (Mitoxantrone for Injection Concentrate); Novolin 70/30 Innolet (70% NPH, Human Insulin Isophane Suspension and 30% Regular, Human Insulin Injection); NovoLog (Insulin Aspart [rDNA origin] Inj); Nplate (romiplostim); Nutropin (Somatropin (rDNA origin) for Inj); Nutropin AQ; Nutropin Depot (Somatropin (rDNA origin) for Inj); Octreotide Acetate Injection (Sandostatin LAR); Ocrelizumab; Ofatumumab Injection (Arzerra); Olanzapine Extended Release Injectable Suspension (Zyprexa Relprevv); Omnitarg; Omnitrope (Somatropin [rDNA origin] Injection); Ondansetron Hydrochloride Injection (Zofran Injection); OptiMARK (Gadoversetamide Injection); Optiray Injection (Ioversol Injection); Orencia; Osmitrol Injection in Aviva (Mannitol Injection in Aviva Plastic Vessel); Osmitrol Injection in Viaflex (Mannitol Injection in Viaflex Plastic Vessel); Osteoprotegrin; Ovidrel (Choriogonadotropin Alfa Injection); Oxacillin (Oxacillin for Injection); Oxaliplatin Injection (Eloxatin); Oxytocin Injection (Pitocin); Paliperidone Palmitate Extended-Release Injectable Suspension (Invega Sustenna); Pamidronate Disodium Injection (Pamidronate Disodium Injection); Panitumumab Injection for Intravenous Use (Vectibix); Papaverine Hydrochloride Injection (Papaverine Injection); Papaverine Injection (Papaverine Hydrochloride Injection); Parathyroid Hormone; Paricalcitol Injection Fliptop Vial (Zemplar Injection); PARP Inhibitor; Pediarix; PEGIntron; Peginterferon; Pegfilgrastim; Penicillin G Benzathine and Penicillin G Procaine; Pentetate Calcium Trisodium Inj (Ca-DTPA); Pentetate Zinc Trisodium Injection (Zn-DTPA); Pepcid Injection (Famotidine Injection); Pergonal; Pertuzumab; Phentolamine Mesylate (Phentolamine Mesylate for Injection); Physostigmine Salicylate (Physostigmine Salicylate (injection)); Physostigmine Salicylate (injection) (Physostigmine Salicylate); Piperacillin and Tazobactam Injection (Zosyn); Pitocin (Oxytocin Injection); Plasma-Lyte 148 (Multiple Electrolytes Inj); Plasma-Lyte 56 and Dextrose (Multiple Electrolytes and Dextrose Injection in Viaflex Plastic Vessel); PlasmaLyte; Plerixafor Injection (Mozobil); Polidocanol Injection (Asclera); Potassium Chloride; Pralatrexate Solution for Intravenous Injection (Folotyn); Pramlintide Acetate Injection (Symlin); Premarin Injection (Conjugated Estrogens for Injection); Prep kit for Technetium Tc99 Sestamibi for Injection (Cardiolite); Prevacid I.V. (Lansoprazole for Injection); Primaxin I.V. (Imipenem and Cilastatin for Injection); Prochymal; Procrit; Progesterone; ProHance (Gadoteridol Injection Solution); Prolia (Denosumab Injection); Promethazine HCl Injection (Promethazine Hydrochloride Injection); Propranolol Hydrochloride Injection (Propranolol Hydrochloride Injection); Quinidine Gluconate Injection (Quinidine Injection); Quinidine Injection (Quinidine Gluconate Injection); R-Gene 10 (Arginine Hydrochloride Injection); Ranibizumab Injection (Lucentis); Ranitidine Hydrochloride Injection (Zantac Injection); Raptiva; Reclast (Zoledronic Acid Injection); Recombivarix HB; Regadenoson Injection (Lexiscan); Reglan Injection (Metoclopramide Injection); Remicade; Renagel; Renvela (Sevelamer Carbonate); Repronex (Menotropins for Injection); Retrovir IV (Zidovudine Injection); rhApo2L/TRAIL; Ringer's and 5% Dextrose Injection (Ringers in Dextrose); Ringer's Injection (Ringers Injection); Rituxan; Rituximab; Rocephin (ceftriaxone); Rocuronium Bromide Injection (Zemuron); Roferon-A (interferon alfa-2a); Romazicon (flumazenil); Romidepsin for Injection (Istodax); Saizen (Somatropin Injection); Sandostatin LAR (Octreotide Acetate Injection); Sclerostin Ab; Sensipar (cinacalcet); Sensorcaine (Bupivacaine HCl Injections); Septocaine (Articane HCl and Epinephrine Injection); Serostim LQ (Somatropin (rDNA origin) Injection); Simponi Injection (Golimumab Injection); Sodium Acetate (Sodium Acetate Injection); Sodium Bicarbonate (Sodium Bicarbonate 5% Injection); Sodium Lactate (Sodium Lactate Injection in AVIVA); Sodium Phenylacetate and Sodium Benzoate Injection (Ammonul); Somatropin (rDNA origin) for Inj (Nutropin); Sporanox Injection (Itraconazole Injection); Stelara Injection (Ustekinumab); Stemgen; Sufenta (Sufentanil Citrate Injection); Sufentanil Citrate Injection (Sufenta); Sumavel; Sumatriptan Injection (Alsuma); Symlin; Symlin Pen; Systemic Hedgehog Antagonist; Synvisc-One (Hylan G-F 20 Single Intraarticular Injection); Tarceva; Taxotere (Docetaxel for Injection); Technetium Tc 99m; Telavancin for Injection (Vibativ); Temsirolimus Injection (Torisel); Tenormin I.V. Injection (Atenolol Inj); Teriparatide (rDNA origin) Injection (Forteo); Testosterone Cypionate; Testosterone Enanthate; Testosterone Propionate; Tev-Tropin (Somatropin, rDNA Origin, for Injection); tgAAC94; Thallous Chloride; Theophylline; Thiotepa (Thiotepa Injection); Thymoglobulin (Anti-Thymocyte Globulin (Rabbit); Thyrogen (Thyrotropin Alfa for Injection); Ticarcillin Disodium and Clavulanate Potassium Galaxy (Timentin Injection); Tigan Injection (Trimethobenzamide Hydrochloride Injectable); Timentin Injection (Ticarcillin Disodium and Clavulanate Potassium Galaxy); TNKase; Tobramycin Injection (Tobramycin Injection); Tocilizumab Injection (Actemra); Torisel (Temsirolimus Injection); Totect (Dexrazoxane for Injection, Intravenous Infusion Only); Trastuzumab-DM1; Travasol (Amino Acids (Injection)); Treanda (Bendamustine Hydrochloride Injection); Trelstar (Triptorelin Pamoate for Injectable Suspension); Triamcinolone Acetonide; Triamcinolone Diacetate; Triamcinolone Hexacetonide Injectable Suspension (Aristospan Injection 20 mg); Triesence (Triamcinolone Acetonide Injectable Suspension); Trimethobenzamide Hydrochloride Injectable (Tigan Injection); Trimetrexate Glucuronate Inj (Neutrexin); Triptorelin Pamoate for Injectable Suspension (Trelstar); Twinject; Trivaris (Triamcinolone Acetonide Injectable Suspension); Trisenox (Arsenic Trioxide Injection); Twinrix; Typhoid Vi; Ultravist (Iopromide Injection); Urofollitropin for Injection (Metrodin); Urokinase Injection (Kinlytic); Ustekinumab (Stelara Injection); Ultralente (U); Valium (diazepam); Valproate Sodium Injection (Depacon); Valtropin (Somatropin Injection); Vancomycin Hydrochloride (Vancomycin Hydrochloride Injection); Vancomycin Hydrochloride Injection (Vancomycin Hydrochloride); Vaprisol (Conivaptan Hcl Injection); VAQTA; Vasovist (Gadofosveset Trisodium Injection for Intravenous Use); Vectibix (Panitumumab Injection for Intravenous Use); Venofer (Iron Sucrose Injection); Verteporfin Inj (Visudyne); Vibativ (Telavancin for Injection); Victoza (Liraglutide [rDNA] Injection); Vimpat (lacosamide Tablet and Injection); Vinblastine Sulfate (Vinblastine Sulfate Injection); Vincasar PFS (Vincristine Sulfate Injection); Victoza; Vincristine Sulfate (Vincristine Sulfate Injection); Visudyne (Verteporfin Inj); Vitamin B-12; Vivitrol (Naltrexone XR Inj); Voluven (Hydroxyethyl Starch in Sodium Chloride Injection); Xeloda; Xenical (orlistat); Xeomin (Incobotulinumtoxin A for Injection); Xolair; Zantac Injection (Ranitidine Hydrochloride Injection); Zemplar Injection (Paricalcitol Injection Fliptop Vial); Zemuron (Rocuronium Bromide Injection); Zenapax (daclizumab); Zevalin; Zidovudine Injection (Retrovir IV); Zithromax Injection (Azithromycin); Zn-DTPA (Pentetate Zinc Trisodium Injection); Zofran Injection (Ondansetron Hydrochloride Injection); Zingo; Zoledronic Acid for Inj (Zometa); Zoledronic Acid Injection (Reclast); Zometa (Zoledronic Acid for Inj); Zosyn (Piperacillin and Tazobactam Injection); Zyprexa Relprevv (Olanzapine Extended Release Injectable Suspension)

LIQUID DRUGS (NON-INJECTABLE)

Abilify; AccuNeb (Albuterol Sulfate Inhalation Solution); Actidose Aqua (Activated Charcoal Suspension); Activated Charcoal Suspension (Actidose Aqua); Advair; Agenerase Oral Solution (Amprenavir Oral Solution); Akten (Lidocaine Hydrochloride Ophthalmic Gel); Alamast (Pemirolast Potassium Ophthalmic Solution); Albumin (Human) 5% Solution (Buminate 5%); Albuterol Sulfate Inhalation Solution; Alinia; Alocril; Alphagan; Alrex; Alvesco; Amprenavir Oral Solution; Analpram-HC; Arformoterol Tartrate Inhalation Solution (Brovana); Aristospan Injection 20 mg (Triamcinolone Hexacetonide Injectable Suspension); Asacol; Asmanex; Astepro; Astepro (Azelastine Hydrochloride Nasal Spray); Atrovent Nasal Spray (Ipratropium Bromide Nasal Spray); Atrovent Nasal Spray 0.06; Augmentin ES-600; Azasite (Azithromycin Ophthalmic Solution); Azelaic Acid (Finacea Gel); Azelastine Hydrochloride Nasal Spray (Astepro); Azelex (Azelaic Acid Cream); Azopt (Brinzolamide Ophthalmic Suspension); Bacteriostatic Saline; Balanced Salt; Bepotastine; Bactroban Nasal; Bactroban; Beclovent; Benzac W; Betimol; Betoptic S; Bepreve; Bimatoprost Ophthalmic Solution; Bleph 10 (Sulfacetamide Sodium Ophthalmic Solution 10%); Brinzolamide Ophthalmic Suspension (Azopt); Bromfenac Ophthalmic Solution (Xibrom); Bromhist; Brovana (Arformoterol Tartrate Inhalation Solution); Budesonide Inhalation Suspension (Pulmicort Respules); Cambia (Diclofenac Potassium for Oral Solution); Capex; Carac; Carboxine-PSE; Carnitor; Cayston (Aztreonam for Inhalation Solution); Cellcept; Centany; Cerumenex; Ciloxan Ophthalmic Solution (Ciprofloxacin HCL Ophthalmic Solution); Ciprodex; Ciprofloxacin HCL Ophthalmic Solution (Ciloxan Ophthalmic Solution); Clemastine Fumarate Syrup (Clemastine Fumarate Syrup); CoLyte (PEG Electrolytes Solution); Combiven; Comtan; Condylox; Cordran; Cortisporin Ophthalmic Suspension; Cortisporin Otic Suspension; Cromolyn Sodium Inhalation Solution (Intal Nebulizer Solution); Cromolyn Sodium Ophthalmic Solution (Opticrom); Crystalline Amino Acid Solution with Electrolytes (Aminosyn Electrolytes); Cutivate; Cuvposa (Glycopyrrolate Oral Solution); Cyanocobalamin (CaloMist Nasal Spray); Cyclosporine Oral Solution (Gengraf Oral Solution); Cyclogyl; Cysview (Hexaminolevulinate Hydrochloride Intravesical Solution); DermOtic Oil (Fluocinolone Acetonide Oil Ear Drops); Desmopressin Acetate Nasal Spray; DDAVP; Derma-Smoothe/FS; Dexamethasone Intensol; Dianeal Low Calcium; Dianeal PD; Diclofenac Potassium for Oral Solution (Cambia); Didanosine Pediatric Powder for Oral Solution (Videx); Differin; Dilantin 125 (Phenytoin Oral Suspension); Ditropan; Dorzolamide Hydrochloride Ophthalmic Solution (Trusopt); Dorzolamide Hydrochloride-Timolol Maleate Ophthalmic Solution (Cosopt); Dovonex Scalp (Calcipotriene Solution); Doxycycline Calcium Oral Suspension (Vibramycin Oral); Efudex; Elaprase (Idursulfase Solution); Elestat (Epinastine HCl Ophthalmic Solution); Elocon; Epinastine HCl Ophthalmic Solution (Elestat); Epivir HBV; Epogen (Epoetin alfa); Erythromycin Topical Solution 1.5% (Staticin); Ethiodol (Ethiodized Oil); Ethosuximide Oral Solution (Zarontin Oral Solution); Eurax; Extraneal (Icodextrin Peritoneal Dialysis Solution); Felbatol; Feridex I.V. (Ferumoxides Injectable Solution); Flovent; Floxin Otic (Ofloxacin Otic Solution);

Flo-Pred (Prednisolone Acetate Oral Suspension); Fluoroplex; Flunisolide Nasal Solution (Flunisolide Nasal Spray 0.025%); Fluorometholone Ophthalmic Suspension (FML); Flurbiprofen Sodium Ophthalmic Solution (Ocufen); FML; Foradil; Formoterol Fumarate Inhalation Solution (Perforomist); Fosamax; Furadantin (Nitrofurantoin Oral Suspension); Furoxone; Gammagard Liquid (Immune Globulin Intravenous (Human) 10%); Gantrisin (Acetyl Sulfisoxazole Pediatric Suspension); Gatifloxacin Ophthalmic Solution (Zymar); Gengraf Oral Solution (Cyclosporine Oral Solution); Glycopyrrolate Oral Solution (Cuvposa); Halcinonide Topical Solution (Halog Solution); Halog Solution (Halcinonide Topical Solution); HEP-LOCK U/P (Preservative-Free Heparin Lock Flush Solution); Heparin Lock Flush Solution (Hepflush 10); Hexaminolevulinate Hydrochloride Intravesical Solution (Cysview); Hydrocodone Bitartrate and Acetaminophen Oral Solution (Lortab Elixir); Hydroquinone 3% Topical Solution (Melquin-3 Topical Solution); IAP Antagonist; Isopto; Ipratropium Bromide Nasal Spray (Atrovent Nasal Spray); Itraconazole Oral Solution (Sporanox Oral Solution); Ketorolac Tromethamine Ophthalmic Solution (Acular LS); Kaletra; Lanoxin; Lexiva; Leuprolide Acetate for Depot Suspension (Lupron Depot 11.25 mg); Levobetaxolol Hydrochloride Ophthalmic Suspension (Betaxon); Levocarnitine Tablets, Oral Solution, Sugar-Free (Carnitor); Levofloxacin Ophthalmic Solution 0.5% (Quixin); Lidocaine HCl Sterile Solution (Xylocaine MPF Sterile Solution); Lok Pak (Heparin Lock Flush Solution); Lorazepam Intensol; Lortab Elixir (Hydrocodone Bitartrate and Acetaminophen Oral Solution); Lotemax (Loteprednol Etabonate Ophthalmic Suspension); Loteprednol Etabonate Ophthalmic Suspension (Alrex); Low Calcium Peritoneal Dialysis Solutions (Dianeal Low Calcium); Lumigan (Bimatoprost Ophthalmic Solution 0.03% for Glaucoma); Lupron Depot 11.25 mg (Leuprolide Acetate for Depot Suspension); Megestrol Acetate Oral Suspension (Megestrol Acetate Oral Suspension); MEK Inhibitor; Mepron; Mesnex; Mestinon; Mesalamine Rectal Suspension Enema (Rowasa); Melquin-3 Topical Solution (Hydroquinone 3% Topical Solution); MetMab; Methyldopate Hcl (Methyldopate Hydrochloride Injection, Solution); Methylin Oral Solution (Methylphenidate HCl Oral Solution 5 mg/5 mL and 10 mg/5 mL); Methylprednisolone Acetate Injectable Suspension (Depo Medrol); Methylphenidate HCl Oral Solution 5 mg/5 ml and 10 mg/5 ml (Methylin Oral Solution); Methylprednisolone sodium succinate (Solu Medrol); Metipranolol Ophthalmic Solution (Optipranolol); Migranal; Miochol-E (Acetylcholine Chloride Intraocular Solution); Micro-K for Liquid Suspension (Potassium Chloride Extended Release Formulation for Liquid Suspension); Minocin (Minocycline Hydrochloride Oral Suspension); Nasacort; Neomycin and Polymyxin B Sulfates and Hydrocortisone; Nepafenac Ophthalmic Suspension (Nevanac); Nevanac (Nepafenac Ophthalmic Suspension); Nitrofurantoin Oral Suspension (Furadantin); Noxafil (Posaconazole Oral Suspension); Nystatin (oral) (Nystatin Oral Suspension); Nystatin Oral Suspension (Nystatin (oral)); Ocufen (Flurbiprofen Sodium Ophthalmic Solution); Ofloxacin Ophthalmic Solution (Ofloxacin Ophthalmic Solution); Ofloxacin Otic Solution (Floxin Otic); Olopatadine Hydrochloride Ophthalmic Solution (Pataday); Opticrom (Cromolyn Sodium Ophthalmic Solution); Optipranolol (Metipranolol Ophthalmic Solution); Patanol; Pediapred; PerioGard; Phenytoin Oral Suspension (Dilantin 125); Phisohex; Posaconazole Oral Suspension (Noxafil); Potassium Chloride Extended Release Formulation for Liquid Suspension (Micro-K for Liquid Suspension); Pataday (Olopatadine Hydrochloride Ophthalmic Solution); Patanase Nasal Spray (Olopatadine Hydrochloride Nasal Spray); PEG Electrolytes Solution (CoLyte); Pemirolast Potassium Ophthalmic Solution (Alamast); Penlac (Ciclopirox Topical Solution); PENNSAID (Diclofenac Sodium Topical Solution); Perforomist (Formoterol Fumarate Inhalation Solution); Peritoneal Dialysis Solution; Phenylephrine Hydrochloride Ophthalmic Solution (Neo-Synephrine); Phospholine Iodide (Echothiophate Iodide for Ophthalmic Solution); Podofilox (Podofilox Topical Solution); Pred Forte (Prednisolone Acetate Ophthalmic Suspension); Pralatrexate Solution for Intravenous Injection (Folotyn); Pred Mild; Prednisone Intensol; Prednisolone Acetate Ophthalmic Suspension (Pred Forte); Prevacid; PrismaSol Solution (Sterile Hemofiltration Hemodiafiltration Solution); ProAir; Proglycem; ProHance (Gadoteridol Injection Solution); Proparacaine Hydrochloride Ophthalmic Solution (Alcaine); Propine; Pulmicort; Pulmozyme; Quixin (Levofloxacin Ophthalmic Solution 0.5%); QVAR; Rapamune; Rebetol; Relacon-HC; Rotarix (Rotavirus Vaccine, Live, Oral Suspension); Rotavirus Vaccine, Live, Oral Suspension (Rotarix); Rowasa (Mesalamine Rectal Suspension Enema); Sabril (Vigabatrin Oral Solution); Sacrosidase Oral Solution (Sucraid); Sandimmune; Sepra; Serevent Diskus; Solu Cortef (Hydrocortisone Sodium Succinate); Solu Medrol (Methylprednisolone sodium succinate); Spiriva; Sporanox Oral Solution (Itraconazole Oral Solution); Staticin (Erythromycin Topical Solution 1.5%); Stalevo; Starlix; Sterile Hemofiltration Hemodiafiltration Solution (PrismaSol Solution); Stimate; Sucralfate (Carafate Suspension); Sulfacetamide Sodium Ophthalmic Solution 10% (Bleph 10); Synarel Nasal Solution (Nafarelin Acetate Nasal Solution for Endometriosis); Taclonex Scalp (Calcipotriene and Betamethasone Dipropionate Topical Suspension); Tamiflu; Tobi; TobraDex; Tobradex ST (Tobramycin/Dexamethasone Ophthalmic Suspension 0.3%/0.05%); Tobramycin/Dexamethasone Ophthalmic Suspension 0.3%/0.05% (Tobradex ST); Timolol; Timoptic; Travatan Z; Treprostinil Inhalation Solution (Tyvaso); Trusopt (Dorzolamide Hydrochloride Ophthalmic Solution); Tyvaso (Treprostinil Inhalation Solution); Ventolin; Vfend; Vibramycin Oral (Doxycycline Calcium Oral Suspension); Videx (Didanosine Pediatric Powder for Oral Solution); Vigabatrin Oral Solution (Sabril); Viokase; Viracept; Viramune; Vitamin K1 (Fluid Colloidal Solution of Vitamin K1); Voltaren Ophthalmic (Diclofenac Sodium Ophthalmic Solution); Zarontin Oral Solution (Ethosuximide Oral Solution); Ziagen; Zyvox; Zymar (Gatifloxacin Ophthalmic Solution); Zymaxid (Gatifloxacin Ophthalmic Solution)

DRUG CLASSES 5-alpha-reductase inhibitors; 5-aminosalicylates; 5HT3 receptor antagonists; adamantane antivirals; adrenal cortical steroids; adrenal corticosteroid inhibitors; adrenergic bronchodilators; agents for hypertensive emergencies; agents for pulmonary hypertension;

aldosterone receptor antagonists; alkylating agents; alpha-adrenoreceptor antagonists; alpha-glucosidase inhibitors; alternative medicines; amebicides; aminoglycosides; aminopenicillins; aminosalicylates; amylin analogs; Analgesic Combinations; Analgesics; androgens and anabolic steroids; angiotensin converting enzyme inhibitors; angiotensin II inhibitors; anorectal preparations; anorexiants; antacids; anthelmintics; antiangiogenic ophthalmic agents; anti-CTLA-4 monoclonal antibodies; anti-infectives; antiadrenergic agents, centrally acting; antiadrenergic agents, peripherally acting; antiandrogens; antianginal agents; antiarrhythmic agents; antiasthmatic combinations; antibiotics/antineoplastics; anticholinergic antiemetics; anticholinergic antiparkinson agents; anticholinergic bronchodilators; anticholinergic chronotropic agents; anticholinergics/antispasmodics; anticoagulants; anticonvulsants; antidepressants; antidiabetic agents; antidiabetic combinations; antidiarrheals; antidiuretic hormones; antidotes; antiemetic/antivertigo agents; antifungals; antigonadotropic agents; antigout agents; antihistamines; antihyperlipidemic agents; antihyperlipidemic combinations; antihypertensive combinations; antihyperuricemic agents; antimalarial agents; antimalarial combinations; antimalarial quinolines; antimetabolites; antimigraine agents; antineoplastic detoxifying agents; antineoplastic interferons; antineoplastic monoclonal antibodies; antineoplastics; antiparkinson agents; antiplatelet agents; antipseudomonal penicillins; antipsoriatics; antipsychotics; antirheumatics; antiseptic and germicides; antithyroid agents; antitoxins and antivenins; antituberculosis agents; antituberculosis combinations; antitussives; antiviral agents; antiviral combinations; antiviral interferons; anxiolytics, sedatives, and hypnotics; aromatase inhibitors; atypical antipsychotics; azole antifungals; bacterial vaccines; barbiturate anticonvulsants; barbiturates; BCR-ABL tyrosine kinase inhibitors; benzodiazepine anticonvulsants; benzodiazepines; beta-adrenergic blocking agents; beta-lactamase inhibitors; bile acid sequestrants; biologicals; bisphosphonates; bone resorption inhibitors; bronchodilator combinations; bronchodilators; calcitonin; calcium channel blocking agents; carbamate anticonvulsants; carbapenems; carbonic anhydrase inhibitor anticonvulsants; carbonic anhydrase inhibitors; cardiac stressing agents; cardioselective beta blockers; cardiovascular agents; catecholamines; CD20 monoclonal antibodies; CD33 monoclonal antibodies; CD52 monoclonal antibodies; central nervous system agents; cephalosporins; cerumenolytics; chelating agents; chemokine receptor antagonist; chloride channel activators; cholesterol absorption inhibitors; cholinergic agonists; cholinergic muscle stimulants; cholinesterase inhibitors; CNS stimulants; coagulation modifiers; colony stimulating factors; contraceptives; corticotropin; coumarins and indandiones; cox-2 inhibitors; decongestants; dermatological agents; diagnostic radiopharmaceuticals; dibenzazepine anticonvulsants; digestive enzymes; dipeptidyl peptidase 4 inhibitors; diuretics; dopaminergic antiparkinsonism agents; drugs used in alcohol dependence; echinocandins; EGFR inhibitors; estrogen receptor antagonists; estrogens; expectorants; factor Xa inhibitors; fatty acid derivative anticonvulsants; fibric acid derivatives; first generation cephalosporins; fourth generation cephalosporins; functional bowel disorder agents; gallstone solubilizing agents; gamma-aminobutyric acid analogs; gamma-aminobutyric acid reuptake inhibitors; gamma-aminobutyric acid transaminase inhibitors; gastrointestinal agents; general anesthetics; genitourinary tract agents; GI stimulants; glucocorticoids; glucose elevating agents; glycopeptide antibiotics; glycoprotein platelet inhibitors; glycylcyclines; gonadotropin releasing hormones; gonadotropin-releasing hormone antagonists; gonadotropins; group I antiarrhythmics; group II antiarrhythmics; group III antiarrhythmics; group IV antiarrhythmics; group V antiarrhythmics; growth hormone receptor blockers; growth hormones; *H. pylori* eradication agents; H2 antagonists; hematopoietic stem cell mobilizer; heparin antagonists; heparins; HER2 inhibitors; herbal products; histone deacetylase inhibitors; hormone replacement therapy; hormones; hormones/antineoplastics; hydantoin anticonvulsants; illicit (street) drugs; immune globulins; immunologic agents; immunosuppressive agents; impotence agents; in vivo diagnostic biologicals; incretin mimetics; inhaled anti-infectives; inhaled corticosteroids; inotropic agents; insulin; insulin-like growth factor; integrase strand transfer inhibitor; interferons; intravenous nutritional products; iodinated contrast media; ionic iodinated contrast media; iron products; ketolides; laxatives; leprostatics; leukotriene modifiers; lincomycin derivatives; lipoglycopeptides; local injectable anesthetics; loop diuretics; lung surfactants; lymphatic staining agents; lysosomal enzymes; macrolide derivatives; macrolides; magnetic resonance imaging contrast media; mast cell stabilizers; medical gas; meglitinides; metabolic agents; methylxanthines; mineralocorticoids; minerals and electrolytes; miscellaneous agents; miscellaneous analgesics; miscellaneous antibiotics; miscellaneous anticonvulsants; miscellaneous antidepressants; miscellaneous antidiabetic agents; miscellaneous antiemetics; miscellaneous antifungals; miscellaneous antihyperlipidemic agents; miscellaneous antimalarials; miscellaneous antineoplastics; miscellaneous antiparkinson agents; miscellaneous antipsychotic agents; miscellaneous antituberculosis agents; miscellaneous antivirals; miscellaneous anxiolytics, sedatives and hypnotics; miscellaneous biologicals; miscellaneous bone resorption inhibitors; miscellaneous cardiovascular agents; miscellaneous central nervous system agents; miscellaneous coagulation modifiers; miscellaneous diuretics; miscellaneous genitourinary tract agents; miscellaneous GI agents; miscellaneous hormones; miscellaneous metabolic agents; miscellaneous ophthalmic agents; miscellaneous otic agents; miscellaneous respiratory agents; miscellaneous sex hormones; miscellaneous topical agents; miscellaneous uncategorized agents; miscellaneous vaginal agents; mitotic inhibitors; monoamine oxidase inhibitors; monoclonal antibodies; mouth and throat products; mTOR inhibitors; mTOR kinase inhibitors; mucolytics; multikinase inhibitors; muscle relaxants; mydriatics; narcotic analgesic combinations; narcotic analgesics; nasal anti-infectives; nasal antihistamines and decongestants; nasal lubricants and irrigations; nasal preparations; nasal steroids; natural penicillins; neuraminidase inhibitors; neuromuscular blocking agents; next generation cephalosporins; nicotinic acid derivatives; nitrates; NNRTIs; non-cardioselective beta blockers; non-iodinated contrast media; non-ionic iodinated contrast media; non-sulfonylureas; nonsteroidal anti-inflammatory agents; norepinephrine reuptake inhibitors;

norepinephrine-dopamine reuptake inhibitors; nucleoside reverse transcriptase inhibitors (NRTIs); nutraceutical products; nutritional products; ophthalmic anesthetics; ophthalmic anti-infectives; ophthalmic anti-inflammatory agents; ophthalmic antihistamines and decongestants; ophthalmic diagnostic agents; ophthalmic glaucoma agents; ophthalmic lubricants and irrigations; ophthalmic preparations; ophthalmic steroids; ophthalmic steroids with anti-infectives; ophthalmic surgical agents; oral nutritional supplements; otic anesthetics; otic anti-infectives; otic preparations; otic steroids; otic steroids with anti-infectives; oxazolidinedione anticonvulsants; parathyroid hormone and analogs; penicillinase resistant penicillins; penicillins; peripheral opioid receptor antagonists; peripheral vasodilators; peripherally acting antiobesity agents; phenothiazine antiemetics; phenothiazine antipsychotics; phenylpiperazine antidepressants; plasma expanders; platelet aggregation inhibitors; platelet-stimulating agents; polyenes; potassium-sparing diuretics; probiotics; progesterone receptor modulators; progestins; prolactin inhibitors; prostaglandin D2 antagonists; protease inhibitors; proton pump inhibitors; psoralens; psychotherapeutic agents; psychotherapeutic combinations; purine nucleosides; pyrrolidine anticonvulsants; quinolones; radiocontrast agents; radiologic adjuncts; radiologic agents; radiologic conjugating agents; radiopharmaceuticals; RANK ligand inhibitors; recombinant human erythropoietins; renin inhibitors; respiratory agents; respiratory inhalant products; rifamycin derivatives; salicylates; sclerosing agents; second generation cephalosporins; selective estrogen receptor modulators; selective serotonin reuptake inhibitors; serotonin-norepinephrine reuptake inhibitors; serotoninergic neuroenteric modulators; sex hormone combinations; sex hormones; skeletal muscle relaxant combinations; skeletal muscle relaxants; smoking cessation agents; somatostatin and somatostatin analogs; spermicides; statins; sterile irrigating solutions; streptomyces derivatives; succinimide anticonvulsants; sulfonamides; sulfonylureas; synthetic ovulation stimulants; tetracyclic antidepressants; tetracyclines; therapeutic radiopharmaceuticals; thiazide diuretics; thiazolidinediones; thioxanthenes; third generation cephalosporins; thrombin inhibitors; thrombolytics; thyroid drugs; tocolytic agents; topical acne agents; topical agents; topical anesthetics; topical anti-infectives; topical antibiotics; topical antifungals; topical antihistamines; topical antipsoriatics; topical antivirals; topical astringents; topical debriding agents; topical depigmenting agents; topical emollients; topical keratolytics; topical steroids; topical steroids with anti-infectives; toxoids; triazine anticonvulsants; tricyclic antidepressants; trifunctional monoclonal antibodies; tumor necrosis factor (TNF) inhibitors; tyrosine kinase inhibitors; ultrasound contrast media; upper respiratory combinations; urea anticonvulsants; urinary anti-infectives; urinary antispasmodics; urinary pH modifiers; uterotonic agents; vaccine; vaccine combinations; vaginal anti-infectives; vaginal preparations; vasodilators; vasopressin antagonists; vasopressors; VEGF/VEGFR inhibitors; viral vaccines; viscosupplementation agents; vitamin and mineral combinations; vitamins

DIAGNOSTIC TESTS

17-Hydroxyprogesterone; ACE (Angiotensin I converting enzyme); Acetaminophen; Acid phosphatase; ACTH; Activated clotting time; Activated protein C resistance; Adrenocorticotropic hormone (ACTH); Alanine aminotransferase (ALT); Albumin; Aldolase; Aldosterone; Alkaline phosphatase; Alkaline phosphatase (ALP); Alpha1-antitrypsin; Alpha-fetoprotein; Alpha-fetoprotien; Ammonia levels; Amylase; ANA (antinuclear antbodies); ANA (antinuclear antibodies); Angiotensin-converting enzyme (ACE); Anion gap; Anticardiolipin antibody; Anticardiolipin antivbodies (ACA); Anti-centromere antibody; Antidiuretic hormone; Anti-DNA; Anti-Dnase-B; Anti-Gliadin antibody; Anti-glomerular basement membrane antibody; Anti-HBC (Hepatitis B core antibodies; Anti-HBs (Hepatitis B surface antibody; Antiphospholipid antibody; Anti-RNA polymerase; Anti-Smith (Sm) antibodies; Anti-Smooth Muscle antibody; Antistreptolysin O (ASO); Antithrombin III; Anti-Xa activity; Anti-Xa assay; Apolipoproteins; Arsenic; Aspartate aminotransferase (AST); B12; Basophil; Beta-2-Microglobulin; Beta-hydroxybutyrate; B-HCG; Bilirubin; Bilirubin, direct; Bilirubin, indirect; Bilirubin, total; Bleeding time; Blood gases (arterial); Blood urea nitrogen (BUN); BUN; BUN (blood urea nitrogen); CA 125; CA 15-3; CA 19-9; Calcitonin; Calcium; Calcium (ionized); Carbon monoxide (CO); Carcinoembryonic antigen (CEA); CBC; CEA; CEA (carcinoembryonic antigen); Ceruloplasmin; CH50Chloride; Cholesterol; Cholesterol, HDL; Clot lysis time; Clot retraction time; CMP; CO2; Cold agglutinins; Complement C3; Copper; Corticotrophin releasing hormone (CRH) stimulation test; Cortisol; Cortrosyn stimulation test; C-peptide; CPK (Total); CPK-MB; C-reactive protein; Creatinine; Creatinine kinase (CK); Cryoglobulins; DAT (Direct antiglobulin test); D-Dimer; Dexamethasone suppression test; DHEA-S; Dilute Russell viper venom; Elliptocytes; Eosinophil; Erythrocyte sedimentation rate (ESR); Estradiol; Estriol; Ethanol; Ethylene glycol; Euglobulin lysis; Factor V Leiden; Factor VIII inhibitor; Factor VIII level; Ferritin; Fibrin split products; Fibrinogen; Folate; Folate (serum; Fractional excretion of sodium (FENA); FSH (follicle stimulating factor); FTA-ABS; Gamma glutamyl transferase (GGT); Gastrin; GGTP (Gamma glutamyl transferase); Glucose; Growth hormone; Haptoglobin; HBeAg (Hepatitis Be antigen); HBs-Ag (Hepatitis B surface antigen); *Helicobacter pylori*; Hematocrit; Hematocrit (HCT); Hemoglobin; Hemoglobin A1C; Hemoglobin electrophoresis; Hepatitis A antibodies; Hepatitis C antibodies; IAT (Indirect antiglobulin test); Immunofixation (IFE); Iron; Lactate dehydrogenase (LDH); Lactic acid (lactate); LDH; LH (Leutinizing hormone; Lipase; Lupus anticoagulant; Lymphocyte; Magnesium; MCH (mean corpuscular hemoglobin; MCHC (mean corpuscular hemoglobin concentration); MCV (mean corpuscular volume); Methylmalonate; Monocyte; MPV (mean platelet volume); Myoglobin; Neutrophil; Parathyroid hormone (PTH); Phosphorus; Platelets (plt); Potassium; Prealbumin; Prolactin; Prostate specific antigen (PSA); Protein C; Protein S; PSA (prostate specific antigen); PT (Prothrombin time); PTT (Partial thromboplastin time); RDW (red cell distribution width); Renin; Rennin; Reticulocyte count; reticulocytes; Rheumatoid factor (RF); Sed Rate; Serum glutamic-pyruvic transaminase (SGPT; Serum protein electrophoresis (SPEP); Sodium; T3-resin uptake (T3RU); T4, Free; Thrombin time; Thyroid stimulating hormone (TSH); Thyroxine (T4); Total iron binding capacity (TIBC); Total protein; Transferrin; Transferrin saturation; Triglyceride (TG); Troponin; Uric acid; Vitamin B12; White blood cells (WBC); Widal test.

13. The vessel of claim 1, in which the lumen contains a pharmaceutical agent.

14. The vessel of claim 13, in which the pharmaceutical agent has a pH between 5 and 9.

15. The vessel of claim 14, in which the pH protective coating or layer contacting the pharmaceutical agent is between 20 and 700 nm thick two years after the invention is assembled.

16. The vessel of claim 14, having a shelf life of at least two years and at most ten years.

17. The vessel of claim 16, in which the shelf life is determined at 3° C.

18. The vessel of claim 17, in which the pH of the fluid composition is between 7 and 8 and the thickness of the pH protective coating or layer is at least 80 nm at the end of the shelf life.

19. The vessel of claim 14, in which the fluid composition removes the pH protective coating or layer at a rate of 1 nm or less of pH protective coating or layer thickness per 44 or 250 hours of contact with the fluid composition.

* * * * *